United States Patent
Hunter et al.

(10) Patent No.: US 11,746,378 B2
(45) Date of Patent: Sep. 5, 2023

(54) DETECTION OF CHROMOSOME INTERACTION RELEVANT TO BREAST CANCER

(71) Applicant: Oxford Biodynamics, PLC, Oxford (GB)

(72) Inventors: Ewan Hunter, Oxford (GB); Howard Womersley, Oxford (GB); Aroul Ramadass, Oxford (GB); Alexandre Akoulitchev, Oxford (GB)

(73) Assignee: OXFORD BIODYNAMICS PLC, Oxford (GB)

( * ) Notice: Subject to any disclaimer, the term of this patent is extended or adjusted under 35 U.S.C. 154(b) by 0 days.

(21) Appl. No.: 16/098,667

(22) PCT Filed: May 8, 2017

(86) PCT No.: PCT/GB2017/051273
§ 371 (c)(1),
(2) Date: Nov. 2, 2018

(87) PCT Pub. No.: WO2017/191477
PCT Pub. Date: Nov. 9, 2017

(65) Prior Publication Data
US 2019/0241964 A1    Aug. 8, 2019

(30) Foreign Application Priority Data
May 6, 2016   (GB) ...................... 1608000

(51) Int. Cl.
*C12Q 1/6886*    (2018.01)
*C12Q 1/6827*    (2018.01)

(52) U.S. Cl.
CPC ......... *C12Q 1/6886* (2013.01); *C12Q 1/6827* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2010/0075861 A1    3/2010    De Laat et al.

FOREIGN PATENT DOCUMENTS

| WO | WO 2007/061876 A2 | 5/2007 |
|----|-------------------|--------|
| WO | WO 2007/093819 A2 | 8/2007 |
| WO | 2009147386 A1 | 12/2009 |
| WO | WO 2009/147386 A1 | 12/2009 |
| WO | 2012159025 A2 | 11/2012 |
| WO | WO 2012/159025 A2 | 11/2012 |
| WO | WO 2013/075059 A1 | 5/2013 |
| WO | 2015071748 A1 | 5/2015 |
| WO | WO 2015/071748 A1 | 5/2015 |
| WO | WO 2015/135035 A2 | 9/2015 |
| WO | 2016207647 A1 | 12/2016 |
| WO | WO 2016/207647 A1 | 12/2016 |
| WO | WO 2016/207653 A1 | 12/2016 |
| WO | WO 2016/207661 A1 | 12/2016 |

OTHER PUBLICATIONS

Merriam-Webster Dictionary definition for "physically." Available via URL: <merriam-webster.com/dictionary/physically, printed Sep. 28, 2021 (Year: 2021).*
Bastonini et al. (2014) "Chromatin barcodes as biomarkers for melanoma," Pigment Cell & Melanoma Research, 27 (5): 788-800.
Simonis et al. (2006) "Nuclear organization of active and inactive chromatin domains uncovered by chromosome conformation capture-on-chip (4C)," Nature Genetics, 38 (11): 1348-1354.
Stadhouders et al. (2013) "Multiplexed chromosome conformation capture sequencing for rapid genome-scale high-resolution detection of long-range chromatin interactions," Nature Protocols, 8 (3): 509-524.
Written Opinion and International Search Report dated Aug. 21, 2017 in International Application No. PCT/GB2017/051273.
Jeznach et al., "Breast cancer: development of early non-invasive diagnostics to reduce disease mortality and psychological outcomes", Psychoonkologia, vol. 2, 2013, pp. 35-49.
Zeitz et al., "Genomic interaction profiles in breast cancer reveal altered chromatin architecture", PLoS ONE, vol. 8, Issue 9, Sep. 2013, e73974, 12 pages.
Bastonini et al., "Chromatin barcodes as biomarkers for melanoma", Pigment Cell and Melanoma Research, 2014, vol. 27, Issue 5, pp. 788-800.
Simonis et al., "Nuclear organization of active and inactive chromatin domains uncovered by chromosome conformation capture-on-chip (4C)", Nature Genetics, 2006, vol. 38, No. 11, pp. 1348-1354.
Stadhouders et al., "Multiplexed Chromosome Conformation Capture Sequencing for Rapid Genome-Scale High-Resolution Detection of Long-Range Chromatin Interactions", Nature Protocols, 2013 Vol. 8, No. 3, pp. 509-524, doi: 10.1038/nprot.2013.018.
Oxford BioDynamics, "Predictive Biomarkers", Oxford BioDynamics Website, 2013-2014, retrieved from: http://web.archive.org/web/20131209081232/http://oxfordbiodynamics.com/applications/predictive-biomarkers.
Cheng et al., "Disease-Associated Chromatin Conformation and Therapeutic Implications In Leukemia", Blood, 2013, vol. 122, Issue 21, p. 4892.
Jakub et al., "A pilot study of chromosomal aberrations and epigenetic changes in peripheral blood samples to identify patients with melanoma", Melanoma Research, 2015, vol. 25, No. 5. pp. 406-411.
Crutchley et al., "Chromatin conformation signatures: ideal human disease biomarkers", Biomarkers in Medicine, 2010, vol. 4, No. 4, pp. 611-629.

(Continued)

*Primary Examiner* — Carla J Myers
(74) *Attorney, Agent, or Firm* — FisherBroyles, LLP; Adam Whiting; Adelaide K. Leitzel

(57) ABSTRACT

A process for analysing chromosome regions and interactions relating to breast cancer.

3 Claims, 25 Drawing Sheets

Specification includes a Sequence Listing.

(56) References Cited

OTHER PUBLICATIONS

McCord R et al., "Abstract 462: Chromatin signatures of DLBCL subtypes", Proceedings of the 105th Annual Meeting of the American Association for Cancer Research, Apr. 5-9, 2014, San Diego, CA, AACR—Cancer Research, 2014, vol. 74, Issue 19 Supplement, doi:10.1158/1538-7445.AM2014-462 [retrieved Aug. 20, 2018] <URL: http://cancerres.aacrjournals.org/content/74/19_Supplement/462>.

Dekker et al., "Capturing Chromosome Conformation", Science, 2002, vol. 295, pp. 1306-1311.

Abstract O-065; Annual Meeting of the Japanese Association of Breast Cancer Screening; Clinical evaluation of EpiSwitch OBD-27, a Breast Cancer Screening Tool, based on Epigenetics Concept on Japanese population; Nov. 10, 2012 [in Japanese].

English translation of D23 [Abstract O-065; Annual Meeting of the Japanese Association of Breast Cancer Screening; Clinical evaluation of EpiSwitch OBD-27, a Breast Cancer Screening Tool, based on Epigenetics Concept on Japanese population; Nov. 10, 2012].

National Cancer Centre Singapore, Poster of Jan. 18, 2011, CMR Seminar Announcement, 1 page.

Oxford BioDynamics, Press Release of Sep. 10, 2010, 1 page.

Oxford BioDynamics, New Frontiers in Epigenetics: Genomic Biomarkers with EpiSwitch™ Technology, Presentation at SingHealth, National Cancer Centre, Singapore (NCCS), Jan. 23, 2012, 7 pages.

\* cited by examiner

Figure 21A

| probe | Genelocus | Probe_Count_Total | Probe_Count_Sig | HyperG_Stats | FDR_HyperG | Percent_Sig | logFC | AveExpr | t | P.Value | adj.P.Val | B | FC | FC_1 | LS | Loop detected |
|---|---|---|---|---|---|---|---|---|---|---|---|---|---|---|---|---|
| ATM_11_108118137_108126372_108355279_108366887_RF | ATM | 54 | 11 | 0.010710258 | 0.319438 | 20.37 | 0.302259 | 0.302259 | 10.26887 | 9E-07 | 5E-05 | 6.228128 | 1.233073 | 1.233073 | 1 | HC |
| CDC6_17_38421089_38423079_38451196_38457050_FF | CDC6 | 18 | 5 | 0.0222213308 | 0.344891 | 27.78 | -0.333066 | -0.333066 | -13.39008 | 8E-07 | 0.00028 | 6.590187 | 0.795173 | -1.257259 | -1 | BrCa |
| TSPYL5_8_98276431_98282736_98318623_98318730_FF | TSPYL5 | 23 | 6 | 0.01713027 | 0.320337 | 26.09 | -0.38273 | -0.38273 | -12.2759 | 2E-06 | 0.000361 | 5.940948 | 0.766984 | -1.30381 | -1 | BrCa |
| ME3_11_86300063_86304401_86420568_86436300_FR | ME3 | 144 | 14 | 0.491902034 | | 9.72 | -0.40222 | -0.40222 | -3.89629 | 0.000417 | 0.017168 | 2.28251 | 0.756691 | -1.321541 | -1 | BrCa |
| SRD5A1_5_6634975_6639025_6667775_6669711_RF | SRD5A1 | 13 | 2 | 0.350038364 | | 15.38 | -0.32108 | -0.32108 | -3.32108 | 0.000138 | 0.002522 | 1.36779 | 0.80047 | -1.24927 | -1 | BrCa |
| VAV3_1_108148301_108159073_108220300_108229538FF | VAV3 | 170 | 7 | 0.99731958 | | 4.12 | -0.461222 | -0.461222 | -7.261115 | 8E-05 | 0.002063 | 1.943909 | 0.726373 | -1.3767 | -1 | BrCa |
| FOXC1_6_1577253_1581989_1604206_1605973_FR | FOXC1 | 28 | 15 | 4E-09 | 1E-06 | 53.57 | -0.47676 | -0.47676 | -7.51826 | 6E-05 | 0.00183 | 2.205023 | 0.718589 | -1.393162 | -1 | BrCa |
| MSH3_5_80021913_80025030_80153948_80159012_RF | MSH3 | 151 | 12 | 0.772883797 | | 7.95 | 0.335831 | 0.335831 | 7.438085 | 7E-05 | 0.0019887 | 2.124415 | 1.264512 | 1.264512 | 1 | HC |

| Probe sequence | | Probe Location | | | | | 4 kb Sequence Location | | | |
|---|---|---|---|---|---|---|---|---|---|---|
| ID_mer | Probe sequence | Chr | Start1 | End1 | Start2 | End2 | Chr | Start1 | End1 | Start2 | End2 |
| TTGGAGGGAAAGTAATTACGTTCAACTTCGACTGTATTCTACAAAGTGCTGGGATTACA | | 11 | 1.08E+08 | 1.08E+08 | 1.08E+08 | 1.08E+08 | 11 | 1.08E+08 | 1.08E+08 | 1.08E+08 | 1.08E+08 |
| GGAAGGAGCCAGAGAAAGAGAATGTGATCGATTTCTAAATACTGTGTGTGTATGTA | | 17 | 38423048 | 38423077 | 38457019 | 38457048 | 17 | 38419078 | 38423077 | 38453049 | 38457048 |
| GGATGGAGGAAGAGGAGGAATTCAAGACTCGAACTAAACAAAAGGAGATGATCCTGGGT | | 8 | 98282705 | 98282734 | 98318689 | 98318718 | 8 | 98278735 | 98282734 | 98314719 | 98318718 |
| ATGATCTCATGATGCTTTGAATACTTTCTCGATACCTTATTATAAATCAGCTTTGTGTT | | 11 | 86304370 | 86304399 | 86420539 | 86420568 | 11 | 86300400 | 86304399 | 86420539 | 86424538 |
| AGCTCAAATTCTTTACTAATTGTACATCGAAAGTTCAAAGTTTCAAAGTTTAAACGTTT | | 5 | 6634975 | 6635004 | 6669680 | 6669709 | 5 | 6634975 | 6638974 | 6665710 | 6669709 |
| AATTTAGAGGAACTCTATATAAACAACATCGAAACTTTGCTTCATGCACAAAATTTAAAA | | 1 | 1.08E+08 | 1.08E+08 | 1.08E+08 | 1.08E+08 | 1 | 1.08E+08 | 1.08E+08 | 1.08E+08 | 1.08E+08 |
| CAGAAATTCGACGCACAGGCACAACAGCATCGAAAACCGGTTCTTTGAGGCTCAGTTTTG | | 6 | 1581956 | 1581987 | 1604208 | 1604237 | 6 | 1577988 | 1581987 | 1604208 | 1608207 |
| CCTACAATATACATGGAATATTCCTGGTATCGAAATATTTTAGGTAATCATTATTGCCTA | | 5 | 80021915 | 80021944 | 80158981 | 80159010 | 5 | 80021915 | 80025914 | 80155011 | 80159010 |

Figure 21B

| probe | PCR_Primer1_ID | PCR_Primer1 | PCR_Primer2_ID | PCR_Primer2 | GLMNET |
|---|---|---|---|---|---|
| ATM_11_108118137_108126372_108135279_108156687_RF | OBD116.53 | TCCAGAGGTTATGGAATTTGAG | OBD116.55 | AAGAAACAGACTGGGCTTG | 0.1394873 |
| CDC6_17_38421089_38423079_38451196_38457050_FF | OBD116.89 | GCATGAAACTTAGGAGGAGAGG | OBD116.103 | TTGCCACCATGTGACTATAC | 0.0081371 |
| TSPYL5_8_98276431_98282736_98316421_98318720_FF | OBD116.129 | GTGCTTGTAAACCATGAAGTG | OBD116.131 | TCGTGGGCATATGACTGAG | 0 |
| ME3_11_86300063_86304401_86420537_86426200_FR | OBD116.173 | ACCCTCCTTCACTCACATAG | OBD116.175 | GCACCTAATCTACCTAACATCAC | 0.0080034 |
| SRD5A1_5_6634973_6639025_6667775_6669711_FR | OBD116.177 | GGCATTGCTTTGCCTTATC | OBD116.179 | CAACTTCCTTGGGTGTAGAG | 0 |
| VAV3_1_108148303_108158073_108220200_108227533_RF | OBD116.185 | TGTTGAGLAAGATGGATAGC | OBD116.187 | ATATTCAGGATGGAACCCAAG | -0.032431 |
| FOXC1_6_1577253_1581989_1604206_1605973_FR | OBD116.197 | GGAGTGTACATCGTTGGTAATG | OBD116.199 | GCAAATAAAGACTGCTGGTTTC | 0.1215176 |
| MSH3_5_80021913_80025030_80153948_80159012_RF | OBD116.301 | AGGACCCATCACCTACATATAC | OBD116.303 | AGCCAAGTTTATGCCAAGAG | -0.266166 |

Figure 21C

| Gene | Marker | GLMNET |
|---|---|---|
| ATM_11 | OBD116.53.55_8 | 0.1394873 |
| CDC6_17 | OBD116.89.103_8 | 0.0081371 |
| TSPYL5_8 | OBD116.129.131.4 | 0 |
| ME3_11 | OBD116.173.175_2 | 0.0080034 |
| SRD5A1_5 | OBD116.177.179_8 | 0 |
| VAV3_1 | OBD116.185.187_16 | -0.032431 |
| FOXC1_6 | OBD116.197.199_8 | 0.1215176 |
| MSH3_5 | OBD116.301.303_2 | -0.266166 |

Figure 21D

Markers showing good GLMNET scores.

| Marker | Estimate | Std. Error | z_value | Pr(>|z|) | Glmnet_0.5 |
|---|---|---|---|---|---|
| OBD116.301.303_2 | 3.592231 | 1.494287 | 2.404 | 0.0162 | -0.266166 |
| OBD116.185.187_16 | 2.135415 | 1.532293 | 1.394 | 0.1634 | -0.032431 |
| OBD116.58.59_8 | -1.78499 | 1.341226 | -1.331 | 0.1832 | 0.1394873 |
| OBD116.161.163_64 | 3.616204 | 2.872291 | 1.259 | 0.208 | -0.267241 |
| OBD116.197.199_8 | -1.87868 | 1.491999 | -1.259 | 0.208 | 0.1215176 |
| OBD116.129.131_4 | 1.560365 | 1.479932 | 1.054 | 0.2917 | 0 |
| OBD116.173.175_2 | -1.39826 | 1.491721 | -0.937 | 0.3486 | 0.0080034 |
| OBD116.89.103_8 | -1.24015 | 1.35114 | -0.918 | 0.3587 | 0.0081371 |
| OBD116.177.179_8 | -1.20884 | 1.323655 | -0.913 | 0.3611 | 0 |
| OBD116.113.87_4 | 1.615246 | 2.060497 | 0.807 | 0.4194 | -0.051646 |

Figure 21E

The final 8 markers were produced using GLMNET

| Marker | Estimate | Std. Error | z_value | Pr(>|z|) | Glmnet_0.5 |
|---|---|---|---|---|---|
| OBD116.301.303_2 | 3.592231 | 1.494287 | 2.404 | 0.0162 | -0.266166 |
| OBD116.185.187_16 | 2.135415 | 1.532293 | 1.394 | 0.1634 | -0.032431 |
| OBD116.58.59_8 | -1.78499 | 1.341226 | -1.331 | 0.1832 | 0.1394873 |
| OBD116.197.199_8 | -1.87868 | 1.491999 | -1.259 | 0.208 | 0.1215176 |
| OBD116.129.131_4 | 1.560365 | 1.479932 | 1.054 | 0.2917 | 0 |
| OBD116.173.175_2 | -1.39826 | 1.491721 | -0.937 | 0.3486 | 0.0080034 |
| OBD116.89.103_8 | -1.24015 | 1.35114 | -0.918 | 0.3587 | 0.0081371 |
| OBD116.177.179_8 | -1.20884 | 1.323655 | -0.913 | 0.3611 | 0 |

| probe | GeneLocus | Probe_Count_Total | Probe_Count_Sig | HyperG_Stats | FDR_HyperG | Percent_Sig | logFC |
|---|---|---|---|---|---|---|---|
| ATM_11_108118137_108126372_108155279_108156687_RF | ATM | 54 | 11 | 0.010710258 | 0.31943808 | 20.37 | 0.454214 |
| CDC6_17_38421089_38423079_38451196_38457050_FF | CDC6 | 18 | 5 | 0.022213308 | 0.344890835 | 27.78 | -0.33066 |
| CDC6_17_38421089_38423079_38467677_38474960_FR | CDC6 | 18 | 5 | 0.022213308 | 0.344890835 | 27.78 | -0.37233 |
| FOXC1_6_1577253_1581989_1604206_1605973_FR | FOXC1 | 28 | 15 | 4.24E-09 | 1.25E-06 | 53.57 | -0.47676 |
| MAP3K1_5_56102259_56110500_56140227_56144076_FF | MAP3K1 | 43 | 9 | 0.01691209 | 0.320337199 | 20.93 | -0.34444 |
| ME3_11_86300063_86304401_86420537_86426200_FR | ME3 | 144 | 14 | 0.491902034 | 1 | 9.72 | -0.40222 |
| MELK_9_36577630_36579243_36637050_36643005_RF | MELK | 13 | 1 | 0.723819061 | 1 | 7.69 | 0.434674 |
| MSH3_5_80021913_80025030_80153948_80159012_RF | MSH3 | 151 | 12 | 0.772883797 | 1 | 7.95 | 0.338581 |
| NF1_17_29477103_29483764_29651799_29657368_FF | NF1 | 139 | 8 | 0.957207644 | 1 | 5.76 | 0.239382 |
| SLC16A10_6_111441989_111447305_111492951_111498431_FR | SLC16A10 | 58 | 9 | 0.091353207 | 0.768704111 | 15.52 | 0.436205 |
| SRD5A1_5_66334973_66339025_66677775_6669711_RF | SRD5A1 | 13 | 2 | 0.350038364 | 1 | 15.38 | -0.32108 |
| TSPYL5_8_98276431_98282736_98316421_98318720_FF | TSPYL5 | 23 | 6 | 0.017130277 | 0.320337199 | 26.09 | -0.38273 |
| VAV3_1_108148303_108158073_108220200_108227533_RF | VAV3 | 170 | 7 | 0.997311958 | 1 | 4.12 | -0.46122 |

| AveExpr | t | P.Value | adj.P.Val | B | FC | FC_1 | LS | Loop detected |
|---|---|---|---|---|---|---|---|---|
| 0.454213671 | 20.03629461 | 3.24E-08 | 0.000245686 | 9.4061079 | 1.3700359 | 1.3700359 | 1 | Healthy Control |
| -0.330659264 | -13.39075625 | 7.88E-07 | 0.00028018 | 6.5901872 | 0.795173 | -1.2575879 | -1 | Breast Cancer |
| -0.372331446 | -14.3873663 | 4.49E-07 | 0.000245686 | 7.11834238 | 0.772533 | -1.294443 | -1 | Breast Cancer |
| -0.476760626 | -7.518259334 | 6.21E-05 | 0.001829905 | 2.20502335 | 0.7185893 | -1.3916155 | -1 | Breast Cancer |
| -0.344442158 | -9.949728159 | 7.79E-06 | 0.000845895 | 4.3410834 | 0.7876125 | -1.26966 | -1 | Breast Cancer |
| -0.402224564 | -3.896290267 | 0.004417342 | 0.017168026 | -2.2825092 | 0.7566906 | -1.3215441 | -1 | Breast Cancer |
| 0.434674411 | 8.417027975 | 2.72E-05 | 0.001398089 | 3.06083302 | 1.3516058 | 1.3516058 | 1 | Healthy Control |
| 0.338580663 | 7.438084892 | 6.71E-05 | 0.001887016 | 2.12441463 | 1.2645119 | 1.2645119 | 1 | Healthy Control |
| 0.239381986 | 5.889898408 | 0.000342343 | 0.003905502 | 0.41306097 | 1.1804869 | 1.1804869 | 1 | Healthy Control |
| 0.436205134 | 12.70357791 | 1.19E-06 | 0.000328931 | 6.19754645 | 1.3530406 | 1.3530406 | 1 | Healthy Control |
| -0.321078087 | -6.719266175 | 0.000138259 | 0.002521703 | 1.36779039 | 0.8004705 | -1.2492653 | -1 | Breast Cancer |
| -0.382732158 | -12.27585147 | 1.55E-06 | 0.000361291 | 5.94034849 | 0.7669837 | -1.3038087 | -1 | Breast Cancer |
| -0.4612178 | -7.26115356 | 7.98E-05 | 0.002061466 | 1.94390864 | 0.7263729 | -1.3767034 | -1 | Breast Cancer |

Figure 22 B

| Probe sequence | | Probe Location | | | | |
|---|---|---|---|---|---|---|
| 60 mer | Chr | Start1 | End1 | Start2 | End2 |
| TTGGAGGGAAAAGTAATTACGTTCAACTTCGACTGTATTCTACAAAGTGCTGGGATTACA | 11 | 108118139 | 108118168 | 108156656 | 108156685 |
| GGAGGAGGCCAGAGAAAAGAGAAATGTGATCGATTTCTAAATACTGTGTGTGTATGTA | 17 | 38423048 | 38423077 | 38457019 | 38457048 |
| GGAGGAGGCCAGAGAAAAGAGAAATGTGATCGATGACCTTAATGTCAGTGTCACTGACTCT | 17 | 38423048 | 38423077 | 38467679 | 38467708 |
| CAGAAATGCACGCACAGGCACAACAGCATCGAAACCGGTTCTTTGGAGGCTCAGTTTTG | 6 | 1581958 | 1581987 | 1604208 | 1604237 |
| CCAAAGACAGCCAAGGAAAAACTAAAGATCGAAAGTTTTATTACTTCCAAATTAGTAAA | 5 | 56110469 | 56110498 | 56144045 | 56144074 |
| AGGATCTCATGATGCTTTGAATACTTTCTCGATACCTTATTATAAAATCAGCTTTGTGTT | 11 | 86304370 | 86304399 | 86420539 | 86420568 |
| CATAATTTTTTTGTAGTTTATTCACCTCGACTAGATTTTAATTTTTAATTTTATTTA | 9 | 36577632 | 36577661 | 36642974 | 36643003 |
| CCTACATATACATGGAATATTCTGGTATCGAAATATTTTAGGTAATCATTATTTGTCTA | 5 | 80021915 | 80021944 | 80158981 | 80159010 |
| ATTTCTTCTTCCCATTTCTAAAATCGATTTTCAAAATTAAAGGTACAAGTTAAGGC | 17 | 29483733 | 29483762 | 29657337 | 29657366 |
| ATACTCATCATAAATGTCAGATTTATAATCGAGATCACAGTGAGCTGAGATTGCACCACT | 6 | 111447274 | 111447303 | 111492953 | 111492982 |
| AGCTCAAATTCTTTACTAAGTGTTACATCGAAAGTTCAAAAGTTCAAAATTTAAACGTTTT | 5 | 6634975 | 6635004 | 6669680 | 6669709 |
| GGATGGAGGAAGAAGAGGAATTCAAGACTCGAACTAAACAAAAGGAGAATGATCCTGGGT | 8 | 98282705 | 98282734 | 98318689 | 98318718 |
| AATTTAGAGGAACTCTATATAACAACATCGAAACATTGCTTCATGCACAAAATTTAAAA | 1 | 108148305 | 108148334 | 108227502 | 108227531 |

Figure 22C

| | 4 kb Sequence Location | | | |
|---|---|---|---|---|
| Chr | Start1 | End1 | Start2 | End2 |
| 11 | 108118139 | 108122138 | 108152686 | 108156685 |
| 17 | 38419078 | 38423077 | 38453049 | 38457048 |
| 17 | 38419078 | 38423077 | 38467679 | 38471678 |
| 6 | 1577988 | 1581987 | 1604208 | 1608207 |
| 5 | 56106499 | 56110498 | 56140075 | 56144074 |
| 11 | 86300400 | 86304399 | 86420539 | 86424538 |
| 9 | 36577632 | 36581631 | 36639004 | 36643003 |
| 5 | 80021915 | 80025914 | 80155011 | 80159010 |
| 17 | 29479763 | 29483762 | 29653367 | 29657366 |
| 6 | 111443304 | 111447303 | 111492953 | 111496952 |
| 5 | 6634975 | 6638974 | 6665710 | 6669709 |
| 8 | 98278735 | 98282734 | 98314719 | 98318718 |
| 1 | 108148305 | 108152304 | 108223532 | 108227531 |

Figure 22 D

SEQUENCE LISTING

```
<160> NUMBER OF SEQ ID NOS: 119

<210> SEQ ID NO 1
<211> LENGTH: 14
<212> TYPE: DNA
<213> ORGANISM: Homo sapiens;
<220> FEATURE:
<221> NAME/KEY: misc_feature
<222> LOCATION: (6)..(9)
<223> OTHER INFORMATION: "n is a, c, g, or t" for nucleic acid sequence

<400> SEQUENCE: 1
ccgcgnggng gcag                                                     14

<210> SEQ ID NO 2
<211> LENGTH: 60
<212> TYPE: DNA
<213> ORGANISM: Homo sapiens;

<400> SEQUENCE: 2
atttctttct tcttcccatt ttctaaaatc gatttttaaa ttaaaggtac aagttaaggc    60

<210> SEQ ID NO 3
<211> LENGTH: 60
<212> TYPE: DNA
<213> ORGANISM: Homo sapiens;

<400> SEQUENCE: 3
ggatggagga agaggaggaa ttcaagactc gaactaaaca aaaaggagat gatcctgggt    60
```

<210> SEQ ID NO 4
<211> LENGTH: 60
<212> TYPE: DNA
<213> ORGANISM: Homo sapiens;

<400> SEQUENCE: 4
agctcaaatt cttttactaa ttgttacatc gaaagttcaa aattaaattt taaacgtttt    60

<210> SEQ ID NO 5
<211> LENGTH: 60
<212> TYPE: DNA
<213> ORGANISM: Homo sapiens;

<400> SEQUENCE: 5
ccaaagacag ccaaggaaaa actaaagatc gaaagttttt attacttcca aattagtaaa    60

<210> SEQ ID NO 6
<211> LENGTH: 60
<212> TYPE: DNA
<213> ORGANISM: Homo sapiens;

<400> SEQUENCE: 6
aatttagagg aactctatat aaacaacatc gaaactttgc ttcatgcaca aaatttaaaa    60

<210> SEQ ID NO 7
<211> LENGTH: 60
<212> TYPE: DNA
<213> ORGANISM: Homo sapiens;

<400> SEQUENCE: 7
ttggagggaa aagtaattac gttcaacttc gactgtattc tacaaagtgc tgggattaca    60

<210> SEQ ID NO 8
<211> LENGTH: 60
<212> TYPE: DNA
<213> ORGANISM: Homo sapiens;

<400> SEQUENCE: 8
atactcatca taaatgtcag atttataatc gagatcacag tgagctgaga ttgcaccact    60

<210> SEQ ID NO 9
<211> LENGTH: 60
<212> TYPE: DNA
<213> ORGANISM: Homo sapiens;

<400> SEQUENCE: 9
aggatctcat gatgctttga atactttctc gataccttat tataaaatca gctttgtgtt    60

<210> SEQ ID NO 10
<211> LENGTH: 22
<212> TYPE: DNA
<213> ORGANISM: Homo sapiens;

<400> SEQUENCE: 10
tgtagtagtt accctgttgt tg                                             22

<210> SEQ ID NO 11
<211> LENGTH: 19
<212> TYPE: DNA
<213> ORGANISM: Homo sapiens;

<400> SEQUENCE: 11
gcctcacagt gctcttatg                                                 19

```
<210> SEQ ID NO 12
<211> LENGTH: 22
<212> TYPE: DNA
<213> ORGANISM: Homo sapiens;

<400> SEQUENCE: 12
gtgctttgta aaccatgaag tg                                              22

<210> SEQ ID NO 13
<211> LENGTH: 19
<212> TYPE: DNA
<213> ORGANISM: Homo sapiens;

<400> SEQUENCE: 13
tcgtgggcat atgactgag                                                  19

<210> SEQ ID NO 14
<211> LENGTH: 19
<212> TYPE: DNA
<213> ORGANISM: Homo sapiens;

<400> SEQUENCE: 14
ggcattgctt tgccttatc                                                  19

<210> SEQ ID NO 15
<211> LENGTH: 20
<212> TYPE: DNA
<213> ORGANISM: Homo sapiens;

<400> SEQUENCE: 15
caacttcctt gggtgtagag                                                 20

<210> SEQ ID NO 16
<211> LENGTH: 21
<212> TYPE: DNA
<213> ORGANISM: Homo sapiens;

<400> SEQUENCE: 16
cgctatatgt ggttctgtac g                                               21

<210> SEQ ID NO 17
<211> LENGTH: 22
<212> TYPE: DNA
<213> ORGANISM: Homo sapiens;

<400> SEQUENCE: 17
cttctctaaa gggagatttg gg                                              22

<210> SEQ ID NO 18
<211> LENGTH: 20
<212> TYPE: DNA
<213> ORGANISM: Homo sapiens;

<400> SEQUENCE: 18
tgttgagcaa gatggatagc                                                 20

<210> SEQ ID NO 19
<211> LENGTH: 21
<212> TYPE: DNA
<213> ORGANISM: Homo sapiens;

<400> SEQUENCE: 19
atattcagga tggaacccaa g                                               21
```

<210> SEQ ID NO 20
<211> LENGTH: 22
<212> TYPE: DNA
<213> ORGANISM: Homo sapiens;

<400> SEQUENCE: 20
tccagaggtt atggaatttg ag                                              22

<210> SEQ ID NO 21
<211> LENGTH: 19
<212> TYPE: DNA
<213> ORGANISM: Homo sapiens;

<400> SEQUENCE: 21
aagaaacaga ctgggcttg                                                  19

<210> SEQ ID NO 22
<211> LENGTH: 22
<212> TYPE: DNA
<213> ORGANISM: Homo sapiens;

<400> SEQUENCE: 22
actcaaatac tgctctacac tg                                              22

<210> SEQ ID NO 23
<211> LENGTH: 20
<212> TYPE: DNA
<213> ORGANISM: Homo sapiens;

<400> SEQUENCE: 23
aaggaagtta agccctatgc                                                 20

<210> SEQ ID NO 24
<211> LENGTH: 20
<212> TYPE: DNA
<213> ORGANISM: Homo sapiens;

<400> SEQUENCE: 24
accctccttc actcacatag                                                 20

<210> SEQ ID NO 25
<211> LENGTH: 23
<212> TYPE: DNA
<213> ORGANISM: Homo sapiens;

<400> SEQUENCE: 25
gcacctaatc tacctaacat cac                                             23

<210> SEQ ID NO 26
<211> LENGTH: 28
<212> TYPE: DNA
<213> ORGANISM: Homo sapiens;

<400> SEQUENCE: 26
tacgttcaac ttcgactgta ttctacaa                                        28

<210> SEQ ID NO 27
<211> LENGTH: 21
<212> TYPE: DNA
<213> ORGANISM: Homo sapiens;

<400> SEQUENCE: 27
gcaagttcct tagttgctta g                                               21

<210> SEQ ID NO 28
<211> LENGTH: 22
<212> TYPE: DNA
<213> ORGANISM: Homo sapiens;

<400> SEQUENCE: 28
caaccatcat cactaattct gg                                              22

<210> SEQ ID NO 29
<211> LENGTH: 22
<212> TYPE: DNA
<213> ORGANISM: Homo sapiens;

<400> SEQUENCE: 29
ccagaattag tgatgatggt tg                                              22

<210> SEQ ID NO 30
<211> LENGTH: 800
<212> TYPE: DNA
<213> ORGANISM: Homo sapiens;

<400> SEQUENCE: 30
aagggataag taaccaaact tggtcaatat tagataaact tcaagggacc tttttttttt      60
ttagtttcct agttatctat attgaaccaa gaaatggaac agcaagttcc ttagttgctt     120
aggtggacct attcagaact ggttgtaagt ctgcagtctg aagggaaatg gtgagcagag     180
gactcctttc ccaaagacag ctggaacaga aataggcact ccagaggtta tggaatttga     240
gagagatact cagcctctag ccactcccat tcaatctccc agcttagtct tctgagcatt     300
cttaatctta ctattctttt cttaatgtat tcaaaccaaa agacagcaat ttttagagcc     360
tgaataggtt ttggagggaa aagtaattac gttcaacttc gactgtattc tacaaagtgc     420
tgggattaca ggcatgagcc accaagccca gtctgtttct tttttgcaat taagctagag     480
ttcacatagc ataaaattca cgattttgag ttgtacattt cagtggtttt tagtattttt     540
actatgttgt acaaccatca tcactaattc tggaaacttt ttttatttta ttttattttt     600
tttgagatgg agtcttgctc tgtcacccag gctggagtgc agtggcacaa tctccgctca     660
ctgcaacctc cctttcccgg gttcaagtga ttctcctgca tcagcctccc gagtagctgg     720
gactacaggt gcctgccacc acgcccagct aattttttgtt ttttagtag agactgggtt     780
tcaccatatt ggccagccta                                                 800

<210> SEQ ID NO 31
<211> LENGTH: 30
<212> TYPE: DNA
<213> ORGANISM: Homo sapiens;

<400> SEQUENCE: 31
aaagagaatg tgatcgattt ctaaaatact                                      30

<210> SEQ ID NO 32
<211> LENGTH: 22
<212> TYPE: DNA
<213> ORGANISM: Homo sapiens;

<400> SEQUENCE: 32 ggggttcaaga atgcaggaat ag                                             22

```
<210> SEQ ID NO 33
<211> LENGTH: 20
<212> TYPE: DNA
<213> ORGANISM: Homo sapiens;

<400> SEQUENCE: 33
gtatagtcac atggtggcaa                                              20

<210> SEQ ID NO 34
<211> LENGTH: 20
<212> TYPE: DNA
<213> ORGANISM: Homo sapiens;

<400> SEQUENCE: 34
ttgccaccat gtgactatac                                              20

<210> SEQ ID NO 35
<211> LENGTH: 800
<212> TYPE: DNA
<213> ORGANISM: Homo sapiens;

<400> SEQUENCE: 35
aggtaagtta aagaccaaga actggcattg gtcttagtat catgggaccc ttttgagtag    60
tttcagtgga gtggtggagg gtgaaagtga aagcttaatt ggagtgggtt caagaatgca   120
ggaataggag gagagaaatt ggagatagca atatagaaat ctcttaaaga gttcgctgta   180
aagtccagga gagagggtg aagataagtg aagtgattgt tggacgaaga tgtgggttg     240 agagttgttt ttttcccatc ccaagatggg agacctattt gtatgctgat ggaatgagta   300
gcatgaaact taggagagag ggaaaaaatt gaatcagaag agagggaaca gattgcctga   360
ataatgacct ggaggaggcc agagaaaaga gaatgtgatc gatttctaaa atactgtgtg   420
tgtgtatgta tgatgagaca gatgatacta agtttgagct aaaggaaatt caagtatagt   480
cacatggtgg caaagcagag gttttaaatc tctaaccaga ggccaaagga tgagagataa   540
tgctattctc ttaaggatgt caaaataatg tgggatgact tgaaaagtag ggttacccct   600
tctctgggcc aaatagtgag ctgttttgtc ctatgaatg taatttaatg tcagaggaac    660
aaaacccacc tcatgaaagg accagagaac tactgtattt tttttttggga caggatctct   720 gtcactcagg ctggagtaca gtggcactat catggctcac tgcagccttg cttcctggg    780 ttcaagtgat cctcctgcct                                              800

<210> SEQ ID NO 36
<211> LENGTH: 25
<212> TYPE: DNA
<213> ORGANISM: Homo sapiens;

<400> SEQUENCE: 36
aaccggtttc gatgctgttg tgcct                                        25

<210> SEQ ID NO 37
<211> LENGTH: 19
<212> TYPE: DNA
<213> ORGANISM: Homo sapiens;

<400> SEQUENCE: 37
gggacacacg ttagtcaag                                               19

<210> SEQ ID NO 38
<211> LENGTH: 18
<212> TYPE: DNA
```

```
<213> ORGANISM: Homo sapiens;

<400> SEQUENCE: 38
ctggaaggaa tgcgtagc                                                  18

<210> SEQ ID NO 39
<211> LENGTH: 18
<212> TYPE: DNA
<213> ORGANISM: Homo sapiens;

<400> SEQUENCE: 39
gctacgcatt ccttccag                                                  18

<210> SEQ ID NO 40
<211> LENGTH: 800
<212> TYPE: DNA
<213> ORGANISM: Homo sapiens;

<400> SEQUENCE: 40
cgccgtccca gcagcgcccc atctcaccaa ctcccacctt catgtgtggc cgcccaccta    60
gagccatgcc tgaagccact gtccctgacc acaaagcttt tggctgatag gaagcatgac   120
agcactgggg ccctacactg gaagcgggac cgtccagaga agaagactgc gcacagggat   180
cgggagctgg gacacacgtt agtcaaggtg tacgagggag gaatcaccgc catgtggagc   240
cactactcgg ggaggacgtg ggccacccgg agctcagtga cagtactccc gggagtgtac   300
atcgttggta atgtccacga cagtgtccct gcctgtgacc caataatttc ccatccaggg   360
acacacttca cagaaatgca cgcacaggca caacagcatc gaaaccggtt ctttggaggc   420 tcagttttg gtaattaaga ctaaggagtg tttaaaaaac agaagtacat tttcctggaa    480
accagcagtc tttatttgca acttttattg caaacctgg ctgccagtaa atacattcct    540
tggcatctcc cacaatgtaa ttcactggat ggagcggcct tgcttttttct gtaacgtgta   600 cgtcaattaa aagggccgcc tggaaggaat gcgtagcgt ggctgaaagc cccagtctcg    660
ggtcacctcc ctccactcca ggaacaaaag cgtccgtggt ctgtgcctgg aagtctgaga   720
gggtctcccc gatggggctg ttcccgcccg gaccctgagg gatgagagtt gcagcctaga   780
aaaccaggtg ccaggccctg                                               800

<210> SEQ ID NO 41
<211> LENGTH: 31
<212> TYPE: DNA
<213> ORGANISM: Homo sapiens;

<400> SEQUENCE: 41
aaaactaaag atcgaaagtt tttattactt c                                   31

<210> SEQ ID NO 42
<211> LENGTH: 20
<212> TYPE: DNA
<213> ORGANISM: Homo sapiens;

<400> SEQUENCE: 42
gtgacattac cgagcacttc                                                20

<210> SEQ ID NO 43
<211> LENGTH: 21
<212> TYPE: DNA
<213> ORGANISM: Homo sapiens;

<400> SEQUENCE: 43
```

```
gtaactcaaa ctcagtgtgc t                                              21
```

<210> SEQ ID NO 44
<211> LENGTH: 21
<212> TYPE: DNA
<213> ORGANISM: Homo sapiens;

<400> SEQUENCE: 44

```
agcacactga gtttgagtta c                                              21
```

<210> SEQ ID NO 45
<211> LENGTH: 800
<212> TYPE: DNA
<213> ORGANISM: Homo sapiens;

<400> SEQUENCE: 45

```
aaaccagctg gaggaaagga aaggaaggaa gaaataaacg caacacagaa gttctcctca    60
gttgacaaaa ggtcaaaaat cattaacgtg taaatgttgc tttttccatc ccaaagcacc   120
ttctcacgta gagtccaggg actaggagga ctcacaacgc agcgatgggc agccaggccc   180
tgcaggagtg gggacagagg gaacccggcc ggtggcccga ccctgcaggg aagaaggacg   240
tgcggcgaga agcatcggat tcggggaggg ccgggacctg gccgagggtg acattaccga   300
gcacttcctg gcacagcgct ggtcccctcc ccaaacgcgc tatatgtggt tctgtacggg   360
actgcctttc ccaaagacag ccaaggaaaa actaaagatc gaaagttttt attacttcca   420
aattagtaaa tttgtaacaa tcatcaggca actaactata ataagaggga atttacaaaa   480
gacagagagc tactagtcag tatcaaatca ttcttaaaag tggcaactct gtatcaattt   540
ttttttttgca gtcaattacc tttgactcag tctataaagt acatgcccaa atctcccttt   600
agagaagaaa agtgaatcaa aaagaaaaat gtatattaac tgtacagttc tcctatacta   660
aatgttctta catgctcaaa atgtatgaat atatttaaag caactgatcc tctattgaat   720
actgaataaa cttgaaggga tttctaagta aattattact ggtaactcaa actcagtgtg   780
ctataaattt cagacaccac                                              800
```

<210> SEQ ID NO 46
<211> LENGTH: 29
<212> TYPE: DNA
<213> ORGANISM: Homo sapiens;

<400> SEQUENCE: 46

```
aataaggtat cgagaaagta ttcaaagca                                      29
```

<210> SEQ ID NO 47
<211> LENGTH: 20
<212> TYPE: DNA
<213> ORGANISM: Homo sapiens;

<400> SEQUENCE: 47

```
accctccttc actcacatag                                                20
```

<210> SEQ ID NO 48
<211> LENGTH: 23
<212> TYPE: DNA
<213> ORGANISM: Homo sapiens;

<400> SEQUENCE: 48

```
gtgatgttag gtagattagg tgc                                            23
```

<210> SEQ ID NO 49
<211> LENGTH: 23
<212> TYPE: DNA
<213> ORGANISM: Homo sapiens;

<400> SEQUENCE: 49
gcacctaatc tacctaacat cac                                           23

<210> SEQ ID NO 50
<211> LENGTH: 800
<212> TYPE: DNA
<213> ORGANISM: Homo sapiens;

<400> SEQUENCE: 50
taaccttcca taggcctcag ctcccttatc tattaacctg gtgaaatgca gaccccctctg    60 catggggtta caaggtttca gcatgactgg gtatgaaaag agaacaaaga agcttcctgg   120
agatgactgt ggccttggct cactgccagg aaaatgactc atttctgtat gccagggtta   180
tagttcactg ttaccctgac aaatgaatgt ggaagaccca tgatttcctc caccctcctt   240
cactcacata gtaaaagtta gctactgcct gcaacatacc aggcaccgta caacacgaaa   300
ctgtaggctc cccctccagg aagtgacaat gtcattccta acctgttgga attttaacac   360
ctgtcataaa aggatctcat gatgctttga atactttctc gataccttat tataaaatca   420
gctttgtgtt gaatgatttt tcccagctgt agactaatgt aaatgttctg agcatgttta   480
aggtaggcta gtctaagctg tgatgttagg tagattaggt gcatttaaat gcattttcaa   540
tgatatttta aatttgcagt gggtttatca ggatgttact ccaagatgct cctccaaggt   600
gaggggcatc tgtgttttag tcagtgaaaa tgtcttgcaa aactgaagat aaaataaata   660
cagttagtca cacttcactt gcactataag aaattctaaa gaaaaattct tcaaattgaa   720
ggaatataat aacataaatt tatatctaca ggaaggaata aagagcaaag aaatgataaa   780
caaatcgctt aaagtgttta                                              800

<210> SEQ ID NO 51
<211> LENGTH: 29
<212> TYPE: DNA
<213> ORGANISM: Homo sapiens;

<400> SEQUENCE: 51
tgtagtttat tcacctcgac tagatttta                                     29

<210> SEQ ID NO 52
<211> LENGTH: 22
<212> TYPE: DNA
<213> ORGANISM: Homo sapiens;

<400> SEQUENCE: 52
atgcttgctg gaatatgctt ac                                            22

<210> SEQ ID NO 53
<211> LENGTH: 20
<212> TYPE: DNA
<213> ORGANISM: Homo sapiens;

<400> SEQUENCE: 53
cagcttcgct tgttacccag                                               20

<210> SEQ ID NO 54
<211> LENGTH: 20

```
<212> TYPE: DNA
<213> ORGANISM: Homo sapiens;

<400> SEQUENCE: 54
ctgggtaaca agcgaagctg                                                20

<210> SEQ ID NO 55
<211> LENGTH: 800
<212> TYPE: DNA
<213> ORGANISM: Homo sapiens;

<400> SEQUENCE: 55
agtagagatg gggttttcacc atgctggcca ggccagtctc aaactcctga cctcaggtga     60
tctgcccgcc ccagcctccc aaaatgctag aattacaggt gtgaactatt gtgcccggca    120
ttgtacaacc gaactttaac aacagttgct cagatgatga tggggataaa gagttgggaa    180
agagcacatc ttcttgaaat gcttgctgga atatgcttac ttcttaaaag attatagaga    240
atattgattc ttccccaaga aattgacaga ttcatgtttt acataatgat atttgattgt    300
ataaagtaat tatgctgatt ttaaaatgtg aaaacattga atatatttgt aattttttgt    360
taataaagtg cataattttt ttttgtagtt tattcacctc gactagattt taattttttaa    420 tttttattta ttttttgag acacagcttc gcttgttacc caggctggag tgcagtggca    480
tgatctcggc tcaccgcaac ctctgcttcc cgggttcaag tgattctcct gcctcagcct    540
ccctagtagc tgggattaca ggcatgggcc accacgcctg gctaattttt tatattttta    600
gtagagacgg ggtttctcca tgttggtcag gctggtcttg aactcccgac ctcaggtgat    660
ccgcctgcct cagcctccca agtgccggg attacaagtg tgagccactg cgcctggctg    720 tttttatt  tagtagaga caaggtcttg ctatattgtc ctggcttgtc ttgaactcca    780
ggcctcaagc aatcctcctg                                               800

<210> SEQ ID NO 56
<211> LENGTH: 30
<212> TYPE: DNA
<213> ORGANISM: Homo sapiens;

<400> SEQUENCE: 56
attcctggta tcgaaatatt ttaggtaatc                                     30

<210> SEQ ID NO 57
<211> LENGTH: 21
<212> TYPE: DNA
<213> ORGANISM: Homo sapiens;

<400> SEQUENCE: 57
aggacccatc acctacatat a                                              21

<210> SEQ ID NO 58
<211> LENGTH: 20
<212> TYPE: DNA
<213> ORGANISM: Homo sapiens;

<400> SEQUENCE: 58
ctcttggcat aaacttggct                                                20

<210> SEQ ID NO 59
<211> LENGTH: 20
<212> TYPE: DNA
<213> ORGANISM: Homo sapiens;
```

```
<400> SEQUENCE: 59
agccaagttt atgccaagag                                                  20

<210> SEQ ID NO 60
<211> LENGTH: 800
<212> TYPE: DNA
<213> ORGANISM: Homo sapiens;

<400> SEQUENCE: 60
taacaaaaat aaactttaaa atggtggagg tgagtgggga aaagtgaaac ctctgcttta      60
cagaatacca acgaataaat gtaggaagaa ttttttaatc aacatttaat aacgactata     120
ataataactg attcagacag caatgatcaa tagattataa aacctttgga tgaaagattg     180
ttggagaaaa ggatattcat atatctcaaa gtgtcatgcc acaggttatt tattaattac     240
aaagggaaaa ggtatagtga agaaatctag tgggtacect cttcaaccag ataatcaaat     300
ttggcatccc cagttatgta aaactgtatat cacgtcccac ctgatgtgat gcactgggaa     360
ggacccatca cctacatata catggaatat tcctggtatc gaaatatttt aggtaatcat     420
tatttgtcta attcacatgt ccacaatcag gcattaatgt ttactttcat ttgtacctca     480
cattcctgcc agtccagctt atgttagggt ccattttgtg gatggtgagg tgaatagaca     540
ttttccctct tggcataaac ttggcttcac tctaatcttc atcctactcc atatggagga     600
aatttatctc tgtcacatgc tagagagtgt tcatcatcag ctccccatca ctgctccatt     660
taagcatcag tgtctagtta gcatttcctt gcatctaggc atcagtgtct tgttagcatg     720
tctctttaat ttcatgatgc cttggtcaaa taaagtgtct gagcgtgtat cccacttctt     780
tttatttttt tctgtaaggt                                                 800

<210> SEQ ID NO 61
<211> LENGTH: 32
<212> TYPE: DNA
<213> ORGANISM: Homo sapiens;

<400> SEQUENCE: 61
aatttaaaaa tcgatttag aaaatgggaa ga                                    32

<210> SEQ ID NO 62
<211> LENGTH: 22
<212> TYPE: DNA
<213> ORGANISM: Homo sapiens;

<400> SEQUENCE: 62
tgtagtagtt accctgttgt tg                                              22

<210> SEQ ID NO 63
<211> LENGTH: 19
<212> TYPE: DNA
<213> ORGANISM: Homo sapiens;

<400> SEQUENCE: 63
cataagagca ctgtgaggc                                                  19

<210> SEQ ID NO 64
<211> LENGTH: 19
<212> TYPE: DNA
<213> ORGANISM: Homo sapiens;

<400> SEQUENCE: 64
gcctcacagt gctcttatg                                                  19
```

```
<210> SEQ ID NO 65
<211> LENGTH: 800
<212> TYPE: DNA
<213> ORGANISM: Homo sapiens;

<400> SEQUENCE: 65
actttcattt taatttatta tttcccttag aaacatctcc tatcttttgt gaccatgtct      60
ccttttccag tatgtttctt gaattaggat ttcatagagc ttttgtggcc tacacgaatt    120
gaccacagta atccattaca catattttc tttagcatct tgtttgaatt tacttacggt     180
tgtcccagcc ctaagtagat gataaaatat gatctcatag tcctaaaatg tggattgatt    240
tttttatgaa gatatgtgtt ttttcttcct tctgtaacct gtgacagatt ctgtagtagt    300
taccctgttg ttgaaacagt ttttctcaaa taccagtttc atcaaataat tccactgtta    360
aaagctcata atttctttct tcttcccatt ttctaaaatc gattttaaa ttaaaggtac     420 aagttaaggc acacagaaga ttataggcag ctgacctagg agaaaacaca aatgaagttg    480
ttttaaaacg tatttttcct tatagttcca aaatttttc ataacataca atttgtgatt    540
ctgttacaaa gtatgatcaa ctatttttaa attttatgat cagttagaaa taagatgtta    600
taattctaca gtaaaaccaa atacccctt aatcatttag ggatttata aaaagggaca     660 cacttgatat aaccataaga gcactgtgag gctcctatga cagaggggcg gggtataggc    720
tttcctaaaa tacatctcac tgagacataa aatatgagag gacttatggt cctaatgtgg    780
atcaatagaa attaagtcag                                                800

<210> SEQ ID NO 66
<211> LENGTH: 27
<212> TYPE: DNA
<213> ORGANISM: Homo sapiens;

<400> SEQUENCE: 66
tactaattgt tacatcgaaa gttcaaa                                         27

<210> SEQ ID NO 67
<211> LENGTH: 19
<212> TYPE: DNA
<213> ORGANISM: Homo sapiens;

<400> SEQUENCE: 67
ggcattgctt tgccttatc                                                  19

<210> SEQ ID NO 68
<211> LENGTH: 20
<212> TYPE: DNA
<213> ORGANISM: Homo sapiens;

<400> SEQUENCE: 68
ctctacaccc aaggaagttg                                                 20

<210> SEQ ID NO 69
<211> LENGTH: 20
<212> TYPE: DNA
<213> ORGANISM: Homo sapiens;

<400> SEQUENCE: 69
caacttcctt gggtgtagag                                                 20

<210> SEQ ID NO 70
```

<211> LENGTH: 800
<212> TYPE: DNA
<213> ORGANISM: Homo sapiens;

<400> SEQUENCE: 70

```
accactttt aagatttatc ctgtttgttc tttgttgatt gaaacataat aattgttaaa    60
attctctaca gccttctttt tcttccatag ctaatcttcc ttctaatagt ttttgctttc   120
tgttttgctg ttgttgcttt gcaaagcttt cccctcatag cctgtacctg ttatcaatat   180
aaaataatct tcctgttgaa tgcttcatga cttgaattct actttgataa aaacattgcc   240
atactgcttt ttatcttgat gaattcatct ggcattgctt tgccttatca tctcatctgg   300
agttttaaa tgccatttgt ttcagttgtc tttaacaaca taataaatag actttgccat    360
ttaacaaggt agctcaaatt cttttactaa ttgttacatc gaaagttcaa aattaaattt   420
taaacgtttt cattcaggct ctggaaagct tcacagttaa aaaggatgtc tctacaccca   480
aggaagttga actcactggc tgtgtgacta tgggcagttt acccaacctt tctgatttgg   540
ggtcccacct taaaacactc acttcccaga gagacaggaa gaactcagtg tgtgtttata   600
agcctctctt ctttctcctg gtgtcatgca ttccagcgaa gagaaagtac acagctccac   660
tacttggaac cagtgttgta cccagcacag tttttggtac ctgagttccc tgaaaaccag   720
caccttaccc tgtaactggt gcagtctgtg tcctcagtgt gctttgatga cttgcacttt   780
aaacaagggc aagtcaacat                                                800
```

<210> SEQ ID NO 71
<211> LENGTH: 23
<212> TYPE: DNA
<213> ORGANISM: Homo sapiens;

<400> SEQUENCE: 71

```
aggaattcaa gactcgaact aaa                                             23
```

<210> SEQ ID NO 72
<211> LENGTH: 20
<212> TYPE: DNA
<213> ORGANISM: Homo sapiens;

<400> SEQUENCE: 72

```
ttgagtcctg gctctactac                                                 20
```

<210> SEQ ID NO 73
<211> LENGTH: 22
<212> TYPE: DNA
<213> ORGANISM: Homo sapiens;

<400> SEQUENCE: 73

```
gaacaaagga ccaagtatag ct                                              22
```

<210> SEQ ID NO 74
<211> LENGTH: 22
<212> TYPE: DNA
<213> ORGANISM: Homo sapiens;

<400> SEQUENCE: 74

```
agctatactt ggtcctttgt tc                                              22
```

<210> SEQ ID NO 75
<211> LENGTH: 800
<212> TYPE: DNA
<213> ORGANISM: Homo sapiens;

<400> SEQUENCE: 75

```
taaagaagtt tcacattcat atgccaactc agattgatgg gcagcaactg gataatccgc    60
tgtgcagaaa gttaaataca ggttctgtgc aaagaagtgt ctagattcat agtgccagac   120
atctgccctg ggccacatgc ttaccgtccc atggatggat ggaacttgga atcagaagac   180
ccaagtttga gtcctggctc tactactttt gtgattttgg tcatttaacc tctttgagcc   240
ttcttatggc atagtagtta taatcaagat aatataagtg aatgtgcttt gtaaaccatg   300
aagtgttggt cacacagatg atagctactg tcttatattt gtcaaacctc agctgaggac   360
caggttgaca ggatggagga agaggaggaa ttcaagactc gaactaaaca aaaaggagat   420
gatcctgggt gggcttgact taatcaagtg aaagccttaa aagcaagagt ctcctgctag   480
tctaggaaaa gcaaacagcc ctgctatgaa tggcctatag aaaggggcag cctctaggag   540
catgggcctc agtcatatgc ccacgaggaa ctgaatattg ccagcaacca tgtgagcatg   600
gaagaggact ctaagcctct gatgagacca cagccctggc caatgctttg attgtggctc   660
tgtgaggcct tgaacaaagg accaagtata gctatgccag gacttctgaa ccacgggaat   720
ggtgagataa taaatgtttg gtgttttaag ccactaagtt tgtgttaatt ttttatgccg   780
caatagaaag cgaatactac                                               800
```

<210> SEQ ID NO 76
<211> LENGTH: 800
<212> TYPE: DNA
<213> ORGANISM: Homo sapiens;

<400> SEQUENCE: 76

```
aggtaagtta aagaccaaga actggcattg gtcttagtat catgggaccc ttttgagtag    60
tttcagtgga gtggtggagg gtgaaagtga agcttaatt ggagtgggtt caagaatgca   120
ggaataggag gagagaaatt ggagatagca atatagaaat ctcttaaaga gttcgctgta   180
aagtccagga gagagggtg aagataagtg aagtgattgt tggacgaaga tgtggggttg   240
agagttgttt ttttcccatc ccaagatggg agacctattt gtatgctgat ggaatgagta   300
gcatgaaact taggagagag ggaaaaaatt gaatcagaag agaggaaaca gattgcctga   360
ataatgacct ggaggaggcc agagaaaaga gaatgtgatc gatgacctta atgtcagtgt   420
cactgactct gacaaggagg aaaggacagc gatgagccag gctgaccccc gccaccccat   480
tcccatagcc ccactttctt ctctcttctt gttcagaaat gtttcacttt gcctcatcta   540
gccccttttgg ccagtaggtc acatctggga gcttctgggg gtgccacatg tctgcctcaa   600
tctgggctgt ttcctcccct ccaagatatt tcactgtctc tgggctgggc gccaggactc   660
ctgggttttcc ctgcctgtgg tgcagggctc ccctgcaggg ctccagagag tcgcttagct   720
ggtttccttc ctcctttgtg gggagggcct tcccctaggg ctgggaggtg tcaggaatcc   780
caggtgggac aggggtgggg                                               800
```

<210> SEQ ID NO 77
<211> LENGTH: 800
<212> TYPE: DNA
<213> ORGANISM: Homo sapiens;

<400> SEQUENCE: 77

```
ttcaattgct atataaaaaa tgtaaagtct gtttactgcc ttaaaccttc tggtgtattt    60
ttatataaag taacacccctt aattctaact tggccaacag gtaggatggt attattatta  120
```

```
tcttcattgt acagataagg aaactgaggc tcagattgac tagatcaaac aggagttttc      180
tggaaaacct aggacacaag cctaaatctt tgaactcaaa tactgctcta cactgaatta      240
cagttatata ctgatttctg ttgtaaattc ttagagaaga cagacataga aattagtaac      300
ttgagtcagt agcggctttg ttcaaacaca ggcacatgca tattttatgg tatatgttta      360
tatctgtgta atactcatca taaatgtcag atttataatc gagatcacag tgagctgaga      420
ttgcaccact gcactccagc ctgggcagcg gagtgagacc ttttctcaaa aaaaaaaaa       480 aaaaaaggca aaaattaaa ttattagtat ggtaaagttt cgtttggact taatatgaaa       540
ctcatttcta gaaatgatga tcatttgcat agggcttaac ttcctttgct aagaaaatag      600
agtagtatac taggagactt ccagagctgc atagagcttc agggtcatct accaagacag      660
acaatttgtt gtcatcatca gtgttaaact ctaaattatt aagtgcttat gtgccagata      720
ctgaagttta tatacacttt ctctaatctt taataattct agaaaggtat gtgtttgatc      780
cattttcaag ataagaaaac                                                  800

<210> SEQ ID NO 78
<211> LENGTH: 800
<212> TYPE: DNA
<213> ORGANISM: Homo sapiens;

<400> SEQUENCE: 78
atgaggtttt tttccagcct tcctaagggc ctcaaagtca tatccagcag acttgcaggg       60
ttctcaggtg aaagcaaatt ggagaaattt ttaaaatgta attttggttt ttactccaac      120
tactttcaac atggatttgt aaaagactgc taggatcatt aaaatcagca ttgaagctat      180
gttgagcaag atggatagct gcactagaaa agctgtaaca agagtcattg tgaatgaaag      240
gaaaattttg ctctagattt gttggtagcc aaggcacaaa aattggaagc ataatgagtt      300
acagactcat gtctgataat atgaagaac actaatttaa agaaaaaatc ttttctgtct        360
gaaattttat aatttagagg aactctatat aaacaacatc gaaactttgc ttcatgcaca      420
aaatttaaaa tattacataa aattaccttc aggctttgtg tataagatat atataaaaca      480
taaataaatt ttgtgtttac acttgggttc catcctgaat atatctcatg atgtttatgc      540
aaatattcca aaatctgaaa aaatctgaaa ttcaaaacac ttccggtccc aagcattttg      600
aataagggat actcaaccta tagctgcatt aattgaatta agacaaccac ataatctacc      660
tgttaatttt ctctggagcc ttttcttctg agccctccac gctcttctaa ttgatactgc      720
ttgctctact aagcctgttg aattactgta gtcctgggac ttctctttgc tccccttttcc     780 tggcttctat atctccctct                                                  800

<210> SEQ ID NO 79
<211> LENGTH: 264
<212> TYPE: DNA
<213> ORGANISM: Homo sapiens;

<400> SEQUENCE: 79
ggggagtgga tgggataagg tggaatgttg ggtgaactaa aaggccttta aggcccctct       60
gaaatccagc atcgaagagg gaaactgcat cacagttgat ggaagtctgt tggcctctta      120
acaaagctaa tgcttgccct tctggcttag cttacataag aaccacaagg aatctttgtt      180
gaattgtttc tttcagatca tcgggacaac tctccttttg atggacctgg aggaaatctt      240
gctcatgctt ttcaaccagg ccca                                             264
```

```
<210> SEQ ID NO 80
<211> LENGTH: 22
<212> TYPE: DNA
<213> ORGANISM: Homo sapiens;

<400> SEQUENCE: 80
ggggagtgga tgggataagg tg                                              22

<210> SEQ ID NO 81
<211> LENGTH: 20
<212> TYPE: DNA
<213> ORGANISM: Homo sapiens;

<400> SEQUENCE: 81
tgggcctggt tgaaaagcat                                                 20

<210> SEQ ID NO 82
<211> LENGTH: 29
<212> TYPE: DNA
<213> ORGANISM: Homo sapiens;

<400> SEQUENCE: 82
atccagcatc gaagagggaa actgcatca                                       29

<210> SEQ ID NO 83
<211> LENGTH: 60
<212> TYPE: DNA
<213> ORGANISM: Homo sapiens;

<400> SEQUENCE: 83
ttggagggaa aagtaattac gttcaacttc gactgtattc tacaaagtgc tgggattaca     60

<210> SEQ ID NO 84
<211> LENGTH: 60
<212> TYPE: DNA
<213> ORGANISM: Homo sapiens;

<400> SEQUENCE: 84
ggaggaggcc agagaaaaga gaatgtgatc gatttctaaa atactgtgtg tgtgtatgta     60

<210> SEQ ID NO 85
<211> LENGTH: 60
<212> TYPE: DNA
<213> ORGANISM: Homo sapiens;

<400> SEQUENCE: 85
ggatggagga agaggaggaa ttcaagactc gaactaaaca aaaggagat gatcctgggt      60

<210> SEQ ID NO 86
<211> LENGTH: 60
<212> TYPE: DNA
<213> ORGANISM: Homo sapiens;

<400> SEQUENCE: 86
aggatctcat gatgctttga atactttctc gataccttat tataaaatca gctttgtgtt     60

<210> SEQ ID NO 87
<211> LENGTH: 60
<212> TYPE: DNA
<213> ORGANISM: Homo sapiens;

<400> SEQUENCE: 87
agctcaaatt cttttactaa ttgttacatc gaaagttcaa aattaaattt taaacgtttt    60
```

<210> SEQ ID NO 88
<211> LENGTH: 60
<212> TYPE: DNA
<213> ORGANISM: Homo sapiens;

<400> SEQUENCE: 88
aatttagagg aactctatat aaacaacatc gaaactttgc ttcatgcaca aaatttaaaa    60

<210> SEQ ID NO 89
<211> LENGTH: 60
<212> TYPE: DNA
<213> ORGANISM: Homo sapiens;

<400> SEQUENCE: 89
cagaaatgca cgcacaggca caacagcatc gaaaccggtt ctttggaggc tcagttttttg   60

<210> SEQ ID NO 90
<211> LENGTH: 60
<212> TYPE: DNA
<213> ORGANISM: Homo sapiens;

<400> SEQUENCE: 90
cctacatata catggaatat tcctggtatc gaaatatttt aggtaatcat tatttgtcta    60

<210> SEQ ID NO 91
<211> LENGTH: 22
<212> TYPE: DNA
<213> ORGANISM: Homo sapiens;

<400> SEQUENCE: 91
tccagaggtt atggaatttg ag                                             22

<210> SEQ ID NO 92
<211> LENGTH: 19
<212> TYPE: DNA
<213> ORGANISM: Homo sapiens;

<400> SEQUENCE: 92
aagaaacaga ctgggcttg                                                 19

<210> SEQ ID NO 93
<211> LENGTH: 21
<212> TYPE: DNA
<213> ORGANISM: Homo sapiens;

<400> SEQUENCE: 93
gcatgaaact taggagagag g                                              21

<210> SEQ ID NO 94
<211> LENGTH: 20
<212> TYPE: DNA
<213> ORGANISM: Homo sapiens;

<400> SEQUENCE: 94
ttgccaccat gtgactatac                                                20

<210> SEQ ID NO 95
<211> LENGTH: 22
<212> TYPE: DNA
<213> ORGANISM: Homo sapiens;

<400> SEQUENCE: 95
gtgctttgta aaccatgaag tg                                             22

<210> SEQ ID NO 96
<211> LENGTH: 19
<212> TYPE: DNA
<213> ORGANISM: Homo sapiens;

<400> SEQUENCE: 96
tcgtgggcat atgactgag                                              19

<210> SEQ ID NO 97
<211> LENGTH: 20
<212> TYPE: DNA
<213> ORGANISM: Homo sapiens;

<400> SEQUENCE: 97
accctccttc actcacatag                                             20

<210> SEQ ID NO 98
<211> LENGTH: 23
<212> TYPE: DNA
<213> ORGANISM: Homo sapiens;

<400> SEQUENCE: 98
gcacctaatc tacctaacat cac                                         23

<210> SEQ ID NO 99
<211> LENGTH: 19
<212> TYPE: DNA
<213> ORGANISM: Homo sapiens;

<400> SEQUENCE: 99
ggcattgctt tgccttatc                                              19

<210> SEQ ID NO 100
<211> LENGTH: 20
<212> TYPE: DNA
<213> ORGANISM: Homo sapiens;

<400> SEQUENCE: 100
caacttcctt gggtgtagag                                             20

<210> SEQ ID NO 101
<211> LENGTH: 20
<212> TYPE: DNA
<213> ORGANISM: Homo sapiens;

<400> SEQUENCE: 101
tgttgagcaa gatggatagc                                             20

<210> SEQ ID NO 102
<211> LENGTH: 21
<212> TYPE: DNA
<213> ORGANISM: Homo sapiens;

<400> SEQUENCE: 102
atattcagga tggaacccaa g                                           21

<210> SEQ ID NO 103
<211> LENGTH: 22
<212> TYPE: DNA
<213> ORGANISM: Homo sapiens;

<400> SEQUENCE: 103

```
ggagtgtaca tcgttggtaa tg                                              22

<210> SEQ ID NO 104
<211> LENGTH: 22
<212> TYPE: DNA
<213> ORGANISM: Homo sapiens;

<400> SEQUENCE: 104
gcaaataaag actgctggtt tc                                              22

<210> SEQ ID NO 105
<211> LENGTH: 22
<212> TYPE: DNA
<213> ORGANISM: Homo sapiens;

<400> SEQUENCE: 105
aggacccatc acctacatat ac                                              22

<210> SEQ ID NO 106
<211> LENGTH: 20
<212> TYPE: DNA
<213> ORGANISM: Homo sapiens;

<400> SEQUENCE: 106
agccaagttt atgccaagag                                                 20

<210> SEQ ID NO 107
<211> LENGTH: 60
<212> TYPE: DNA
<213> ORGANISM: Homo sapiens;

<400> SEQUENCE: 107
ttggagggaa aagtaattac gttcaacttc gactgtattc tacaaagtgc tgggattaca     60

<210> SEQ ID NO 108
<211> LENGTH: 60
<212> TYPE: DNA
<213> ORGANISM: Homo sapiens;

<400> SEQUENCE: 108
ggaggaggcc agagaaaaga gaatgtgatc gatttctaaa atactgtgtg tgtgtatgta     60

<210> SEQ ID NO 109
<211> LENGTH: 60
<212> TYPE: DNA
<213> ORGANISM: Homo sapiens;

<400> SEQUENCE: 109
ggaggaggcc agagaaaaga gaatgtgatc gatgacctta atgtcagtgt cactgactct     60

<210> SEQ ID NO 110
<211> LENGTH: 60
<212> TYPE: DNA
<213> ORGANISM: Homo sapiens;

<400> SEQUENCE: 110
cagaaatgca cgcacaggca caacagcatc gaaaccggtt ctttggaggc tcagttttg     60

<210> SEQ ID NO 111
<211> LENGTH: 60
<212> TYPE: DNA
<213> ORGANISM: Homo sapiens;

<400> SEQUENCE: 111
```
ccaaagacag ccaaggaaaa actaaagatc gaaagttttt attacttcca aattagtaaa        60

<210> SEQ ID NO 112
<211> LENGTH: 60
<212> TYPE: DNA
<213> ORGANISM: Homo sapiens;

<400> SEQUENCE: 112
aggatctcat gatgctttga atactttctc gataccttat tataaaatca gctttgtgtt        60

<210> SEQ ID NO 113
<211> LENGTH: 60
<212> TYPE: DNA
<213> ORGANISM: Homo sapiens;

<400> SEQUENCE: 113
cataattttt ttttgtagtt tattcacctc gactagattt taatttttaa tttttattta        60

<210> SEQ ID NO 114
<211> LENGTH: 60
<212> TYPE: DNA
<213> ORGANISM: Homo sapiens;

<400> SEQUENCE: 114
cctacatata catggaatat tcctggtatc gaaatatttt aggtaatcat tatttgtcta        60

<210> SEQ ID NO 115
<211> LENGTH: 60
<212> TYPE: DNA
<213> ORGANISM: Homo sapiens;

<400> SEQUENCE: 115
atttctttct tcttcccatt ttctaaaatc gattttaaa ttaaaggtac aagttaaggc         60

<210> SEQ ID NO 116
<211> LENGTH: 60
<212> TYPE: DNA
<213> ORGANISM: Homo sapiens;

<400> SEQUENCE: 116
atactcatca taaatgtcag atttataatc gagatcacag tgagctgaga ttgcaccact        60

<210> SEQ ID NO 117
<211> LENGTH: 60
<212> TYPE: DNA
<213> ORGANISM: Homo sapiens;

<400> SEQUENCE: 117
agctcaaatt cttttactaa ttgttacatc gaaagttcaa aattaaattt taaacgtttt       60

<210> SEQ ID NO 118
<211> LENGTH: 60
<212> TYPE: DNA
<213> ORGANISM: Homo sapiens;

<400> SEQUENCE: 118
ggatggagga agaggaggaa ttcaagactc gaactaaaca aaaaggagat gatcctgggt       60

```
<210> SEQ ID NO 119
<211> LENGTH: 60
<212> TYPE: DNA
<213> ORGANISM: Homo sapiens;

<400> SEQUENCE: 119
aatttagagg aactctatat aaacaacatc gaaactttgc ttcatgcaca aaatttaaaa    60
```

DETECTION OF CHROMOSOME INTERACTION RELEVANT TO BREAST CANCER

CROSS-REFERENCE TO RELATED APPLICATIONS

This application is a 35 U.S.C. § 371 filing of International Patent Application No. PCT/GB2017/051273, filed May 8, 2017, which claims priority to Great Britain Patent Application No. 1608000.4, filed May 6, 2016, the entire contents of which are incorporated herein by reference.

FIELD OF THE INVENTION

The invention relates to detecting chromosome interactions.

BACKGROUND OF THE INVENTION

Cancer is caused by the loss of regulation in cell growth and division. This occurs when mutations in the DNA of a cell occur, without the cell being able fix the mutation, the mutations can either be inherited (germline) or developed (acquired). There are two types of cancer: benign and malignant, benign cancers occur when a loss of regulation in cell division occurs but the tumour does not spread to other parts of the body. Malignant (or metastatic) cancers are more severe and occur when the cancerous cells migrate to other parts of the body via the bloodstream or lymph system. Breast cancer is the name for cancers that start in the breast and is the second most common cancer worldwide. An estimated 14.1 million new cancer cases occurred in 2012. Presently cancer screening using a mammogram is the gold standard to check for any breast abnormalities and if a lump is detected then a biopsy is carried out. Histological grading of invasive mammary carcinoma is used to separate patients with invasive breast cancer into three groups with distinct prognosis: good, intermediate, and poor.

SUMMARY OF THE INVENTION

Specific Chromosome Conformation Signatures (CCSs) at loci either exist or are absent due to the regulatory epigenetic control settings associated with pathology or treatment. CCSs have mild off-rates and when representing a particular phenotype or pathology, they will only change with a physiologically signalled transition to a new phenotype, or as a result of external intervention. In addition, the measurement of these events is binary, and so this read-out is in stark contrast to the continuum readout of varying levels of DNA methylation, histone modifications and most of the non-coding RNAs. The continuum read-out used for most molecular biomarkers to date offers a challenge to data analysis, in that the magnitude of change for particular biomarkers varies greatly from patient to patient, which causes problems for classification statistics when they are used to stratify cohorts of patients. These classification statistics are better-suited to using biomarkers that are absent of magnitude and offer just a "yes or no" binary score of phenotypic differences—signifying that EpiSwitch™ biomarkers are an excellent resource for potential diagnostic, prognostic and predictive biomarkers.

The inventors have identified regions of the genome where chromosomal interactions are relevant to breast cancer using an approach which allows identification of subgroups in a population. Accordingly, the invention provides a process for detecting a chromosome state which represents a subgroup in a population comprising determining whether a chromosome interaction is present or absent within a defined disease-associated region of the genome, wherein said disease is breast cancer. The chromosome interaction may optionally have been identified, or be identifiable (or derivable), by a method of determining which chromosomal interactions are relevant to a chromosome state corresponding to a breast cancer subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to a breast cancer subgroup.

BRIEF DESCRIPTION OF THE DRAWINGS

FIGS. 21A-F show data corresponding to marker set 2 of Example 2. The loop detection data shows whether the marker is associated with a cancer disease sample or a control sample. This figure shows the following sequences:

Figure 1:
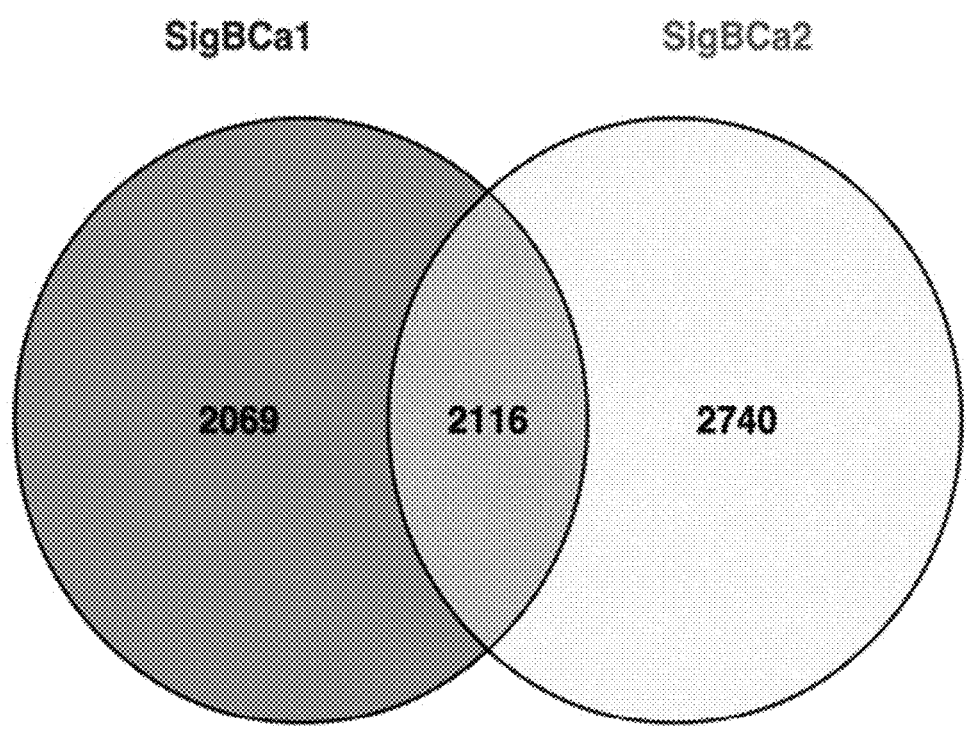
FIG. 1. Comparison of significant probes from BCa1 and BCa2 arrays. Probes adjusted p-value <0.05.
Figure 2:
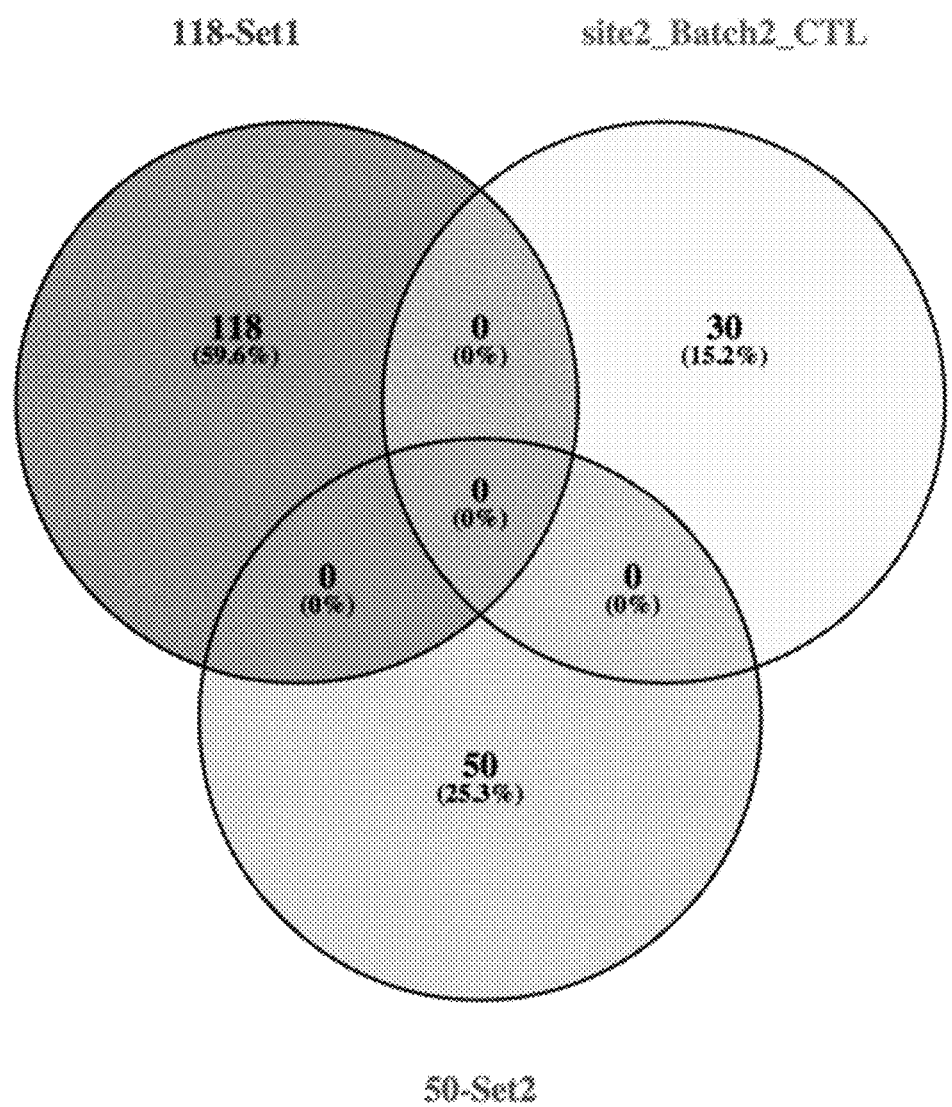
FIG. 2. This Venn diagram shows the patient set broken into maker reduction set (118, set 1) and model validation set (50, sett). The other patient set refers to the controls excluded from site 2 shipment 122.

```
                                              (SEQ ID NO:83)
TTGGAGGGAAAAGTAATTACGTTCAACTTCGACTGTATTCTACAAAGTG
CTGGGATTACA;

(SEQ ID NO:84)
GGAGGAGGCCAGAGAAAAGAGAATGTGATCGATTTCTAAAATACTGTGT
GTGTGTATGTA;

(SEQ ID NO:85)
GGATGGAGGAAGAGGAGGAATTCAAGACTCGAACTAAACAAAAAGGAGA
TGATCCTGGGT;

(SEQ ID NO:86)
AGGATCTCATGATGCTTTGAATACTTTCTCGATACCTTATTATAAAATC
AGCTTTGTGTT;

(SEQ ID NO:87)
AGCTCAAATTCTTTTACTAATTGTTACATCGAAAGTTCAAAATTAAATT
TTAAACGTTTT;

(SEQ ID NO:88)
AATTTAGAGGAACTCTATATAAACAACATCGAAACTTTGCTTCATGCAC
AAAATTTAAAA;

(SEQ ID NO: 89)
CAGAAATGCACGCACAGGCACAACAGCATCGAAACCGGTTCTTTGGAGG
CTCAGTTTTTG;

(SEQ ID NO:90)
CCTACATATACATGGAATATTCCTGGTATCGAAATATTTTAGGTAATCA
TTATTTGTCTA.

(SEQ ID NO:91)
TCCAGAGGTTATGGAATTTGAG (SEQ ID NO:92)
AAGAAACAGACTGGGCTTG (SEQ ID NO:93)
GCATGAAACTTAGGAGAGAGG (SEQ ID NO:94)
TTGCCACCATGTGACTATAC (SEQ ID NO:95)
GTGCTTTGTAAACCATGAAG TG (SEQ ID NO:96)
TCGTGGGCATATGACTGAG (SEQ ID NO:97)
ACCCTCCTTCACTCACATAG
```

-continued

GCACCTAATCTACCTAACATCAC
(SEQ ID NO:98)

GGCATTGCTTTGCCTTATC
(SEQ ID NO:99)

CAACTTCCTTGGGTGTAGAG
(SEQ ID NO:100)

TGTTGAGCAAGATGGATAGC
(SEQ ID NO:101)

ATATTCAGGATGGAACCCAAG
(SEQ ID NO:102)

GGAGTGTACATCGTTGGTAATG
(SEQ ID NO:103)

GCAAATAAAGACTGCTGGTTTC
(SEQ ID NO:104)

AGGACCCATCACCTACATATAC
(SEQ ID NO:105)

AGCCAAGTTTATGCCAAGAG
(SEQ ID NO:106)

FIGS. 22A-D show data corresponding to marker set 3 of Example 3. The loop detection data shows whether the marker is associated with a malignant disease sample or a control sample. The statistics shown are for the nested PCR work. This figure shows the following sequences:

(SEQ ID NO:107)
TTGGAGGGAAAAGTAATTACGTTCAACTTCGACTGTATTCTACAAAGTG
CTGGGATTACA;

(SEQ ID NO:108)
GGAGGAGGCCAGAGAAAAGAGAATGTGATCGATTTCTAAAATACTGTGT
GTGTGTATGTA;

(SEQ ID NO:109)
GGAGGAGGCCAGAGAAAAGAGAATGTGATCGATGACCTTAATGTCAGTG
TCACTGACTCT;

(SEQ ID NO:110)
CAGAAATGCACGCACAGGCACAACAGCATCGAAACCGGTTCTTTGGAGG
CTCAGTTTTTG;

(SEQ ID NO:111)
CCAAAGACAGCCAAGGAAAAACTAAAGATCGAAAGTTTTTATTACTTCC
AAATTAGTAAA;

(SEQ ID NO:112)
AGGATCTCATGATGCTTTGAATACTTTCTCGATACCTTATTATAAAATC
AGCTTTGTGTT;

(SEQ ID NO:113)
CATAATTTTTTTTGTAGTTTATTCACCTCGACTAGATTTTAATTTTTA
ATTTTTATTTA;

(SEQ ID NO:114)
CCTACATATACATGGAATATTCCTGGTATCGAAATATTTTAGGTAATCA
TTATTTGTCTA;

(SEQ ID NO:115)
ATTTCTTTCTTCTTCCCATTTTCTAAAATCGATTTTTAAATTAAAGGTA
CAAGTTAAGGC;

(SEQ ID NO:116)
ATACTCATCATAAATGTCAGATTTATAATCGAGATCACAGTGAGCTGAG
ATTGCACCACT;

(SEQ ID NO:117)
AGCTCAAATTCTTTTACTAATTGTTACATCGAAAGTTCAAAATTAAATT
TTAAACGTTTT;

(SEQ ID NO: 118)
GGATGGAGGAAGAGGAGGAATTCAAGACTCGAACTAAACAAAAAGGAGA
TGATCCTGGGT;

(SEQ ID NO:119)
AATTTAGAGGAACTCTATATAAACAACATCGAAACTTTGCTTCATGCAC
AAAATTTAAAA.

For all figures showing amplification curves the Y-axis is RFU, the X-axis is cycles; and for wells in row C the amplification lines for the patient samples are marked with an X, in row D the patient amplification curves are designated with triangles (Δ).

For all figures showing standard curves the Y-axis is Cq, the X-axis is log starting quantity; and the circles are standard and the crosses are unknown.

DETAILED DESCRIPTION OF THE INVENTION

The Process of the Invention

The process of the invention comprises a typing system for detecting chromosome interactions relevant to breast cancer. This typing may be performed using the EpiSwitch™ system mentioned herein which is based on cross-linking regions of chromosome which have come together in the chromosome interaction, subjecting the chromosomal DNA to cleavage and then ligating the nucleic acids present in the cross-linked entity to derive a ligated nucleic acid with sequence from both the regions which formed the chromosomal interaction. Detection of this ligated nucleic acid allows determination of the presence or absence of a particular chromosome interaction.

The chromosomal interactions may be identified using the above described method in which populations of first and second nucleic acids are used. These nucleic acids can also be generated using EpiSwitch™ technology.

The Epigenetic Interactions Relevant to the Invention

As used herein, the term 'epigenetic' and 'chromosome' interactions typically refers to interactions between distal regions of a chromosome, said interactions being dynamic and altering, forming or breaking depending upon the status of the region of the chromosome.

In particular processes of the invention chromosome interactions are detected by first generating a ligated nucleic acid that comprises sequence from both regions of the chromosomes that are part of the interactions. In such processes the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Para-formaldehyde can cross link DNA chains which are 4 Angstroms apart.

The chromosome interaction may reflect the status of the region of the chromosome, for example, if it is being transcribed or repressed in response to change of the physiological conditions. Chromosome interactions which are specific to subgroups as defined herein have been found to be stable, thus providing a reliable means of measuring the differences between the two subgroups.

In addition, chromosome interactions specific to a characteristic (such as a disease condition) will normally occur early in a biological process, for example compared to other epigenetic markers such as methylation or changes to binding of histone proteins. Thus the process of the invention is able to detect early stages of a biological process. This allows early intervention (for example treatment) which may as a consequence be more effective. Furthermore there is little variation in the relevant chromosome interactions between individuals within the same subgroup. Detecting chromosome interactions is highly informative with up to 50 different possible interactions per gene, and so processes of the invention can interrogate 500,000 different interactions.

Preferred Marker Sets

Specific markers are disclosed herein, any of which may used in the invention. Further sets of markers may be used, for example in the combinations or numbers disclosed herein. Marker sets 1, 2 and 3 are preferred. These may be typed by any suitable method, for example the PCR or probe based methods disclosed herein, including a qPCR method. The markers are defined herein by location or by probe and/or primer sequences.

Location and Causes of Epigenetic Interactions

Epigenetic chromosomal interactions may overlap and include the regions of chromosomes shown to encode relevant or undescribed genes, but equally may be in intergenic regions. It should further be noted that the inventors have discovered that epigenetic interactions in all regions are equally important in determining the status of the chromosomal locus. These interactions are not necessarily in the coding region of a particular gene located at the locus and may be in intergenic regions.

The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The changes which lead to the chromosome interactions may be caused by changes to the underlying nucleic acid sequence, which themselves do not directly affect a gene product or the mode of gene expression. Such changes may be for example, SNPs within and/or outside of the genes, gene fusions and/or deletions of intergenic DNA, microRNA, and non-coding RNA. For example, it is known that roughly 20% of SNPs are in non-coding regions, and therefore the process as described is also informative in non-coding situation. In one embodiment the regions of the chromosome which come together to form the interaction are less than 5 kb, 3 kb, 1 kb, 500 base pairs or 200 base pairs apart on the same chromosome.

The chromosome interaction which is detected is preferably within any of the genes mentioned in Table 9. The chromosome interaction which is detected may be within any of the genes mentioned for marker set 1, 2 or 3. However it may also be upstream or downstream of the gene, for example up to 50,000, up to 30,000, up to 20,000, up to 10,000 or up to 5000 bases upstream or downstream from the gene or from the coding sequence.

Subgroups, Diagnosis and Personalised Treatment

The aim of the present invention is to permit detection of chromosome interactions relevant to a breast cancer subgroup. Therefore the process may or may not be used for diagnosis of breast cancer. The process of the invention may be used for diagnosis of malignant breast cancer, and preferably markers from marker set 3 are used in such an embodiment.

As used herein, a "subgroup" preferably refers to a population subgroup (a subgroup in a population), more preferably a subgroup in the population of a particular animal such as a particular eukaryote, or mammal (e.g. human, non-human, non-human primate, or rodent e.g. mouse or rat). Most preferably, a "subgroup" refers to a subgroup in the human population.

The invention includes detecting and treating particular subgroups in a population. The inventors have discovered that chromosome interactions differ between subsets (for example two or at least two subsets) in a given population. Identifying these differences will allow physicians to categorize their patients as a part of one subset of the population as described in the process. The invention therefore provides physicians with a process of personalizing medicine for the patient based on their epigenetic chromosome interactions.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method described herein uses generation of such ligated nucleic acids to detect chromosome interactions.

Thus a process of the invention may comprise a step of generating ligated nucleic acids (e.g. DNA) by the following steps (including a method comprising these steps):
  (i) cross-linking of epigenetic chromosomal interactions present at the chromosomal locus, preferably in vitro;
  (ii) optionally isolating the cross-linked DNA from said chromosomal locus;
  (iii) subjecting said cross-linked DNA to cutting, for example by restriction digestion with an enzyme that cuts it at least once (in particular an enzyme that cuts at least once within said chromosomal locus);
  (iv) ligating said cross-linked cleaved DNA ends (in particular to form DNA loops); and
  (v) optionally identifying the presence of said ligated DNA and/or said DNA loops, in particular using techniques such as PCR (polymerase chain reaction), to identify the presence of a specific chromosomal interaction.

These steps may be carried out to detect the chromosome interactions for any embodiment mentioned herein, such as for determining whether the individual is part of a breast cancer subgroup. The steps may also be carried out to generate the first and/or second set of nucleic acids mentioned herein.

PCR (polymerase chain reaction) may be used to detect or identify the ligated nucleic acid, for example the size of the PCR product produced may be indicative of the specific chromosome interaction which is present, and may therefore be used to identify the status of the locus. In preferred embodiments at least 1, 2, 3, 4, 5, 6, 7 or 8 primers or primer pairs as shown in Table 10 are used in the PCR reaction. In other preferred embodiments at least 1, 2, 3, 4, 5, 6, 7 or 8 primers or primer pairs relevant to or as shown for marker set 2 or 3 are used in the PCR reaction. The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is TaqI.

Embodiments Such as EpiSwitch™ Technology

The EpiSwitch™ Technology also relates to the use of microarray EpiSwitch™ marker data in the detection of epigenetic chromosome conformation signatures specific for phenotypes. Embodiments such as EpiSwitch™ which utilise ligated nucleic acids in the manner described herein have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 hours to 6 hours.

Samples and Sample Treatment

The process of the invention will normally be carried out on a sample. The sample will normally contain DNA from the individual. It will normally contain cells. In one embodiment a sample is obtained by minimally invasive means, and may for example be a blood sample. DNA may be extracted and cut up with a standard restriction enzyme. This can pre-determine which chromosome conformations are retained and will be detected with the EpiSwitch™ platforms. Due to the synchronisation of chromosome interactions between tissues and blood, including horizontal transfer, a blood sample can be used to detect the chromosome interactions in tissues, such as tissues relevant to disease. For certain conditions, such as cancer, genetic noise due to mutations can affect the chromosome interaction 'signal' in the relevant tissues and therefore using blood is advantageous.

Properties of Nucleic Acids of the Invention

The invention relates to certain nucleic acids, such as the ligated nucleic acids which are described herein as being used or generated in the process of the invention. These may be the same as, or have any of the properties of, the first and second nucleic acids mentioned herein. The nucleic acids of the invention typically comprise two portions each comprising sequence from one of the two regions of the chromosome which come together in the chromosome interaction. Typically each portion is at least 8, 10, 15, 20, 30 or 40 nucleotides in length, for example 10 to 40 nucleotides in length. Preferred nucleic acids comprise sequence from any of the genes mentioned in any of the tables. Typically preferred nucleic acids comprise the specific probe sequences mentioned in Table 9; or fragments and/or homologues of such sequences. Typically preferred nucleic acids also comprise the specific probe sequences relevant to and/or mentioned for marker set 2 or 3; or fragments and/or homologues of such sequences. Preferably the nucleic acids are DNA. It is understood that where a specific sequence is provided the invention may use the complementary sequence as required in the particular embodiment.

The primers shown in Table 10 may also be used in the invention as mentioned herein. In one embodiment primers are used which comprise any of: the sequences shown in Table 10; or fragments and/or homologues of any sequence shown in Table 10. The primers relevant for and/or shown for marker set 2 or 3 may also be used in the invention as mentioned herein. In one embodiment primers are used which comprise any of: the sequences shown for marker set 2 or 3; or fragments and/or homologues of any sequence shown for marker set 2 or 3.

The Second Set of Nucleic Acids—the 'Index' Sequences

The second set of nucleic acid sequences has the function of being a set of index sequences, and is essentially a set of nucleic acid sequences which are suitable for identifying subgroup specific sequence. They can represents the 'background' chromosomal interactions and might be selected in some way or be unselected. They are in general a subset of all possible chromosomal interactions.

The second set of nucleic acids may be derived by any suitable process. They can be derived computationally or they may be based on chromosome interaction in individuals. They typically represent a larger population group than the first set of nucleic acids. In one particular embodiment, the second set of nucleic acids represents all possible epigenetic chromosomal interactions in a specific set of genes. In another particular embodiment, the second set of nucleic acids represents a large proportion of all possible epigenetic chromosomal interactions present in a population described herein. In one particular embodiment, the second set of nucleic acids represents at least 50% or at least 80% of epigenetic chromosomal interactions in at least 20, 50, 100 or 500 genes, for example in 20 to 100 or 50 to 500 genes.

The second set of nucleic acids typically represents at least 100 possible epigenetic chromosome interactions which modify, regulate or in any way mediate a disease state/phenotype in population. The second set of nucleic acids may represent chromosome interactions that affect a disease state in a species, for example chromosome interactions in genes that encode cytokines, kinases, or regulators associated with any disease state, predisposition to a disease or a disease phenotype. The second set of nucleic acids typically comprises sequences representing epigenetic interactions relevant and not relevant to a breast cancer subgroup.

In one particular embodiment the second set of nucleic acids derive at least partially from naturally occurring sequences in a population, and are typically obtained by in silico processes. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one particular embodiment, the second set of nucleic acids may comprise sequence representing a homologue and/or orthologue with at least 70% sequence identity to the corresponding portion of nucleic acids present in the naturally occurring species. In another particular embodiment, at least 80% sequence identity or at least 90% sequence identity to the corresponding portion of nucleic acids present in the naturally occurring species is provided.

Properties of the Second Set of Nucleic Acids

In one particular embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All or at least 90% or at least 50% or these would correspond to different chromosomal interactions.

In one particular embodiment, the second set of nucleic acids represent chromosome interactions in at least 20 different loci or genes, preferably at least 40 different loci or genes, and more preferably at least 100, at least 500, at least 1000 or at least 5000 different loci or genes, such as 100 to 10,000 different loci or genes. The lengths of the second set of nucleic acids are suitable for them to specifically hybridise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprises nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different characteristics.

The First Set of Nucleic Acids

The first set of nucleic acids are normally from individuals with breast cancer. The first nucleic acids may have any of the characteristics and properties of the second set of nucleic acids mentioned herein. The first set of nucleic acids is normally derived from a sample from the individuals which has undergone treatment and processing as described herein, particularly the EpiSwitch™ cross-linking and cleaving steps. Typically the first set of nucleic acids represents all or at least 80% or 50% of the chromosome interactions present in the samples taken from the individuals.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interactions in a defined set of loci or genes.

Library of Nucleic Acids

Any of the types of nucleic acid populations mentioned herein may be present in the form of a library comprising at least 200, at least 500, at least 1000, at least 5000 or at least 10000 different nucleic acids of that type, such as 'first' or 'second' nucleic acids. Such a library may be in the form of being bound to an array.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used.

Labelled Nucleic Acids and Pattern of Hybridisation

The nucleic acids mentioned herein may be labelled, preferably using an independent label such as a fluorophore (fluorescent molecule) or radioactive label which assists detection of successful hybridisation. Certain labels can be detected under UV light. The pattern of hybridisation, for example on an array described herein, represents differences in epigenetic chromosome interactions between the two subgroups, and thus provides a process of comparing epigenetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it not limited to any particular assay or technique, or the need to have a surface or array on which a 'pattern' can be detected.

Selecting a Subgroup with Particular Characteristics

The invention provides a process which comprises detecting the presence or absence of chromosome interactions, typically 5 to 20 or 5 to 500 such interactions, preferably 20 to 300 or 50 to 100 interactions, in order to determine the presence or absence of a characteristic relating to breast cancer in an individual. Preferably the chromosome interactions are those in any of the genes mentioned herein. In one embodiment the chromosome interactions which are typed are those represented by the nucleic acids in Table 9. The column titled 'Loop Detected' in Table 9 shows which subgroup is detected (breast cancer or control) by each probe. As can be seen the process of the invention can detect either a breast cancer subgroup and/or a control subgroup (non-breast cancer) as part of the testing.

The Individual that is Tested

Examples of the species that the individual who is tested is from are mentioned herein. In addition the individual that is tested in the process of the invention may have been selected in some way. The individual may be female, for example.

Preferred Gene Regions, Loci, Genes and Chromosome Interactions

For all aspects of the invention preferred gene regions, loci, genes and chromosome interactions are mentioned in the Table 9. Typically in the processes of the invention chromosome interactions are detected from at least 1, 2, 3, 4, 5, 6, 7 or 8 of the relevant genes listed in Table 9. Preferably the presence or absence of at least 1, 2, 3, 4, 5, 6, 7 or 8 of the relevant specific chromosome interactions represented by the probe sequences in Table 9 are detected. The disease-associated region may be upstream or downstream of any of the genes mentioned herein, for example 50 kb upstream or 20 kb downstream, for example from the coding sequence.

For all aspects of the invention preferred gene regions, loci, genes and chromosome interactions are mentioned in other tables. Typically in the processes of the invention chromosome interactions are detected from at least 1, 2, 3, 4, 5, 6, 7 or 8 of the relevant genes listed in tables, for example for marker set 2 or 3. Preferably the presence or absence of at least 1, 2, 3, 4, 5, 6, 7 or 8 of the relevant specific chromosome interactions represented by the probe sequences in tables are detected. The disease-associated region may be upstream or downstream of any of the genes mentioned herein, for example 50 kb upstream or 20 kb downstream, for example from the coding sequence.

In one embodiment the locus (including the gene and/or place where the chromosome interaction is detected) may comprise a CTCF binding site. This is any sequence capable of binding transcription repressor CTCF. That sequence may consist of or comprise the sequence CCCTC which may be present in 1, 2 or 3 copies at the locus. The CTCF binding site sequence may comprise the sequence CCGCGNGG-NGGCAG (SEQ ID NO:1) (in IUPAC notation). The CTCF binding site may be within at least 100, 500, 1000 or 4000 bases of the chromosome interaction or within any of the chromosome regions shown Table 9. The CTCF binding site may be within at least 100, 500, 1000 or 4000 bases of the chromosome interaction or within any of the chromosome regions shown in any table, for example for marker set 2 or 3.

In one embodiment the chromosome interactions which are detected are present at any of the gene regions shown Table 9. In the case where a ligated nucleic acid is detected in the process then sequence shown in any of the probe sequences in Table 9 may be detected. In another embodiment the chromosome interactions which are detected are present at any of the gene regions shown in other tables, for example for marker set 2 or 3. In the case where a ligated nucleic acid is detected in the process then sequence shown in any of the probe sequences in a table may be detected, for example for marker set 2 or 3.

Thus typically sequence from both regions of the probe (i.e. from both sites of the chromosome interaction) could be detected. In preferred embodiments probes are used in the process which comprise or consist of the same or complementary sequence to a probe shown in any table. In some embodiments probes are used which comprise sequence which is homologous to any of the probe sequences shown in the tables.

Tables Provided Herein

Table 9 shows probe (Episwitch™ marker) data and gene data representing chromosome interactions relevant to breast cancer. Other probe and gene data is shown in other tables, for example for marker set 2 or 3. The probe sequences show sequence which can be used to detect a ligated product generated from both sites of gene regions that have come together in chromosome interactions, i.e. the probe will comprise sequence which is complementary to sequence in the ligated product. The first two sets of Start-End positions show probe positions, and the second two sets of Start-End positions show the relevant 4 kb region. The following information is provided in the probe data table:

HyperG_Stats: p-value for the probability of finding that number of significant EpiSwitch™ markers in the locus based on the parameters of hypergeometric enrichment Probe Count Total: Total number of EpiSwitch™ Conformations tested at the locus Probe Count Sig: Number of EpiSwitch™ Conformations found to be statistical significant at the locus FDR HyperG: Multi-test (False Discovery Rate) corrected hypergeometric p-value Percent Sig: Percentage of significant EpiSwitch™ markers relative the number of markers tested at the locus log FC: logarithm base 2 of Epigenetic Ratio (FC)

AveExpr: average log 2-expression for the probe over all arrays and channels

T: moderated t-statistic p-value: raw p-value adj. p-value: adjusted p-value or q-value B—B-statistic (lods or B) is the log-odds that that gene is differentially expressed.

FC—non-log Fold Change

FC_1—non-log Fold Change centred around zero

LS—Binary value this relates to FC_1 values. FC_1 value below −1.1 it is set to −1 and if the FC_1 value is above 1.1 it is set to 1. Between those values the value is 0

Table 9 shows genes where a relevant chromosome interaction has been found to occur. Other tables show similar data. The p-value in the loci table is the same as the HyperG_Stats (p-value for the probability of finding that number of significant EpiSwitch™ markers in the locus based on the parameters of hypergeometric enrichment).

The probes are designed to be 30 bp away from the Taq1 site. In case of PCR, PCR primers are also designed to detect ligated product but their locations from the Taq1 site vary.

Probe locations:
Start 1-30 bases upstream of TaqI site on fragment 1
End 1—TaqI restriction site on fragment 1
Start 2—TaqI restriction site on fragment 2
End 2-30 bases downstream of TaqI site on fragment 2
4 kb Sequence Location:
Start 1-4000 bases upstream of TaqI site on fragment 1
End 1—TaqI restriction site on fragment 1
Start 2—TaqI restriction site on fragment 2
End 2-4000 bases downstream of TaqI site on fragment 2

Table 10 and other tables show for each of the top PCR markers: GLMNET™-procedures for fitting the entire lasso or elastic-net regularization. Lambda set to 0.5 (elastic-net)

Preferred Embodiments for Sample Preparation and Chromosome Interaction Detection Methods of preparing samples and detecting chromosome conformations are described herein. Optimised (non-conventional) versions of these methods can be used, for example as described in this section.

Typically the sample will contain at least $2 \times 10^5$ cells. The sample may contain up to $5 \times 10^5$ cells. In one embodiment, the sample will contain $2 \times 10^5$ to $5.5 \times 10^5$ cells Crosslinking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55° C. to about 70° C., such as for about 65° C., for a period of about 10 to 30 minutes, such as about 20 minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs. In one embodiment, the typical fragment size is from 200 base pairs to 4,000 base pairs, such as 400 to 2,000 or 500 to 1,000 base pairs.

In one embodiment of the EpiSwitch™ method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step.

In one embodiment PCR detection is capable of detecting a single copy of the ligated nucleic acid, preferably with a binary read-out for presence/absence of the ligated nucleic acid.

Processes and Uses of the Invention

The process of the invention can be described in different ways. It can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:

the locus may be any of the loci, regions or genes mentioned in Table 9, and/or wherein the chromosomal interaction may be any of the chromosome interactions mentioned herein or corresponding to any of the probes disclosed in Table 9, and/or wherein the ligated product may have or comprise (i) sequence which is the same as or homologous to any of the probe sequences disclosed in Table 9; or (ii) sequence which is complementary to (ii).

The process of the invention can be described as a process for detecting chromosome states which represent different subgroups in a population comprising determining whether a chromosome interaction is present or absent within a defined epigenetically active (disease associated) region of the genome, wherein preferably:

the subgroup is defined by presence or absence of breast cancer, and/or the chromosome state may be at any locus, region or gene mentioned in Table 9; and/or the chromosome interaction may be any of those mentioned in Table 9 or corresponding to any of the probes disclosed in that table.

The invention includes detecting chromosome interactions at any locus, gene or regions mentioned Table 9. The invention includes use of the nucleic acids and probes mentioned herein to detect chromosome interactions, for example use of at least 1, 2, 4, 6 or 8 such nucleic acids or probes to detect chromosome interactions in at least 1, 2, 4, 6 or 8 different loci or genes. The invention includes detection of chromosome interactions using any of the primers or primer pairs listed in Table 10 or using variants of these primers as described herein (sequences comprising the primer sequences or comprising fragments and/or homologues of the primer sequences).

In particular embodiments:

the locus may be any of the loci, regions or genes mentioned in any table, for example for marker set 2 or 3, and/or wherein the chromosomal interaction may be any of the chromosome interactions mentioned herein or corresponding to any of the probes disclosed in any table, for example for marker set 2 or 3, and/or wherein the ligated product may have or comprise (i) sequence which is the same as or homologous to any of the probe sequences disclosed in any table, for example for marker set 2 or 3; or (ii) sequence which is complementary to (ii).

The process of the invention can be described as a process for detecting chromosome states which represent different subgroups in a population comprising determining whether a chromosome interaction is present or absent within a defined epigenetically active (disease associated) region of the genome, wherein preferably:

the subgroup is defined by presence or absence of breast cancer, and/or the chromosome state may be at any locus, region or gene mentioned in any table, for example for marker set 2 or 3; and/or the chromosome interaction may be any of those mentioned in any table, for example for marker set 2 or 3; or corresponding to any of the probes disclosed in that table.

The invention includes detecting chromosome interactions at any locus, gene or regions mentioned in any table, for example for marker set 2 or 3. The invention includes use of the nucleic acids and probes mentioned herein to detect chromosome interactions, for example use of at least 1, 2, 4, 6 or 8 such nucleic acids or probes to detect chromosome interactions in at least 1, 2, 4, 6 or 8 different loci or genes. The invention includes detection of chromosome interactions using any of the primers or primer pairs listed in any table, for example for marker set 2 or 3, or using variants of these primers as described herein (sequences comprising the primer sequences or comprising fragments and/or homologues of the primer sequences).

Use of the Method of the Invention to Identify New Treatments

Knowledge of chromosome interactions can be used to identify new treatments for conditions. The invention provides methods and uses of chromosomes interactions defined here to identify or design new therapeutic agents for breast cancer.

Homologues

Homologues of polynucleotide/nucleic acid (e.g. DNA) sequences are referred to herein. Such homologues typically have at least 70% homology, preferably at least 80%, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

Therefore, in a particular embodiment, homologues of polynucleotide/nucleic acid (e.g. DNA) sequences are referred to herein by reference to percentage sequence identity. Typically such homologues have at least 70% sequence identity, preferably at least 80%, at least 85%, at least 90%, at least 95%, at least 97%, at least 98% or at least 99% sequence identity, for example over a region of at least 10, 15, 20, 30, 100 or more contiguous nucleotides, or across the portion of the nucleic acid which is from the region of the chromosome involved in the chromosome interaction.

For example the UWGCG™ Package provides the BESTFIT™ program which can be used to calculate homology and/or % sequence identity (for example used on its default settings) (Devereux et al (1984) Nucleic Acids Research 12, p 387-395). The PILEUP' and BLAST™ algorithms can be used to calculate homology and/or % sequence identity and/or line up sequences (such as identifying equivalent or corresponding sequences (typically on their default settings)), for example as described in Altschul S. F. (1993) J Mol Evol 36:290-300; Altschul, S, F et al (1990) J Mol Biol 215:403-10.

Software for performing BLAST™ analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased.

Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST™ algorithm parameters W5 T and X determine the sensitivity and speed of the alignment. The BLAST™ program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST™ algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides). These changes may be measured across any of the regions mentioned above in relation to calculating homology and/or % sequence identity.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array may be based on an Agilent™ SurePrint™ G3 Custom CGH microarray platform. Detection of binding of first nucleic acids to the array may be performed by a dual colour system.

Therapeutic Agents

Therapeutic agents are mentioned herein. The invention provides such agents for use in preventing or treating the breast cancer in certain individuals, for example those identified by a process of the invention. This may comprise administering to an individual in need a therapeutically effective amount of the agent. The invention provides use of the agent in the manufacture of a medicament to prevent or treat breast cancer in certain individuals.

Preferred therapeutic agents are cytotoxic drugs which are used to disrupt the growth of cancer cells. There are a number of different chemotherapy drugs that are commonly used to treat breast cancer. These include Cyclophosphamide, Fluorouracil (SFU), Methotrexate, Mitomycin™, Mitozantrone™, Doxorubicin™, Docetaxel (Taxotere™) and Gemcitabine™ (Gemzar™). Usually patients have a combination of about three chemotherapy drugs together. The therapeutic agent may reduce the level of hormones that trigger the growth of cancerous cells. The various drugs used for hormonotherapy include Anastrozole (Arimidex™), Exemestane™ (Aromasin™), Letrozole™ (Femara™) and Tamoxifen™. The therapeutic agent may be a biological therapy, such as drugs that interrupt interactions between cancerous cells, and thereby stop cell division and growth. Commonly used drugs for biological therapy include Herceptin™ (Trastuzumab™), Lapatinib™ (Tyverb™), Pertuzumab™ (Perjeta™) and Everolimus™ (Afinitor™).

The formulation of the agent will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. The agent may be formulated for parenteral, intravenous, intramuscular, subcutaneous, transdermal or oral administration.

The dose of an agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

Forms of the Substance Mentioned Herein

Any of the substances, such as nucleic acids or therapeutic agents, mentioned herein may be in purified or isolated form. They may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all of the specific nucleic acid sequences mentioned herein in single or double stranded form, and thus includes the complementary strand to any sequence which is disclosed.

The invention also provides a kit for carrying out any process of the invention, including detection of a chromosomal interaction associated with breast cancer or diagnosis of breast cancer. Such a kit can include a specific binding agent capable of detecting the relevant chromosomal interaction, such as agents capable of detecting a ligated nucleic acid generated by processes of the invention. Preferred agents present in the kit include probes capable of hybridising to the ligated nucleic acid or primer pairs, for example as described herein, capable of amplifying the ligated nucleic acid in a PCR reaction.

The invention also provides a device that is capable of detecting the relevant chromosome interactions. The device preferably comprises any specific binding agents, probe or primer pair capable of detecting the chromosome interaction, such as any such agent, probe or primer pair described herein.

Detection Methods

In one embodiment quantitative detection of the ligated sequence which is relevant to a chromosome interaction is carried out using a probe which is detectable upon activation during a PCR reaction, wherein said ligated sequence comprises sequences from two chromosome regions that come together in an epigenetic chromosome interaction, wherein said method comprises contacting the ligated sequence with the probe during a PCR reaction, and detecting the extent of activation of the probe, and wherein said probe binds the ligation site. The method typically allows particular interactions to be detected in a MIQE compliant manner using a dual labelled fluorescent hydrolysis probe.

The probe is generally labelled with a detectable label which has an inactive and active state, so that it is only detected when activated. The extent of activation will be related to the extent of template (ligation product) present in the PCR reaction. Detection may be carried out during all or some of the PCR, for example for at least 50% or 80% of the cycles of the PCR.

The probe can comprise a fluorophore covalently attached to one end of the oligonucleotide, and a quencher attached to the other end of the nucleotide, so that the fluorescence of the fluorophore is quenched by the quencher. In one embodiment the fluorophore is attached to the 5' end of the oligonucleotide, and the quencher is covalently attached to the 3' end of the oligonucleotide. Fluorophores that can be used in the methods of the invention include FAM™, TET™, JOE™, Yakima Yellow™, HEX™, Cyanine3™, ATTO 550™, TAMRA™, ROX™, Texas Red™, Cyanine 3.5™, LC610™, LC 640™, ATTO 647N™, Cyanine 5™, Cyanine 5.5™ and ATTO 680™. Quenchers that can be used with the appropriate fluorophore include TAM™, BHQ1™, DAB™, Eclip™, BHQ2™ and BBQ650™, optionally wherein said fluorophore is selected from HEX™, Texas Red™ and FAM™. Preferred combinations of fluorophore and quencher include FAM™ with BHQ1™ and Texas Red™ with BHQ2™.

Use of the Probe in a qPCR Assay

Hydrolysis probes of the invention are typically temperature gradient optimised with concentration matched negative controls. Preferably single-step PCR reactions are optimized. More preferably a standard curve is calculated. An advantage of using a specific probe that binds across the junction of the ligated sequence is that specificity for the ligated sequence can be achieved without using a nested PCR approach. The methods described herein allow accurate and precise quantification of low copy number targets. The target ligated sequence can be purified, for example gel-purified, prior to temperature gradient optimization. The target ligated sequence can be sequenced. Preferably PCR reactions are performed using about 10 ng, or 5 to 15 ng, or 10 to 20 ng, or 10 to 50 ng, or 10 to 200 ng template DNA. Forward and reverse primers are designed such that one primer binds to the sequence of one of the chromosome regions represented in the ligated DNA sequence, and the other primer binds to other chromosome region represented in the ligated DNA sequence, for example, by being complementary to the sequence.

Choice of Ligated DNA Target

The invention includes selecting primers and a probe for use in a PCR method as defined herein comprising selecting primers based on their ability to bind and amplify the ligated sequence and selecting the probe sequence based properties of the target sequence to which it will bind, in particular the curvature of the target sequence.

Probes are typically designed/chosen to bind to ligated sequences which are juxtaposed restriction fragments spanning the restriction site. In one embodiment of the invention, the predicted curvature of possible ligated sequences relevant to a particular chromosome interaction is calculated, for example using a specific algorithm referenced herein. The curvature can be expressed as degrees per helical turn, e.g. 10.5° per helical turn. Ligated sequences are selected for targeting where the ligated sequence has a curvature propensity peak score of at least 5° per helical turn, typically at least 10°, 15° or 20° per helical turn, for example 5° to 20° per helical turn. Preferably the curvature propensity score per helical turn is calculated for at least 20, 50, 100, 200 or 400 bases, such as for 20 to 400 bases upstream and/or downstream of the ligation site. Thus in one embodiment the target sequence in the ligated product has any of these levels of curvature. Target sequences can also be chosen based on lowest thermodynamic structure free energy.

Particular Embodiments

In particular embodiments chromosome interactions in IGFBP3 are not typed/detected.

In certain embodiments chromosome interactions in any of the genes mentioned herein are not typed/detected. In one embodiment any of the following genes are not typed/detected:

BCAS1, ZNF217, TSHZ2, SUMO1P1, MIR4756, BCAS3, TBX2, C17orf82, TBX4, BCA54, LINC00651, UBE2V1, TMEM189, CEBPB, LOC284751, PTPNI, MIR645, FAM65C PARD68, ADNP, LINC00494, PREX1, ARFGEF2, CSE1L, PDE4DIP, SEC22B, NOTCH2NL NBP10, HFE2, TXNIP, POLR3GL, ANKRD34A, LIX1L, RBM8A, GNRHR2, PEX11B, ITGA10, ANKRD35, PIAS3, NUDT17, POLR3C, RNF115, CD160, PDZK1, GPR89A, ZNF334. OCSTAMP, SLC13A3, TP53RK, SLC2A10, EYA2, MIR3616, ZMYND8, L0C100131496, DLG1, MIR4797, DLG1-AS1, BDH1, LOC220729, KIAA0226, MIR922, FYTTDI, LRCH3, IQCG, RPL35A, LMLN, ANKRD18DP, DDX59, CAMSAP2, GPR25, C1orf10[6], KIF21B, CACNA15, ASCLS, TMEM9, IGFN1, PKP1, TNN2, LAD1, TNNI1, PHLDA3, NCOA1, PTRHD1, CENPO, ADCY3, DNAJC27, DNAJC27-AS1, EFR3B. POMC, DNMT3A, MIR1301, DTNB, SPON2, LOC100130872, CTBP1, CTBP1-AS1, MAEA, UVSSA, CRIPAK, FAM53A, SLBP, TMEM129, TACC3, FGFR3, LETM1, WHSC1, SCARNA22, WHSC2, MIR943, C4orf48, NAT8L, POLN, HAUS3, MXD4, MIR4800, ZFYVE28, LOC402160, RNF4, LOC100506190, C9orf50, NTMT1, ASB6, PRRX2, PTGES, TOR1B, TOR1A, C9orf78, USP20, FNBP1, GPR107, NC51, ASS1.

In one embodiment only intrachromosomal interactions are typed/detected, and no extrachromosomal interactions (between different chromosomes) are typed/detected.

Publications

The contents of all publications mentioned herein are incorporated by reference into the present specification and may be used to further define the features relevant to the invention.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent™ SurePrint™ G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent™ SureScan™ Scanner and the resultant features extracted using the Agilent™ Feature Extraction software. The data is then processed using the EpiSwitch™ array processing scripts in R. The arrays are processed using standard dual colour packages in Bioconductor in R: Limma*. The normalisation of the arrays is done using the normalisedWithinArrays function in Limma* and this is done to the on chip Agilent™ positive controls and EpiSwitch™ positive controls. The data is filtered based on the Agilent™ Flag calls, the Agilent™ control probes are removed and the technical replicate probes are averaged, in order for them to be analysed using Limma*. The probes are modelled based on their difference between the 2 scenarios being compared and then corrected by using False Discovery Rate. Probes with Coefficient of Variation (CV)<=30% that are <=−1.1 or =>1.1 and pass the p<=0.1 FDR p-value are used for further screening. To reduce the probe set further Multiple Factor Analysis is performed using the FactorMineR package in R.

Note: LIMMA is Linear Models and Empirical Bayes Processes for Assessing Differential Expression in Microarray Experiments. Limma is an R package for the analysis of gene expression data arising from microarray or RNA-Seq.

The pool of probes is initially selected based on adjusted p-value, FC and CV<30% (arbitrary cut off point) parameters for final picking. Further analyses and the final list are drawn based only on the first two parameters (adj. p-value; FC).

Genes Mentioned Herein

TSPYL5—TSPY-like 5
SRD5A1—steroid 5 alpha-reductase 1
MAP3K1—mitogen-activated protein kinase kinase kinase 1
VAV3—vav guanine nucleotide exchange factor 3
ATM—ATM serine/threonine kinase
SLC16A10—solute carrier family 16 member 10
ME3—malic enzyme 3

The invention is illustrated by the following non-limiting examples.

Example 1

Statistical Pipeline

EpiSwitch™ screening arrays are processed using the EpiSwitch™ Analytical Package in R in order to select high value EpiSwitch™ markers for translation on to the EpiSwitch™ PCR platform.

Step 1

Probes are selected based on their corrected p-value (False Discovery Rate, FDR), which is the product of a modified linear regression model. Probes below p-value <=0.1 are selected and then further reduced by their Epigenetic ratio (ER), probes ER have to be <=−1.1 or =>1.1 in order to be selected for further analysis. The last filter is a coefficient of variation (CV), probes have to be below <=0.3.

Step 2

The top 40 markers from the statistical lists are selected based on their ER for selection as markers for PCR translation. The top 20 markers with the highest negative ER load and the top 20 markers with the highest positive ER load form the list.

Step 3

The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation. Genetic locations below p-value of 0.3 or 0.2 are selected. The statistical probes mapping to these genetic locations, with the markers from step 2, form the high value markers for EpiSwitch™ PCR translation.

Array Design and Processing

Array Design

1. Genetic loci are processed using the SII software (currently v3.2) to:
    a. Pull out the sequence of the genome at these specific genetic loci (gene sequence with 50 kb upstream and 20 kb downstream)
    b. Define the probability that a sequence within this region is involved in CCs
    c. Cut the sequence using a specific RE
    d. Determine which restriction fragments are likely to interact in a certain orientation
    e. Rank the likelihood of different CCs interacting together.
2. Determine array size and therefore number of probe positions available (x)
3. Pull out x/4 interactions.
4. For each interaction define sequence of 30 bp to restriction site from part 1 and 30 bp to restriction site of part 2. Check those regions aren't repeats, if so exclude and take next interaction down on the list. Join both 30 bp to define probe.
5. Create list of x/4 probes plus defined control probes and replicate 4 times to create list to be created on array
6. Upload list of probes onto Agilent™ Sure design website for custom CGH array.
7. Use probe group to design Agilent™ custom CGH array.

Array Processing
1. Process samples using EpiSwitch™ Standard Operating Procedure (SOP) for template production.
2. Clean up with ethanol precipitation by array processing laboratory.
3. Process samples as per Agilent™ SureTag™ complete DNA labelling kit—Agilent™ Oligonucleotide Array-based CGH for Genomic DNA Analysis Enzymatic labelling for Blood, Cells or Tissues
4. Scan using Agilent™ C Scanner using Agilent™ feature extraction software.

Breast Cancer Overview

Age-specific incidence rates indicate that the age effects for invasive breast cancer are more similar among Asian and Western populations. In fact, the Asian breast cancer rates in recent generations are even surpassing the historically high rates in the United States, highlighting an urgent need for efficient prevention and treatment strategies among Asian populations. However, the results of a large scale 25 year study showed that mammography did not reduce breast cancer associated mortality. Early detection of breast cancer, before tumours become macroscopic, would mean that medical intervention could initiate at a stage when the cancer is more treatable.

EpiSwitch™ Technology Overview

The EpiSwitch™ platform offers a highly effective means of screening, early detection, companion-diagnosis, monitoring and prognostic analysis of major diseases associated with aberrant and responsive gene expression. The major advantages of this approach is that it is non-invasive, rapid, and relies on highly stable DNA based targets as part of chromosomal signatures, rather than unstable protein/RNA molecules.

EpiSwitch™ biomarker signatures demonstrate high robustness, sensitivity and specificity in the stratification of complex disease phenotypes. This technology takes advantage of the latest breakthroughs in the science of epigenetics, monitoring and evaluation of chromosome conformation signatures as a highly informative class of epigenetic biomarkers. Current research methodologies deployed in academic environment require from 3 to 7 days for biochemical processing of cellular material in order to detect CCSs. Those procedures have limited sensitivity, and reproducibility; and furthermore, do not have the benefit of the targeted insight provided by the EpiSwitch" Analytical Package at the design stage.

EpiSwitch™ Analytical Package

The EpiSwitch™ platform technology detects changes in the higher order structure of human chromosomes as part of the main epigenetic framework of regulation. Juxtaposing distant sites in the chromosome forms a specific type of biomarker—regulatory chromosome conformation signatures. One of the biggest challenges in this process is to identify the potential sites in the gene/loci in the chromosome that forms part of the higher order structure. This is performed by use of proprietary pattern recognition software that identifies the potential sites within a given sequence. The EpiSwitch™ Analytical Package software, which includes a machine-learning algorithm, identifies patterns in DNA that are likely to form higher order structures of CCSs.

EpiSwitch™ Array in Silico Marker Identification

CCS sites across the genome are directly evaluated by the EpiSwitch™ Array on clinical samples from testing cohorts for identification of all relevant stratifying lead biomarkers. The EpiSwitch™ Array platform is used for marker identification due to its high-throughput capacity, and its ability to screen large numbers of loci rapidly. The array used was the Agilent™ custom-CGH array, which allows markers identified through the in silico software to be interrogated.

EpiSwitch™ PCR

Potential markers identified by EpiSwitch™ Array are then validated either by EpiSwitch™ PCR or DNA sequencers (i.e. Roche™ 454, Nanopore™ MinION™, etc.). The top PCR markers which are statistically significant and display the best reproducibility are selected for further reduction into the final EpiSwitch™ Signature Set, and validated on an independent cohort of samples. EpiSwitch™ PCR can be performed by a trained technician following a standardised operating procedure protocol established. All protocols and manufacture of reagents are performed under ISO 13485 and 9001 accreditation to ensure the quality of the work and the ability to transfer the protocols. EpiSwitch™ PCR and EpiSwitch™ Array biomarker platforms are compatible with analysis of both whole blood and cell lines. The tests are sensitive enough to detect abnormalities in very low copy numbers using small volumes of blood.

Summary

The inventors have used epigenetic chromosomal interactions as the basis for identifying biomarkers to be used as a companion diagnostic method in breast cancer diagnosis. The EpiSwitch™ biomarker discovery platform was developed by the inventors to detect epigenetic regulatory signature changes such as those driving phenotypic changes implicated in breast cancer. The EpiSwitch™ biomarker discovery platform identifies CCSs which define the initial regulatory process in integrating environmental cues into the epigenetic and transcriptional machinery. As such, CCSs are the primary step in a cascade of gene regulation. The CCSs isolated by the EpiSwitch™ biomarker discovery platform have several well documented advantages: severe biochemical and physiological stability; their binary nature and readout; and their primary position in the eukaryotic cascade of gene regulation.

The EpiSwitch™ Array screening platform was applied in this invention and its results translated onto the EpiSwitch™ PCR platform to meet the following aims:
1. Identify EpiSwitch™ markers that differentiate patients with breast cancer from healthy individuals;
2. Identify EpiSwitch™ markers that can be developed into a test that offers standards of sensitivity, specificity or positive predictive value (PPV), in relation to current existing clinical practice. In this breast cancer biomarker discovery project an 8×60 k array was utilised, which allows for the study of up to 56,964 potential chromosome conformations in quadruplicates. Two arrays were produced using eight stage II/III breast cancer patient samples from a range of backgrounds individually tested against eight pooled healthy control patient samples. Each array contained 56,964 EpiSwitch™ probes. The EpiSwitch™ template was prepared for each of the samples. The first array was carried out on Asian breast cancer samples. The second array used European and Asian samples. Asian and European breast cancers can differ between ER+ and ER− status. Overlapping probes were found for similar cancers in multiple populations. Each of the probes were then tested for statistical quality of the data, and then analysed as described subsequently.

Blood Sample Quality Control Results

The samples used in the study were from Malaysia. Biochemical quality of blood samples suitable for the EpiSwitch™ Assay is directly affected by the extent of sample oxidation and protein denaturation, as exemplified by haemoglobin. These two parameters are the standard means of assessing blood quality prior to sample processing. Briefly, when oxygenated haemoglobin (oxyhaemoglobin) is oxidized methaemoglobin is formed, and if the globin domains are denatured methaemoglobin is converted to hemichrome. Spectral changes were used to calculate the abundance of each fraction by the quality control method described by Winterbourn (1990), Oxidative reactions of hemoglobin. Methods Enzymol. 1990; 186: 265-72, which is based on the extinction coefficient of each haemoglobin fraction. In accordance with this document, as part of the quality control for each sample, blood was diluted in PBS and analysed on a spectrophotometer (Epoch Microplate (BioTek)) at 560, 577 and 630 nm. The micromolar concentrations of each of the three haemoglobin fractions were monitored according to standard calculations: µM oxyhaemoglobin=$119*A_{577}-39*A_{630}-89*A_{560}$, µM methaemoglobin=$28*A_{577}+307*A_{630}-55*A_{560}$, µM hemichrome=$-133*A_{577}-114*A_{630}+233*A_{560}$. Samples that demonstrated an oxyhaemoglobin:methaemoglobin ratio ≥0.75 were cleared on quality control and considered suitable for EpiSwitch™ processing. 11 samples failed haemoglobin QC (samples BrCaMa132, BrCaMa136, BrCaMa137, BrCaMa147, BrCaMa164, BrCaMa165, BrCaMa166, BrCaMa167, BrCaMa168, BrCaMa169, and BrCaMa170) and were excluded on the basis of their biochemical state of oxidation and denaturation.

TABLE 1

Oxy/met-Hb ratio thresholds of the samples and their usage within the statistical processes.
Epigenetic profiling of all the processed samples included a second quality control for the outliers.
Shipment 122 (site 2 batch 2 controls) demonstrated fundamentally different distribution and quality
from all the other sites and shipments. According to the standard practice of outlier control, 30 samples
from Site 2 batch 2 (shipment 122) were excluded from the development of the test.

| Sample ID | Client ID | Basic annotation | OD 577 nm | OD 630 nm | OD 560 nm | QC: nM oxYes-Hb est | QC: µM met-Hb est | QC: oxYes/met-Hb ratio | Development Cohort | Independent Validation Cohort | QC: Outliers |
|---|---|---|---|---|---|---|---|---|---|---|---|
| BrCaMa-002 | 022-Site 01 | BrCa Control | 1.924 | 0.296 | 1.243 | 1067.85 | 763.79 | 1.398 | Yes | | |
| BrCaMa-005 | 013-Site 01 | BrCa Control | 2.602 | 0.205 | 1.572 | 1617.35 | 493.31 | 3.279 | Yes | | |
| BrCaMa-006 | 024-Site 01 | BrCa Control | 1.887 | 0.269 | 1.204 | 1069.06 | 691.99 | 1.545 | Yes | | |
| BrCaMa-007 | 015-Site 01 | BrCa Control | 2.384 | 0.196 | 1.44 | 1478.92 | 477.24 | 3.099 | Yes | | |
| BrCaMa-012 | 019-Site 01 | BrCa Control | 1.861 | 0.341 | 1.232 | 985.12 | 890.35 | 1.106 | Yes | | |
| BrCaMa-014 | 020-Site 01 | BrCa Control | 1.851 | 0.284 | 1.192 | 1031.05 | 734.56 | 1.404 | Yes | | |
| BrCaMa-015 | 008-Site 01 | BrCa Control | 2.752 | 0.25 | 1.681 | 1681.29 | 613.51 | 2.74 | Yes | | |
| BrCaMa-016 | 007-Site 01 | BrCa Control | 2.56 | 0.225 | 1.557 | 1572.92 | 551.2 | 2.854 | | Yes | |
| BrCaMa-017 | 009-Site 01 | BrCa Control | 2.492 | 0.203 | 1.504 | 1547.75 | 493.77 | 3.135 | | Yes | |
| BrCaMa-018 | 010-Site 01 | BrCa Control | 2.246 | 0.182 | 1.353 | 1397.59 | 443.47 | 3.151 | | Yes | |
| BrCaMa-019 | 038-Site 01 | BrCa | 1.756 | 0.326 | 1.158 | 931.88 | 855.6 | 1.089 | Yes | | |
| BrCaMa-020 | 037-Site 01 | BrCa | 1.68 | 0.317 | 1.114 | 884.11 | 830.89 | 1.064 | Yes | | |
| BrCaMa-021 | 031-Site 01 | BrCa Control | 2.074 | 0.271 | 1.318 | 1189.35 | 687.79 | 1.729 | | Yes | |
| BrCaMa-022 | 032-Site 01 | BrCa Control | 2.767 | 0.216 | 1.67 | 1722.19 | 519.38 | 3.316 | | Yes | |
| BrCaMa-023 | 030-Site 01 | BrCa Control | 1.566 | 0.235 | 1 | 881.89 | 609.93 | 1.446 | | Yes | |
| BrCaMa-024 | 035-Site 01 | BrCa | 2.18 | 0.32 | 1.402 | 1221.62 | 821.7 | 1.487 | Yes | | |
| BrCaMa-025 | 036-Site 01 | BrCa | 1.844 | 0.326 | 1.212 | 988.54 | 850.54 | 1.162 | Yes | | |
| BrCaMa-026 | 034-Site 01 | BrCa Control | 2.021 | 0.391 | 1.351 | 1050.11 | 1023.2 | 1.026 | | Yes | |
| BrCaMa-027 | 033-Site 01 | BrCa Control | 1.761 | 0.208 | 1.101 | 1034.58 | 526.09 | 1.967 | | Yes | |
| BrCaMa-028 | 026-Site 01 | BrCa Control | 1.485 | 0.32 | 1.003 | 749.68 | 846.55 | 0.886 | Yes | | |
| BrCaMa-029 | 025-Site 01 | BrCa Control | 1.595 | 0.234 | 1.022 | 897.21 | 602.88 | 1.488 | Yes | | |
| BrCaMa-030 | 027-Site 01 | BrCa Control | 2.044 | 0.326 | 1.321 | 1129.53 | 846.59 | 1.334 | Yes | | |
| BrCaMa-031 | 029-Site 01 | BrCa Control | 1.944 | 0.379 | 1.296 | 1012.11 | 995.05 | 1.017 | Yes | | |
| BrCaMa-032 | 028-Site 01 | BrCa | 1.634 | 0.26 | 1.056 | 903.22 | 674.92 | 1.338 | | Yes | |
| BrCaMa-036 | 005-Site 01 | BrCa | 2.678 | 0.241 | 1.629 | 1643.02 | 593.76 | 2.767 | | Yes | |
| BrCaMa-039 | 001-Site 04 | BrCa | 1.986 | 0.346 | 1.304 | 1067.84 | 901.1 | 1.185 | Yes | | |
| BrCaMa-040 | 002-Site 04 | BrCa | 1.635 | 0.245 | 1.056 | 910.26 | 629.15 | 1.447 | Yes | | |
| BrCaMa-041 | 003-Site 04 | BrCa | 1.847 | 0.365 | 1.235 | 956.43 | 958.46 | 0.998 | Yes | | |
| BrCaMa-042 | 007-Site 04 | BrCa | 1.874 | 0.28 | 1.213 | 1041.29 | 717.17 | 1.452 | Yes | | |
| BrCaMa-043 | 004-Site 04 | BrCa Control | 2.452 | 0.208 | 1.494 | 1507.1 | 503.42 | 2.994 | Yes | | |
| BrCaMa-044 | 005-Site 04 | BrCa Control | 1.802 | 0.424 | 1.256 | 861.18 | 1115.44 | 0.772 | Yes | | |
| BrCaMa-045 | 006-Site 04 | BrCa Control | 1.733 | 0.376 | 1.18 | 865.43 | 990.56 | 0.874 | Yes | | |
| BrCaMa-046 | 008-Site 04 | BrCa Control | 1.888 | 0.329 | 1.241 | 1013.92 | 856.12 | 1.184 | Yes | | |
| BrCaMa-050 | 039-Site 01 | BrCa | 1.537 | 0.312 | 1.034 | 787.09 | 819.5 | 0.96 | | Yes | |
| BrCaMa-051 | 040-Site 01 | BrCa | 1.951 | 0.316 | 1.265 | 1072.6 | 820.65 | 1.307 | | Yes | |
| BrCaMa-055 | 044-Site 01 | BrCa Control | 2.984 | 0.217 | 1.803 | 1861.66 | 510.06 | 3.65 | Yes | | |
| BrCaMa-056 | 045-Site 01 | BrCa Control | 2.545 | 0.235 | 1.555 | 1552.95 | 578.8 | 2.683 | Yes | | |
| BrCaMa-057 | 046-Site 01 | BrCa Control | 2.455 | 0.202 | 1.484 | 1521.65 | 491.34 | 3.097 | Yes | | |
| BrCaMa-058 | 047-Site 01 | BrCa Control | 1.507 | 0.292 | 1.003 | 786.78 | 766.75 | 1.026 | Yes | | |
| BrCaMa-059 | 048-Site 01 | BrCa Control | 2.69 | 0.236 | 1.638 | 1651.24 | 576.82 | 2.863 | Yes | | |
| BrCaMa-060 | 049-Site 01 | BrCa | 1.863 | 0.341 | 1.238 | 982.16 | 887.61 | 1.107 | | Yes | |
| BrCaMa-061 | 050-Site 01 | BrCa | 2.119 | 0.36 | 1.397 | 1137.88 | 930.17 | 1.223 | | Yes | |
| BrCaMa-062 | 051-Site 01 | BrCa | 1.752 | 0.334 | 1.165 | 917.77 | 875.19 | 1.049 | | Yes | |
| BrCaMa-063 | 052-Site 01 | BrCa | 1.758 | 0.331 | 1.169 | 922.52 | 865.46 | 1.066 | | Yes | |
| BrCaMa-064 | 053-Site 01 | BrCa | 1.898 | 0.297 | 1.222 | 1055.21 | 771.13 | 1.368 | | Yes | |
| BrCaMa-065 | 054-Site 01 | BrCa | 1.599 | 0.227 | 1.02 | 906.48 | 583.61 | 1.553 | | Yes | |
| BrCaMa-066 | 055-Site 01 | BrCa | 1.5 | 0.286 | 0.996 | 787.02 | 750.22 | 1.049 | Yes | | |
| BrCaMa-067 | 001-Site 02 | BrCa | 1.821 | 0.36 | 1.227 | 934.56 | 940.23 | 0.994 | Yes | | |
| BrCaMa-068 | 002-Site 02 | BrCa | 2.476 | 0.231 | 1.51 | 1512.45 | 571.95 | 2.644 | Yes | | |
| BrCaMa-069 | 003-Site 02 | BrCa | 2.461 | 0.452 | 1.644 | 1289.15 | 1172.52 | 1.099 | Yes | | |
| BrCaMa-070 | 004-Site 02 | BrCa | 2.156 | 0.377 | 1.425 | 1150.36 | 977.32 | 1.177 | Yes | | |
| BrCaMa-071 | 005-Site 02 | BrCa | 1.898 | 0.346 | 1.262 | 1000.5 | 899.56 | 1.112 | Yes | | |

TABLE 1-continued

Oxy/met-Hb ratio thresholds of the samples and their usage within the statistical processes.
Epigenetic profiling of all the processed samples included a second quality control for the outliers.
Shipment 122 (site 2 batch 2 controls) demonstrated fundamentally different distribution and quality
from all the other sites and shipments. According to the standard practice of outlier control, 30 samples
from Site 2 batch 2 (shipment 122) were excluded from the development of the test.

| Sample ID | Client ID | Basic annotation | OD 577 nm | OD 630 nm | OD 560 nm | QC: nM oxYes-Hb est | QC: μM met-Hb est | QC: oxYes/met-Hb ratio | Development Cohort | Independent Validation Cohort | QC: Outliers |
|---|---|---|---|---|---|---|---|---|---|---|---|
| BrCaMa-072 | 006-Site 02 | BrCa | 1.807 | 0.411 | 1.24 | 886.44 | 1085.73 | 0.816 | Yes | | |
| BrCaMa-073 | 007-Site 02 | BrCa | 1.839 | 0.378 | 1.247 | 931.16 | 989.53 | 0.941 | Yes | | |
| BrCaMa-074 | 008-Site 02 | BrCa | 1.767 | 0.317 | 1.176 | 932.46 | 821.15 | 1.136 | Yes | | |
| BrCaMa-075 | 009-Site 02 | BrCa | 2.141 | 0.343 | 1.398 | 1169.8 | 883.59 | 1.324 | | Yes | |
| BrCaMa-076 | 010-Site 02 | BrCa | 2.148 | 0.409 | 1.438 | 1116.79 | 1066.17 | 1.047 | | Yes | |
| BrCaMa-077 | 011-Site 02 | BrCa | 1.721 | 0.344 | 1.156 | 884.99 | 902.16 | 0.981 | | Yes | |
| BrCaMa-078 | 012-Site 02 | BrCa | 2.142 | 0.448 | 1.454 | 1080.2 | 1175.42 | 0.919 | | Yes | |
| BrCaMa-079 | 013-Site 02 | BrCa | 1.888 | 0.281 | 1.213 | 1057.56 | 724.16 | 1.46 | | Yes | |
| BrCaMa-080 | 014-Site 02 | BrCa | 1.97 | 0.301 | 1.264 | 1101.95 | 780.47 | 1.412 | | Yes | |
| BrCaMa-081 | 015-Site 02 | BrCa | 2.128 | 0.312 | 1.373 | 1188.67 | 798.53 | 1.489 | Yes | | |
| BrCaMa-082 | 016-Site 02 | BrCa | 1.978 | 0.332 | 1.303 | 1064.67 | 856.43 | 1.243 | Yes | | |
| BrCaMa-083 | 017-Site 02 | BrCa | 2.025 | 0.389 | 1.357 | 1050.31 | 1014.88 | 1.035 | Yes | | |
| BrCaMa-084 | 018-Site 02 | BrCa | 2.048 | 0.362 | 1.358 | 1087.32 | 937.88 | 1.159 | Yes | | |
| BrCaMa-085 | 019-Site 02 | BrCa | 2.216 | 0.388 | 1.457 | 1188.99 | 1010.29 | 1.177 | Yes | | |
| BrCaMa-086 | 020-Site 02 | BrCa | 1.549 | 0.354 | 1.066 | 756.51 | 934.2 | 0.81 | Yes | | |
| BrCaMa-087 | 021-Site 02 | BrCa | 2.064 | 0.366 | 1.363 | 1100.35 | 951.89 | 1.156 | Yes | | |
| BrCaMa-088 | 022-Site 02 | BrCa | 1.734 | 0.362 | 1.172 | 879.2 | 952.26 | 0.923 | Yes | | |
| BrCaMa-089 | 023-Site 02 | BrCa | 2.063 | 0.431 | 1.393 | 1047.11 | 1134.66 | 0.923 | Yes | | |
| BrCaMa-090 | 024-Site 02 | BrCa | 1.966 | 0.429 | 1.349 | 971.62 | 1125.56 | 0.863 | Yes | | |
| BrCaMa-091 | 025-Site 02 | BrCa | 1.697 | 0.309 | 1.124 | 898.56 | 805.59 | 1.115 | Yes | | |
| BrCaMa-093 | 001-Site 02 | BrCa Control | 1.539 | 0.295 | 1.025 | 804.11 | 772.82 | 1.04 | Yes | | |
| BrCaMa-094 | 002-Site 02 | BrCa Control | 1.634 | 0.311 | 1.089 | 853.96 | 813.34 | 1.05 | Yes | | |
| BrCaMa-095 | 003-Site 02 | BrCa Control | 1.381 | 0.313 | 0.947 | 678.47 | 826.74 | 0.821 | | Yes | |
| BrCaMa-096 | 004-Site 02 | BrCa Control | 1.545 | 0.286 | 1.021 | 818.32 | 749.07 | 1.092 | | Yes | |
| BrCaMa-097 | 005-Site 02 | BrCa Control | 1.817 | 0.297 | 1.177 | 998.87 | 773.2 | 1.292 | | Yes | |
| BrCaMa-098 | 006-Site 02 | BrCa Control | 1.753 | 0.375 | 1.194 | 877.16 | 985.39 | 0.89 | | Yes | |
| BrCaMa-099 | 007-Site 02 | BrCa Control | 2.129 | 0.336 | 1.381 | 1173.38 | 868.09 | 1.352 | | Yes | |
| BrCaMa-100 | 008-Site 02 | BrCa Control | 1.693 | 0.274 | 1.102 | 927.03 | 709.12 | 1.307 | | Yes | |
| BrCaMa-101 | 009-Site 02 | BrCa Control | 0.988 | 0.147 | 0.634 | 554.13 | 379.23 | 1.461 | | Yes | |
| BrCaMa-102 | 010-Site 02 | BrCa Control | 2.017 | 0.274 | 1.279 | 1155.06 | 702.49 | 1.644 | | Yes | |
| BrCaMa-103 | 011-Site 02 | BrCa Control | 2.011 | 0.287 | 1.283 | 1139.29 | 738.52 | 1.543 | Yes | | |
| BrCaMa-104 | 012-Site 02 | BrCa Control | 1.853 | 0.356 | 1.231 | 970.64 | 934.71 | 1.038 | Yes | | |
| BrCaMa-105 | 013-Site 02 | BrCa Control | 1.802 | 0.379 | 1.214 | 916.11 | 1000.39 | 0.916 | Yes | | |
| BrCaMa-106 | 014-Site 02 | BrCa Control | 1.943 | 0.271 | 1.244 | 1099.32 | 691.81 | 1.589 | Yes | | |
| BrCaMa-107 | 015-Site 02 | BrCa Control | 1.933 | 0.288 | 1.248 | 1077.23 | 739 | 1.458 | Yes | | |
| BrCaMa-108 | 016-Site 02 | BrCa Control | 1.774 | 0.374 | 1.209 | 889.19 | 979.95 | 0.907 | Yes | | |
| BrCaMa-109 | 017-Site 02 | BrCa Control | 1.774 | 0.316 | 1.166 | 950.08 | 825.54 | 1.151 | Yes | | |
| BrCaMa-110 | 018-Site 02 | BrCa Control | 1.639 | 0.31 | 1.087 | 862.08 | 812.77 | 1.061 | Yes | | |
| BrCaMa-111 | 019-Site 02 | BrCa Control | 2.169 | 0.399 | 1.435 | 1148.35 | 1043 | 1.101 | Yes | | |
| BrCaMa-112 | 020-Site 02 | BrCa Control | 2.017 | 0.359 | 1.324 | 1081.86 | 938.69 | 1.153 | Yes | | |
| BrCaMa-113 | 021-Site 02 | BrCa Control | 1.817 | 0.323 | 1.189 | 978.05 | 846.42 | 1.156 | Yes | | |
| BrCaMa-114 | 022-Site 02 | BrCa Control | 1.716 | 0.296 | 1.13 | 920.9 | 767.7 | 1.2 | Yes | | |
| BrCaMa-115 | 023-Site 02 | BrCa Control | 1.609 | 0.242 | 1.038 | 896.51 | 622.56 | 1.44 | Yes | | |
| BrCaMa-116 | 024-Site 02 | BrCa Control | 2.054 | 0.348 | 1.349 | 1107.93 | 901.53 | 1.229 | Yes | | |
| BrCaMa-117 | 025-Site 02 | BrCa Control | 1.956 | 0.362 | 1.304 | 1025.9 | 941.82 | 1.089 | Yes | | |
| BrCaMa-118 | 056-Site 01 | BrCa | 1.153 | 0.203 | 0.755 | 620.95 | 530.8 | 1.17 | Yes | | |
| BrCaMa-119 | 057-Site 01 | BrCa | 1.79 | 0.326 | 1.185 | 948.31 | 850.27 | 1.115 | Yes | | |
| BrCaMa-120 | 058-Site 01 | BrCa | 1.383 | 0.286 | 0.933 | 703.86 | 752.11 | 0.936 | Yes | | |
| BrCaMa-121 | 059-Site 01 | BrCa | 1.043 | 0.171 | 0.672 | 576.4 | 447.41 | 1.288 | Yes | | |
| BrCaMa-122 | 060-Site 01 | BrCa | 1.834 | 0.316 | 1.198 | 993 | 824.74 | 1.204 | Yes | | |
| BrCaMa-123 | 061-Site 01 | BrCa | 1.782 | 0.315 | 1.168 | 958.21 | 823.61 | 1.163 | Yes | | |
| BrCaMa-124 | 062-Site 01 | BrCa | 1.166 | 0.184 | 0.754 | 644.72 | 476.66 | 1.353 | Yes | | |
| BrCaMa-125 | 063-Site 01 | BrCa | 1.638 | 0.293 | 1.075 | 878.2 | 766.9 | 1.145 | Yes | | |
| BrCaMa-126 | 064-Site 01 | BrCa | 1.542 | 0.274 | 1.011 | 828.33 | 716.89 | 1.155 | Yes | | |
| BrCaMa-127 | 065-Site 01 | BrCa | 1.349 | 0.352 | 0.943 | 628.76 | 939.71 | 0.669 | | Yes | |
| BrCaMa-129 | 009-Site 04 | BrCa | 1.727 | 0.31 | 1.139 | 920.52 | 808.81 | 1.138 | | Yes | |
| BrCaMa-130 | 010-Site 04 | BrCa | 2.016 | 0.303 | 1.308 | 1116.75 | 775.29 | 1.44 | | Yes | |
| BrCaMa-131 | 001-Site 03 | BrCa | 2.063 | 0.379 | 1.386 | 1073.62 | 978.87 | 1.097 | Yes | | |
| BrCaMa-132 | 002-Site 03 | BrCa Control | 1.719 | 0.428 | 1.211 | 800.9 | 1129.23 | 0.709 | | | |
| BrCaMa-133 | 003-Site 03 | BrCa Control | 1.825 | 0.322 | 1.221 | 959.48 | 827.99 | 1.159 | Yes | | |
| BrCaMa-134 | 004-Site 03 | BrCa | 1.855 | 0.383 | 1.256 | 940.24 | 1004.41 | 0.936 | | Yes | |
| BrCaMa-135 | 005-Site 03 | BrCa Control | 2.024 | 0.402 | 1.365 | 1036.93 | 1050.11 | 0.987 | Yes | | |
| BrCaMa-136 | Site 3_006 | BrCa | 0.134 | 0.11 | 0.136 | −4.48 | 300.42 | −0.015 | | | |
| BrCaMa-137 | Site 3_007 | BrCa | 0.139 | 0.116 | 0.141 | −5.32 | 317.49 | −0.017 | | | |
| BrCaMa-138 | 008-Site 03 | BrCa Control | 1.308 | 0.514 | 1.021 | 447.37 | 1382.67 | 0.324 | | Yes | |
| BrCaMa-139 | 009-Site 03 | BrCa Control | 1.595 | 0.532 | 1.188 | 633.25 | 1426.44 | 0.444 | | Yes | |
| BrCaMa-140 | 010-Site 03 | BrCa | 0.217 | 0.069 | 0.155 | 93.37 | 187.34 | 0.498 | | Yes | |
| BrCaMa-141 | 026-Site 02 | BrCa | 1.715 | 0.397 | 1.182 | 834.04 | 1048.89 | 0.795 | Yes | | |
| BrCaMa-142 | 027-Site 02 | BrCa | 1.626 | 0.276 | 1.063 | 881.23 | 717.95 | 1.227 | Yes | | |
| BrCaMa-143 | 028-Site 02 | BrCa | 0.218 | 0.062 | 0.153 | 99.07 | 167.23 | 0.592 | Yes | | |

TABLE 1-continued

Oxy/met-Hb ratio thresholds of the samples and their usage within the statistical processes.
Epigenetic profiling of all the processed samples included a second quality control for the outliers.
Shipment 122 (site 2 batch 2 controls) demonstrated fundamentally different distribution and quality
from all the other sites and shipments. According to the standard practice of outlier control, 30 samples
from Site 2 batch 2 (shipment 122) were excluded from the development of the test.

| Sample ID | Client ID | Basic annotation | OD 577 nm | OD 630 nm | OD 560 nm | QC: nM oxYes-Hb est | QC: μM met-Hb est | QC: oxYes/met-Hb ratio | Development Cohort | Independent Validation Cohort | QC: Outliers |
|---|---|---|---|---|---|---|---|---|---|---|---|
| BrCaMa-144 | 029-Site 02 | BrCa | 1.704 | 0.341 | 1.142 | 878.39 | 895.89 | 0.98 | Yes | | |
| BrCaMa-145 | 030-Site 02 | BrCa | 1.721 | 0.311 | 1.143 | 909.43 | 808 | 1.126 | Yes | | |
| BrCaMa-146 | 031-Site 02 | BrCa | 1.96 | 0.385 | 1.317 | 1010.12 | 1006.4 | 1.004 | Yes | | |
| BrCaMa-147 | 032-Site 02 | BrCa | 0.227 | 0.071 | 0.162 | 98.26 | 192.43 | 0.511 | | | |
| BrCaMa-148 | 033-Site 02 | BrCa | 1.502 | 0.317 | 1.018 | 757.73 | 833.85 | 0.909 | Yes | | |
| BrCaMa-149 | 035-Site 02 | BrCa | 1.7 | 0.336 | 1.141 | 876.47 | 879.97 | 0.996 | Yes | | |
| BrCaMa-150 | 036-Site 02 | BrCa | 1.955 | 0.339 | 1.283 | 1052.37 | 882.48 | 1.193 | Yes | | |
| BrCaMa-151 | 037-Site 02 | BrCa | 1.66 | 0.333 | 1.112 | 855.85 | 875.51 | 0.978 | Yes | | |
| BrCaMa-152 | 038-Site 02 | BrCa | 2.434 | 0.491 | 1.637 | 1248.04 | 1288.54 | 0.969 | Yes | | |
| BrCaMa-153 | 039-Site 02 | BrCa | 1.77 | 0.324 | 1.175 | 934.19 | 844.03 | 1.107 | Yes | | |
| BrCaMa-154 | 040-Site 02 | BrCa | 1.871 | 0.35 | 1.247 | 980.16 | 912.53 | 1.074 | Yes | | |
| BrCaMa-155 | 041-Site 02 | BrCa | 1.694 | 0.363 | 1.159 | 842.78 | 951.28 | 0.886 | Yes | | |
| BrCaMa-156 | 042-Site 02 | BrCa | 1.828 | 0.371 | 1.231 | 935.04 | 973.76 | 0.96 | Yes | | |
| BrCaMa-157 | 043-Site 02 | BrCa | 1.75 | 0.337 | 1.17 | 909.77 | 881.09 | 1.033 | Yes | | |
| BrCaMa-158 | 044-Site 02 | BrCa | 1.851 | 0.356 | 1.238 | 962.03 | 930.3 | 1.034 | Yes | | |
| BrCaMa-159 | 045-Site 02 | BrCa | 1.77 | 0.321 | 1.171 | 938.92 | 837.02 | 1.122 | Yes | | |
| BrCaMa-160 | 046-Site 02 | BrCa | 1.67 | 0.347 | 1.126 | 849.83 | 913.59 | 0.93 | Yes | | |
| BrCaMa-161 | 047-Site 02 | BrCa | 0.18 | 0.06 | 0.131 | 74.21 | 162.55 | 0.457 | | Yes | |
| BrCaMa-162 | 048-Site 02 | BrCa | 1.846 | 0.393 | 1.257 | 924.74 | 1032.04 | 0.896 | Yes | | |
| BrCaMa-163 | 049-Site 02 | BrCa | 1.63 | 0.436 | 1.161 | 736.37 | 1156.37 | 0.637 | | Yes | |
| BrCaMa-164 | 050-Site 02 | BrCa | 1.08 | 0.75 | 1.028 | 77.78 | 2039.5 | 0.038 | | Yes | |
| BrCaMa-165 | Site 2_051 | BrCa | 0.135 | 0.098 | 0.125 | 11.18 | 269.91 | 0.041 | | | |
| BrCaMa-166 | Site 2_052 | BrCa | 0.578 | 0.388 | 0.567 | 31.87 | 1041.15 | 0.031 | | | |
| BrCaMa-167 | 053-Site 02 | BrCa | 1.021 | 0.692 | 0.974 | 78.25 | 1874.62 | 0.042 | | Yes | |
| BrCaMa-168 | 054-Site 02 | BrCa | 0.899 | 0.63 | 0.849 | 68.5 | 1718.87 | 0.04 | | Yes | |
| BrCaMa-169 | 055-Site 02 | BrCa | 1.799 | 1.162 | 1.754 | 126.57 | 3106.36 | 0.041 | | Yes | |
| BrCaMa-170 | 056-Site 02 | BrCa | 1.497 | 0.939 | 1.431 | 141.63 | 2514.84 | 0.056 | | Yes | |
| BrCaMa-171 | 026-Site 02 | BrCa Control | 1.495 | 0.373 | 1.048 | 700.86 | 987.31 | 0.71 | | | Yes |
| BrCaMa-172 | 027-Site 02 | BrCa Control | 1.92 | 0.448 | 1.328 | 928.16 | 1182.56 | 0.785 | Yes | | Yes |
| BrCaMa-173 | 028-Site 02 | BrCa Control | 2.1 | 0.392 | 1.392 | 1107.24 | 1025.84 | 1.079 | Yes | | Yes |
| BrCaMa-174 | 029-Site 02 | BrCa Control | 2.125 | 0.335 | 1.377 | 1172.57 | 866.1 | 1.354 | | | Yes |
| BrCaMa-175 | 030-Site 02 | BrCa Control | 1.935 | 0.41 | 1.313 | 974.18 | 1078.35 | 0.903 | | | Yes |
| BrCaMa-176 | 031-Site 02 | BrCa Control | 1.812 | 0.314 | 1.186 | 978.28 | 819.04 | 1.194 | Yes | | Yes |
| BrCaMa-177 | 032-Site 02 | BrCa Control | 1.821 | 0.344 | 1.213 | 953.26 | 898.81 | 1.061 | Yes | | Yes |
| BrCaMa-178 | 033-Site 02 | BrCa Control | 1.617 | 0.324 | 1.08 | 836.67 | 853.44 | 0.98 | | | Yes |
| BrCaMa-179 | 034-Site 02 | BrCa Control | 1.429 | 0.255 | 0.942 | 762.68 | 664.87 | 1.147 | | | Yes |
| BrCaMa-180 | 035-Site 02 | BrCa Control | 1.44 | 0.217 | 0.921 | 809.28 | 562.84 | 1.438 | Yes | | Yes |
| BrCaMa-181 | 036-Site 02 | BrCa Control | 1.882 | 0.358 | 1.253 | 984.79 | 936.87 | 1.051 | Yes | | Yes |
| BrCaMa-182 | 037-Site 02 | BrCa Control | 1.752 | 0.329 | 1.16 | 924.17 | 862.59 | 1.071 | Yes | | Yes |
| BrCaMa-183 | 038-Site 02 | BrCa Control | 2 | 0.363 | 1.321 | 1062.74 | 947.86 | 1.121 | Yes | | Yes |
| BrCaMa-184 | 039-Site 02 | BrCa Control | 1.852 | 0.289 | 1.196 | 1026.73 | 747.99 | 1.373 | Yes | | Yes |
| BrCaMa-185 | 040-Site 02 | BrCa Control | 1.618 | 0.361 | 1.103 | 802.96 | 954.66 | 0.841 | | | Yes |
| BrCaMa-186 | 041-Site 02 | BrCa Control | 1.762 | 0.325 | 1.166 | 932.29 | 849.81 | 1.097 | | | Yes |
| BrCaMa-187 | 042-Site 02 | BrCa Control | 1.818 | 0.309 | 1.186 | 987.37 | 805.37 | 1.226 | | | Yes |
| BrCaMa-188 | 043-Site 02 | BrCa Control | 1.935 | 0.318 | 1.255 | 1061.68 | 827.81 | 1.283 | | | Yes |
| BrCaMa-189 | 044-Site 02 | BrCa Control | 1.723 | 0.297 | 1.127 | 931.51 | 774.38 | 1.203 | | | Yes |
| BrCaMa-190 | 045-Site 02 | BrCa Control | 1.875 | 0.36 | 1.248 | 980.13 | 943.8 | 1.038 | | | Yes |
| BrCaMa-191 | 046-Site 02 | BrCa Control | 1.784 | 0.267 | 1.146 | 998.89 | 688.91 | 1.45 | | | Yes |
| BrCaMa-192 | 047-Site 02 | BrCa Control | 1.742 | 0.413 | 1.202 | 842.13 | 1094.57 | 0.769 | | | Yes |
| BrCaMa-193 | 048-Site 02 | BrCa Control | 1.872 | 0.309 | 1.217 | 1024.04 | 803.44 | 1.275 | | | Yes |
| BrCaMa-194 | 049-Site 02 | BrCa Control | 1.616 | 0.257 | 1.046 | 891.87 | 666.17 | 1.339 | | | Yes |
| BrCaMa-195 | 050-Site 02 | BrCa Control | 1.265 | 0.209 | 0.823 | 691.37 | 543.18 | 1.273 | | | Yes |
| BrCaMa-196 | 051-Site 02 | BrCa Control | 1.601 | 0.358 | 1.096 | 790.13 | 944.54 | 0.837 | | | Yes |
| BrCaMa-197 | 052-Site 02 | BrCa Control | 1.661 | 0.24 | 1.061 | 938.7 | 618.33 | 1.518 | | | Yes |
| BrCaMa-198 | 053-Site 02 | BrCa Control | 1.546 | 0.272 | 1.015 | 830.31 | 709.67 | 1.17 | | | Yes |
| BrCaMa-199 | 054-Site 02 | BrCa Control | 1.505 | 0.314 | 1.019 | 761.58 | 824.93 | 0.923 | | | Yes |
| BrCaMa-200 | 055-Site 02 | BrCa Control | 1.939 | 0.309 | 1.256 | 1069.06 | 800.75 | 1.335 | | | Yes |
| BrCaMa-201 | Site 05-001 | BrCa | 1.077 | 0.083 | 0.645 | 675.655 | 201.895 | 3.347 | | Yes | |
| BrCaMa-202 | Site 05-002 | BrCa Control | 0.985 | 0.084 | 0.592 | 612.213 | 208.01 | 2.943 | Yes | | |
| BrCaMa-203 | Site 05-003 | BrCa | 0.858 | 0.079 | 0.52 | 527.805 | 196.073 | 2.692 | | Yes | |
| BrCaMa-204 | Site 05-004 | BrCa | 0.929 | 0.088 | 0.563 | 570.093 | 218.958 | 2.604 | Yes | | |
| BrCaMa-205 | Site 05-005 | BrCa | 0.82 | 0.072 | 0.494 | 507.638 | 177.965 | 2.852 | Yes | | |
| BrCaMa-206 | Site 05-006 | BrCa | 0.821 | 0.071 | 0.494 | 509.685 | 174.75 | 2.917 | Yes | | |
| BrCaMa-207 | Site 05-007 | BrCa | 0.993 | 0.085 | 0.599 | 615.535 | 210.445 | 2.925 | Yes | | |
| BrCaMa-208 | Site 05-008 | BrCa Control | 0.846 | 0.079 | 0.512 | 521.188 | 196.62 | 2.651 | Yes | | |
| BrCaMa-209 | Site 05-009 | BrCa Control | 0.534 | 0.059 | 0.327 | 320.603 | 150.523 | 2.13 | Yes | | |
| BrCaMa-210 | Site 05-010 | BrCa Control | 0.854 | 0.074 | 0.515 | 528.775 | 182.28 | 2.901 | Yes | | |
| BrCaMa-211 | Site 05-011 | BrCa Control | 0.806 | 0.079 | 0.492 | 490.5 | 198.583 | 2.47 | Yes | | |
| BrCaMa-212 | Site 05-012 | BrCa | 1.13 | 0.083 | 0.673 | 712.738 | 199.248 | 3.577 | Yes | | |
| BrCaMa-213 | Site 05-013 | BrCa Control | 1.005 | 0.085 | 0.605 | 623.435 | 210.09 | 2.967 | Yes | | |

TABLE 1-continued

Oxy/met-Hb ratio thresholds of the samples and their usage within the statistical processes.
Epigenetic profiling of all the processed samples included a second quality control for the outliers.
Shipment 122 (site 2 batch 2 controls) demonstrated fundamentally different distribution and quality
from all the other sites and shipments. According to the standard practice of outlier control, 30 samples
from Site 2 batch 2 (shipment 122) were excluded from the development of the test.

| Sample ID | Client ID | Basic annotation | OD 577 nm | OD 630 nm | OD 560 nm | QC: nM oxYes-Hb est | QC: μM met-Hb est | QC: oxYes/met-Hb ratio | Development Cohort | Independent Validation Cohort | QC: Outliers |
|---|---|---|---|---|---|---|---|---|---|---|---|
| BrCaMa-214 | Site 05-014 | BrCa | 1.233 | 0.086 | 0.732 | 781.85 | 204.985 | 3.814 | | Yes | |
| BrCaMa-215 | Site 05-015 | BrCa Control | 1.081 | 0.093 | 0.655 | 667.788 | 227.38 | 2.937 | Yes | | |
| BrCaMa-216 | Site 05-016 | BrCa | 1.112 | 0.092 | 0.667 | 693.89 | 225.483 | 3.077 | | Yes | |
| BrCaMa-217 | Site 05-017 | BrCa Control | 0.973 | 0.082 | 0.585 | 605.285 | 201.03 | 3.011 | Yes | | |
| BrCaMa-218 | Site 05-018 | BrCa Control | 1.088 | 0.087 | 0.65 | 682.81 | 214.438 | 3.184 | Yes | | |
| BrCaMa-219 | Site 05-019 | BrCa Control | 1.018 | 0.082 | 0.609 | 637.258 | 202.665 | 3.144 | Yes | | |
| BrCaMa-220 | Site 05-020 | BrCa | 1.451 | 0.098 | 0.861 | 921.855 | 231.848 | 3.976 | Yes | | |
| ISH-1008 | N/A | BrCa | 2.358 | 0.269 | 1.464 | 1398.15 | 680.87 | 2.053 | Yes | | |
| MM-5013 | N/A | BrCa control | 2.528 | 0.365 | 1.617 | 1426.84 | 939.04 | 1.519 | Yes | | |
| PAH-1004 | N/A | BrCa | 2.06 | 0.312 | 1.334 | 1142.46 | 800.94 | 1.426 | Yes | | |
| PAH-1007 | N/A | BrCa | 1.921 | 0.232 | 1.214 | 1115.05 | 582.42 | 1.915 | Yes | | |

EpiSwitch™ Array Results

Both data sets produced many significant probes;

Array 1, BCa1 4185 significant EpiSwitch™ markers identified in the analysis of breast cancer versus healthy controls;

Array 2, BCa2 4856 significant EpiSwitch™ markers identified in the analysis of breast cancer versus healthy controls;

However there was an overlap between both analyses of 2116 significant probes consistent between the 2 studies (see FIG. 1)

All data was originally taken and all saturated probes were removed. They were then normalised to even up the data between the channels. All of the four replicates for each data set were then combined together, and the co-efficient of variation was determined. The 2116 probes were narrowed down using normalised correlation values to rank the most changed genes on the array. Enrichment analysis was used to find the most differentially expressed genes above that of random chance. Altogether there were 138 markers from the combined BCa1 and BCa2 arrays that showed differential up-regulated or down-regulated expression. The top 80 EpiSwitch™ markers (see Appendix I) including 41 markers from array 1 and 39 markers from array 2 were taken on for validation with the EpiSwitch™ PCR assay to stratify between breast cancer and healthy controls.

EpiSwitch™ PCR Platform and Marker Verification

Primers were designed using the Integrated DNA Technologies™ (IDT) software (and Primer3web™ version 4.0.0 software if required) from markers identified on the microarray. Primer testing was carried out on each primer set. Each set was tested on a pooled subset of samples to ensure that appropriate primers could study the potential interactions. If the primer testing was successful then the primer sets were taken through to screening.

168 samples were used. These samples were split into 2 sets: 118 patient samples (68 BrCa & 50 Control) were used in marker reduction and model development, and the remaining 50 samples (31 BrCa & 19 Control) were used as an independent cohort to validate the final model developed from the initial 118 patient set. 30 Control samples from site 2, shipment 122 (defined as batch 2) were not used in the final patient set as they proved to be outliers in quality control procedures.

Primer Screen

This test was used to eliminate non-specific primers, and to determine whether the primers are enabling the detection of the 3C conformational looping. All extracted blood samples were diluted from 1:2-1:64. Initial results were produced in a binary format; i.e. '1'—yes, a band is present at the correct size or '0'—no, a band is not present at the correct size. All read-outs by EpiSwitch™ PCR were performed in presence of and with >95% accuracy of detecting both positive and negative controls.

Screen 1

51 primer sets successfully passed the primer testing stage and were tested on the 8 BrCa and 8 control blood samples. In the first screen the samples were matched to those used on the array.

TABLE 2

Samples used on Array 1 and in further PCR validation.

| BrCa Sample ID | Patient ID | Control Sample ID | Patient ID |
|---|---|---|---|
| BrCaMa050 | 039 site 1 | BrCaMa057 | 046 site 1 |
| BrCaMa051 | 040 site 1 | BrCaMa058 | 047 site 1 |
| BrCaMa060 | 049 site 1 | BrCaMa055 | 044 site 1 |
| BrCaMa061 | 050 site 1 | BrCaMa056 | 045 site 1 |
| BrCaMa062 | 051 site 1 | BrCaMa096 | 004 site 2 |
| BrCaMa064 | 053 site 1 | BrCaMa097 | 005 site 2 |
| BrCaMa089 | 023 site 2 | BrCaMa043 | 004 site 4 |
| BrCaMa041 | 003 site 4 | BrCaMa045 | 006 site 4 |

Screen 2

Primer sets showing differentiation were then screened with a further 12 BrCa and 12 control blood samples. A 1:2 to 1:64 dilution series was used to identify the range of assay sensitivity. Results from screen 1 and 2 were merged together to give a full representation of all the 20 samples used. A further 24 BrCa and 24 controls and finally the remainder of the samples were tested.

Screen 3

The final 20 BrCa and 20 control samples were then screened using the most informative three dilutions, covering the sensitive range of detection for the assay for each primer set. 13 markers in total were used in the final 20 samples screen. The results from screen 3 were merged together with the 90 BrCa and 90 control samples to give a full representation of 100 samples used for both BrCa and controls. These were then tested for efficacy in differentiating BrCa patients from control samples. A chi-square test (Fisher's exact) was produced to give the final markers.

TABLE 3

The final markers and primer sets.

| PROBES | OUTERS | INNERS |
| --- | --- | --- |
| MELK_9_36577630_36579243_36637050_36643005_RF | PRMR-2/4 | PRMR-1/3 |
| ATM_11_108118137_108126372_108155279_108156687_RF | PRMR-54/56 | PRMR-53/55 |
| CDC6_17_38421089_38423079_38467677_38474960_FR | PRMR-90/92 | PRMR-89/91 |
| CDC6_17_38421089_38423079_38451196_38457050_FF | PRMR-102/104 | PRMR-101/103 |
| SLC16A10_6_111441989_111447305_111492951_111498421_FR | PRMR-114/80 | PRMR-113/115 |
| TSPYL5_8_98276431_98282736_98316421_98318720_FF | PRMR-130/132 | PRMR-129/131 |
| MAP3K1_5_56102259_56110500_56140227_56144076_FF | PRMR-162/164 | PRMR-161/163 |
| ME3_11_86300063_86304401_86420537_86426200_FR | PRMR-174/176 | PRMR-173/175 |
| SRD5A1_5_6634973_6639025_6667775_6669711_RF | PRMR-178/180 | PRMR-177/179 |
| VAV3_1_108148303_108158073_108220200_108227533_RF | PRMR-186/188 | PRMR-185/187 |
| FOXC1_6_1577253_1581989_1604206_1605973_FR | PRMR-198/200 | PRMR-197/199 |
| NF1_17_29477103_29483764_29651799_29657368_FF | PRMR-262/264 | PRMR-261/263 |
| MSH3_5_80021913_80025030_80153948_80159012_RF | PRMR-302/304 | PRMR-301/303 |

Marker Reduction 13 Primer Combinations with 3 Dilution Factors, 39 Markers

Figure 3:
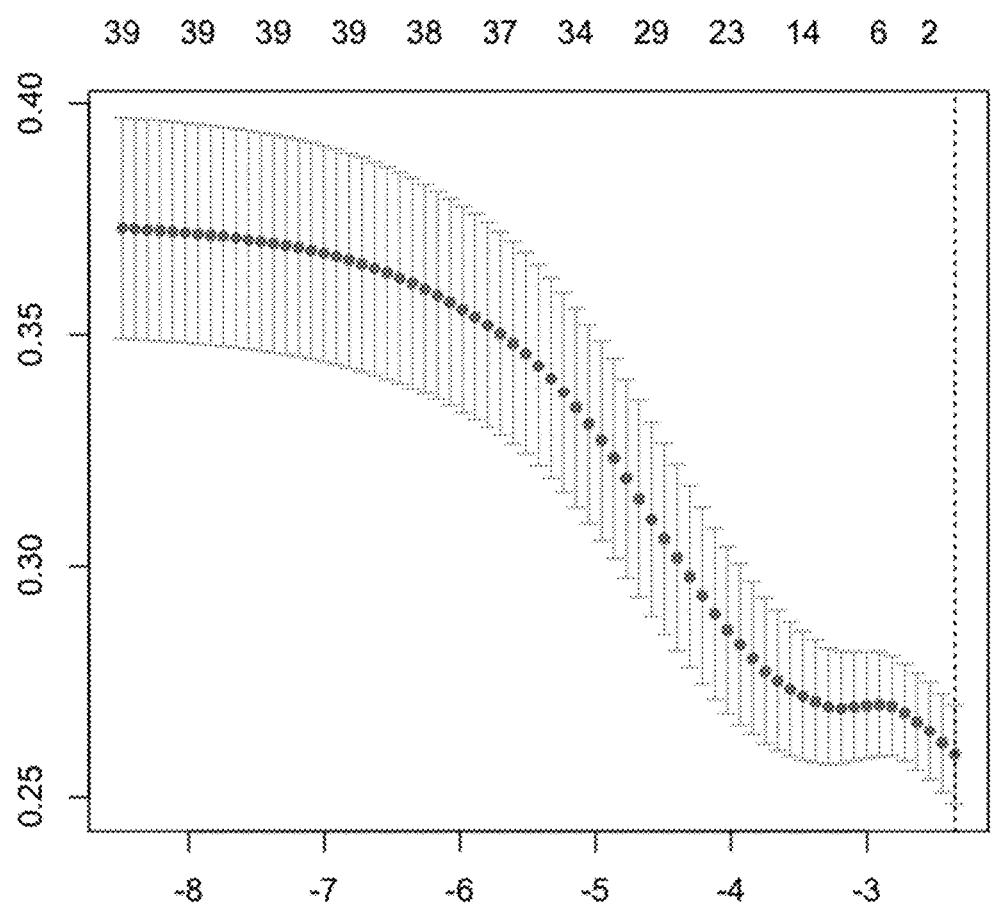
FIG. 3. Cross validation plot of the GLMNET™ model is used to choose lambda (penalized value for logistic model) and coefficients (at min error). Y-axis is mean-squared error. X-axis is log (lambda).
Figure 4:
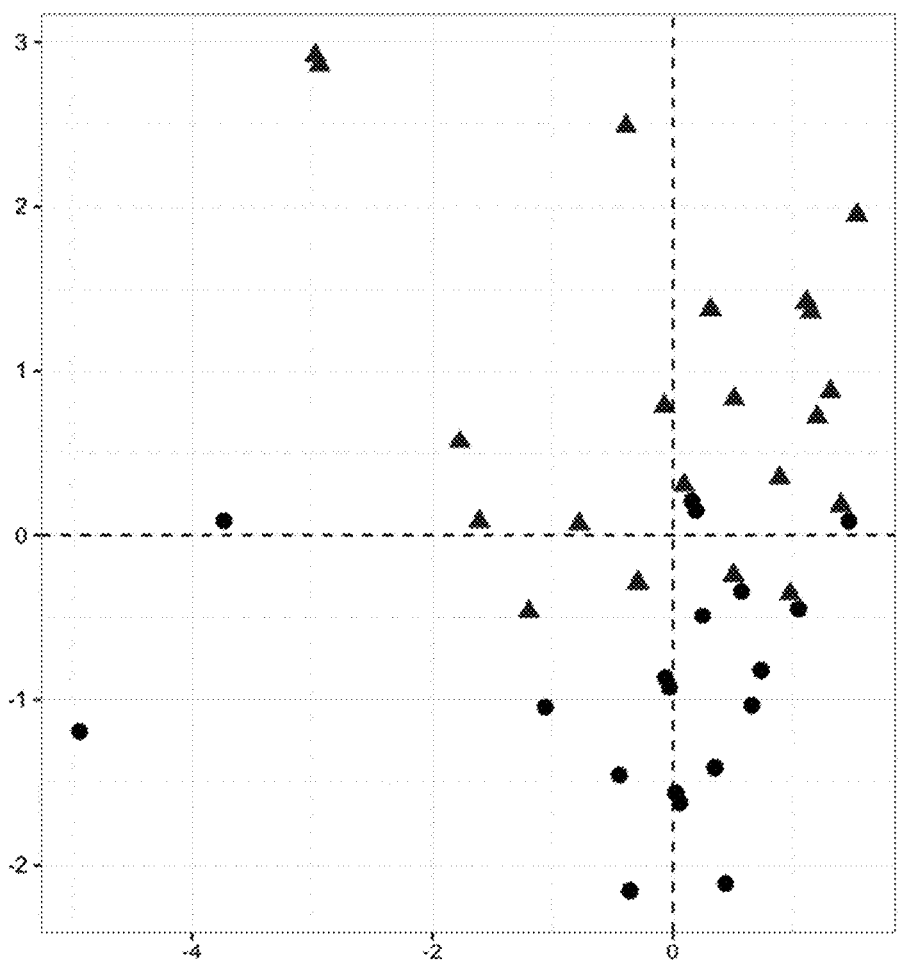
FIG. 4. Outlier quality control for shipment 122. Factor analysis (principle component analysis) plot of the control samples from site 2 using the 8 markers from the final BrCa model. The patients shown as triangles (site2_b2) are from shipment 122 (30 patients) and these were excluded from the total analysis, the patients shown as circles (site_2) are site 2 control from shipment 113 (25 patients), which were used. This plot shows that within these controls from the same location, there is a large variation component which separates patients that are meant to be biologically similar in context of comparison to BrCa. This is of a concern as this variation will compete for the difference between BrCa and control in the final model; hence site 2 batch 2 shipment 122 samples were removed. Y-axis is Dim 2 16.79%. X-axis is Dim 1 18.11%.
Figure 5:
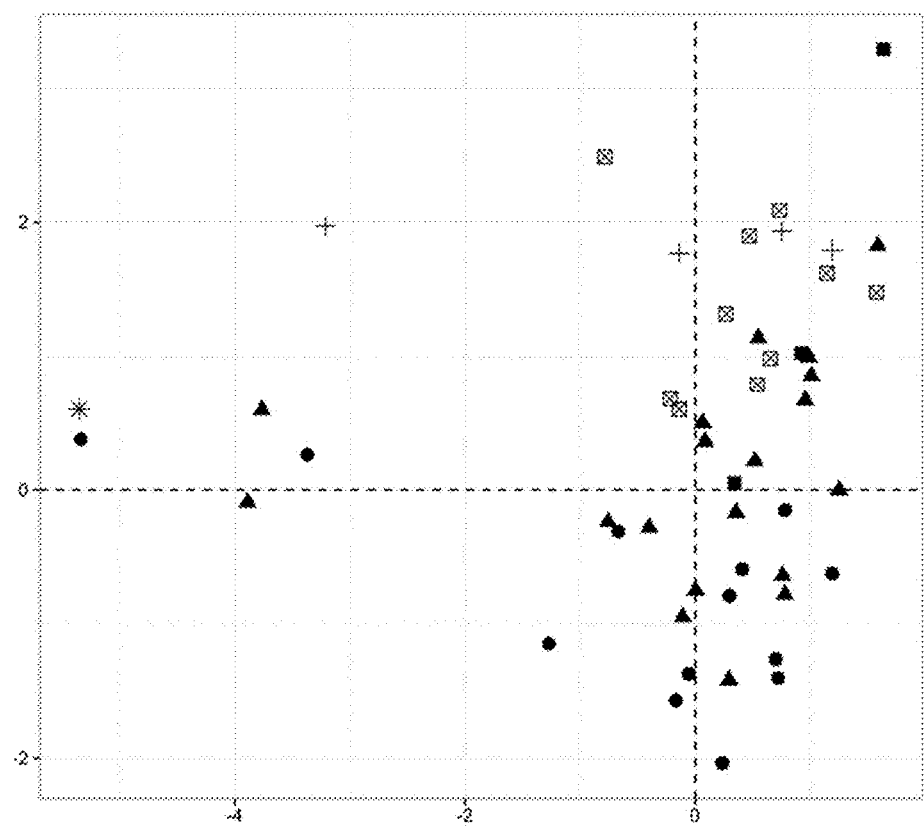
FIG. 5 shows a factor analysis (principle component analysis) plot for all control samples used in the analysis (69 controls) using the 8 markers from the final BrCa model. There is slight geographical variation in the patients but this is smaller than the variation with the outlier group of the site 2 controls (shipment 122). Circles are site 1. Triangles are site 2. Dark squares are site 3. Crosses are site 4. Crossed boxes are site 5. Y-axis is Dim2 11.57%. Y-axis is Dim 1 15.47%.
Figure 6:
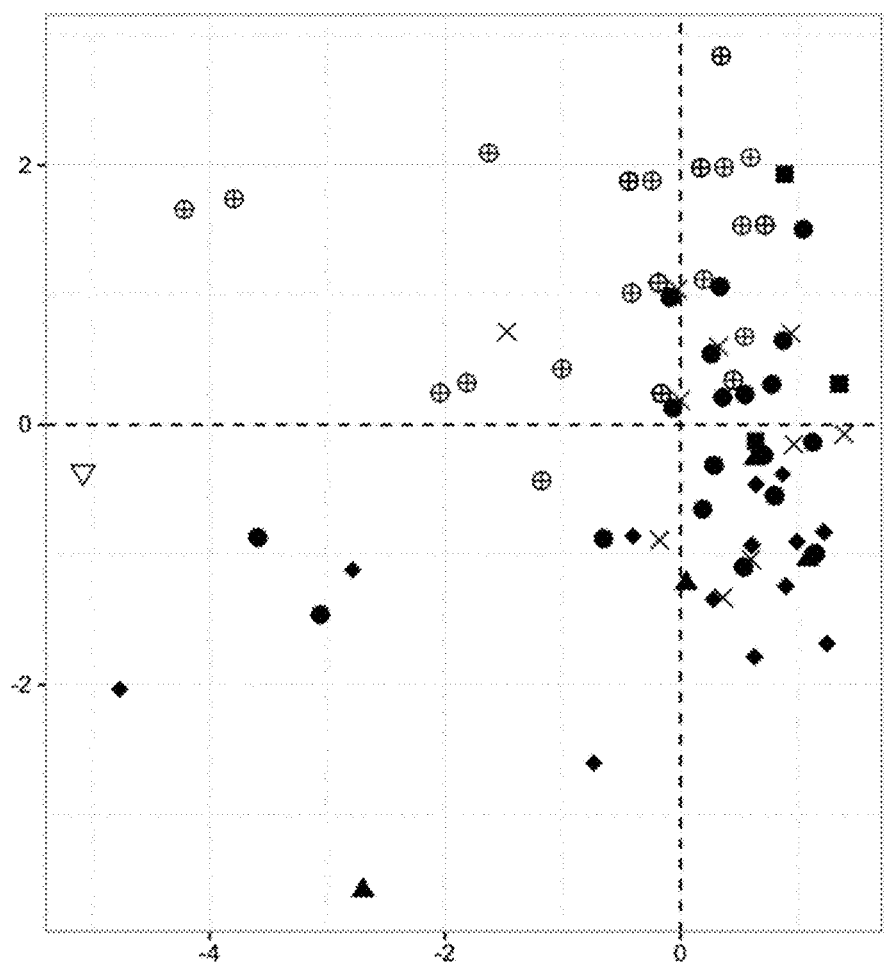
FIG. 6 shows a factor analysis (principle component analysis) plot for all control samples used in the analysis (69 controls), plus the 30 excluded outlier group of site 2 (shipment 122—shown as crossed circles) using the 8 markers from the final BrCa model. The spread in the data is predominantly due to the issues in the site 2 shipment 122. Dark diamonds are site 1. Dark circles are site 2. Dark squares are site 3. Dark triangles are site 4. Crosses are site 5. Light triangles are site 6. Crossed circles are site 2_b2. Y-axis is Dim 2 11.14%. X-axis is Dim 1 12.36%.
Figure 7:
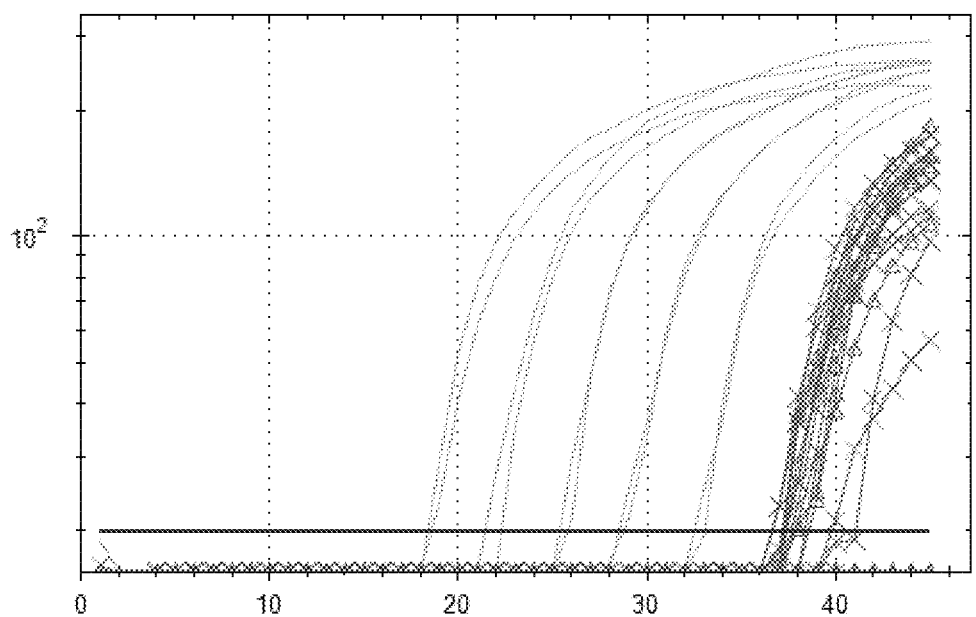
FIG. 7 shows results for marker ATM_11_108118137_108126372_108155279_ 108156687_RF. The first figure shows amplification with ATM primers 54 and 56, 472 bp analysis two. The second figure shows the standard curve. FAM™ is used. The efficiency is found to be 91.7%, $R^2$ is 0.996, slope is −3.539, y-int is 39.706.
Figure 7:
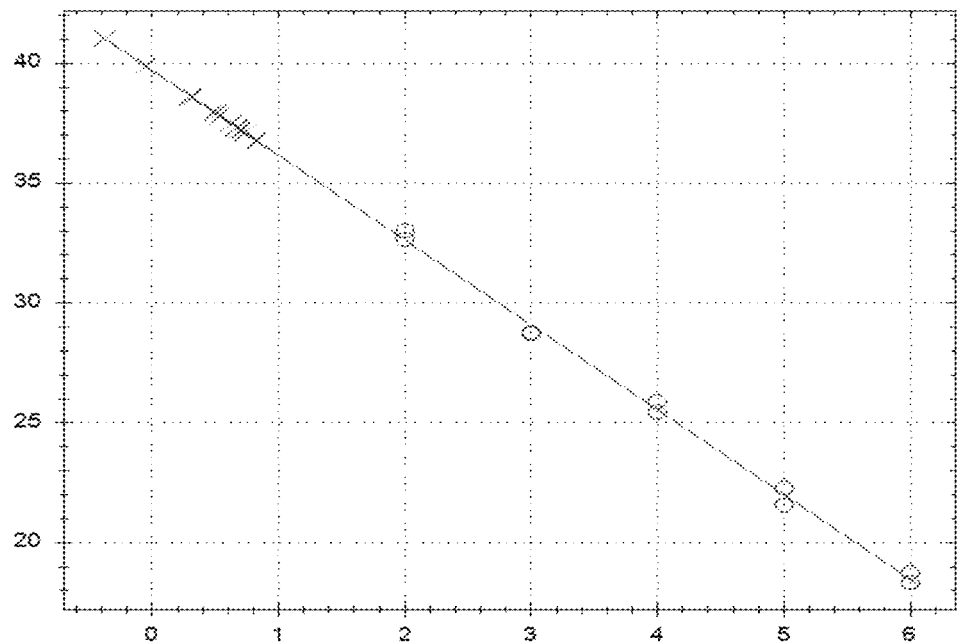
Figure 8:
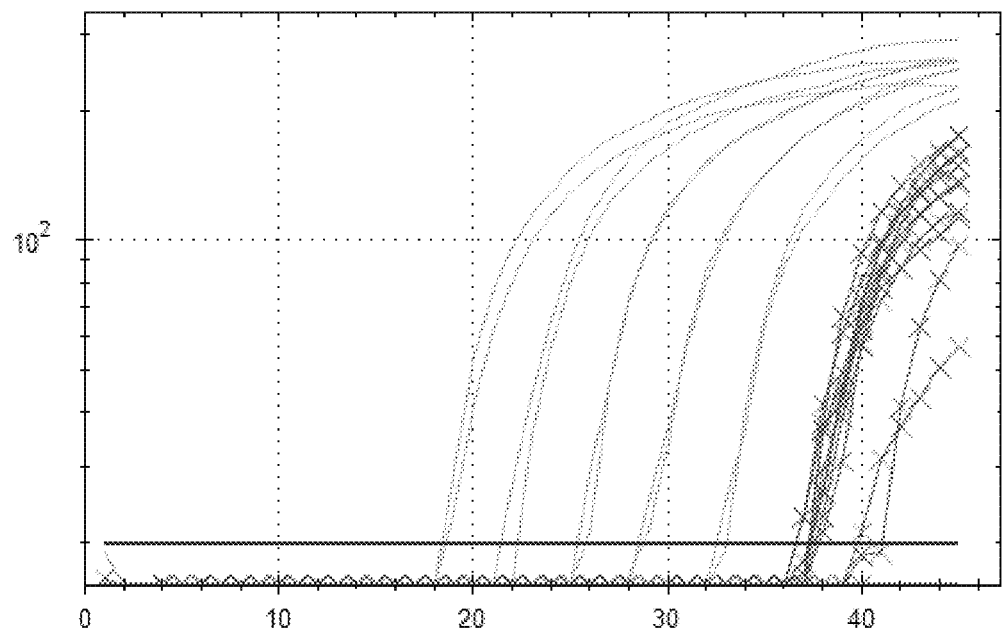
FIG. 8 shows amplification lines for ATM_11_108118137_108126372_108155279_ 108156687_RF. The first Figure shows amplification with ATM primers 54 and 56, 472 bp analysis two, row C. The second figure shows amplification with ATM primers 54 and 56, 472 bp analysis two, row D.
Figure 8:
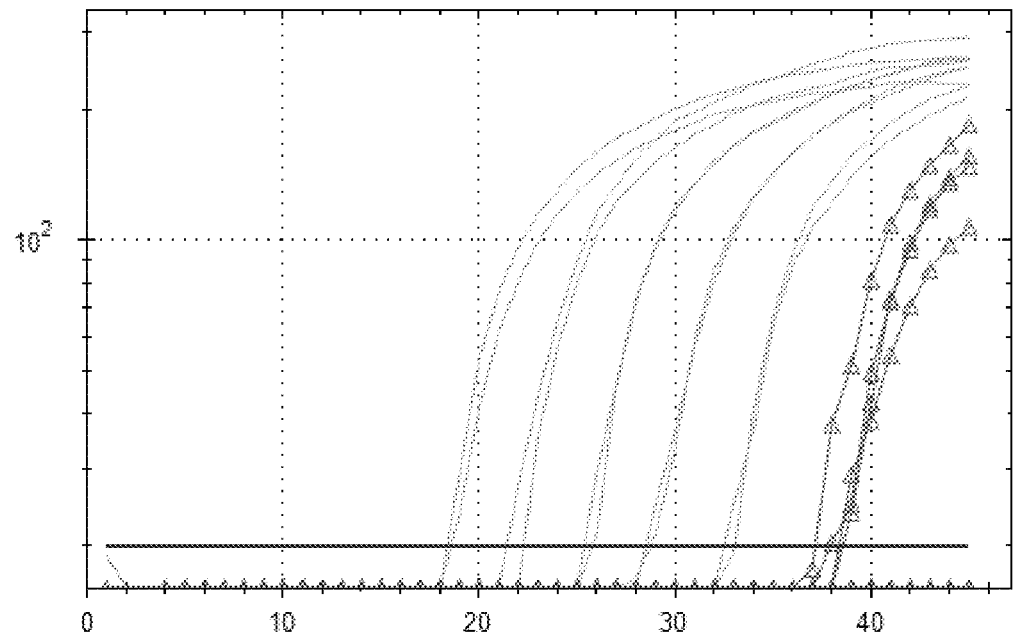
Figure 9:
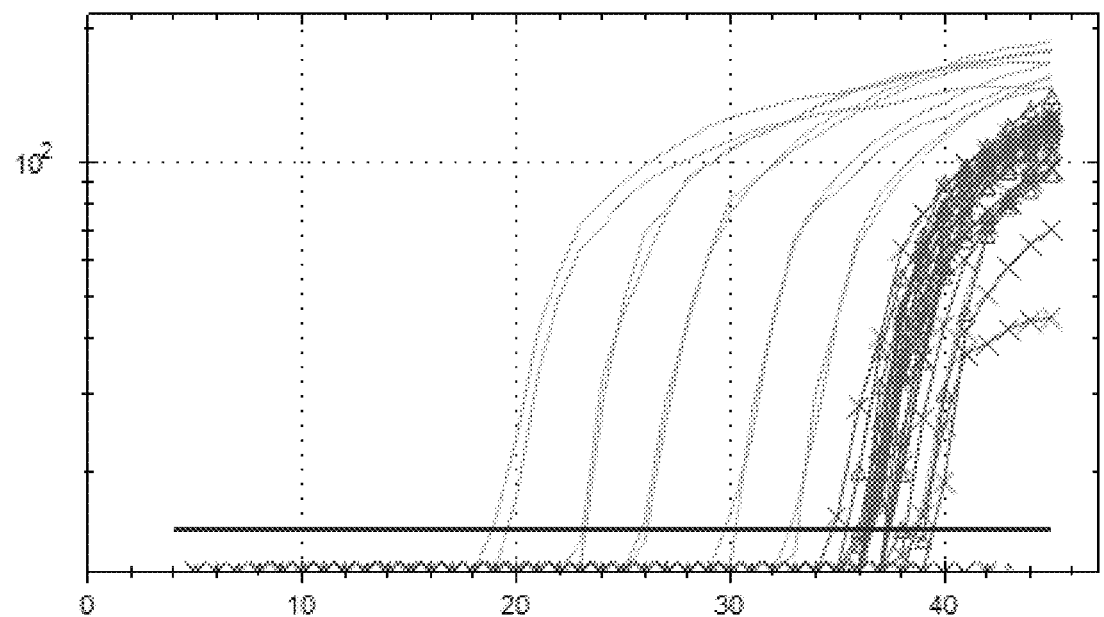
FIG. 9 shows results for marker CDC6_17_38421089_38423079_38451196_38457050_FF. The first figure shows amplification with PCR 2 CDC6 FF. The second figure shows the standard curve. FAM™ is used. The efficiency is found to be 90.7%, $R^2$ is 0.990, slope is −3.568, y-int is 40.652.
Figure 9:
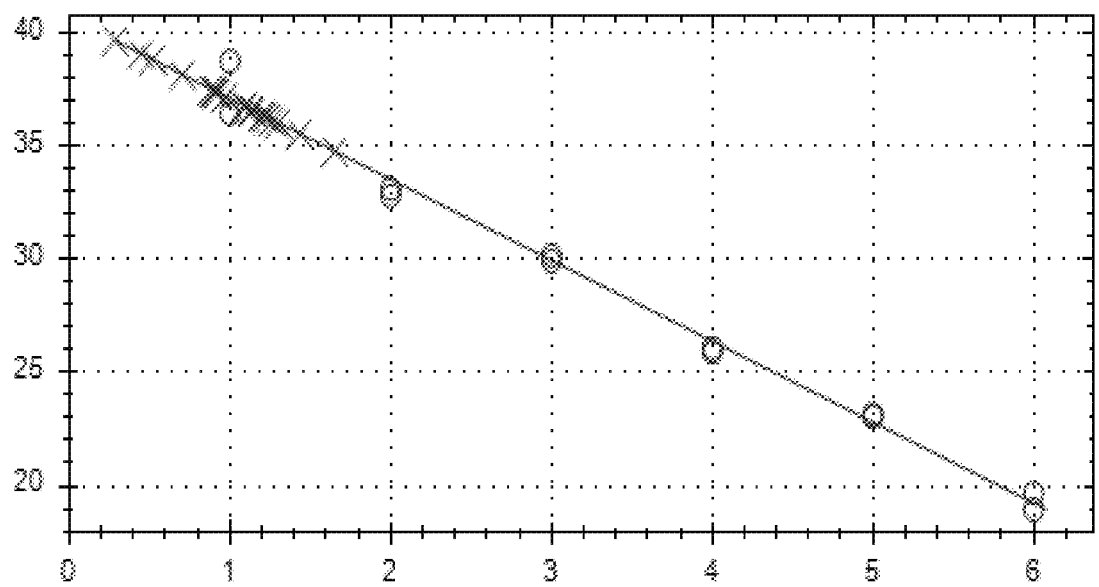
Figure 10:
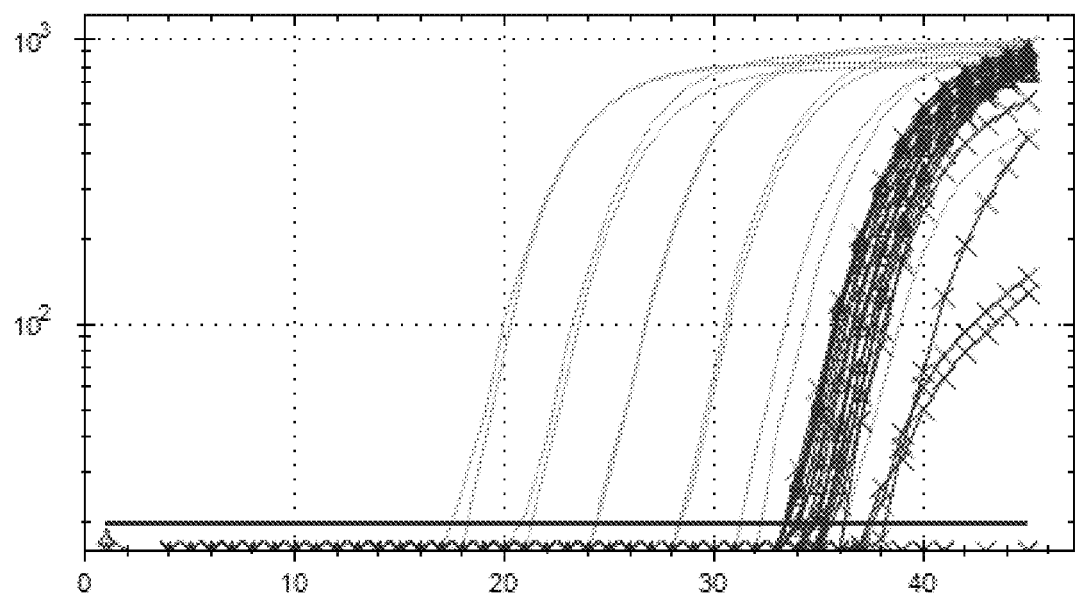
FIG. 10 shows results for marker FOXC1_6_1577253_1581989_1604206_1605973_FR. The first FIG. shows amplification with ATM 208 bp FOXC1. The second figure shows the standard curve. FAM™ is used. The efficiency is found to be 101.6%, $R^2$ is 0.992, slope is −3.284, y-int is 37.746.
Figure 10:
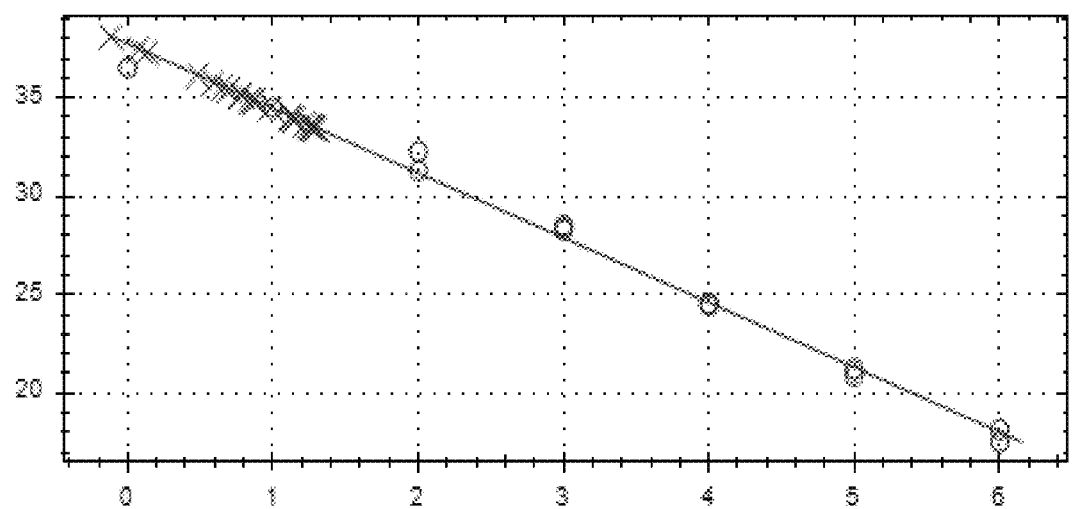
Figure 11:
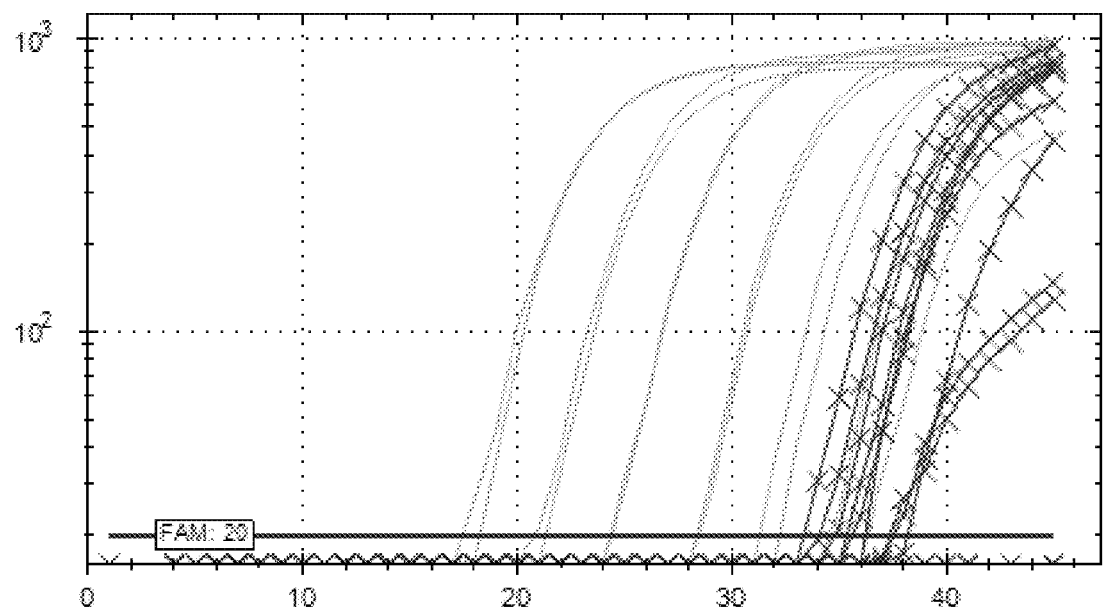
FIG. 11 shows amplification lines for marker FOXC1_6_1577253_1581989_1604206_1605973_FR. The first Figure shows amplification with ATM 208 bp, row C. The second figure shows amplification with ATM 208 bp, row D.
Figure 11:
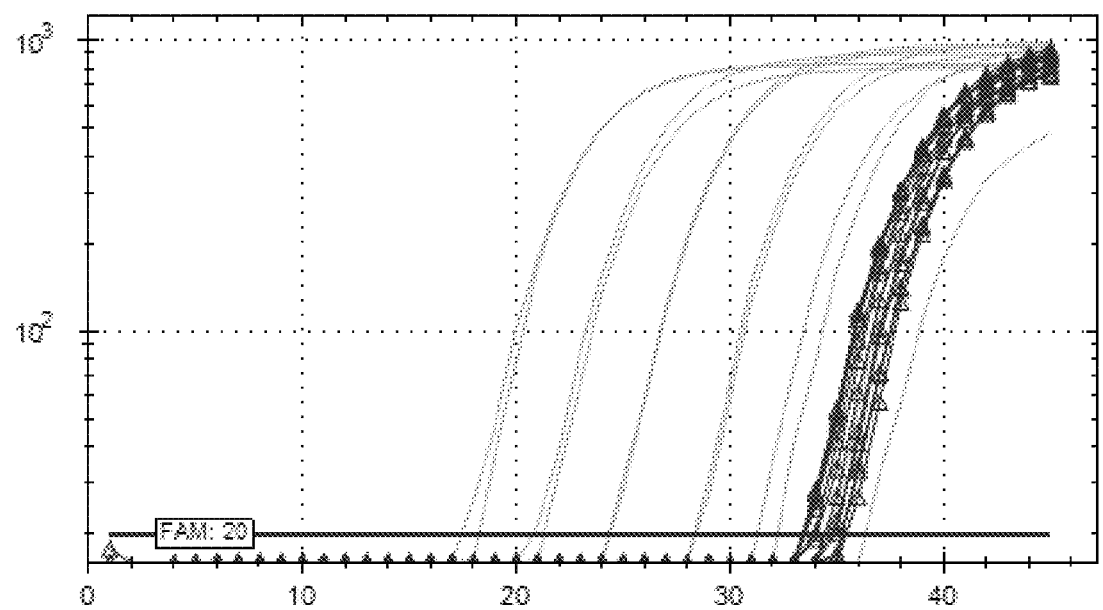
Figure 12:
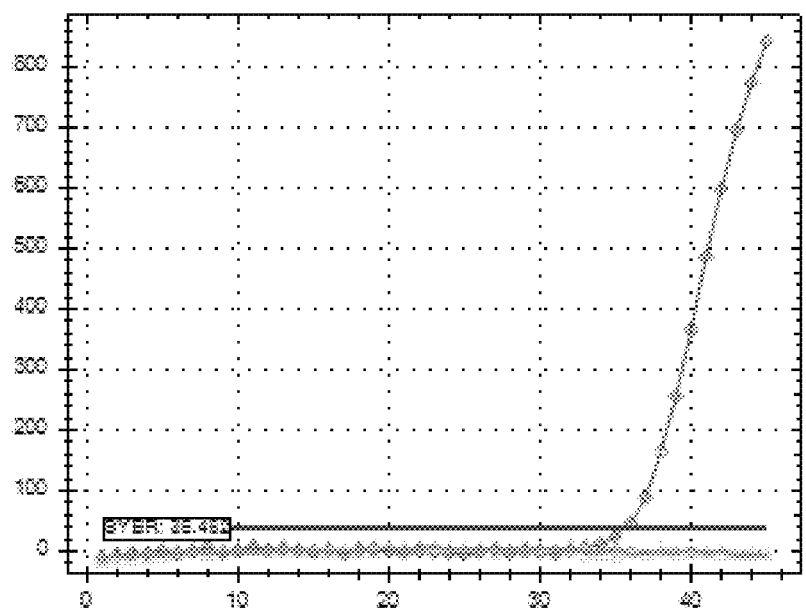
FIG. 12 shows results for marker MAP3K1_5_56102259_56110500_56140227_ 56144076_FF. The first figure shows amplification PCR 9 MAP3K1 cells C1-C6 (RFU versus cycles). The second figure shows melt peak for well C1 to C6. The y-axis shows −d(RFU)/dt. The x-axis shows temperature in Celsius.
Figure 12:
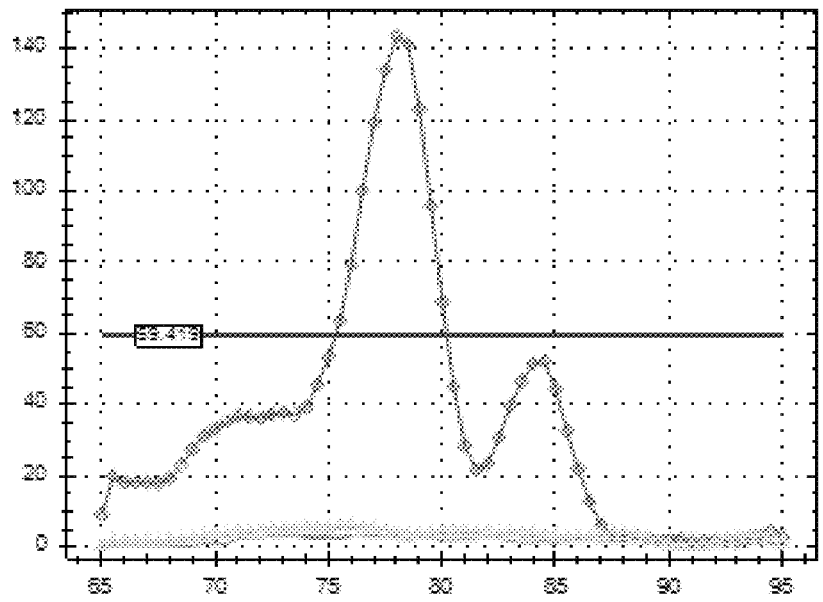
Figure 13:
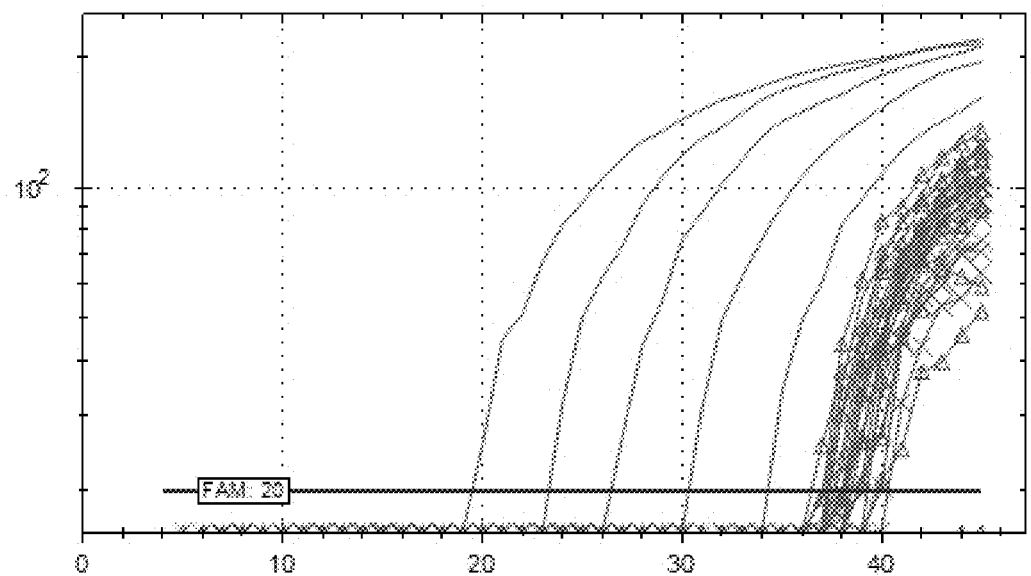
FIG. 13 shows results for marker MAP3K1_5_56102259_56110500_56140227_ 56144076_FF. The first figure shows amplification with MAP3K1 495 bp. The second figure shows the standard curve. FAM™ is used. The efficiency is found to be 91.9%, $R^2$ is 0.999, slope is −3.533, y-int is 40.940.
Figure 13:
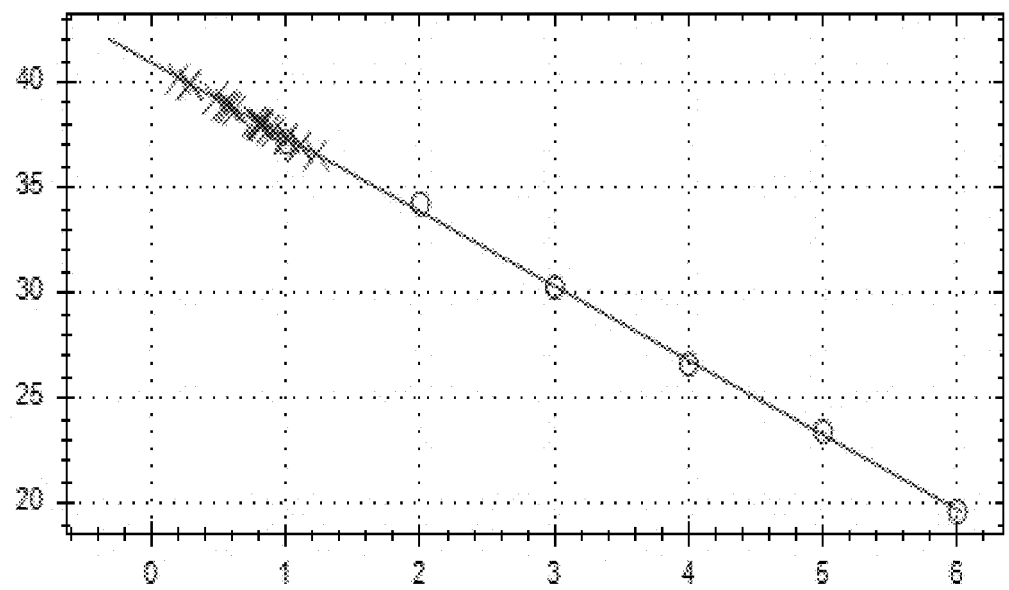
Figure 14:
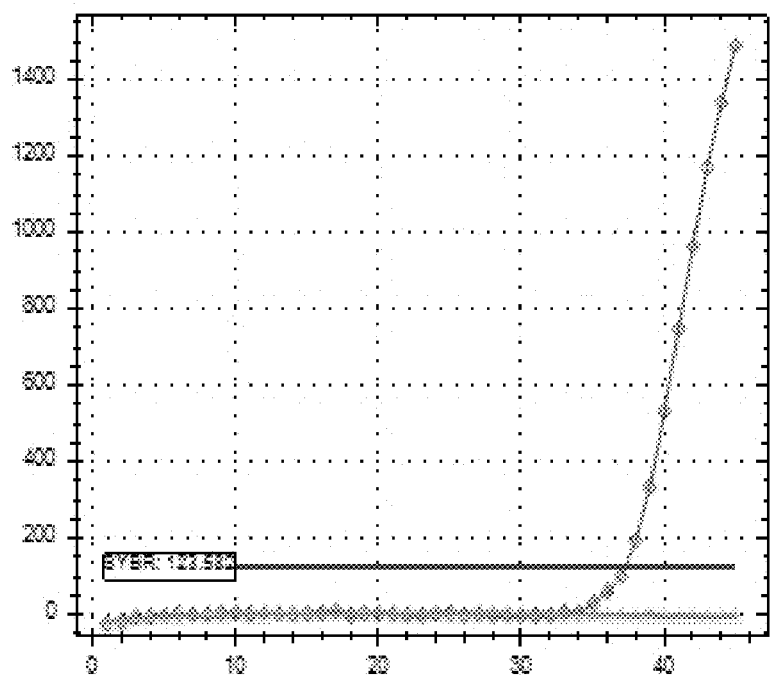
FIG. 14 shows results for marker ME3_11_86300063_86304401_86420537_86426200_FR. The first figure shows amplification ME3 PCR 12, A7-A12 (RFU versus cycles). The second figure shows melt peak. The y-axis shows −d(RFU)/dt. The x-axis shows temperature in Celsius.
Figure 14:
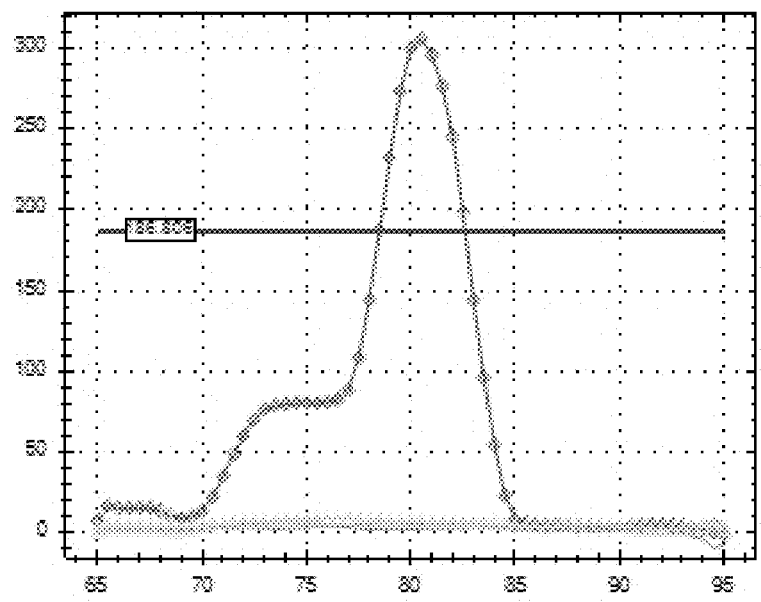
Figure 15:
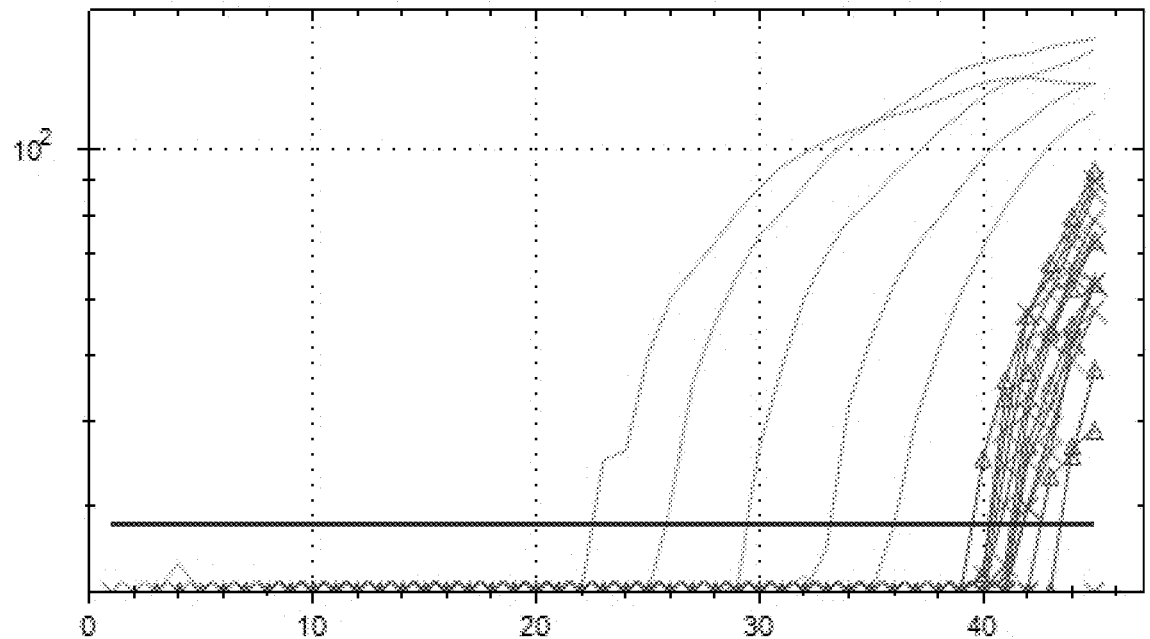
FIG. 15 shows results for marker ME3_11_86300063_86304401_86420537_86426200_FR. The first figure shows amplification with ME3 291 bp. The second figure shows the standard curve. FAM™ is used. The efficiency is found to be 96.8%, $R^2$ is 0.998, slope is −3.400, y-int is 39.596.
Figure 15:
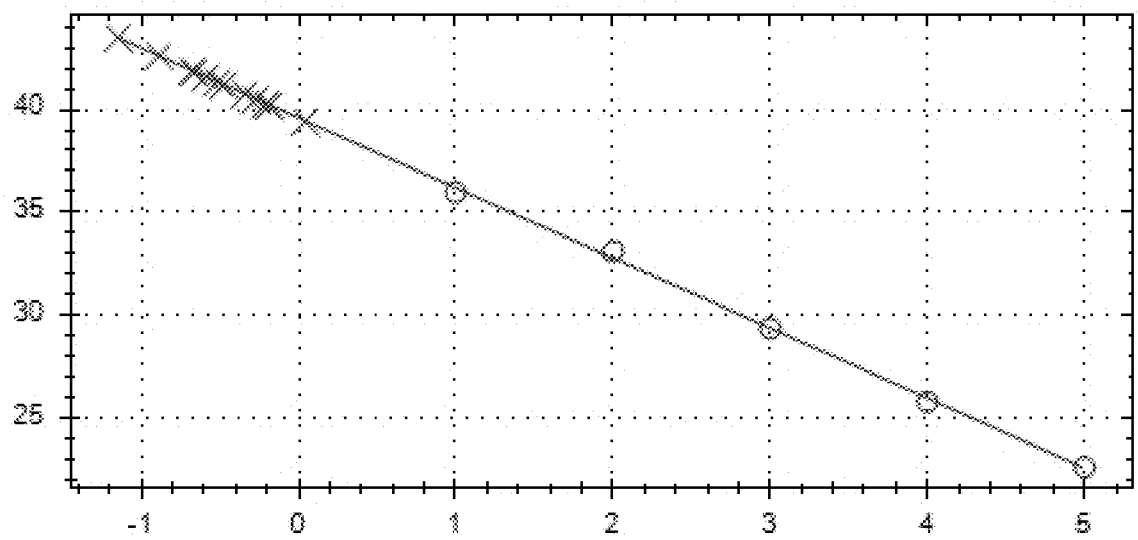
Figure 16:
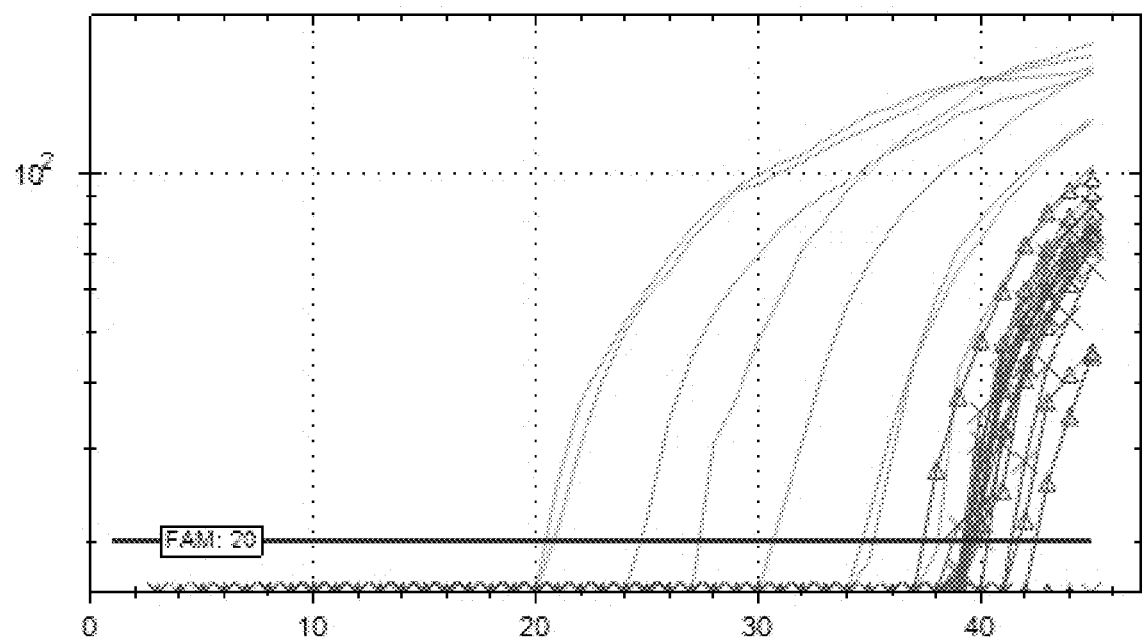
FIG. 16 shows results for marker MELK_9_36577630_36579243_36637050_36643005_RF. The first figure shows amplification with MELK 207 bp. The second figure shows the standard curve. FAM™ is used. The efficiency is found to be 91.3%, $R^2$ is 0.995, slope is −3.550, y-int is 42.000.
Figure 16:
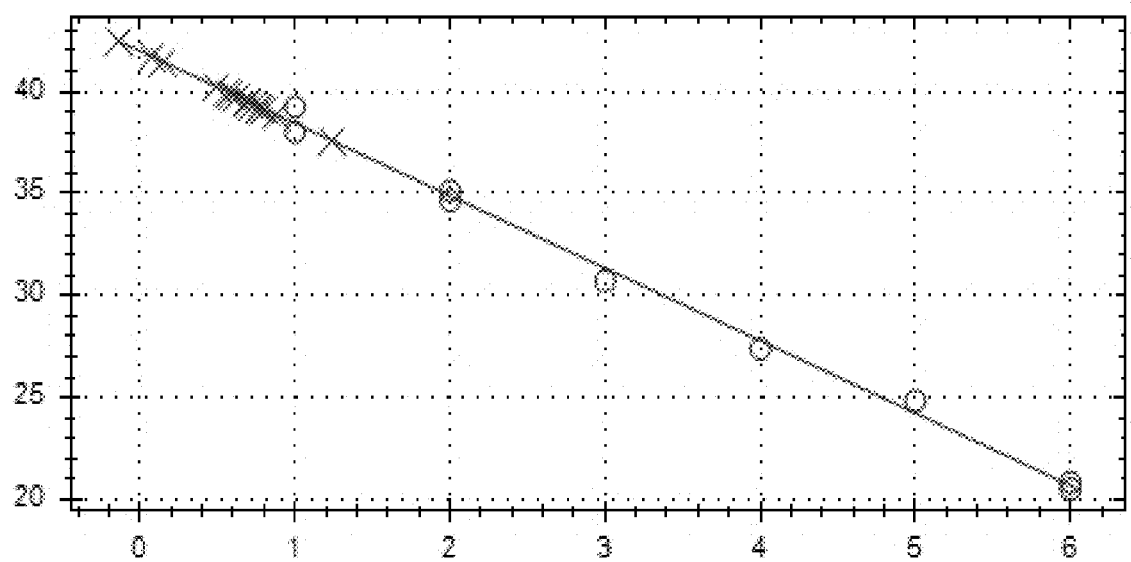
Figure 17:
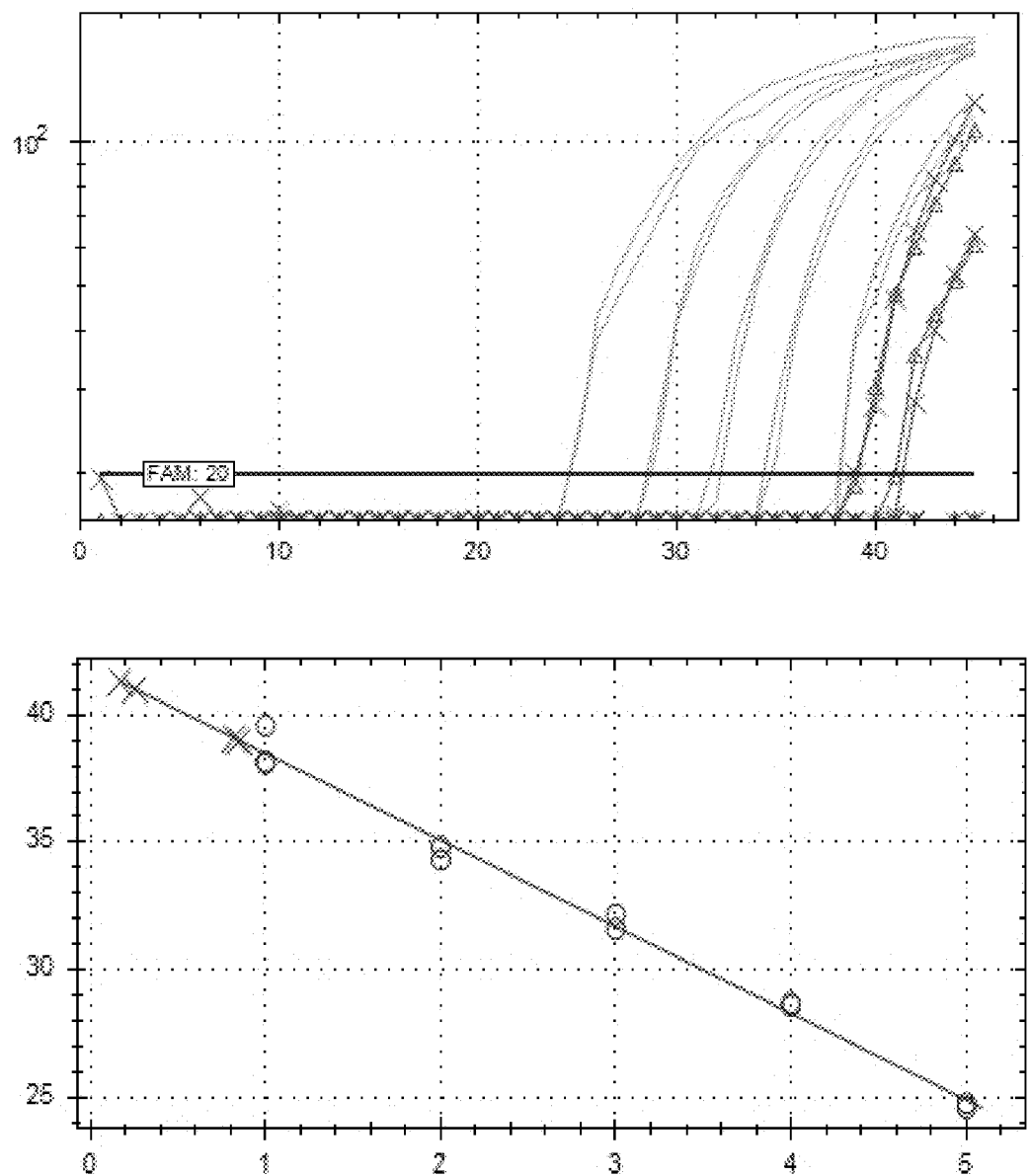
FIG. 17 shows results for marker MSH3_5_80021913_80025030_80153948_80159012_RF. The first figure shows amplification with MSH3 207 bp. The second figure shows the standard curve. FAM™ is used. The efficiency is found to be 97.1%, $R^2$ is 0.990, slope is −3.394, y-int is 41.876.
Figure 18:
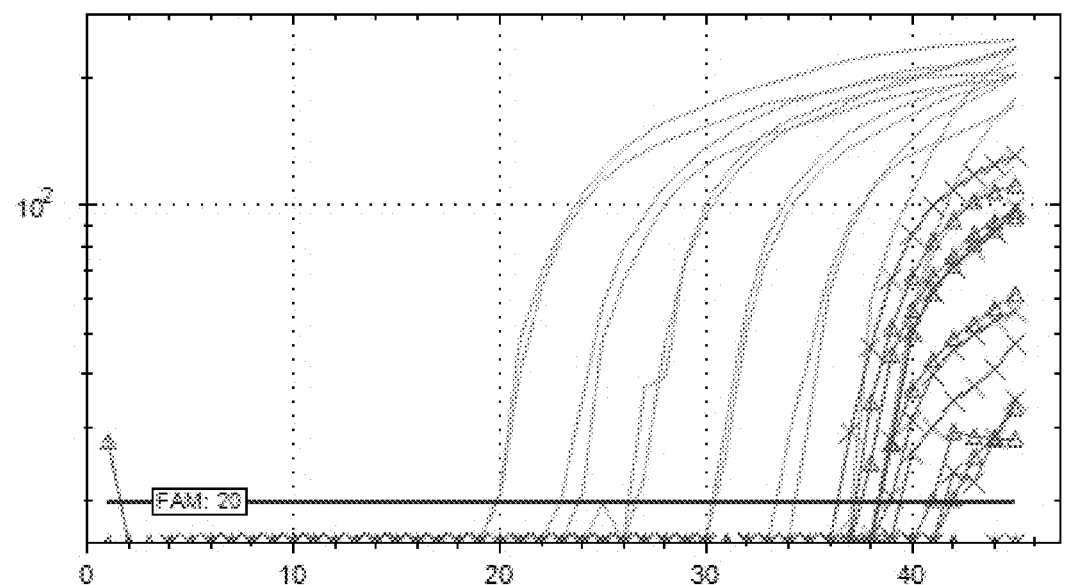
FIG. 18 shows results for marker NF1_17_29477103_29483764_29651799_29657368_FF. The first figure shows amplification with NF1 401 bp. The second figure shows the standard curve. FAM™ is used. The efficiency is found to be 99.0%, $R^2$ is 0.987, slope is −3.347, y-int is 40.192.
Figure 18:
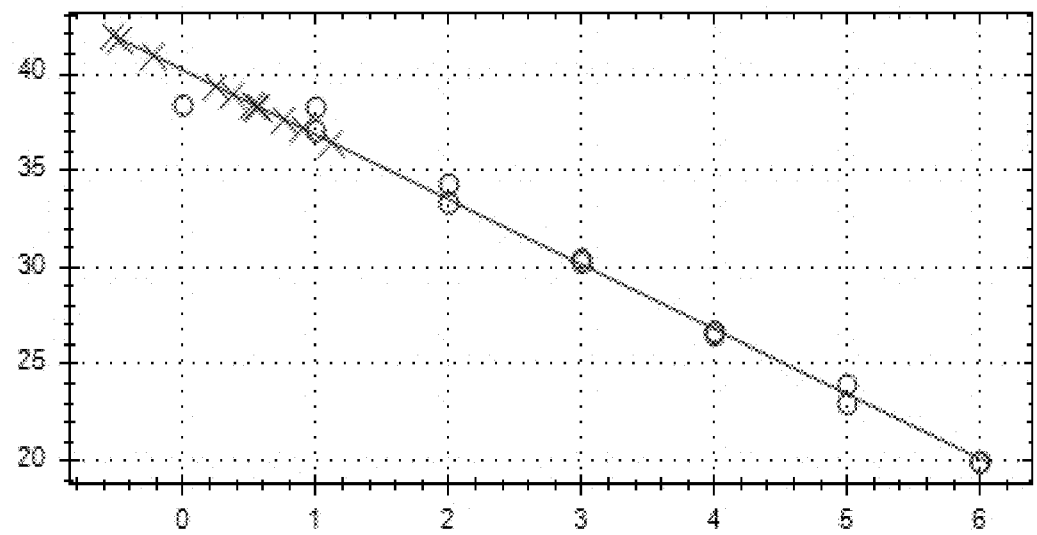
Figure 19:
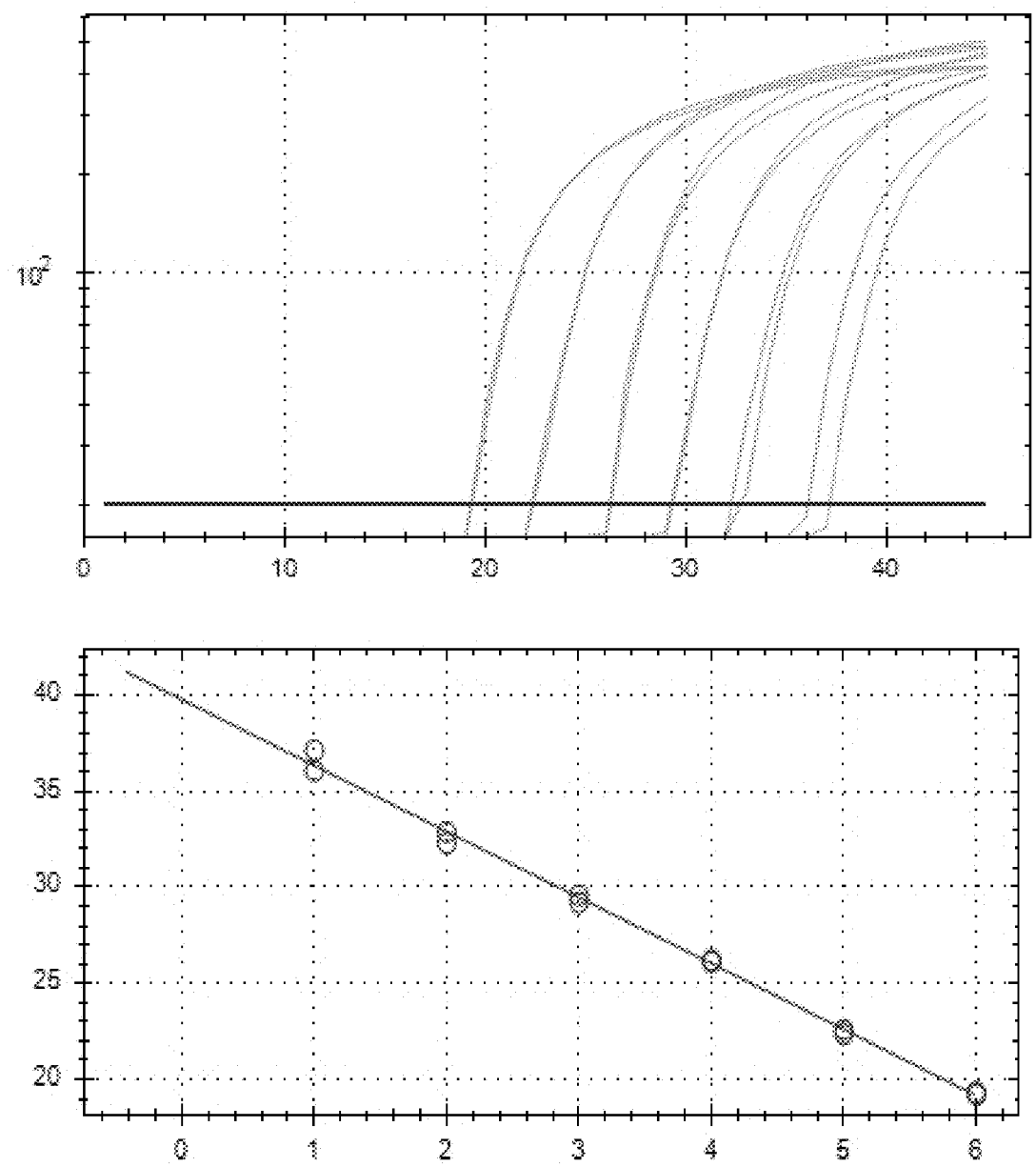
FIG. 19 shows results for marker SRD5A1_5_6634973_6639025_6667775_6669711_RF. Only standard curves are shown with no patient data. The first figure shows amplification with SRDA51. The second figure shows the standard curve. FAM" is used. The efficiency is found to be 95.5%, $R^2$ is 0.997, slope is −3.434, y-int is 39.761.
Figure 20:
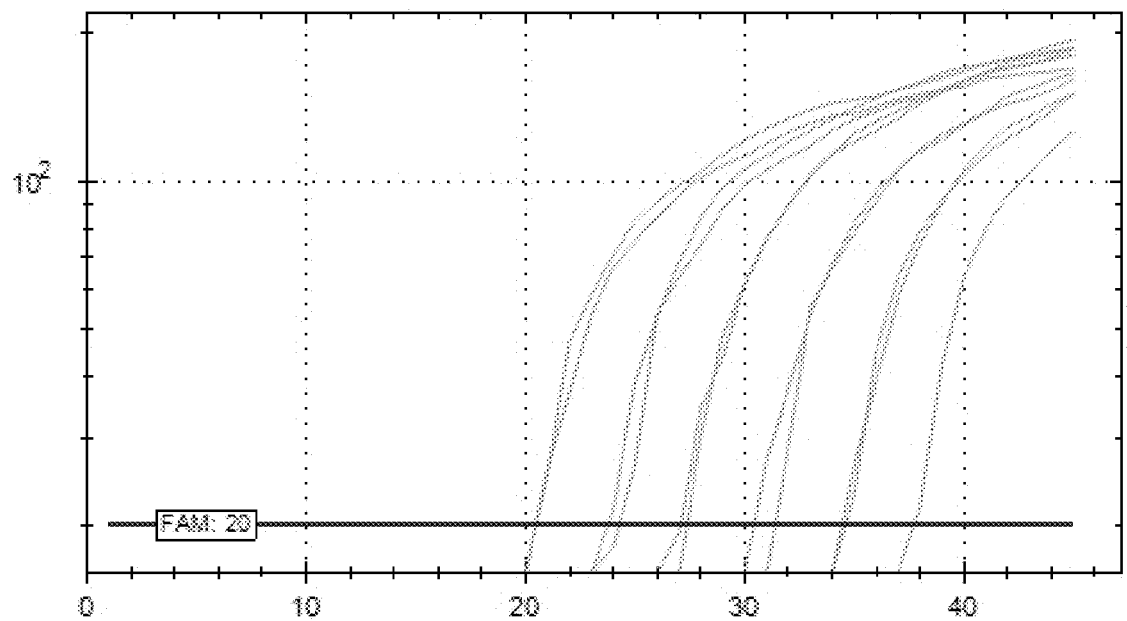
FIG. 20 shows results for marker TSPYL5_8_98276431_98282736_98316421_98318720_ FF. Only standard curves are shown with no patient data. The first figure shows amplification with TSPYL5. The second figure shows the standard curve. FAM™ is used. The efficiency is found to be 94.2%, $R^2$ is 0.998, slope is −3.469, y-int is 41.344.
Figure 20:
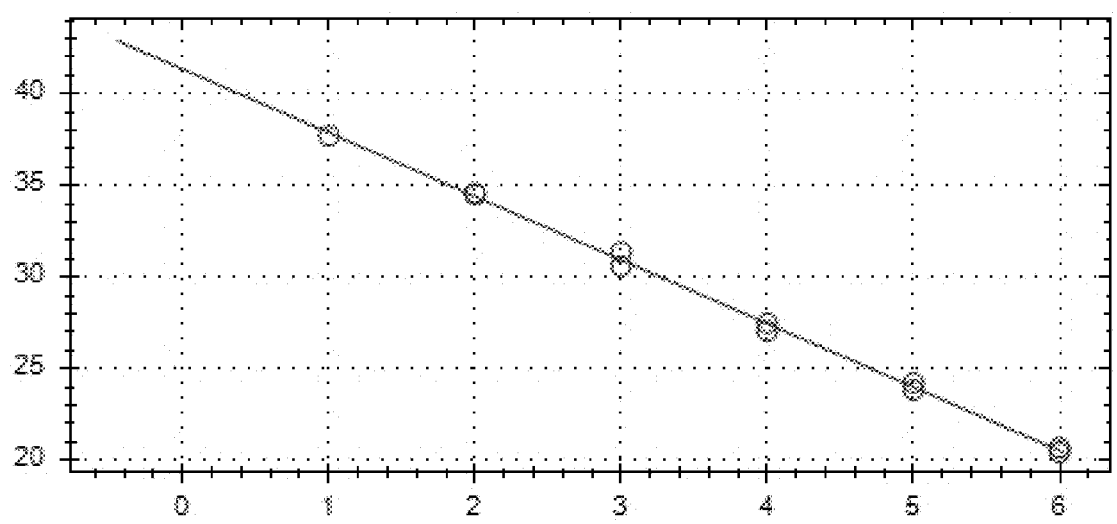

To reduce the finally selected 13 locations and 39 markers to a working classifying model, the GLMNET™ package with the R statistical language was used. GLMNET™ performs penalized (elastic-net penalty) regression modelling allowing ridge or lasso regression (which omits co-linearity of markers). Multivariate logistic regression analysis using lasso regression was performed on patient set 1. [See FIG. 3]

TABLE 4

The 13-marker set with their 3 dilutions were reduced down to an 8 marker set using the 118 patients from 1; the GLMNET ™ coefficients for the markers are shown in the table above. The top 4 markers are ones that trend with the BrCa phenotype and the bottom four markers in blue are ones that trend with the Control phenotype.

| Gene | Marker | GLMNET ™ |
| --- | --- | --- |
| SRD5A1_5 | PRMR.177.179_2 | 0.233358596 |
| NF1_17 | PRMR.261.263_4 | 0.145129097 |
| TSPYL5_8 | PRMR.129.131_2 | 0.04597074 |
| ME3_11 | PRMR.173.175_4 | 0.019318541 |
| VAV3_1 | PRMR.185.187_8 | −0.008248717 |
| ATM_11 | PRMR.53.55_32 | −0.029412806 |
| MAP3K1_5 | PRMR.161.163_8 | −0.045528058 |
| SLC16A10_6 | PRMR.113.115_4 | −0.0174300311 |

Logistic Regression Analysis

Logistic regression analysis was carried out using the Waikato™ to Environment for Knowledge Analysis (WEKA™) software version 3.6.12. Using this analysis the classification function of sensitivity and specificity was established for patient set 1 (118 patients, 68 BrCa and 50 Control), with the 8 markers identified by the GLMNET™ analysis.

TABLE 5

Above shows the model test statistics for the 118 patient, 8 marker model. The classification was based on 80% Training (94 known samples) and 20% Test (24 blinded samples) analysis. The AUC for this model is 0.832.

| | | 95% Confidence Interval (CI) |
| --- | --- | --- |
| Sensitivity | 85.71% | 57.2%-98.2% |
| Specificity | 80.00% | 44.4%-97.2% |
| PPV | 85.71% | 57.2%-98.2% |
| NPV | 80.00% | 44.4%-97.2% |

Model Validation

The 8 marker logistic model was then tested on patient set 2, (31 BrCa & 19 control), these patients were not used to reduce the markers and are an independent data set.

TABLE 6

The table above shows the model test statistics for the 8-marker model on the independent 50 patient set. The classification was based on 80% Training (40 known samples) and 20% Test (10 blinded samples) analysis, The AUC for this model is 0.98.

| | | 95% Confidence Interval (CI) |
| --- | --- | --- |
| Sensitivity | 83.3% | 35.9%-99.6% |
| Specificity | 100.0% | 39.8%-100.0% |
| PPV | 100.0% | 47.8%-100.0% |
| NPV | 80.0% | 28.4%-99.5% |

Principal Components Analysis (PCA) is an exploratory multivariate statistical technique for simplifying complex data sets. Given m observations on n variables, the goal of PCA is to reduce the dimensionality of the data matrix by finding r new variables, where r is less than n. Termed principal components, these r new variables together account for as much of the variance in the original n variables as possible while remaining mutually uncorrelated and orthogonal. Each principal component is a linear combination of the original variables, and so it is often possible to ascribe meaning to what the components represent. Principal components analysis has been used in a wide range of biomedical problems, including the analysis of microarray data in search of outlier genes as well as the analysis of other types of expression data.

TABLE 7

Shows factor analysis data (principle component analysis) for the 8-marker BrCa model validated signature using all the 168 samples used in the analysis: development (118 patients) and validation (50 patients) steps of the project.

| Patient | Dim.1 | Dim.2 | Dim.3 | Dim.4 | Dim.5 |
|---|---|---|---|---|---|
| MM5013 | −1.800071608 | 0.492729305 | 0.6019709 | 0.438989393 | 1.26872044 |
| BrCaMa219 | −0.785966577 | 0.47223154 | 1.51829263 | −1.895977084 | −3.11799252 |
| BrCaMa218 | 0.173347221 | 1.548046183 | −0.91822436 | 0.767768358 | −0.14166967 |
| BrCaMa217 | 0.802477895 | 1.191180105 | 0.33952978 | −0.318075596 | 1.27316931 |
| BrCaMa215 | 1.113161481 | 1.960102724 | −0.36790426 | 1.04353295 | −0.62147173 |
| BrCaMa213 | 0.350909675 | 1.263048827 | −0.49646041 | 0.70813229 | 0.19512773 |
| BrCaMa211 | −0.120178677 | 1.753308317 | 1.88817334 | −2.596145659 | −1.63044319 |
| BrCaMa210 | −0.89241577 | 0.371232864 | −1.64136315 | −0.663666676 | −0.27700782 |
| BrCaMa209 | −0.137336365 | 0.779123564 | −0.21079032 | −0.593840188 | 1.75297137 |
| BrCaMa208 | 0.595430617 | 0.127397803 | −0.49637741 | −0.378540735 | −1.98291708 |
| BrCaMa202 | −0.894770738 | 3.078346899 | 1.37016687 | 1.491976975 | 0.74357301 |
| BrCaMa135 | 1.076504256 | 0.322159869 | 0.51996917 | 0.657857571 | −0.69418208 |
| BrCaMa133 | −0.130163964 | 1.068286761 | −1.51280699 | −0.328266016 | −1.09360727 |
| BrCaMa117 | 1.261218517 | 1.40847458 | −0.1264967 | −1.07870931 | −0.49536775 |
| BrCaMa116 | 0.809650296 | 1.480343302 | −0.96248689 | −0.052501424 | −1.57340933 |
| BrCaMa115 | 0.321404256 | 0.996418039 | −0.6768168 | −1.354473902 | −0.01556569 |
| BrCaMa114 | 0.624915441 | 1.476177461 | −0.08223417 | −0.258439528 | 0.93637191 |
| BrCaMa113 | 1.224561292 | −0.229468275 | 0.76137673 | −1.464384689 | −0.56807811 |
| BrCaMa112 | 0.802477895 | 1.191180105 | 0.33952978 | −0.318075596 | 1.27316931 |
| BrCaMa111 | −0.440847549 | 0.299364142 | −0.80537296 | −1.689874562 | 0.80103376 |
| BrCaMa110 | 0.802477895 | 1.191180105 | 0.33952978 | −0.318075596 | 1.27316931 |
| BrCaMa109 | −0.89241577 | 0.371232864 | −1.64136315 | −0.663666676 | −0.27700782 |
| BrCaMa108 | −1.375844377 | 2.883584833 | 0.35382028 | 0.455578669 | −0.54516199 |
| BrCaMa107 | 0.624915441 | 1.476177461 | −0.08223417 | −0.258439528 | 0.93637191 |
| BrCaMa106 | 0.350909675 | 1.263048827 | −0.49646041 | 0.70813229 | 0.19512773 |
| BrCaMa105 | −3.181468802 | 0.837563041 | 2.61664094 | −1.078446956 | 0.133645 |
| BrCaMa104 | −0.89241577 | 0.371232864 | −1.64136315 | −0.663666676 | −0.27700782 |
| BrCaMa103 | 1.838756062 | 1.019213766 | 0.64852532 | 0.993258231 | −1.51078154 |
| BrCaMa094 | −0.137336365 | 0.779123564 | −0.21079032 | −0.593840188 | 1.75297137 |
| BrCaMa093 | 0.321404256 | 0.996418039 | −0.6768168 | −1.354473902 | −0.01556569 |
| BrCaMa059 | 0.321404256 | 0.996418039 | −0.6768168 | −1.354473902 | −0.01556569 |
| BrCaMa058 | −0.440847549 | 0.299364142 | −0.80537296 | −1.689874562 | 0.80103376 |
| BrCaMa057 | −0.89241577 | 0.371232864 | −1.64136315 | −0.663666676 | −0.27700782 |
| BrCaMa056 | −4.427149215 | 2.652861113 | 4.48326822 | −0.294602271 | 0.68209028 |
| BrCaMa055 | −1.822244743 | 0.644197879 | 1.20929708 | −3.207310911 | −0.33404168 |
| BrCaMa046 | 0.595430617 | 0.127397803 | −0.49637741 | −0.378540735 | −1.98291708 |
| BrCaMa045 | −0.588904585 | 0.850992286 | −1.04678051 | 0.432367698 | 0.67492979 |
| BrCaMa044 | 0.04739849 | 0.783289405 | −1.09104305 | −0.387902084 | −0.75680988 |
| BrCaMa043 | −3.936548207 | 0.429672342 | 1.18606812 | −1.148273444 | −1.89633418 |
| BrCaMa031 | 0.321404256 | 0.996418039 | −0.6768168 | −1.354473902 | −0.01556569 |
| BrCaMa030 | −0.89241577 | 0.371232864 | −1.64136315 | −0.663666676 | −0.27700782 |
| BrCaMa029 | 0.183332507 | 2.233067739 | 2.48275597 | −1.500111286 | −0.67850559 |
| BrCaMa028 | 0.173347221 | 1.548046183 | −0.91822436 | 0.767768358 | −0.14166967 |
| BrCaMa015 | 0.809650296 | 1.480343302 | −0.96248689 | −0.052501424 | −1.57340933 |
| BrCaMa014 | 0.624915441 | 1.476177461 | −0.08223417 | −0.258439528 | 0.93637191 |
| BrCaMa012 | 0.624915441 | 1.476177461 | −0.08223417 | −0.258439528 | 0.93637191 |
| BrCaMa007 | 1.261218517 | 1.40847458 | −0.1264967 | −1.07870931 | −0.49536775 |
| BrCaMa006 | 0.321404256 | 0.996418039 | −0.6768168 | −1.354473902 | −0.01556569 |
| BrCaMa005 | −0.440847549 | 0.299364142 | −0.80537296 | −1.689874562 | 0.80103376 |
| BrCaMa002 | −2.735068436 | 3.076949995 | 1.76116414 | 2.584442624 | −0.07747531 |
| PAH1010-BRCA | 2.155416969 | −0.944242691 | 1.21265768 | −0.457038415 | −1.12641136 |
| PAH1007-BRCA | 1.429822388 | −0.003353733 | 0.19622809 | −0.406763696 | −0.23710155 |
| PAH1004-BRCA | 0.038439907 | −0.343541552 | −1.1900822 | 0.343679598 | −0.83534107 |
| ISH1008-BRCA | 0.667570582 | −0.70040763 | 0.06767194 | −0.742164356 | 0.57949791 |
| BrCaMa220 | 0.490008128 | −0.415410274 | −0.35409201 | −0.682528288 | 0.24270051 |
| BrCaMa212 | 1.703848748 | −0.872373969 | 0.37666749 | 0.569169471 | −2.20445294 |
| BrCaMa207 | 0.341951092 | 0.13621787 | −0.59549956 | 1.439713972 | 0.11659654 |
| BrCaMa206 | 0.27343348 | 0.938758261 | 3.12354749 | 1.147076052 | 0.85377359 |
| BrCaMa205 | −0.723811899 | −1.040595449 | −1.31863835 | 0.008278938 | −0.01874161 |
| BrCaMa204 | 0.001782682 | −1.981484407 | −0.30220877 | −0.041995781 | −0.90805142 |
| BrCaMa162 | 1.733333573 | 0.476405689 | 0.79081073 | 0.689270678 | 0.71483606 |
| BrCaMa160 | 0.031267506 | −0.632704749 | 0.11193447 | 0.078105426 | 2.01123757 |
| BrCaMa159 | 1.429822388 | −0.003353733 | 0.19622809 | −0.406763696 | −0.23710155 |
| BrCaMa158 | −0.420300714 | −0.560836027 | −0.72405572 | 1.104313312 | 0.93319599 |
| BrCaMa157 | 0.971081767 | −0.220648208 | 0.66225457 | 0.353870018 | 1.53143551 |
| BrCaMa156 | −2.590781534 | −1.994913652 | 3.36121269 | −1.552810435 | −1.44933621 |
| BrCaMa155 | 0.490008128 | −0.415410274 | −0.35409201 | −0.682528288 | 0.24270051 |
| BrCaMa154 | −0.272243678 | −1.112464171 | −0.48264816 | −1.017928948 | 1.05929997 |
| BrCaMa153 | 2.155416969 | −0.944242691 | 1.21265768 | −0.457038415 | −1.12641136 |
| BrCaMa152 | 0.764034488 | −1.28443051 | −0.17365262 | 0.293404879 | −1.72465088 |
| BrCaMa151 | −0.578109831 | 1.114890442 | 1.93429922 | 0.041680329 | 1.12794319 |

TABLE 7-continued

Shows factor analysis data (principle component analysis) for the 8-marker BrCa model validated signature using all the 168 samples used in the analysis: development (118 patients) and validation (50 patients) steps of the project.

| Patient | Dim.1 | Dim.2 | Dim.3 | Dim.4 | Dim.5 |
|---|---|---|---|---|---|
| BrCaMa150 | −0.272243678 | −1.112464171 | −0.48264816 | −1.017928948 | 1.05929997 |
| BrCaMa149 | 0.341951092 | 0.13621787 | −0.59549956 | 1.439713972 | 0.11659654 |
| BrCaMa148 | −2.083035957 | −0.847230287 | 0.08870551 | 2.137142893 | 0.44894507 |
| BrCaMa146 | −2.083035957 | −0.847230287 | 0.08870551 | 2.137142893 | 0.44894507 |
| BrCaMa145 | −0.272243678 | −1.112464171 | −0.48264816 | −1.017928948 | 1.05929997 |
| BrCaMa144 | −0.417627116 | −1.376062704 | 1.65545519 | 2.362632767 | −0.9201668 |
| BrCaMa143 | 0.756862087 | −1.573593707 | 1.12836406 | 0.027830707 | 1.12192776 |
| BrCaMa142 | −0.898700755 | −1.57082477 | 0.63910861 | 1.326234461 | −2.2089018 |
| BrCaMa141 | 0.031267506 | −0.632704749 | 0.11193447 | 0.078105426 | 2.01123757 |
| BrCaMa131 | −0.272243678 | −1.112464171 | −0.48264816 | −1.017928948 | 1.05929997 |
| BrCaMa126 | −2.386547141 | −1.326989709 | −0.50587713 | 1.04110852 | −0.50299254 |
| BrCaMa125 | −0.723811899 | −1.040595449 | −1.31863835 | 0.008278938 | −0.01874161 |
| BrCaMa124 | −2.386547141 | −1.326989709 | −0.50587713 | 1.04110852 | −0.50299254 |
| BrCaMa123 | 1.733333573 | 0.476405689 | 0.79081073 | 0.689270678 | 0.71483606 |
| BrCaMa122 | 1.696676347 | −1.161537166 | 1.67868416 | 0.303595299 | 0.6421257 |
| BrCaMa121 | 0.453350903 | −2.053353129 | 0.53378142 | −1.068203667 | 0.16999016 |
| BrCaMa120 | 1.733333573 | 0.476405689 | 0.79081073 | 0.689270678 | 0.71483606 |
| BrCaMa119 | −0.272243678 | −1.112464171 | −0.48264816 | −1.017928948 | 1.05929997 |
| BrCaMa118 | 0.031267506 | −0.632704749 | 0.11193447 | 0.078105426 | 2.01123757 |
| BrCaMa091 | 0.453350903 | −2.053353129 | 0.53378142 | −1.068203667 | 0.16999016 |
| BrCaMa090 | 0.667570582 | −0.70040763 | 0.06767194 | −0.742164356 | 0.57949791 |
| BrCaMa089 | −0.723811899 | −1.040595449 | −1.31863835 | 0.008278938 | −0.01874161 |
| BrCaMa088 | −0.272243678 | −1.112464171 | −0.48264816 | −1.017928948 | 1.05929997 |
| BrCaMa087 | 1.519113893 | −0.87653981 | 1.25692021 | 0.363231367 | 0.30532831 |
| BrCaMa086 | 0.031267506 | −0.632704749 | 0.11193447 | 0.078105426 | 2.01123757 |
| BrCaMa085 | 0.031267506 | −0.632704749 | 0.11193447 | 0.078105426 | 2.01123757 |
| BrCaMa084 | 0.667570582 | −0.70040763 | 0.06767194 | −0.742164356 | 0.57949791 |
| BrCaMa083 | −0.928046291 | −1.708519392 | 2.54845146 | −2.585640016 | −0.96508529 |
| BrCaMa082 | −1.624295336 | −0.629935812 | −0.37732097 | 1.37650918 | −1.31959199 |
| BrCaMa081 | −2.386547141 | −1.326989709 | −0.50587713 | 1.04110852 | −0.50299254 |
| BrCaMa074 | 0.453350903 | −2.053353129 | 0.53378142 | −1.068203667 | 0.16999016 |
| BrCaMa073 | 0.764034488 | −1.28443051 | −0.17365262 | 0.293404879 | −1.72465088 |
| BrCaMa072 | 0.341951092 | 0.13621787 | −0.59549956 | 1.439713972 | 0.11659654 |
| BrCaMa071 | −3.767944336 | −0.982155972 | 1.50879291 | −0.47632783 | −1.63806798 |
| BrCaMa070 | 0.793519312 | 0.064349148 | 0.24049063 | 0.413506086 | 1.19463812 |
| BrCaMa069 | −0.869215931 | −0.222045112 | 1.05325185 | 1.446335667 | 0.71038719 |
| BrCaMa068 | 1.733333573 | 0.476405689 | 0.79081073 | 0.689270678 | 0.71483606 |
| BrCaMa067 | −1.624295336 | −0.629935812 | −0.37732097 | 1.37650918 | −1.31959199 |
| BrCaMa066 | 0.756862087 | −1.573593707 | 1.12836406 | 0.027830707 | 1.12192776 |
| BrCaMa042 | −1.624295336 | −0.629935812 | −0.37732097 | 1.37650918 | −1.31959199 |
| BrCaMa041 | −0.723811899 | −1.040595449 | −1.31863835 | 0.008278938 | −0.01874161 |
| BrCaMa040 | −0.723811899 | −1.040595449 | −1.31863835 | 0.008278938 | −0.01874161 |
| BrCaMa039 | 0.038439907 | −0.343541552 | −1.1900822 | 0.343679598 | −0.83534107 |
| BrCaMa025 | −0.272243678 | −1.112464171 | −0.48264816 | −1.017928948 | 1.05929997 |
| BrCaMa024 | 2.458928153 | −0.464483269 | 1.80724031 | 0.638995959 | −0.17447375 |
| BrCaMa020 | −2.083035957 | −0.847230287 | 0.08870551 | 2.137142893 | 0.44894507 |
| BrCaMa019 | −0.272243678 | −1.112464171 | −0.48264816 | −1.017928948 | 1.05929997 |
| BrCaMa101 | −0.166821189 | −0.569656094 | −0.62493357 | −0.713941395 | −1.16631763 |
| BrCaMa138 | 0.173347221 | 1.548046183 | −0.91822436 | 0.767768358 | −0.14166967 |
| BrCaMa016 | 0.321404256 | 0.996418039 | −0.6768168 | −1.354473902 | −0.01556569 |
| BrCaMa017 | 0.04739849 | 0.783289405 | −1.09104305 | −0.387902084 | −0.75680988 |
| BrCaMa018 | −0.130163964 | 1.068286761 | −1.51280699 | −0.328266016 | −1.09360727 |
| BrCaMa021 | −0.89241577 | 0.371232864 | −1.64136315 | −0.663666676 | −0.27700782 |
| BrCaMa022 | 0.173347221 | 1.548046183 | −0.91822436 | 0.767768358 | −0.14166967 |
| BrCaMa023 | 0.04739849 | 0.783289405 | −1.09104305 | −0.387902084 | −0.75680988 |
| BrCaMa026 | 0.809650296 | 1.480343302 | −0.96248689 | −0.052501424 | −1.57340933 |
| BrCaMa027 | 0.624915441 | 1.476177461 | −0.08223417 | −0.258439528 | 0.93637191 |
| BrCaMa095 | −0.130163964 | 1.068286761 | −1.51280699 | −0.328266016 | −1.09360727 |
| BrCaMa096 | 0.284747031 | −0.641524816 | 0.21105663 | −1.740149281 | −0.08827605 |
| BrCaMa097 | −3.349263206 | 1.828267955 | 1.87401555 | 0.126799705 | 0.86522812 |
| BrCaMa098 | −0.588904585 | 0.850992286 | −1.04678051 | 0.432367698 | 0.67492979 |
| BrCaMa099 | −0.588904585 | 0.850992286 | −1.04678051 | 0.432367698 | 0.67492979 |
| BrCaMa100 | 1.113161481 | 1.960102724 | −0.36790426 | 1.04353295 | −0.62147173 |
| BrCaMa102 | 0.321404256 | 0.996418039 | −0.6768168 | −1.354473902 | −0.01556569 |
| BrCaMa130 | 1.113161481 | 1.960102724 | −0.36790426 | 1.04353295 | −0.62147173 |
| BrCaMa139 | −0.440847549 | 0.299364142 | −0.80537296 | −1.689874562 | 0.80103376 |
| BrCaMa036 | 2.007359933 | −0.392614547 | 0.97125012 | 1.665203845 | −1.25251533 |
| BrCaMa080 | −0.723811899 | −1.040595449 | −1.31863835 | 0.008278938 | −0.01874161 |
| BrCaMa032 | 2.458928153 | −0.464483269 | 1.80724031 | 0.638995959 | −0.17447375 |
| BrCaMa050 | −2.386547141 | −1.326989709 | −0.50587713 | 1.04110852 | −0.50299254 |
| BrCaMa051 | 0.216002362 | −0.628538908 | −0.76831825 | 0.28404353 | −0.49854367 |
| BrCaMa060 | −0.723811899 | −1.040595449 | −1.31863835 | 0.008278938 | −0.01874161 |
| BrCaMa061 | −0.861883648 | 0.19605425 | 1.84093442 | −0.137358446 | −0.68168151 |
| BrCaMa062 | 0.941596942 | −1.569427866 | 0.24811133 | 0.233768811 | −1.38785348 |

TABLE 7-continued

Shows factor analysis data (principle component analysis) for the 8-marker BrCa model validated signature using all the 168 samples used in the analysis: development (118 patients) and validation (50 patients) steps of the project.

| Patient | Dim.1 | Dim.2 | Dim.3 | Dim.4 | Dim.5 |
|---|---|---|---|---|---|
| BrCaMa063 | 0.756862087 | −1.573593707 | 1.12836406 | 0.027830707 | 1.12192776 |
| BrCaMa064 | −0.420300714 | −0.560836027 | −0.72405572 | 1.104313312 | 0.93319599 |
| BrCaMa065 | 2.155416969 | −0.944242691 | 1.21265768 | −0.457038415 | −1.12641136 |
| BrCaMa075 | 1.281765352 | 0.548274411 | −0.04517946 | 1.715478564 | −0.36320552 |
| BrCaMa076 | −1.143221697 | −0.435173746 | 0.63902561 | 2.412907486 | −0.03085699 |
| BrCaMa077 | 0.305293867 | −1.501724985 | 0.29237387 | 1.054038593 | 0.04388618 |
| BrCaMa078 | 1.733333573 | 0.476405689 | 0.79081073 | 0.689270678 | 0.71483606 |
| BrCaMa079 | 0.216002362 | −0.628538908 | −0.76831825 | 0.28404353 | −0.49854367 |
| BrCaMa127 | −0.420300714 | −0.560836027 | −0.72405572 | 1.104313312 | 0.93319599 |
| BrCaMa129 | −0.723811899 | −1.040595449 | −1.31863835 | 0.008278938 | −0.01874161 |
| BrCaMa134 | 0.978254168 | 0.068514989 | −0.6397621 | 0.61944419 | −1.31514313 |
| BrCaMa140 | −0.723811899 | −1.040595449 | −1.31863835 | 0.008278938 | −0.01874161 |
| BrCaMa161 | 0.341951092 | 0.13621787 | −0.59549956 | 1.439713972 | 0.11659654 |
| BrCaMa163 | 2.458928153 | −0.464483269 | 1.80724031 | 0.638995959 | −0.17447375 |
| BrCaMa164 | −0.420300714 | −0.560836027 | −0.72405572 | 1.104313312 | 0.93319599 |
| BrCaMa167 | 0.341951092 | 0.13621787 | −0.59549956 | 1.439713972 | 0.11659654 |
| BrCaMa168 | 2.458928153 | −0.464483269 | 1.80724031 | 0.638995959 | −0.17447375 |
| BrCaMa169 | −0.420300714 | −0.560836027 | −0.72405572 | 1.104313312 | 0.93319599 |
| BrCaMa170 | 0.453350903 | −2.053353129 | 0.53378142 | −1.068203667 | 0.16999016 |
| BrCaMa201 | 1.519113893 | −0.87653981 | 1.25692021 | 0.363231367 | 0.30532831 |
| BrCaMa203 | −0.272243678 | −1.112464171 | −0.48264816 | −1.017928948 | 1.05929997 |
| BrCaMa214 | 0.031267506 | −0.632704749 | 0.11193447 | 0.078105426 | 2.01123757 |
| BrCaMa216 | 1.703848748 | −0.872373969 | 0.37666749 | 0.569169471 | −2.20445294 |

Conclusion

Quality control procedure identified and excluded shipment 122 (site 2 controls) as samples fundamentally different in their profiles and quality from all other samples from other sites and shipments. Chromosome conformation analysis and logistic regression of the results by the EpiSwitch™ methodology has developed a signature of 8 biomarkers that stratified 118 samples of breast cancer patients and healthy controls with cross-validation results of 85.7% sensitivity, 80% specificity, 85.7% PPV and 80% NPV. Independent cohort validation on 50 samples demonstrated 83.3% sensitivity, 100% specificity, 100% PPV and 80% NPV of the biomarkers.

TABLE 8

80 markers identified via EpiSwitch ™ technology which stratify breast cancer from control samples.
Appendix I: Leading marker List

| NUMBER | PROBES |
|---|---|
| Array 1 | |
| Marker 1 | MELK_9_36577630_36579243_36637050_36643005_RF |
| Marker 2 | TPRG1_3_188933689_188940214_188962938_188970637_FF |
| Marker 3 | LYPD6_2_150146782_150153111_150236512_150246806_RR |
| Marker 4 | KCNE4_2_223978296_223985382_224015903_224024643_FR |
| Marker 5 | SYT9_11_7410026_7412890_7469239_7478268_RF |
| Marker 6 | NOS1AP_1_162209626_162215852_162277389_162286110_RF |
| Marker 7 | STK32B_4_5251609_5261154_5459392_5462470_FF |
| Marker 8 | CENPK_5_64812989_64817647_64878910_64881785_RF |
| Marker 9 | ATM_11_108055477_108058111_108208085_108223747_FF |
| Marker 10 | AR_X_66911452_66916150_66961257_66967450_FF |
| Marker 11 | MAPT_17_43962855_43965625_44076167_44084076_FR |
| Marker 12 | CCNG2_4_78068534_78075153_78309908_78315095_FR |
| Marker 13 | ADCY1_7_45624230_45629168_45722424_45731328_FF |
| Marker 14 | ATM_11_108118137_108126372_108155279_108156687_RF |
| Marker 15 | ESR1_6_152307023_152319013_152333402_152336355_FR |
| Marker 16 | FMNL2_2_153432680_153440869_153479856_153483982_FF |
| Marker 17 | MAP3K1_5_56069013_56071773_56102259_56110500_RF |
| Marker 18 | SKP2_5_36136526_36142109_36155505_36160932_FR |
| Marker 19 | SLC16A10_6_111430971_111434623_111492951_111498421_RR |
| Marker 20 | SLC16A10_6_111393624_111400094_111492951_111498421_RR |
| Marker 21 | SLC16A10_6_111388697_111391406_111492951_111498421_FR |
| Marker 22 | CDC6_17_38421089_38423079_38467677_38474960_FR |
| Marker 23 | NOS1AP_1_162189941_162197873_162209626_162215852_FR |
| Marker 24 | SOX11_2_5786050_5796562_5820335_5823500_RF |
| Marker 25 | CDC6_17_38421089_38423079_38451196_38457050_FF |
| Marker 26 | SLC16A10_6_111430971_111434623_111492951_111498421_RF |
| Marker 27 | BLVRA_7_43784657_43787628_43835273_43842181_FR |
| Marker 28 | SLC16A10_6_111441989_111447305_111492951_111498421_FR |

TABLE 8-continued 80 markers identified via EpiSwitch ™ technology which stratify breast cancer from control samples.
Appendix I: Leading marker List

| NUMBER | PROBES |
|---|---|
| Marker 29 | MAP3K1_5_56102259_56110500_56137105_56140227_FR |
| Marker 30 | NOS1AP_1_162189941_162197873_162354198_162360018_FR |
| Marker 31 | SLC16A10_6_111438349_111441989_111492951_111498421_FR |
| Marker 32 | TSPYL5_8_98276431_98282736_98316421_98318720_FF |
| Marker 33 | PCM1_8_17764504_17769874_17830373_17837849_FR |
| Marker 34 | CDC6_17_38421089_38423079_38457050_38462370_FR |
| Marker 35 | NOS1AP_1_162247113_162253340_162264341_162270934_FR |
| Marker 36 | TSPYL5_8_98276431_98282736_98295938_98301017_FR |
| Marker 37 | ESR1_6_152082003_152085698_152307023_152319013_RF |
| Marker 38 | BARD1_2_215635297_215642717_215688320_215695844_RF |
| Marker 39 | ESR1_6_152082003_152085698_152307023_152319013_FF |
| Marker 40 | MAP3K1_5_56102259_56110500_56140227_56144076_FF |
| Marker 41 | SCUBE2_11_9094735_9101051_9144362_9152463_RF |
| ARRAY 2 | |
| Marker 42 | SYBU_8_110644489_110652424_110667554_110675383_FR |
| Marker 43 | ME3_11_86300063_86304401_86420537_86426200_FR |
| Marker 44 | SRD5A1_5_6634973_6639025_6667775_6669711_RF |
| Marker 45 | SYTL2_11_85446267_85449759_85489426_85497695_FF |
| Marker 46 | VAV3_1_108148303_108158073_108220200_108227533_RF |
| Marker 47 | FOXC1_6_1577253_1581989_1622941_1624186_FR |
| Marker 48 | SYTL2_11_85458295_85462105_85489426_85497695_FF |
| Marker 49 | FOXC1_6_1577253_1581989_1604206_1605973_FR |
| Marker 50 | FOXC1_6_1577253_1581989_1616641_1619635_FF |
| Marker 51 | FOXC1_6_1577253_1581989_1608642_1611166_FF |
| Marker 52 | AR_X_66736338_66750729_66911452_66916150_FR |
| Marker 53 | FOXC1_6_1577253_1581989_1608642_1611166_FR |
| Marker 54 | FOXC1_6_1577253_1581989_1621017_1622239_FF |
| Marker 55 | AR_X_66875649_66881776_66911452_66916150_RF |
| Marker 56 | FOXC1_6_1577253_1581989_1606219_1607879_FR |
| Marker 57 | FOXC1_6_1577253_1581989_1622941_1624186_FF |
| Marker 58 | FOXC1_6_1577253_1581989_1612413_1614478_FF |
| Marker 59 | FMNL2_2_153385935_153395520_153444403_153446929_FR |
| Marker 60 | GFRA1_10_117851659_117860183_117872774_117878186_RR |
| Marker 61 | FOXC1_6_1577253_1581989_1606219_1607879_FF |
| Marker 62 | RERG_12_15275463_15281772_15426692_15434723_FF |
| Marker 63 | MSH3_5_80104716_80118379_80153948_80159012_FF |
| Marker 64 | GPR126_6_142730628_142735943_142754471_142757840_FR |
| Marker 65 | NF1_17_29477103_29483764_29651799_29657368_FF |
| Marker 66 | AR_X_66750729_66754087_66950367_66956132_FF |
| Marker 67 | FMNL2_2_153328638_153335686_153385935_153395520_RF |
| Marker 68 | GFRA1_10_117891959_117898614_117911689_117919592_RR |
| Marker 69 | NOSTRIN_2_169646544_169651214_169732611_169738179_RF |
| Marker 70 | ADCY1_7_45638428_45640651_45722424_45731328_FF |
| Marker 71 | CCNG2_4_78068534_78075153_78338468_78342587_RR |
| Marker 72 | TPRG1_3_188814108_188822963_188962938_188970637_FF |
| Marker 73 | GFRA1_10_117891959_117898614_117944517_117949325_RR |
| Marker 74 | DACH1_13_71994847_72006255_72288568_72291811_RR |
| Marker 75 | MSH3_5_80021913_80025030_80153948_80159012_RF |
| Marker 76 | NOSTRIN_2_169599544_169606207_169732611_169738179_RF |
| Marker 77 | FMNL2_2_153193445_153196492_153385935_153395520_RF |
| Marker 78 | TPRG1_3_188823929_188830326_188962938_188970637_RF |
| Marker 79 | BMPR1A_10_88534921_88537932_88549709_88557473_RF |
| Marker 80 | PTPRT_20_40761966_40770575_40995945_41003669_FR |

| Probe | GeneLocus | Probe_Count_Total | Probe_Count_Sig |
|---|---|---|---|
| 17_29477103_29483764_29651799_29657368_FF | NF1 | 139 | 8 |
| 8_98276431_98282736_98316421_98318720_FF | TSPYL5 | 23 | 6 |
| 5_6634973_6639025_6667775_6669711_FF | SRD5A1 | 13 | 2 |
| 5_56102259_56110500_56140227_56144076_FF | MAP3K1 | 43 | 9 |
| 11_108148303_108158073_108220200_108227533_RF | VAV3 | 170 | 7 |
| 11_108118137_108126372_108155279_108156687_RF | ATM | 54 | 11 |
| 6_111441989_111447305_111492951_111498421_FR | SLC16A10 | 58 | 9 |
| 11_86300063_86304401_86420537_86426200_FR | ME3 | 144 | 14 |

| Probe | HyperG_Stats | FDR_HyperG | Percent_Sig | t |
|---|---|---|---|---|
| 17_29477103_29483764_29651799_29657368_FF | 0.957207644 | 1 | 5.76 | 5.889898 |
| 8_98276431_98282736_98316421_98318720_FF | 0.017130277 | 0.3203372 | 26.09 | -12.2759 |
| 5_6634973_6639025_6667775_6669711_FF | 0.350038364 | 1 | 15.38 | -6.71927 |
| 5_56102259_56110500_56140227_56144076_FF | 0.01691209 | 0.3203372 | 20.93 | -9.94973 |
| 11_108148303_108158073_108220200_108227533_RF | 0.997319158 | 1 | 4.12 | -7.26115 |
| 11_108118137_108126372_108155279_108156687_RF | 0.010710258 | 0.3194381 | 20.37 | 12.70358 |
| 6_111441989_111447305_111492951_111498421_FR | 0.091353207 | 0.7687041 | 15.52 | 12.70358 |
| 11_86300063_86304401_86420537_86426200_FR | 0.491902034 | 1 | 9.72 | -3.89629 |

| Probe | logFC | AveExpr | Probe sequece 60mer |
|---|---|---|---|
| 17_29477103_29483764_29651799_29657368_FF | 0.239382 | 0.239382 | ATTTCTTTCTTCTCCCATTTCTAAAT CGATTTTAAATTAAAGTACAAGTTAAG GC (SEQ ID NO: 2) |
| 8_98276431_98282736_98316421_98318720_FF | -0.38273 | -0.38273 | GGATGGAGAAGAGGAGGAATTCAAGACT CGAACTAAACAAAAGGAGGATGATCCTGG GT (SEQ ID NO: 3) |
| 5_6634973_6639025_6667775_6669711_FF | -0.32108 | -0.32108 | |
| 5_56102259_56110500_56140227_56144076_FF | -0.34444 | -0.34444 | |
| 11_108148303_108158073_108220200_108227533_RF | -0.46122 | -0.46122 | |
| 11_108118137_108126372_108155279_108156687_RF | 0.436205 | 0.436205 | AGCTCAAATTCTTTTACTAATTGTTACAT CGAAAGTTCAAAATTAAATTTAAACGTT TT (SEQ ID NO: 4) |
| 6_111441989_111447305_111492951_111498421_FR | 0.436205 | 0.436205 | |
| 11_86300063_86304401_86420537_86426200_FR | -0.40222 | -0.40222 | CCAAAGACAGCCAAGGAAAAACTAAAGAT CGAAAGTTTTTATTACTTCCAAATTAGTA AA (SEQ ID NO: 5) |

| P.Value | adj.P.Val | B | FC | FC_1 | LS | Loop detected |
|---|---|---|---|---|---|---|
| 0.000342 | 0.003906 | 0.413061 | 1.180487 | 1.180487 | 1 | CTL |
| 1.55E-06 | 0.000361 | 5.940348 | 0.766984 | -1.30381 | -1 | BrCa |
| 0.000138 | 0.002522 | 1.36779 | 0.80047 | -1.24927 | -1 | BrCa |
| 7.79E-06 | 0.000846 | 4.341083 | 0.787612 | -1.26966 | -1 | BrCa |

-continued

| | | | | | | | |
|---|---|---|---|---|---|---|---|
| 7.98E-05 | 1.943909 | 0.726373 | -1.3767 | -1 | BrCa | AATTTAGAGGAACTCTATATAAACACAT CGAAACTTTGCTTCATGCACAAATTTAA AA (SEQ ID NO: 6) |
| 1.19E-06 | 6.197546 | 1.353041 | 1.353041 | 1 | CTL | TTGGAGGGAAAAGTAATTACGTTCAACTT CGACTGTATTCTACAAAGTGCTGGGATTA CA (SEQ ID NO: 7) |
| 1.19E-06 | 6.197546 | 1.353041 | 1.353041 | 1 | CTL | ATACTCATCATAAATGTCAGATTTATAAT CGAGATCACAGTGAGCTGAGATTGCACCA CT (SEQ ID NO: 8) |
| 0.004417 | -2.28251 | 0.756691 | -1.32154 | -1 | BrCa | AGGATCTCATGATGCTTTGAATACTTTCT CGATACCTTATTATAAAATCAGCTTTGTG TT (SEQ ID NO: 9) |

| Probe Location | | | | | 4 kb Sequence Location | | | |
|---|---|---|---|---|---|---|---|---|
| Chr | Start1 | End1 | Start2 | End2 | Chr | Start1 | End1 | Start2 | End2 |
| 17 | 29483735 | 29483764 | 29657339 | 29657368 | 17 | 29479765 | 29483764 | 29653369 | 29657368 |
| 8 | 98282707 | 98282736 | 98318691 | 98318720 | 8 | 98278737 | 98282736 | 98314721 | 98318720 |
| 5 | 6634973 | 6635002 | 6669682 | 6669711 | 5 | 6634973 | 6638972 | 6665712 | 6669711 |
| 5 | 56110471 | 56110500 | 56144047 | 56144076 | 5 | 56106501 | 56110500 | 56140077 | 56144076 |
| 1 | 108148303 | 108148332 | 108227504 | 108227533 | 1 | 108148303 | 108152302 | 108223534 | 108227533 |
| 11 | 108118137 | 108118166 | 108156658 | 108156687 | 11 | 108118137 | 108122136 | 108152688 | 108156687 |
| 6 | 111447276 | 111447305 | 111492951 | 111492980 | 6 | 111443306 | 111447305 | 111492951 | 111496950 |
| 11 | 86304372 | 86304401 | 86420537 | 86420566 | 11 | 86300402 | 86304401 | 86420537 | 86424536 |

The three sections of Table 9 above provide information on the final 8 markers for marker set 1.

TABLE 10

PCR Primers for the 8 markers

| Probe | PCR-Primer1_ID | PCR_Primer1 | PCR-Primer2_ID |
|---|---|---|---|
| 17_29477103_29483764_29651799_29657368_FF | PRMR-261 | TGTAGTAGTTACCCTGTTGTTG (SEQ ID NO: 10) | PRMR-263 |
| 8_98276431_98282736_98316421_68318720_FF | PRMR-129 | GTGCTTTGTAAACCATGAAGTG (SEQ ID NO: 12) | PRMR-131 |
| 5_6634973_6639028_6667775_6669711_RF | PRMR-177 | GGCATTGCTTTGCCTTATC (SEQ ID NO: 14) | PRMR-179 |
| 5_56102259_56110500_56140227_56144076_FF | PRMR-161 | CGCTATATGTGGTTCCTGTACG (SEQ ID NO: 16) | PRMR-163 |
| 1_108148303_108158073_108220200_108227533_RF | PRMR-185 | TGTTGAGCAAGATGGATAGC (SEQ ID NO: 18) | PRMR-187 |
| 11_108118137_108126372_108155279_108156687_RF | PRMR-53 | TCCAGAGGTTATGGAATTTGAG (SEQ ID NO: 20) | PRMR-55 |
| 6_111441989_111447305_111492951_111498421_FR | PRMR-113 | ACTCAAATACTGCTCTACACTG (SEQ ID NO: 22) | PRMR-115 |
| 11_86300063_86304401_86420537_86426200_FR | PRMR-173 | ACCCTCCTTCACTCACATAG (SEQ ID NO: 24) | PRMR-175 |

| Probe | PCR_Primer2 | GLMNET |
|---|---|---|
| 17_29477103_29483764_29651799_29657368_FF | GCCTCACGTGCTCTTATG (SEQ ID NO: 11) | 0.1451291 |
| 8_98276431_98282736_98316421_68318720_FF | TCGTGGGCATATGACTGAG (SEQ ID NO: 13) | 0.0459707 |
| 5_6634973_6639028_6667775_6669711_RF | CAACTTCCTTGGGTGTAGAG (SEQ ID NO: 15) | 0.2333586 |
| 5_56102259_56110500_56140227_56144076_FF | CTTCTCTAAAGGGAGATTTGGG (SEQ ID NO: 17) | -0.0455281 |
| 1_108148303_108158073_108220200_108227533_RF | ATATTCAGGATGGAACCCAAG (SEQ ID NO: 19) | -0.0082487 |
| 11_108118137_108126372_108155279_108156687_RF | AAGAAACAGACTGGGCCTTG (SEQ ID NO: 21) | -0.0294128 |
| 6_111441989_111447305_111492951_111498421_FR | AAGGAAGTTAAGCCCTATGC (SEQ ID NO: 23) | -0.01743 |
| 11_86300063_86304401_86420537_86426200_FR | GCACCTAATCTACCTAACATCAC (SEQ ID NO: 25) | 0.0193185 |

Example 2

Oxford BioDynamics™ (OBD) is a healthcare service company offering a novel patented platform technology in the field of aberrant gene expression and epigenetics. The patented EpiSwitch™ platform technology detects epigenetic regulatory signature changes. The EpiSwitch™ biomarker discovery platform identifies Chromosome Conformation Signatures (CCSs), which define the initial regulatory process in integrating environmental cues into the epigenetic and transcriptional machinery. As such, CCSs are the primary step in a cascade of gene regulation.

The CCSs isolated by the EpiSwitch™ biomarker discovery platform have several advantages:
Severe biochemical and physiological stability;
Their binary nature and readout;
Their primary position in the eukaryotic cascade of gene regulation.

Specific conformation signatures at loci either exist or are absent due to the regulatory epigenetic control settings associated with pathology or treatment. CCSs have mild off-rates and when representing a particular phenotype or pathology, they will only change with a physiologically signalled transition to a new phenotype or as a result of external intervention. In addition, the measurement of these events is binary, and so this read out is in stark contrast to the continuum readout of varying levels of DNA methylation, histone modifications and most of the non-coding RNAs. The continuum read-out for most of the molecular biomarkers used to date offers a challenge to data analysis, in that the magnitude of change for particular biomarkers varies greatly from patient to patient, causing problems for classification statistics, which are used to stratify patients. These classification statistics and inference approaches are better-suited using biomarkers that are absent of magnitude and offer just a "yes or no" binary score of phenotypic differences signifying that EpiSwitch™ CCS biomarkers are an excellent resource for potential diagnostic, prognostic and predictive biomarkers.

OBD has consistently observed highly disseminating EpiSwitch™ markers in all its developed applications, with high concordance to the primary and secondary affected tissues and strong validation results. EpiSwitch™ biomarker signatures demonstrated high robustness and high sensitivity and specificity in the stratification of complex disease phenotypes. The OBD technology takes advantage of the latest breakthroughs in the science of epigenetics and offers a unique and the only industrial-quality ISO certified platform for the discovery, monitoring and evaluation of chromosome conformation signatures, as a highly informative class of epigenetic biomarkers.

The EpiSwitch™ technology offers a highly effective means of screening; early detection; companion diagnostic; monitoring and prognostic analysis of major diseases associated with aberrant and responsive gene expression. A major advantage of the OBD approach is that it is non-invasive, rapid, and relies on highly stable DNA based targets as part of chromosomal signatures, rather than unstable protein/RNA molecules.

Technology Overview

CCSs form a stable regulatory framework of epigenetic controls and access to genetic information across the whole genome of the cell. Changes in CCSs reflect early changes in the mode of regulation and gene expression well before the results manifest themselves as obvious abnormalities. A simple way of thinking of CCSs is that they are topological arrangements where different distant regulatory parts of the DNA are brought in close proximity to influence each other's function. These connections are not done randomly; they are highly regulated and are well recognised as high level regulatory mechanisms with significant biomarker stratification power. In the fast developing field of applied epigenetics, CCSs offer significant advantages against alternative biomarker platforms. As a new biomarker entity, discovery, monitoring and validation of CCSs requires a technology acceptable to the industry for its performance on quality, stability, sensitivity, reproducibility, cost and time of operational turnover.

DNA that is likely to form higher order structures of CCSs across the genome are directly evaluated by the EpiSwitch™ Array on clinical samples from testing cohorts for identification of all relevant stratifying lead biomarkers. Following the EpiSwitch™ Array screening, the pools of statistically significant stratifying biomarkers normally exceed 300 leads. A number of leads are then translated into the EpiSwitch™ CR. The minimal signature of stratifying biomarkers (<15) undergoes standard validation and, once confirmed Validated signatures contain binary CCSs which are either present, or absent as conditional biomarkers of epigenetic regulation in patients with specific pathology. The OBD technology takes advantage of the latest breakthroughs in the science of epigenetics and offers a unique and the only industrial-quality ISO certified platform for the discovery, monitoring and evaluation of chromosome conformation signatures.

Episwitch™ Assay

Proprietary biochemical processing of clinical samples offer quick and effective (<4 hrs) conversion of epigenetic CCS biomarkers into sequence based analytes which are then read by the EpiSwitch™ Array (a modified version of Agilent™ CGH array platform), EpiSwitch™ PCR or DNA sequencers i.e. Roche™ 454, Nanopore™ MinION™, etc EpiSwitch™ Array Analysis The EpiSwitch™ array platform is used for marker identification due to its high-throughput, and ability to screen large numbers of loci rapidly. The array used in this project is the Agilent™ custom-CGH array, which allows OBD to interrogate the markers identified through the in silico software.

The project was to be carried out using an array with samples from group 1 (stage I, II, III & IV) using a 15K EpiSwitch™ array, but to increase the scope of the analysis the samples were used in collaboration with different ethnicity to increase the breadth of data sourced from the array. So instead we used two 8×60 k array, which allows the study of up to 56,964 potential chromosome conformations in quadruplicate, so a 60 k array was used in this project. This can be used to look at the chromosomal conformation signatures in up to 14,000 probes in four replicates. Two arrays were produced using 8 stage II/III breast cancer patient samples from a range of backgrounds individually tested against 8 pooled healthy control patient samples. The EpiSwitch™ template was prepared for each of the samples. The first array was carried out on Asian breast cancer samples procured by OBD. The second array used Polish cohort and an independent Asian samples cohort. Asian and European breast cancers can differ between ER+ and ER- status, as well as in prevalence of other subtypes and epigenetic profiles. Overlapping probes were found for similar cancers in multiple populations.

The main outcomes of the analysis were:

Both data sets produced a lot of significant probes;

Array 1, BrCa1 4185 significant EpiSwitch™ markers identified in the analysis of breast cancer versus healthy controls;

Array 2, BrCa2 4856 significant EpiSwitch™ markers identified in the analysis of breast cancer versus healthy controls;

There was an overlap between both analyses of 2116 significant probes consistent between the 2 studies.

FIG. 1 shows a comparison of significant probes from BrCa1 (table 11) and BrCa2 (table 12, Polish cohort included) arrays. The probes adjusted p-value <0.05.

All data was originally taken and all saturated probes were removed. Normalisation occurred to even up the data between the channels. All the four replicates for each data set were then combined together and co-efficient of variation was determined. The 2116 probes were narrowed down using normalised correlation values to rank the most changed genes on the array. Enrichment analysis was used to find the most differentially expressed genes above that of random chance. So altogether there were 138 markers from the combined BrCa1 and BrCa2 arrays that showed differential up-regulated or down-regulated expression. The samples used in the array were matched as closely as possible in ages, array, age range 33-68 years, array 2 32 to 65 years.

TABLE 11

Samples used on BrCa array 1.

| Sample ID | Patient ID | Ethnicity | Age | Type | Stage | Pathology | ER | PR | HER |
|---|---|---|---|---|---|---|---|---|---|
| BrCaMa050 | 039 site 1 | Indian | 46 | IDC | T3, N1, 0 | IIIA | + | + | − |
| BrCaMa051 | 040 site 1 | Malaysian | 47 | IDC | T3, N2, 0 | IIIA | N/A | N/A | N/A |
| BrCaMa060 | 049 site 1 | Chinese | 68 | IDC | 4c, N2, 0 | IIIB | N/A | N/A | N/A |
| BrCaMa061 | 050 site 1 | Indian | 59 | IDC | 4a, 0, 0 | IIIB | N/A | N/A | N/A |
| BrCaMa062 | 051 site 1 | Malaysian | 33 | IDC | T3, 0, 0 | IIB | N/A | N/A | N/A |
| BrCaMa064 | 053 site 1 | Malaysian | 50 | IDC | 4c, N1, 0 | IIIB | (−) | (−) | (−) |
| BrCaMa089 | 023 site 2 | Indian | 66 | IDC | Ct4, N+, 0 | IIIB | (−) | (−) | + |
| BrCaMa041 | 003 site 4 | Indian | 48 | ILC | T2 0, 0 | III | + | + | (−) |

TABLE 12

Samples used on the BrCa array 2.

| Sample ID | Patient ID | Ethnicity | Age | Type | Stage | Pathology | | | ER | PR | HER |
|---|---|---|---|---|---|---|---|---|---|---|---|
| | | | | | | NG | G | Mi | | | |
| ISH1008 | 24925/14 | Chinese | 45 | BC | T3, X, X | | | | N/A | N/A | N/A |
| PAH1004 | 0491895 | Chinese | 65 | BC | T2, N1, 0 | | | | + | + | 2+ |
| PAH1007 | 0488720 | Indian | 55 | BC | T2, N1, 0 | | | | + | + | 2+ |
| PAH1008 | 0494750 | Chinese | 54 | BC | T2, N3, 1 | | | | + | + | (−) |
| 10782 | 10782 | European | 49 | ILC | B5 | — | X | Luminal A | + | + | (−) |
| 10892 | 10892 | European | 62 | IC NST | B5b | 2 | 2 | 3/10 | + | + | + |
| 11015 | 11015 | European | 32 | IC NST | B5 | 3 | 3 | 36/10 | (−) | (−) | (−) |
| 11081 | 11081 | European | 54 | IC NST | B5 | 3 | X | Necrosis | (−) | (−) | + |

Screen1, EpiSwitch™ Marker Validation

The EpiSwitch™ PCR assay is a molecular biology test that can be performed by a trained technician following a standardised operating procedure protocol. All protocols and reagent manufacture are performed according to ISO 13485 and 9001 specifications to ensure the quality of the work and the ability to transfer the protocols.

Primers were designed using the Integrated DNA Technologies (IDT) software (and Primer3web version 4.0.0 software if required) from markers identified from the microarray. Sample quality control was carried out using MMP1 primers on singlicate extracted samples. All samples showed a positive result for MMP1, allowing the samples to continue onto the EpiSwitch™ PCR. All extracted blood samples were diluted from 1:2-1:64 and nested PCR carried out. Initial results were produced in a binary format, i.e. '1'—yes, a band is present at the correct size or '0'—no, a band is not present at the correct size.

After statistical analysis the top 80 EpiSwitch™ markers including 41 markers from array 1 and 39 markers from array 2 were taken on for validation with the EpiSwitch™ PCR assay to stratify between breast cancer samples.

After the first round of screening on 8 BrCa and 8 control samples the markers were reduced to 51, the second round used a further 36 BrCa and 36 control samples the markers were reduced to 13 good markers (table 13) that were able to stratify between BrCa and control patients.

TABLE 13

Good markers used for evaluation by PCR on Gliwice samples

| PROBES | OUTERS | INNERS |
|---|---|---|
| MELK_9_36577630_36579243_36637050_36643005_RF | OBD116-2/4 | OBD116-1/3 |
| ATM_11_108118137_108126372_108155279_108156687_RF | OBD116-54/56 | OBD116-53/55 |
| CDC6_17_38421089_38423079_38467677_38474960_FR | OBD116-90/92 | OBD116-89/91 |
| CDC6_17_38421089_38423079_38451196_38457050_FF | OBD116-102/104 | OBD116-101/103 |
| SLC16A10_6_111441989_111447305_111492951_111498421_FR | OBD116-114/80 | OBD116-113/115 |
| TSPYL5_8_98276431_98282736_98316421_98318720_FF | OBD116-130/132 | OBD116-129/131 |
| MAP3K1_5_56102259_56110500_56140227_56144076_FF | OBD116-162/164 | OBD116-161/163 |
| ME3_11_86300063_86304401_86420537_86426200_FR | OBD116-174/176 | OBD116-173/175 |
| SRD5A1_5_6634973_6639025_6667775_6669711_RF | OBD116-178/180 | OBD116-177/179 |
| VAV3_1_108148303_108158073_108220200_108227533_RF | OBD116-186/188 | OBD116-185/187 |
| FOXC1_6_1577253_1581989_1604206_1605973_FR | OBD116-198/200 | OBD116-197/199 |
| NF1_17_29477103_29483764_29651799_29657368_FF | OBD116-262/264 | OBD116-261/263 |
| MSH3_5_80021913_80025030_80153948_80159012_RF | OBD116-302/304 | OBD116-301/303 |

Screen 2, EpiSwitch™ PCR Validation on the Gliwice Samples

Screening was carried out using the 13 good markers on the 50 Gliwice samples and 22 control samples, using a 1:2 to 1:64 dilution series. See table 18 in appendix for the binary data results. After screening was carried out the binary results were tested for efficacy in differentiating the BrCa from control samples by the use of a chi-square test (Fisher's exact) was produced to give the final markers.

The results of the 13 markers were then assessed using GLMNET™ and Bayes logistic Modelling statistics. markers (table 4) were then highlighted having good scores

TABLE 14

Markers showing good GLMNET™ scores

| Marker | Estimate | Std. Error | z_value | Pr (>|z|) | Glmnet™_0.5 |
|---|---|---|---|---|---|
| OBD116.301.303_2 | 3.592231 | 1.494287 | 2.404 | 0.0162 | −0.266166 |
| OBD116.185.187_16 | 2.135415 | 1.532293 | 1.394 | 0.1634 | −0.032431 |
| OBD116.53.55_8 | −1.78499 | 1.341226 | −1.331 | 0.1832 | 0.1394873 |
| OBD116.161.163_64 | 3.616204 | 2.872291 | 1.259 | 0.208 | −0.267241 |
| OBD116.197.199_8 | −1.87868 | 1.491999 | −1.259 | 0.208 | 0.1215176 |
| OBD116.129.131_4 | 1.560365 | 1.479932 | 1.054 | 0.2917 | 0 |
| OBD116.173.175_2 | −1.39826 | 1.491721 | −0.937 | 0.3486 | 0.0080034 |
| OBD116.89.103_8 | −1.24015 | 1.35114 | −0.918 | 0.3587 | 0.0081371 |
| OBD116.177.179_8 | −1.20884 | 1.323655 | −0.913 | 0.3611 | 0 |
| OBD116.113.87_4 | 1.615246 | 2.000497 | 0.807 | 0.4194 | −0.051646 |

Additional statistical analysis reduced the markers further; using a classification random tree with a 66% training set and a 34% test set, in which 24 samples were used.

Correctly classified instances were 19 (79.1667%), incorrectly classified instances were 5 (20.8333%), and this gave a Kappa statistic of 0.5 and a mean absolute error of 0.2322. The mean absolute error was 0.4656, with the relative absolute error being 55.2934%, the root squared error was 108.4286%

| TP Rate | FP Rate | Precision | Recall | F-Measure | ROC Area | Class |
|---|---|---|---|---|---|---|
| 0.75 | 0 | 1 | 0.75 | 0.857 | 0.925 | BrCa |
| 1 | 0.25 | 0.444 | 1 | 0.615 | 0.925 | Control |
| 0.792 | 0.042 | 0.907 | 0.792 | 0.817 | 0.925 | |

Confusion Matrix

| a | b | |
|---|---|---|
| 15 | 5 | a = BrCa |
| 0 | 4 | b = Control |

The final 8 markers were produced using GLMNET™

TABLE 15 the final 8 markers

| Marker | Estimate | Std. Error | z_value | Pr (>|z|) | Glmnet™_0.5 |
|---|---|---|---|---|---|
| OBD116.301.303_2 | 3.592231 | 1.494287 | 2.404 | 0.0162 | −0.266166 |
| OBD116.185.187_16 | 2.135415 | 1.532293 | 1.394 | 0.1634 | −0.032431 |
| OBD116.53.55_8 | −1.78499 | 1.341226 | −1.331 | 0.1832 | 0.1394873 |
| OBD116.197.199_8 | −1.87868 | 1.491999 | −1.259 | 0.208 | 0.1215176 |
| OBD116.129.131_4 | 1.560365 | 1.479932 | 1.054 | 0.2917 | 0 |
| OBD116.173.175_2 | −1.39826 | 1.491721 | −0.937 | 0.3486 | 0.0080034 |
| OBD116.89.103_8 | −1.24015 | 1.35114 | −0.918 | 0.3587 | 0.0081371 |
| OBD116.177.179_8 | −1.20884 | 1.323655 | −0.913 | 0.3611 | 0 |

Independent Classification of Samples

The final stage was to test the markers stratification on an independent cohort of 25 samples using logistic modelling and 5 fold cross validation.

| | |
|---|---|
| True positive rate | 0.836 |
| Num true positives | 8.36 |
| False positive rate | 0.09 |
| Num_false positives | 0.44 |
| True negative rate | 0.91 |
| Num true negatives | 4.08 |
| False negative rate | 0.164 |
| Num false negatives | 1.64 |
| IR precision | 0.953505 |
| IR recall | 0.836 |
| F measure | 0.887459 |
| Area under ROC | 0.9026 |

This shows that in the independent cohort validation the classifier based on the selected markers that were capable of 83.6% sensitivity and 91.0% specificity with a ROC value of 0.903. This means that the performance of the binary classifier is of a high standard, the highest ROC being 1 and the lowest being 0.5.

Conclusion

The aim of the study was to determine the epigenetic changes in whole blood of women with breast cancer or predisposed to breast cancer then to use the biomarkers for diagnostic stratification.

A 60K EpiSwitch™ array was developed to look at 56964 potential chromosome interactions in relation to the diagnosis of breast cancer patients from control patients.

Two arrays were produced the first having Asian BrCa and control patient samples, the second having both Asian and Polish BrCa samples and controls, this was to allow us to see if there were any similar markers between the two arrays. This would ultimately allow a greater depth of markers to be found between different ethnic groups. After analysis of the arrays 4185 and 4856 probes were found with an overlap of 2116 significant probes. Correction normalisation of the probes was carried out and 138 potential markers were found that could be used to determine a diagnosis of breast cancer from control patients. Further statistical reductions were carried out to produce the top 80 markers that went onto PCR screening. After several rounds of screening 13 markers showed robustness in their screening abilities, each having p-values >0.3. These 13 markers were then used to screen the 50 BrCa samples from the Memorial CancerCenter and Institute of Oncology, Gliwice Branch (IOG) plus 22 control patient samples. After the serial dilution nested PCR screen was carried out, the binary read out was then analysed to determine which markers were able to distinguish between BrCa and controls, 8 markers were finally narrowed down, please see table 16.

TABLE 16 showing the final markers produced

| Marker | Probe |
|---|---|
| OBD116.53.55_8 | ATM_11_108118137_108126372_108155279_108156687_RF |
| OBD116.89.103_8 | CDC6_17_38421089_38423079_38451196_38457050_FF |
| OBD116.129.131_4 | TSPYL5_8_98276431_98282736_98316421_98318720_FF |
| OBD116.173.175_2 | ME3_11_86300063_86304401_86420537_86426200_FR |
| OBD116.177.179_8 | SRD5A1_5_6634973_6639025_6667775_6669711_RF |
| OBD116.185.187_16 | VAV3_1_108148303_108158073_108220200_108227533_RF |
| OBD116.197.199_8 | FOXC1_6_1577253_1581989_1604206_1605973_FR |
| OBD116.301.303_2 | MSH3_5_80021913_80025030_80153948_80159012_RF |

The final stage in the analysis was to determine if the 8 markers could be used for diagnosis of breast cancer patients from control patients. An independent subset of 25 samples was used to run logistic modelling to determine if the markers could predict the samples correctly. Out of the 25 samples the markers showed 83.6% sensitivity and 91.0% specificity with a ROC value of 0.903.

The markers found by the EpiSwitch™ screen also show interesting features in cancer diagnosis. Ataxia telangiectasia mutated kinase (ATM) plays key role in DNA damage response, loss of function may lead to cancer development; they are also linked to signalling pathways in sustained tumour growth. ATM promotes tumourigencity of HER2 (Human epidermal growth factor receptor 2) in a positive breast cancer cell line. ATM participates in a trimeric compound with HSP90 (heat shock protein) and HER2 and has been identified in several tumours. Significant risk of breast cancer is associated with CHEK2, PALB2 and TP53, plus moderate risk with mutations in ATM.

The gene SLC16A10, Solute carrier family 16 (aromatic amino acid transporter), member 10, is involved in system T which is a Na+ independent transporter system that selectively transports aromatic amino acids it is known to be strongly expressed in kidney, liver and intestines. Among its related pathways are the transport of glucose and other sugars, bile salts and organic acids, metal ions and amine compounds, protein digestion and absorption. GO annotations related to this gene include transporter activity. The uniporter TAT1 (Slc16a10) is required to equilibrate the concentration of AAAs across specific membranes.

Vav3 is an oncogene that plays a significant role in prostate cancer tumorigenesis, it is also expressed and up regulated in breast cancer. Vav proteins are guanine nucleotide exchange factors for GTPases of the Rho family. They are involved in cell signalling and tumorigenesis. Vav3 enhances cell growth and proliferation. Breast and prostate cancers are hormone independent tumours whose growth is mediated by their respective hormone receptors. Vav3 is epigenetically regulated in the development of breast cancer.

MSH3, MutS homolog 3 has been associated with several different types of cancer such as colorectal, breast, prostate, bladder, thyroid, ovarian and oesophageal cancers. Mismatch repair pathways are involved in cell cycle regulation, apoptosis and DNA damage. In humans there are 7 mismatch repair genes, there has been 180 SNPs reported for the MSH3 gene. Loss of MSH3 protein expression is associated with colorectal cancer and a polymorphism rs26279G is associated with the risk of breast cancer.

FOXC1, Forkhead box C1 is a transcription factor involved in the development of mesoderm, brain and eye during embryogenesis, it may be a key diagnostic marker for basal like breast cancer. Elevated levels of FOXC1 predict poor survival in cancers such as lung and hepatocellular carcinoma. FOXC1 protein is exclusively expressed in basal cell. FOXC1 has been identified as a Smoothhead (SMO)-independent activator of Hedgehog signalling via direct interaction of Gli2 transcription factor.

These results show a very robust and specific set of markers, monitored as epigenetic deregulation at the level of 3D chromatin architecture of specific genetic loci, that can help stratify the breast cancer patient samples from control samples with a high degree of reliability.

TABLE 17

Appendix II
BCa samples from Maria Sklodowska-Curie Memorial Cancer Center and Institute of Oncology,
Gliwice Branch (IOG)

| Sample No | Patient's age at Diagnosis (yrs) | Clinical Diagnosis | NG | G | IM Histopathology | Cat | ER | PR | HER2 |
|---|---|---|---|---|---|---|---|---|---|
| 10692 | 47.75 | carcinoma infiltrans | 3 | 3 | IM: 21 mitotic figures/10HPF | B5 | +++ | +++ | (−) |
| 10693 | 66.91 | Invasive ductal carcinoma | 3 | 3 | IM: 41/10 HPF. Type luminal B (HER 2 negative) | B5b | + | + | |
| 10695 | 29.87 | Invasive carcinoma of NST | 3 | 3 | IM: 25/10 HPF | B5b | + | + | + |
| 10698 | 58.06 | Invasive carcinoma NST | 2 | 3 | IM: 26 mitotic figures/10 HPF Type: luminal B (HER-2 negative) | B5 | +++ | (−) | + |
| 10715 | 49.85 | carcinoma lobulare infiltrans | 2 | 2 | IM: 3 mitotic figures/10HPF. Type: luminal A | B5 | +++ | ++ | + |
| 10717 | 67.58 | Invasive lobular carcinoma | 2 | 2 | IM: 2/10 HPF | | +++ | +++ | (−) |
| 10726 | 37.39 | Invasive carcinoma NST | 3 | 3 | IM 18/10 HPF. DCIS NG2 in single canals. Type: luminal B (HER 2 positive) | B5 | ++ | +++ | +++ |
| 10731 | 43.03 | Invasive carcinoma | 3 | 3 | IM: 20/10 HPF. Wide necrosis | B5 | +++ | (−) | +++ |
| 10732 | 45.65 | Invasive lobular carcinoma | 2 | | LCIS. DCIS comedo type with microcalcfications. Type: luminal A | B5 | +++ | +++ | + |

TABLE 17-continued

Appendix II
BCa samples from Maria Sklodowska-Curie Memorial Cancer Center and Institute of Oncology,
Gliwice Branch (IOG)

| Sample No | Patient's age at Diagnosis (yrs) | Clinical Diagnosis | NG | G | IM Histopathology | Cat | ER | PR | HER2 |
|---|---|---|---|---|---|---|---|---|---|
| 10752 | 62.68 | Invasive carcinoma NST | | 2 | IM: 4/10 HPF | B5 | +++ | +++ | ++ |
| 10754 | 67.93 | carcinoma ductale infiltrans | 2 | 3 | IM: 39 mitotic figures/10HPF Type: Luminal B (HER-2 negative) | B5 | +++ | +++ | + |
| 10764 | 34.31 | Invasive carcinoma NST | | 3 | IM: 18/10 HPF Triple negative (ductal). | B5b | (−) | (−) | (−) |
| 10775 | 50.36 | Invasive carcinoma NST | | 3 | Severe lymphocyte infiltrates in microenvironment IM: 45 mitotic figures/10HPF Triple negative. | B5 | + | (−) | + |
| 10782 | 49.09 | carcinoma lobulare infiltrans | | X | LCIS Widening LCIS in adenoma region (adenosis). Type: luminal A | B5 | +++ | +++ | (−) |
| 10791 | 63.86 | Invasive carcinoma | 3 | 2 | Invasive ductal carcinoma Type: luminal B (HER-2 negative). | | +++ | +++ | + |
| 10794 | 33.94 | Invasive carcinoma NST et invasive micropapillary carcinoma | 2 | 3 | IM: 34 mitotic figures/10HPF | B5 | +++ | + | +++ |
| 10830 | 56.67 | carcinoma ductale invasivum | | 2 | IM: 11/10HPF | | +++ | + | |
| 10832 | 45.39 | Intraductal carcinoma in situ (CDIS) visible taking approx 10% of the tumour | 2 | 2 | Examined tissue biopsy of mixed type: approx. 90%-Carcinoma mucinosum; 10%-IM: 14/10HPF. | | +++ | ++ | + |
| 10836 | 32.31 | Carcinoma ductale invasivum NST | 2 | 2 | IM 9/10 HPF. | | | | + |
| 10853 | 62.82 | Invasive carcinoma with low grade DCIS. NST | 2 | 1 | IM: 2/10 HPF. Type: luminal B HER 2 negative) | B5b | +++ | +++ | (−) |
| 10855 | 38.75 | Invasive carcinoma NST | 3 | 3 | IM: 29 mitotic figures/10HPF Type: Luminal B (HER-2 negative) | B5 | +++ | + | (−) |
| 10861 | 45.69 | Invasive carcinoma NST | 2 | 2 | IM: 6/10 HPF Type: luminal B; (HER 2 positive). | B5b | +++ | ++ | +++ |
| 10865 | 63.80 | Invasive carcinoma NST | 3 | 3 | IM: 11/10 HPF. Triple negative (ductal). Type: basal-like | B5b | (−) | (−) | (−) |
| 10876 | 47.10 | Invasive carcinoma NST | 3 | 3 | IM: 37/10 HPF | B5b | +++ | (−) | (−) |
| 10883 | 48.65 | Invasive carcinoma NST | 3 | 3 | IM: 31 mitotic figures/10HPF Severe lymphocyte infiltrates in microenvironment. Type: Luminal B (HER-2 negative) | B5 | +++ | +++ | (−) |
| 10885 | 45.37 | Invasive carcinoma NST | 3 | 3 | IM 44/10 HPF | B5b | (−) | (−) | ++ |
| 10891 | 64.11 | Invasive carcinoma | 3 | 3 | IM: 24/10 HPF. Severe lymphocyte infiltrates in microenvironment Triple negative | B5 | (−) | (−) | (−) |
| 10892 | 62.44 | Invasive carcinoma NST | 2 | 2 | IM: 3/10 HPF. Type: luminal B (HER 2 negative). | B5b | +++ | +++ | + |
| 10903 | 64.13 | Invasive lobular carcinoma | 3 | 3 | Mitotic activity: 16 mitotic figures/ 10 ipf. Type: luminal B (HER2 negative) | B5 | +++ | +++ | + |
| 10915 | 48.03 | Invasive carcinoma | 2 | 2 | IM: 1/10 HPF Type: luminal B; HER 2 negative. | B5 | +++ | +++ | + |
| 10942 | 46.33 | Invasive carcinoma | 3 | 3 | IM: 58 mitotic figures/10 HPF Type: luminal B (HER-2 positive). | B5 | + | + | +++ |
| 10947 | 52.78 | NST | 3 | 3 | IM: 34/10 HPF Type: luminal B; HER 2 positive. | B5 | + | (−) | +++ |
| 10955 | 68.82 | Invasive carcinoma NST | 2 | 2 | IM: 3/10 HPF. Type: luminal B (HER 2 negative). Invasive carcinoma | B5b | +++ | + | + |
| 10963 | 65.42 | invasive lobular carcinoma- tubulo-lobular variant | 2 | 2 | IM: 4/10 HPF A mixed tumour differentiating towards lobular and ductal carcinoma. | B5 | +++ | (−) | ++ |
| 11015 | 32.48 | Invasive carcinoma NST | 3 | 3 | IM: 36/10 HPF | B5 | (−) | (−) | (−) |
| 11035 | 59.62 | Invasive carcinoma NST | 1 | | (dim. 2 mm). DCIS NG-2. DCIS | B5 | +++ | + | + |
| 11036 | 47.37 | Invasive carcinoma NST | 2 | 1 | IM: 2/10 HPF. DCIS NG2. Type: luminal B-HER 2 negative. | B5 | +++ | +++ | + |
| 11053 | 63.00 | carcinoma ductale infiltrans | 2 | 2 | NG-2, G-2. DCIS NG-2, cribriform type with necrosis. Cat: B5. | B5 | | | |
| 11059 | 39.45 | Invasive carcinoma NST | 2 | 1 | IM: 1/10 HPF. Multiple microcalcifications around tumour site. Type: luminal A | | +++ | +++ | + |
| 11081 | 54.28 | Invasive carcinoma NST | 3 | X | DCIS with focal necrosis | B5 | (−) | (−) | +++ |
| 11083 | 59.55 | Invasive carcinoma NST | 3 | 2 | IM: 16 mitotic figures/10HPF DCIS NG-2 Type: Luminal B | | +++ | ++ | ++ |
| 11097 | 36.19 | Carcinoma ductale invasivum | | 2 | Tumour diameter 1 cm. Desmoplasia in microenvironment. | | +++ | +++ | ++ |
| 11099 | 44.00 | Invasive carcinoma NST | 3 | 3 | IM: 59 mitotic figures/10 HPF. Type: triple negative. | B5 | (−) | (−) | + |
| 11122 | 60.62 | Invasive carcinoma NST | 2 | | (B2) et DCIS NG-2, solid type with microcalcifications. | B5 | +++ | + | |

TABLE 17-continued

Appendix II
BCa samples from Maria Sklodowska-Curie Memorial Cancer Center and Institute of Oncology,
Gliwice Branch (IOG)

| Sample No | Patient's age at Diagnosis (yrs) | Clinical Diagnosis | NG | G | IM Histopathology | Cat | ER | PR | HER2 |
|---|---|---|---|---|---|---|---|---|---|
| 11136 | 57.50 | Invasive carcinoma NST | 2 | 1 | IM: 5 mitotic figures/10 HPF | B5 | +++ | ++ | ++ |
| 11153 | 43.38 | Invasive carcinoma NST | 2 | 2 | IM 6/10 HPF | B5b | +++ | ++ | + |
| 11180 | 42.56 | Invasive carcinoma NST | 3 | 2 | pT1c NO(sn) IM 8/10 HPF | | +++ | +++ | (−) |
| 11187 | 44.19 | Invasive carcinoma | 2 | 2 | IM: 16/10 HPF. DCIS NG 2 cribriform type. | B5 | +++ | +++ | (−) |
| 11217 | 52.04 | Invasive carcinoma of NST differentiation | | 3 | index mit. IM [/10HPF]: 14/10 | | (−) | (−) | (−) |
| 11245 | 35.35 | Invasive carcinoma NST | 3 | 3 | IM: 13/10 HPF | B5 | +++ | +++ | ++ |

TABLE 18

Binary analysis results using the top 13 markers. Darker results showing a p-value > 0.3. Lighter results show best dilution.
OBD116 Gliwice results

| | State. 1 | | | | | | State. 2 | | | | | |
|---|---|---|---|---|---|---|---|---|---|---|---|---|
| | BrCa | BrCa | BrCa | BrCa | BrCa | BrCa | BrCa | BrCa | BrCa | BrCa | BrCa | BrCa |
| | 10692 | 10693 | 10695 | 10698 | 10715 | 10717 | 10726 | 10731 | 10732 | 10752 | 10754 | 10764 |
| OBD116.1.3_2 | 1 | 1 | 1 | 1 | 1 | 1 | 1 | 1 | 1 | 1 | 1 | 1 |
| OBD116.1.3_4 | 1 | 0 | 0 | 1 | 1 | 1 | 1 | 1 | 1 | 1 | 1 | 1 |
| OBD116.1.3_8 | 1 | 0 | 0 | 0 | 0 | 0 | 0 | 1 | 1 | 1 | 1 | 1 |
| OBD116.1.3_16 | 0 | 0 | 0 | 0 | 0 | 0 | 0 | 0 | 1 | 1 | 0 | 0 |
| OBD116.1.3_32 | 0 | 0 | 0 | 0 | 0 | 0 | 0 | 0 | 0 | 0 | 0 | 0 |
| OBD116.1.3_64 | 0 | 0 | 0 | 0 | 0 | 0 | 0 | 0 | 0 | 0 | 0 | 0 |
| OBD116.53.55_2 | 0 | 1 | 1 | 1 | 1 | 1 | 1 | 1 | 1 | 1 | 1 | 1 |
| OBD116.53.55_4 | 0 | 1 | 1 | 1 | 1 | 1 | 1 | 1 | 1 | 1 | 1 | 1 |
| OBD116.53.55_8 | 0 | 0 | 1 | 1 | 1 | 1 | 1 | 1 | 1 | 1 | 1 | 1 |
| OBD116.53.55_16 | 0 | 0 | 0 | 1 | 1 | 0 | 0 | 0 | 1 | 1 | 1 | 1 |
| OBD116.53.55_32 | 0 | 0 | 0 | 1 | 1 | 0 | 0 | 0 | 1 | 0 | 1 | 0 |
| OBD116.53.55_64 | 0 | 0 | 0 | 0 | 0 | 0 | 0 | 0 | 0 | 1 | 0 | 0 |
| OBD116.89.91_2 | 1 | 1 | 1 | 0 | 1 | 1 | 1 | 1 | 1 | 1 | 0 | 1 |
| OBD116.89.91_4 | 1 | 0 | 0 | 0 | 0 | 1 | 0 | 1 | 0 | 0 | 0 | 1 |
| OBD116.89.91_8 | 0 | 0 | 0 | 0 | 0 | 0 | 0 | 0 | 0 | 0 | 0 | 1 |
| OBD116.89.91_16 | 0 | 0 | 0 | 0 | 0 | 0 | 0 | 0 | 0 | 0 | 0 | 0 |
| OBD116.89.91_32 | 0 | 0 | 0 | 0 | 0 | 0 | 0 | 0 | 0 | 0 | 0 | 0 |
| OBD116.89.91_64 | 0 | 0 | 0 | 0 | 0 | 0 | 0 | 0 | 0 | 0 | 0 | 0 |
| OBD116.89.103_2 | 1 | 1 | 1 | 1 | 1 | 1 | 1 | 1 | 1 | 1 | 1 | 0 |
| OBD116.89.103_4 | 1 | 1 | 0 | 0 | 1 | 1 | 0 | 1 | 1 | 0 | 1 | 0 |
| OBD116.89.103_8 | 0 | 1 | 0 | 0 | 1 | 1 | 0 | 1 | 1 | 0 | 1 | 0 |
| OBD116.89.103_16 | 0 | 0 | 0 | 0 | 0 | 1 | 0 | 0 | 1 | 0 | 1 | 0 |
| OBD116.89.103_32 | 0 | 0 | 0 | 0 | 0 | 0 | 0 | 0 | 0 | 0 | 0 | 0 |
| OBD116.89.103_64 | 0 | 0 | 0 | 0 | 0 | 0 | 0 | 0 | 0 | 0 | 0 | 0 |
| OBD116.113.87_2 | 1 | 1 | 1 | 1 | 1 | 1 | 1 | 1 | 1 | 1 | 1 | 1 |
| OBD116.113.87_4 | 1 | 1 | 1 | 1 | 1 | 1 | 1 | 0 | 1 | 1 | 1 | 1 |
| OBD116.113.87_8 | 1 | 1 | 1 | 1 | 1 | 1 | 1 | 0 | 1 | 0 | 1 | 1 |
| OBD116.113.87_16 | 0 | 1 | 0 | 0 | 1 | 0 | 1 | 0 | 1 | 0 | 0 | 0 |
| OBD116.113.87_32 | 0 | 0 | 1 | 0 | 1 | 0 | 1 | 0 | 1 | 0 | 0 | 0 |
| OBD116.113.87_64 | 0 | 0 | 0 | 0 | 0 | 0 | 0 | 0 | 0 | 0 | 0 | 0 |
| OBD116.129.131_2 | 1 | 0 | 1 | 1 | 1 | 1 | 1 | 1 | 1 | 1 | 1 | 1 |
| OBD116.129.131_4 | 1 | 0 | 1 | 0 | 1 | 1 | 1 | 1 | 1 | 1 | 1 | 0 |
| OBD116.129.131_8 | 1 | 0 | 0 | 0 | 1 | 1 | 1 | 1 | 0 | 0 | 1 | 0 |
| OBD116.129.131_16 | 1 | 0 | 0 | 0 | 1 | 0 | 0 | 0 | 0 | 0 | 0 | 0 |
| OBD116.129.131_32 | 0 | 0 | 0 | 0 | 0 | 0 | 0 | 0 | 0 | 0 | 0 | 0 |
| OBD116.129.131_64 | 0 | 0 | 0 | 0 | 0 | 0 | 0 | 0 | 0 | 0 | 0 | 0 |
| OBD116.161.163_2 | 1 | 1 | 1 | 1 | 1 | 0 | 1 | 1 | 1 | 1 | 1 | 1 |
| OBD116.161.163_4 | 1 | 1 | 1 | 1 | 1 | 0 | 1 | 1 | 1 | 1 | 1 | 0 |
| OBD116.161.163_8 | 1 | 1 | 0 | 0 | 0 | 0 | 1 | 1 | 1 | 0 | 1 | 0 |
| OBD116.161.163_16 | 1 | 1 | 0 | 0 | 0 | 0 | 1 | 0 | 1 | 0 | 0 | 0 |
| OBD116.161.163_32 | 0 | 1 | 0 | 0 | 0 | 0 | 1 | 0 | 1 | 0 | 0 | 0 |
| OBD116.161.163_64 | 0 | 0 | 0 | 0 | 0 | 0 | 0 | 0 | 0 | 0 | 0 | 0 |
| OBD116.173.175_2 | 0 | 1 | 0 | 0 | 1 | 1 | 0 | 1 | 1 | 1 | 0 | 0 |
| OBD116.173.175_4 | 0 | 1 | 0 | 0 | 0 | 0 | 1 | 0 | 1 | 1 | 0 | 0 |
| OBD116.173.175_8 | 0 | 0 | 0 | 0 | 0 | 0 | 0 | 0 | 1 | 0 | 0 | 0 |
| OBD116.173.175_16 | 0 | 0 | 0 | 0 | 0 | 0 | 0 | 1 | 0 | 0 | 0 | 0 |
| OBD116.173.175_32 | 0 | 0 | 0 | 0 | 0 | 0 | 0 | 1 | 0 | 0 | 0 | 0 |
| OBD116.173.175_64 | 0 | 0 | 0 | 0 | 0 | 0 | 0 | 0 | 0 | 0 | 0 | 0 |
| OBD116.177.179_2 | 1 | 1 | 1 | 1 | 1 | 1 | 1 | 1 | 1 | 1 | 1 | 1 |

TABLE 18-continued

Binary analysis results using the top 13 markers. Darker results showing a p-value > 0.3. Lighter results show best dilution. OBD116 Gliwice results

| | | | | | | | | | | | | |
|---|---|---|---|---|---|---|---|---|---|---|---|---|
| OBD116.177.179_4 | 1 | 1 | 1 | 1 | 1 | 0 | 1 | 1 | 1 | 1 | 1 | 1 |
| OBD116.177.179_8 | 1 | 1 | 1 | 1 | 1 | 0 | 1 | 1 | 1 | 0 | 1 | 0 |
| OBD116.177.179_16 | 1 | 1 | 1 | 1 | 1 | 0 | 0 | 1 | 1 | 0 | 0 | 0 |
| OBD116.177.179_32 | 0 | 1 | 0 | 1 | 0 | 0 | 0 | 1 | 0 | 0 | 0 | 0 |
| OBD116.177.179_64 | 0 | 1 | 0 | 0 | 0 | 0 | 0 | 0 | 0 | 0 | 0 | 0 |
| OBD116.185.187_2 | 1 | 1 | 1 | 1 | 1 | 1 | 1 | 1 | 1 | 1 | 1 | 1 |
| OBD116.185.187_4 | 1 | 1 | 1 | 1 | 1 | 1 | 1 | 1 | 1 | 1 | 1 | 1 |
| OBD116.185.187_8 | 1 | 0 | 1 | 1 | 1 | 1 | 1 | 0 | 1 | 1 | 0 | 0 |
| OBD116.185.187_16 | 1 | 0 | 0 | 0 | 0 | 0 | 0 | 0 | 1 | 0 | 0 | 0 |
| OBD116.185.187_32 | 0 | 0 | 0 | 0 | 0 | 0 | 0 | 0 | 0 | 0 | 0 | 0 |
| OBD116.185.187_64 | 0 | 0 | 0 | 0 | 0 | 0 | 0 | 0 | 0 | 0 | 0 | 0 |
| OBD116.197.199_2 | 1 | 1 | 1 | 1 | 1 | 1 | 1 | 1 | 1 | 1 | 1 | 0 |
| OBD116.197.199_4 | 0 | 0 | 1 | 1 | 0 | 1 | 1 | 1 | 1 | 1 | 1 | 0 |
| OBD116.197.199_8 | 0 | 0 | 1 | 1 | 0 | 0 | 0 | 1 | 0 | 0 | 1 | 0 |
| OBD116.197.199_16 | 0 | 0 | 1 | 0 | 0 | 0 | 0 | 0 | 0 | 0 | 0 | 0 |
| OBD116.197.199_32 | 0 | 0 | 0 | 0 | 0 | 0 | 0 | 0 | 0 | 0 | 0 | 0 |
| OBD116.197.199_64 | 0 | 0 | 0 | 0 | 0 | 0 | 0 | 0 | 0 | 0 | 0 | 0 |
| OBD116.261.263_2 | 1 | 1 | 0 | 1 | 0 | 0 | 0 | 0 | 1 | 0 | 1 | 1 |
| OBD116.261.263_4 | 0 | 0 | 0 | 1 | 0 | 0 | 0 | 0 | 1 | 0 | 0 | 0 |
| OBD116.261.263_8 | 0 | 0 | 0 | 1 | 0 | 0 | 0 | 0 | 0 | 0 | 0 | 0 |
| OBD116.261.263_16 | 0 | 0 | 0 | 0 | 0 | 0 | 0 | 0 | 0 | 0 | 0 | 0 |
| OBD116.261.263_32 | 0 | 0 | 0 | 0 | 0 | 0 | 0 | 0 | 0 | 0 | 0 | 0 |
| OBD116.261.263_64 | 0 | 0 | 0 | 0 | 0 | 0 | 0 | 0 | 0 | 0 | 0 | 0 |
| OBD116.301.303_2 | 0 | 0 | 1 | 0 | 1 | 0 | 1 | 0 | 1 | 0 | 1 | 0 |
| OBD116.301.303_4 | 0 | 0 | 1 | 0 | 0 | 0 | 1 | 0 | 1 | 0 | 0 | 0 |
| OBD116.301.303_8 | 0 | 0 | 0 | 0 | 0 | 0 | 1 | 0 | 0 | 0 | 0 | 0 |
| OBD116.301.303_16 | 0 | 0 | 0 | 0 | 0 | 0 | 0 | 0 | 0 | 0 | 0 | 0 |
| OBD116.301.303_32 | 0 | 0 | 0 | 0 | 0 | 0 | 0 | 0 | 0 | 0 | 0 | 0 |
| OBD116.301.303_64 | 0 | 0 | 0 | 0 | 0 | 0 | 0 | 0 | 0 | 0 | 0 | 0 |

| | State. 1 | | | | | | | | | | | |
|---|---|---|---|---|---|---|---|---|---|---|---|---|
| | BrCa | BrCa | BrCa | BrCa | BrCa | BrCa | BrCa | BrCa | BrCa | BrCa | BrCa | BrCa |
| | | | | | | State. 2 | | | | | | |
| | 10775 | 10782 | 10791 | 10794 | 10830 | 10832 | 10836 | 10853 | 10855 | 10861 | 10865 | 10876 |
| OBD116.1.3_2 | 0 | 1 | 1 | 1 | 1 | 1 | 1 | 1 | 1 | 0 | 1 | 1 |
| OBD116.1.3_4 | 0 | 0 | 1 | 1 | 1 | 1 | 1 | 1 | 1 | 0 | 1 | 1 |
| OBD116.1.3_8 | 0 | 0 | 0 | 1 | 1 | 1 | 1 | 0 | 1 | 0 | 1 | 0 |
| OBD116.1.3_16 | 0 | 0 | 0 | 0 | 0 | 0 | 1 | 0 | 0 | 0 | 1 | 0 |
| OBD116.1.3_32 | 0 | 0 | 0 | 0 | 0 | 0 | 0 | 0 | 0 | 0 | 0 | 0 |
| OBD116.1.3_64 | 0 | 0 | 0 | 0 | 0 | 0 | 0 | 0 | 0 | 0 | 0 | 0 |
| OBD116.53.55_2 | 1 | 1 | 1 | 1 | 1 | 1 | 1 | 1 | 1 | 1 | 1 | 1 |
| OBD116.53.55_4 | 1 | 0 | 1 | 1 | 1 | 1 | 1 | 1 | 1 | 1 | 1 | 1 |
| OBD116.53.55_8 | 1 | 0 | 1 | 1 | 1 | 0 | 1 | 1 | 1 | 1 | 1 | 1 |
| OBD116.53.55_16 | 1 | 0 | 1 | 1 | 0 | 0 | 1 | 1 | 1 | 1 | 1 | 0 |
| OBD116.53.55_32 | 0 | 0 | 0 | 1 | 0 | 0 | 0 | 0 | 0 | 0 | 0 | 0 |
| OBD116.53.55_64 | 0 | 0 | 0 | 0 | 0 | 0 | 0 | 0 | 0 | 0 | 0 | 0 |
| OBD116.89.91_2 | 1 | 1 | 1 | 1 | 0 | 0 | 0 | 1 | 1 | 0 | 1 | 1 |
| OBD116.89.91_4 | 0 | 1 | 0 | 1 | 0 | 0 | 0 | 0 | 0 | 0 | 1 | 0 |
| OBD116.89.91_8 | 0 | 0 | 0 | 0 | 0 | 0 | 0 | 0 | 0 | 0 | 0 | 0 |
| OBD116.89.91_16 | 0 | 0 | 0 | 0 | 0 | 0 | 0 | 0 | 0 | 0 | 0 | 0 |
| OBD116.89.91_32 | 0 | 0 | 0 | 0 | 0 | 0 | 0 | 0 | 0 | 0 | 0 | 0 |
| OBD116.89.91_64 | 0 | 0 | 0 | 0 | 0 | 0 | 0 | 0 | 0 | 0 | 0 | 0 |
| OBD116.89.103_2 | 1 | 0 | 1 | 1 | 1 | 1 | 1 | 1 | 1 | 1 | 1 | 1 |
| OBD116.89.103_4 | 1 | 0 | 1 | 1 | 1 | 1 | 1 | 0 | 1 | 0 | 1 | 1 |
| OBD116.89.103_8 | 1 | 0 | 1 | 0 | 1 | 0 | 0 | 0 | 0 | 0 | 1 | 0 |
| OBD116.89.103_16 | 0 | 0 | 0 | 0 | 1 | 0 | 0 | 0 | 0 | 0 | 1 | 0 |
| OBD116.89.103_32 | 0 | 0 | 0 | 0 | 0 | 0 | 0 | 0 | 0 | 0 | 0 | 0 |
| OBD116.89.103_64 | 0 | 0 | 0 | 0 | 0 | 0 | 0 | 0 | 0 | 0 | 0 | 0 |
| OBD116.113.87_2 | 1 | 1 | 1 | 1 | 1 | 0 | 0 | 1 | 1 | 1 | 1 | 0 |
| OBD116.113.87_4 | 1 | 1 | 1 | 1 | 1 | 0 | 0 | 1 | 0 | 1 | 1 | 0 |
| OBD116.113.87_8 | 1 | 1 | 1 | 0 | 0 | 0 | 0 | 1 | 0 | 0 | 1 | 0 |
| OBD116.113.87_16 | 0 | 1 | 1 | 0 | 0 | 0 | 0 | 0 | 0 | 0 | 1 | 0 |
| OBD116.113.87_32 | 0 | 0 | 0 | 0 | 0 | 0 | 0 | 0 | 0 | 0 | 0 | 0 |
| OBD116.113.87_64 | 0 | 0 | 0 | 0 | 0 | 0 | 0 | 0 | 0 | 0 | 0 | 0 |
| OBD116.129.131_2 | 1 | 1 | 1 | 1 | 1 | 1 | 1 | 1 | 1 | 1 | 1 | 1 |
| OBD116.129.131_4 | 1 | 0 | 1 | 1 | 1 | 1 | 1 | 0 | 1 | 0 | 1 | 1 |
| OBD116.129.131_8 | 1 | 0 | 1 | 1 | 1 | 1 | 1 | 0 | 1 | 0 | 1 | 1 |
| OBD116.129.131_16 | 0 | 0 | 0 | 0 | 1 | 0 | 1 | 0 | 1 | 0 | 0 | 1 |
| OBD116.129.131_32 | 0 | 0 | 0 | 0 | 0 | 1 | 0 | 0 | 1 | 0 | 0 | 1 |
| OBD116.129.131_64 | 0 | 0 | 0 | 0 | 0 | 1 | 0 | 0 | 1 | 0 | 0 | 1 |
| OBD116.161.163_2 | 1 | 1 | 1 | 1 | 1 | 1 | 1 | 1 | 1 | 1 | 1 | 1 |
| OBD116.161.163_4 | 1 | 0 | 1 | 1 | 1 | 1 | 1 | 1 | 1 | 0 | 1 | 1 |
| OBD116.161.163_8 | 1 | 0 | 1 | 1 | 0 | 0 | 1 | 1 | 1 | 0 | 1 | 0 |
| OBD116.161.163_16 | 0 | 0 | 0 | 1 | 0 | 0 | 0 | 0 | 0 | 0 | 0 | 0 |

TABLE 18-continued

Binary analysis results using the top 13 markers. Darker results showing a p-value > 0.3. Lighter results show best dilution.
OBD116 Gliwice results

| | | | | | | | | | | | | |
|---|---|---|---|---|---|---|---|---|---|---|---|---|
| OBD116.161.163_32 | 0 | 0 | 0 | 0 | 0 | 0 | 0 | 0 | 0 | 0 | 0 | 0 |
| OBD116.161.163_64 | 0 | 0 | 0 | 0 | 0 | 0 | 0 | 0 | 0 | 0 | 0 | 0 |
| OBD116.173.175_2 | 0 | 0 | 1 | 0 | 0 | 0 | 0 | 0 | 1 | 1 | 0 | 1 |
| OBD116.173.175_4 | 0 | 0 | 0 | 0 | 0 | 0 | 0 | 0 | 0 | 0 | 1 | 1 |
| OBD116.173.175_8 | 0 | 0 | 0 | 0 | 0 | 0 | 0 | 0 | 0 | 0 | 0 | 0 |
| OBD116.173.175_16 | 0 | 0 | 0 | 0 | 0 | 0 | 0 | 0 | 0 | 0 | 0 | 0 |
| OBD116.173.175_32 | 0 | 0 | 0 | 0 | 0 | 0 | 0 | 0 | 0 | 0 | 0 | 0 |
| OBD116.173.175_64 | 0 | 0 | 0 | 0 | 0 | 0 | 0 | 0 | 0 | 0 | 0 | 0 |
| OBD116.177.179_2 | 1 | 1 | 1 | 1 | 1 | 1 | 1 | 1 | 1 | 1 | 1 | 1 |
| OBD116.177.179_4 | 1 | 1 | 1 | 1 | 1 | 1 | 1 | 1 | 0 | 1 | 1 | 1 |
| OBD116.177.179_8 | 0 | 1 | 1 | 0 | 1 | 1 | 1 | 0 | 0 | 0 | 0 | 1 |
| OBD116.177.179_16 | 0 | 0 | 0 | 0 | 0 | 1 | 1 | 0 | 0 | 0 | 0 | 1 |
| OBD116.177.179_32 | 0 | 0 | 0 | 0 | 0 | 0 | 0 | 0 | 0 | 0 | 0 | 0 |
| OBD116.177.179_64 | 0 | 0 | 0 | 0 | 0 | 0 | 0 | 0 | 0 | 0 | 0 | 0 |
| OBD116.185.187_2 | 1 | 1 | 1 | 1 | 1 | 0 | 1 | 1 | 1 | 0 | 1 | 1 |
| OBD116.185.187_4 | 1 | 1 | 0 | 1 | 1 | 0 | 1 | 1 | 0 | 0 | 1 | 1 |
| OBD116.185.187_8 | 1 | 1 | 0 | 1 | 1 | 0 | 1 | 1 | 0 | 0 | 1 | 0 |
| OBD116.185.187_16 | 0 | 0 | 0 | 1 | 1 | 0 | 1 | 1 | 0 | 0 | 1 | 0 |
| OBD116.185.187_32 | 0 | 0 | 0 | 1 | 0 | 0 | 1 | 0 | 0 | 0 | 1 | 0 |
| OBD116.185.187_64 | 0 | 0 | 0 | 0 | 0 | 0 | 0 | 0 | 0 | 0 | 0 | 0 |
| OBD116.197.199_2 | 1 | 1 | 1 | 1 | 0 | 1 | 1 | 1 | 1 | 0 | 1 | 1 |
| OBD116.197.199_4 | 0 | 1 | 1 | 1 | 0 | 1 | 1 | 0 | 0 | 1 | 1 | 1 |
| OBD116.197.199_8 | 0 | 0 | 0 | 1 | 0 | 0 | 1 | 0 | 0 | 0 | 1 | 1 |
| OBD116.197.199_16 | 0 | 0 | 0 | 0 | 0 | 0 | 0 | 0 | 0 | 0 | 0 | 1 |
| OBD116.197.199_32 | 0 | 0 | 0 | 0 | 0 | 0 | 0 | 0 | 0 | 0 | 0 | 0 |
| OBD116.197.199_64 | 0 | 0 | 0 | 0 | 0 | 0 | 0 | 0 | 0 | 0 | 0 | 0 |
| OBD116.261.263_2 | 1 | 1 | 0 | 0 | 0 | 1 | 0 | 0 | 1 | 1 | 0 | 0 |
| OBD116.261.263_4 | 0 | 0 | 0 | 0 | 0 | 0 | 0 | 0 | 1 | 0 | 0 | 0 |
| OBD116.261.263_8 | 0 | 0 | 0 | 0 | 0 | 0 | 0 | 0 | 1 | 0 | 0 | 0 |
| OBD116.261.263_16 | 0 | 0 | 0 | 0 | 0 | 0 | 0 | 0 | 0 | 0 | 0 | 0 |
| OBD116.261.263_32 | 0 | 0 | 0 | 0 | 0 | 0 | 0 | 0 | 0 | 0 | 0 | 0 |
| OBD116.261.263_64 | 0 | 0 | 0 | 0 | 0 | 0 | 0 | 0 | 0 | 0 | 0 | 0 |
| OBD116.301.303_2 | 0 | 0 | 0 | 0 | 1 | 0 | 1 | 0 | 1 | 1 | 1 | 1 |
| OBD116.301.303_4 | 0 | 0 | 0 | 0 | 0 | 0 | 1 | 0 | 0 | 1 | 1 | 1 |
| OBD116.301.303_8 | 0 | 0 | 0 | 0 | 0 | 0 | 1 | 0 | 0 | 1 | 1 | 0 |
| OBD116.301.303_16 | 0 | 0 | 0 | 0 | 0 | 0 | 1 | 0 | 0 | 1 | 0 | 0 |
| OBD116.301.303_32 | 0 | 0 | 0 | 0 | 0 | 0 | 1 | 0 | 0 | 0 | 0 | 0 |
| OBD116.301.303_64 | 0 | 0 | 0 | 0 | 0 | 0 | 1 | 0 | 0 | 0 | 0 | 0 |

| | State. 1 | | | | | | | | | | | |
|---|---|---|---|---|---|---|---|---|---|---|---|---|
| | BrCa | BrCa | BrCa | BrCa | BrCa | BrCa | BrCa | BrCa | BrCa | BrCa | BrCa | BrCa |
| | | | | | | State. 2 | | | | | | |
| | 10883 | 10885 | 10891 | 10892 | 10903 | 10915 | 10942 | 10947 | 10955 | 10963 | 11015 | 11035 |
| OBD116.1.3_2 | 1 | 1 | 1 | 1 | 1 | 1 | 1 | 1 | 1 | 1 | 1 | 1 |
| OBD116.1.3_4 | 1 | 1 | 1 | 1 | 0 | 1 | 1 | 1 | 0 | 1 | 1 | 1 |
| OBD116.1.3_8 | 1 | 1 | 0 | 0 | 0 | 0 | 1 | 0 | 0 | 0 | 1 | 1 |
| OBD116.1.3_16 | 1 | 0 | 0 | 0 | 0 | 0 | 1 | 1 | 0 | 0 | 1 | 1 |
| OBD116.1.3_32 | 1 | 0 | 0 | 0 | 0 | 0 | 1 | 0 | 0 | 0 | 1 | 1 |
| OBD116.1.3_64 | 0 | 0 | 0 | 0 | 0 | 0 | 1 | 0 | 0 | 0 | 0 | 0 |
| OBD116.53.55_2 | 1 | 1 | 1 | 1 | 1 | 1 | 1 | 1 | 1 | 1 | 1 | 1 |
| OBD116.53.55_4 | 1 | 1 | 1 | 1 | 1 | 1 | 1 | 1 | 1 | 1 | 1 | 1 |
| OBD116.53.55_8 | 1 | 0 | 1 | 1 | 1 | 0 | 1 | 1 | 1 | 1 | 1 | 1 |
| OBD116.53.55_16 | 1 | 0 | 1 | 1 | 1 | 0 | 0 | 0 | 1 | 0 | 0 | 1 |
| OBD116.53.55_32 | 1 | 0 | 0 | 0 | 0 | 0 | 0 | 0 | 0 | 0 | 0 | 1 |
| OBD116.53.55_64 | 0 | 0 | 0 | 0 | 0 | 0 | 0 | 0 | 0 | 0 | 0 | 1 |
| OBD116.89.91_2 | 1 | 0 | 1 | 0 | 1 | 1 | 1 | 1 | 1 | 0 | 1 | 0 |
| OBD116.89.91_4 | 0 | 0 | 1 | 0 | 1 | 1 | 1 | 0 | 0 | 0 | 0 | 0 |
| OBD116.89.91_8 | 0 | 0 | 1 | 0 | 0 | 0 | 0 | 0 | 0 | 0 | 0 | 0 |
| OBD116.89.91_16 | 0 | 0 | 0 | 0 | 0 | 0 | 0 | 0 | 0 | 0 | 0 | 0 |
| OBD116.89.91_32 | 0 | 0 | 0 | 0 | 0 | 0 | 0 | 0 | 0 | 0 | 0 | 0 |
| OBD116.89.91_64 | 0 | 0 | 0 | 0 | 0 | 0 | 0 | 0 | 0 | 0 | 0 | 0 |
| OBD116.89.103_2 | 1 | 1 | 1 | 1 | 1 | 1 | 1 | 1 | 1 | 1 | 0 | 0 |
| OBD116.89.103_4 | 0 | 1 | 0 | 1 | 1 | 1 | 1 | 1 | 1 | 1 | 0 | 0 |
| OBD116.89.103_8 | 0 | 1 | 0 | 1 | 1 | 0 | 0 | 1 | 1 | 1 | 0 | 0 |
| OBD116.89.103_16 | 0 | 1 | 0 | 1 | 0 | 0 | 0 | 1 | 1 | 0 | 0 | 0 |
| OBD116.89.103_32 | 0 | 1 | 0 | 0 | 0 | 0 | 0 | 0 | 0 | 0 | 0 | 0 |
| OBD116.89.103_64 | 0 | 0 | 0 | 0 | 0 | 0 | 0 | 0 | 0 | 0 | 0 | 0 |
| OBD116.113.87_2 | 1 | 1 | 1 | 1 | 1 | 1 | 1 | 1 | 1 | 1 | 1 | 1 |
| OBD116.113.87_4 | 1 | 1 | 1 | 1 | 1 | 1 | 1 | 1 | 1 | 1 | 1 | 0 |
| OBD116.113.87_8 | 1 | 0 | 1 | 0 | 1 | 1 | 1 | 1 | 1 | 1 | 1 | 0 |
| OBD116.113.87_16 | 1 | 0 | 1 | 0 | 1 | 1 | 0 | 1 | 0 | 0 | 0 | 0 |
| OBD116.113.87_32 | 0 | 0 | 1 | 0 | 0 | 1 | 0 | 0 | 1 | 0 | 0 | 0 |
| OBD116.113.87_64 | 0 | 0 | 0 | 0 | 0 | 0 | 0 | 0 | 1 | 0 | 0 | 0 |
| OBD116.129.131_2 | 1 | 1 | 1 | 1 | 1 | 1 | 1 | 1 | 1 | 1 | 0 | 0 |

TABLE 18-continued

Binary analysis results using the top 13 markers. Darker results showing a p-value > 0.3. Lighter results show best dilution. OBD116 Gliwice results

| | | | | | | | | | | | | |
|---|---|---|---|---|---|---|---|---|---|---|---|---|
| OBD116.129.131_4 | 1 | 0 | 0 | 1 | 1 | 0 | 1 | 1 | 1 | 1 | 0 | 0 |
| OBD116.129.131_8 | 1 | 0 | 0 | 1 | 1 | 0 | 1 | 1 | 1 | 1 | 0 | 0 |
| OBD116.129.131_16 | 1 | 0 | 0 | 1 | 0 | 0 | 0 | 1 | 1 | 0 | 0 | 0 |
| OBD116.129.131_32 | 1 | 0 | 0 | 1 | 0 | 0 | 0 | 1 | 0 | 0 | 0 | 0 |
| OBD116.129.131_64 | 1 | 0 | 0 | 0 | 0 | 0 | 0 | 1 | 0 | 0 | 0 | 0 |
| OBD116.161.163_2 | 1 | 1 | 1 | 1 | 1 | 1 | 1 | 1 | 1 | 1 | 1 | 0 |
| OBD116.161.163_4 | 1 | 1 | 1 | 0 | 1 | 1 | 1 | 1 | 1 | 0 | 0 | 0 |
| OBD116.161.163_8 | 1 | 1 | 0 | 0 | 1 | 1 | 1 | 1 | 0 | 0 | 0 | 0 |
| OBD116.161.163_16 | 0 | 1 | 0 | 0 | 1 | 1 | 1 | 1 | 0 | 0 | 0 | 0 |
| OBD116.161.163_32 | 0 | 0 | 0 | 0 | 0 | 0 | 1 | 0 | 0 | 0 | 0 | 0 |
| OBD116.161.163_64 | 0 | 0 | 0 | 0 | 0 | 0 | 0 | 0 | 0 | 0 | 0 | 0 |
| OBD116.173.175_2 | 1 | 1 | 0 | 1 | 1 | 0 | 0 | 1 | 1 | 0 | 0 | 0 |
| OBD116.173.175_4 | 1 | 1 | 0 | 1 | 1 | 0 | 0 | 1 | 1 | 0 | 0 | 0 |
| OBD116.173.175_8 | 1 | 1 | 0 | 0 | 1 | 0 | 0 | 0 | 1 | 0 | 0 | 0 |
| OBD116.173.175_16 | 0 | 0 | 0 | 0 | 1 | 0 | 0 | 0 | 0 | 0 | 0 | 0 |
| OBD116.173.175_32 | 0 | 0 | 0 | 0 | 0 | 0 | 0 | 0 | 0 | 0 | 0 | 0 |
| OBD116.173.175_64 | 0 | 0 | 0 | 0 | 0 | 0 | 0 | 0 | 0 | 0 | 0 | 0 |
| OBD116.177.179_2 | 1 | 1 | 1 | 1 | 1 | 0 | 1 | 1 | 1 | 1 | 1 | 1 |
| OBD116.177.179_4 | 0 | 1 | 1 | 1 | 1 | 0 | 1 | 1 | 1 | 1 | 1 | 1 |
| OBD116.177.179_8 | 0 | 1 | 1 | 0 | 1 | 0 | 1 | 1 | 1 | 1 | 1 | 0 |
| OBD116.177.179_16 | 0 | 0 | 0 | 0 | 0 | 0 | 1 | 0 | 0 | 1 | 1 | 0 |
| OBD116.177.179_32 | 0 | 0 | 0 | 0 | 0 | 0 | 1 | 0 | 0 | 1 | 0 | 0 |
| OBD116.177.179_64 | 0 | 0 | 0 | 0 | 0 | 0 | 0 | 0 | 0 | 1 | 0 | 0 |
| OBD116.185.187_2 | 1 | 1 | 1 | 1 | 1 | 1 | 1 | 1 | 1 | 1 | 0 | 1 |
| OBD116.185.187_4 | 1 | 1 | 1 | 1 | 1 | 0 | 1 | 1 | 1 | 1 | 0 | 1 |
| OBD116.185.187_8 | 1 | 0 | 1 | 0 | 0 | 0 | 1 | 0 | 1 | 1 | 0 | 0 |
| OBD116.185.187_16 | 1 | 0 | 0 | 0 | 0 | 0 | 1 | 0 | 0 | 0 | 0 | 0 |
| OBD116.185.187_32 | 1 | 0 | 0 | 0 | 0 | 0 | 1 | 0 | 0 | 0 | 0 | 0 |
| OBD116.185.187_64 | 0 | 0 | 0 | 0 | 0 | 0 | 1 | 0 | 0 | 0 | 0 | 0 |
| OBD116.197.199_2 | 1 | 1 | 1 | 1 | 1 | 0 | 1 | 0 | 1 | 1 | 1 | 1 |
| OBD116.197.199_4 | 1 | 1 | 1 | 0 | 1 | 0 | 0 | 0 | 1 | 1 | 0 | 1 |
| OBD116.197.199_8 | 1 | 0 | 1 | 0 | 0 | 0 | 0 | 0 | 0 | 0 | 0 | 1 |
| OBD116.197.199_16 | 1 | 0 | 1 | 0 | 0 | 0 | 0 | 0 | 0 | 0 | 0 | 0 |
| OBD116.197.199_32 | 0 | 0 | 0 | 0 | 0 | 0 | 0 | 0 | 0 | 0 | 0 | 0 |
| OBD116.197.199_64 | 0 | 0 | 0 | 0 | 0 | 0 | 0 | 0 | 0 | 0 | 0 | 0 |
| OBD116.261.263_2 | 1 | 0 | 1 | 0 | 0 | 1 | 0 | 0 | 1 | 0 | 0 | 1 |
| OBD116.261.263_4 | 1 | 0 | 0 | 0 | 0 | 0 | 0 | 0 | 1 | 0 | 0 | 0 |
| OBD116.261.263_8 | 1 | 0 | 0 | 0 | 0 | 0 | 0 | 0 | 0 | 0 | 0 | 0 |
| OBD116.261.263_16 | 0 | 0 | 0 | 0 | 0 | 0 | 0 | 0 | 0 | 0 | 0 | 0 |
| OBD116.261.263_32 | 0 | 0 | 0 | 0 | 0 | 0 | 0 | 0 | 0 | 0 | 0 | 0 |
| OBD116.261.263_64 | 0 | 0 | 0 | 0 | 0 | 0 | 0 | 0 | 0 | 0 | 0 | 0 |
| OBD116.301.303_2 | 1 | 0 | 1 | 1 | 0 | 0 | 0 | 0 | 1 | 0 | 0 | 1 |
| OBD116.301.303_4 | 0 | 0 | 0 | 0 | 0 | 0 | 0 | 0 | 0 | 0 | 0 | 0 |
| OBD116.301.303_8 | 0 | 0 | 0 | 0 | 0 | 0 | 0 | 0 | 0 | 0 | 0 | 0 |
| OBD116.301.303_16 | 0 | 0 | 0 | 0 | 0 | 0 | 0 | 0 | 0 | 0 | 0 | 0 |
| OBD116.301.303_32 | 0 | 0 | 0 | 0 | 0 | 0 | 0 | 0 | 0 | 0 | 0 | 0 |
| OBD116.301.303_64 | 0 | 0 | 0 | 0 | 0 | 0 | 0 | 0 | 0 | 0 | 0 | 0 |

| | State. 1 | | | | | | | | | | | |
|---|---|---|---|---|---|---|---|---|---|---|---|---|
| | BrCa | BrCa | BrCa | BrCa | BrCa | BrCa | BrCa | BrCa | BrCa | BrCa | BrCa | BrCa |
| | | | | | | | State. 2 | | | | | |
| | 11036 | 11053 | 11059 | 11081 | 11083 | 11097 | 11099 | 11122 | 11136 | 11153 | 11180 | 11187 |
| OBD116.1.3_2 | 1 | 1 | 1 | 0 | 1 | 1 | 1 | 1 | 1 | 1 | 1 | 0 |
| OBD116.1.3_4 | 1 | 1 | 0 | 0 | 1 | 1 | 0 | 1 | 1 | 1 | 1 | 0 |
| OBD116.1.3_8 | 0 | 1 | 0 | 0 | 1 | 0 | 0 | 0 | 1 | 1 | 0 | 0 |
| OBD116.1.3_16 | 0 | 1 | 0 | 0 | 0 | 0 | 0 | 0 | 1 | 0 | 0 | 0 |
| OBD116.1.3_32 | 0 | 0 | 0 | 0 | 0 | 0 | 0 | 0 | 0 | 0 | 0 | 0 |
| OBD116.1.3_64 | 0 | 0 | 0 | 0 | 0 | 0 | 0 | 0 | 0 | 0 | 0 | 0 |
| OBD116.53.55_2 | 1 | 1 | 1 | 1 | 1 | 1 | 1 | 1 | 1 | 1 | 1 | 1 |
| OBD116.53.55_4 | 1 | 1 | 1 | 1 | 1 | 1 | 1 | 0 | 1 | 1 | 1 | 1 |
| OBD116.53.55_8 | 1 | 1 | 1 | 0 | 1 | 1 | 1 | 0 | 1 | 0 | 1 | 0 |
| OBD116.53.55_16 | 1 | 0 | 0 | 0 | 0 | 0 | 1 | 1 | 0 | 0 | 1 | 0 |
| OBD116.53.55_32 | 1 | 0 | 0 | 0 | 0 | 0 | 0 | 1 | 0 | 0 | 1 | 0 |
| OBD116.53.55_64 | 0 | 0 | 0 | 0 | 0 | 0 | 0 | 1 | 0 | 0 | 0 | 0 |
| OBD116.89.91_2 | 0 | 1 | 0 | 0 | 1 | 0 | 1 | 1 | 0 | 0 | 1 | 0 |
| OBD116.89.91_4 | 0 | 0 | 0 | 0 | 0 | 0 | 1 | 1 | 0 | 0 | 0 | 0 |
| OBD116.89.91_8 | 0 | 0 | 0 | 0 | 0 | 0 | 0 | 0 | 0 | 0 | 0 | 0 |
| OBD116.89.91_16 | 0 | 0 | 0 | 0 | 0 | 0 | 0 | 0 | 0 | 0 | 0 | 0 |
| OBD116.89.91_32 | 0 | 0 | 0 | 0 | 0 | 0 | 0 | 0 | 0 | 0 | 0 | 0 |
| OBD116.89.91_64 | 0 | 0 | 0 | 0 | 0 | 0 | 0 | 0 | 0 | 0 | 0 | 0 |
| OBD116.89.103_2 | 1 | 1 | 1 | 0 | 1 | 1 | 1 | 1 | 1 | 1 | 1 | 1 |
| OBD116.89.103_4 | 1 | 1 | 1 | 0 | 1 | 1 | 0 | 1 | 0 | 1 | 1 | 1 |
| OBD116.89.103_8 | 1 | 1 | 1 | 0 | 0 | 1 | 0 | 1 | 0 | 1 | 1 | 0 |
| OBD116.89.103_16 | 1 | 1 | 0 | 0 | 0 | 1 | 0 | 0 | 0 | 0 | 1 | 0 |

TABLE 18-continued

Binary analysis results using the top 13 markers. Darker results showing a p-value > 0.3. Lighter results show best dilution.
OBD116 Gliwice results

| | | | | | | | | | | | | |
|---|---|---|---|---|---|---|---|---|---|---|---|---|
| OBD116.89.103_32 | 0 | 1 | 0 | 0 | 0 | 0 | 0 | 0 | 0 | 0 | 1 | 0 |
| OBD116.89.103_64 | 0 | 0 | 0 | 0 | 0 | 0 | 0 | 0 | 0 | 0 | 0 | 0 |
| OBD116.113.87_2 | 1 | 1 | 1 | 1 | 1 | 1 | 1 | 1 | 1 | 1 | 1 | 1 |
| OBD116.113.87_4 | 1 | 1 | 1 | 1 | 1 | 1 | 1 | 1 | 1 | 1 | 1 | 1 |
| OBD116.113.87_8 | 1 | 1 | 1 | 0 | 1 | 1 | 1 | 1 | 1 | 1 | 1 | 1 |
| OBD116.113.87_16 | 1 | 1 | 1 | 0 | 1 | 0 | 1 | 1 | 0 | 1 | 0 | 1 |
| OBD116.113.87_32 | 1 | 0 | 1 | 0 | 0 | 0 | 0 | 0 | 0 | 0 | 0 | 0 |
| OBD116.113.87_64 | 0 | 0 | 0 | 0 | 0 | 0 | 0 | 0 | 0 | 0 | 0 | 0 |
| OBD116.129.131_2 | 1 | 1 | 1 | 1 | 1 | 1 | 1 | 1 | 1 | 1 | 1 | 1 |
| OBD116.129.131_4 | 1 | 1 | 1 | 0 | 1 | 1 | 0 | 1 | 1 | 1 | 1 | 1 |
| OBD116.129.131_8 | 0 | 0 | 1 | 0 | 1 | 1 | 0 | 0 | 1 | 1 | 0 | 0 |
| OBD116.129.131_16 | 0 | 0 | 0 | 0 | 1 | 0 | 0 | 0 | 0 | 0 | 0 | 0 |
| OBD116.129.131_32 | 0 | 0 | 0 | 0 | 0 | 0 | 0 | 0 | 0 | 0 | 0 | 0 |
| OBD116.129.131_64 | 0 | 0 | 0 | 0 | 0 | 0 | 0 | 0 | 0 | 0 | 0 | 0 |
| OBD116.161.163_2 | 1 | 1 | 1 | 0 | 1 | 1 | 1 | 1 | 1 | 1 | 1 | 1 |
| OBD116.161.163_4 | 1 | 1 | 1 | 0 | 1 | 1 | 1 | 0 | 1 | 1 | 1 | 1 |
| OBD116.161.163_8 | 0 | 0 | 0 | 0 | 1 | 1 | 1 | 0 | 1 | 0 | 1 | 1 |
| OBD116.161.163_16 | 0 | 0 | 0 | 0 | 1 | 1 | 1 | 0 | 1 | 0 | 1 | 1 |
| OBD116.161.163_32 | 0 | 0 | 0 | 0 | 0 | 0 | 0 | 0 | 0 | 0 | 1 | 1 |
| OBD116.161.163_64 | 0 | 0 | 0 | 0 | 0 | 0 | 0 | 0 | 0 | 0 | 0 | 0 |
| OBD116.173.175_2 | 0 | 1 | 0 | 1 | 1 | 0 | 1 | 0 | 0 | 1 | 1 | 0 |
| OBD116.173.175_4 | 0 | 1 | 0 | 0 | 1 | 0 | 1 | 0 | 0 | 1 | 0 | 0 |
| OBD116.173.175_8 | 0 | 0 | 0 | 0 | 0 | 0 | 0 | 0 | 0 | 0 | 0 | 0 |
| OBD116.173.175_16 | 0 | 0 | 0 | 0 | 0 | 0 | 0 | 0 | 0 | 0 | 0 | 0 |
| OBD116.173.175_32 | 0 | 0 | 0 | 0 | 0 | 0 | 0 | 0 | 0 | 0 | 0 | 0 |
| OBD116.173.175_64 | 0 | 0 | 0 | 0 | 0 | 0 | 0 | 0 | 0 | 0 | 0 | 0 |
| OBD116.177.179_2 | 1 | 1 | 1 | 1 | 1 | 1 | 1 | 1 | 1 | 1 | 1 | 1 |
| OBD116.177.179_4 | 0 | 1 | 1 | 0 | 1 | 1 | 1 | 0 | 1 | 1 | 1 | 1 |
| OBD116.177.179_8 | 0 | 1 | 1 | 0 | 1 | 1 | 1 | 0 | 0 | 0 | 1 | 0 |
| OBD116.177.179_16 | 0 | 0 | 1 | 0 | 1 | 1 | 0 | 0 | 0 | 0 | 1 | 0 |
| OBD116.177.179_32 | 0 | 0 | 0 | 0 | 0 | 1 | 0 | 0 | 0 | 0 | 1 | 0 |
| OBD116.177.179_64 | 0 | 0 | 0 | 0 | 0 | 0 | 0 | 0 | 0 | 0 | 0 | 0 |
| OBD116.185.187_2 | 1 | 1 | 1 | 0 | 1 | 1 | 1 | 1 | 1 | 1 | 1 | 1 |
| OBD116.185.187_4 | 1 | 0 | 1 | 0 | 1 | 1 | 1 | 1 | 0 | 1 | 0 | 1 |
| OBD116.185.187_8 | 0 | 0 | 0 | 0 | 1 | 1 | 0 | 1 | 0 | 1 | 0 | 0 |
| OBD116.185.187_16 | 0 | 0 | 0 | 0 | 1 | 1 | 0 | 0 | 0 | 0 | 0 | 0 |
| OBD116.185.187_32 | 0 | 0 | 0 | 0 | 1 | 0 | 0 | 0 | 0 | 0 | 0 | 0 |
| OBD116.185.187_64 | 0 | 0 | 0 | 0 | 0 | 0 | 0 | 0 | 0 | 0 | 0 | 0 |
| OBD116.197.199_2 | 1 | 1 | 1 | 1 | 1 | 1 | 0 | 1 | 1 | 1 | 1 | 1 |
| OBD116.197.199_4 | 1 | 1 | 1 | 1 | 1 | 0 | 0 | 1 | 1 | 0 | 1 | 1 |
| OBD116.197.199_8 | 0 | 0 | 0 | 1 | 1 | 0 | 0 | 0 | 1 | 0 | 1 | 1 |
| OBD116.197.199_16 | 0 | 0 | 0 | 0 | 0 | 0 | 0 | 0 | 0 | 0 | 0 | 1 |
| OBD116.197.199_32 | 0 | 0 | 0 | 0 | 0 | 0 | 0 | 0 | 0 | 0 | 0 | 0 |
| OBD116.197.199_64 | 0 | 0 | 0 | 0 | 0 | 0 | 0 | 0 | 0 | 0 | 0 | 0 |
| OBD116.261.263_2 | 1 | 0 | 1 | 0 | 0 | 0 | 1 | 0 | 0 | 0 | 0 | 0 |
| OBD116.261.263_4 | 0 | 0 | 1 | 0 | 0 | 0 | 0 | 0 | 0 | 0 | 0 | 0 |
| OBD116.261.263_8 | 0 | 0 | 0 | 0 | 0 | 0 | 0 | 0 | 0 | 0 | 0 | 0 |
| OBD116.261.263_16 | 0 | 0 | 0 | 0 | 0 | 0 | 0 | 0 | 0 | 0 | 0 | 0 |
| OBD116.261.263_32 | 0 | 0 | 0 | 0 | 0 | 0 | 0 | 0 | 0 | 0 | 0 | 0 |
| OBD116.261.263_64 | 0 | 0 | 0 | 0 | 0 | 0 | 0 | 0 | 0 | 0 | 0 | 0 |
| OBD116.301.303_2 | 0 | 1 | 0 | 0 | 0 | 0 | 1 | 0 | 1 | 1 | 1 | 1 |
| OBD116.301.303_4 | 0 | 0 | 0 | 0 | 0 | 0 | 0 | 0 | 1 | 1 | 0 | 1 |
| OBD116.301.303_8 | 0 | 0 | 0 | 0 | 0 | 0 | 0 | 1 | 1 | 0 | 0 | 1 |
| OBD116.301.303_16 | 0 | 0 | 0 | 0 | 0 | 0 | 0 | 0 | 1 | 0 | 0 | 1 |
| OBD116.301.303_32 | 0 | 0 | 0 | 0 | 0 | 0 | 0 | 0 | 0 | 0 | 0 | 0 |
| OBD116.301.303_64 | 0 | 0 | 0 | 0 | 0 | 0 | 0 | 0 | 0 | 0 | 0 | 0 |

| | State. 1 | | | | | | | | | | | |
|---|---|---|---|---|---|---|---|---|---|---|---|---|
| | BrCa | BrCa | Control | Control | Control | Control State. 2 | Control | Control | Control | Control | Control | Control |
| | 11217 | 11245 | 30003 | 30004 | 30011 | 30015 | 30016 | 30021 | 30024 | 30029 | 30030 | 30041 |
| OBD116.1.3_2 | 1 | 1 | 1 | 0 | 1 | 1 | 1 | 1 | 1 | 1 | 1 | 1 |
| OBD116.1.3_4 | 0 | 1 | 0 | 0 | 1 | 1 | 1 | 1 | 1 | 1 | 1 | 1 |
| OBD116.1.3_8 | 0 | 0 | 0 | 0 | 1 | 1 | 1 | 1 | 0 | 1 | 1 | 1 |
| OBD116.1.3_16 | 0 | 0 | 0 | 0 | 0 | 0 | 0 | 0 | 0 | 1 | 0 | 1 |
| OBD116.1.3_32 | 0 | 0 | 0 | 0 | 0 | 0 | 0 | 0 | 0 | 1 | 0 | 0 |
| OBD116.1.3_64 | 0 | 0 | 0 | 0 | 0 | 0 | 0 | 0 | 0 | 0 | 0 | 0 |
| OBD116.53.55_2 | 1 | 1 | 1 | 1 | 1 | 1 | 1 | 1 | 1 | 1 | 1 | 1 |
| OBD116.53.55_4 | 1 | 1 | 1 | 1 | 1 | 1 | 1 | 1 | 1 | 1 | 1 | 1 |
| OBD116.53.55_8 | 1 | 1 | 1 | 1 | 0 | 1 | 0 | 1 | 0 | 1 | 0 | 0 |
| OBD116.53.55_16 | 1 | 0 | 1 | 1 | 1 | 0 | 1 | 0 | 1 | 0 | 0 | 0 |
| OBD116.53.55_32 | 0 | 0 | 0 | 1 | 1 | 0 | 0 | 0 | 1 | 0 | 0 | 0 |
| OBD116.53.55_64 | 0 | 0 | 0 | 1 | 1 | 0 | 0 | 0 | 0 | 0 | 0 | 0 |
| OBD116.89.91_2 | 1 | 0 | 1 | 1 | 1 | 0 | 1 | 1 | 0 | 1 | 1 | 1 |

TABLE 18-continued

Binary analysis results using the top 13 markers. Darker results showing a p-value > 0.3. Lighter results show best dilution. OBD116 Gliwice results

| | | | | | | | | | | | | |
|---|---|---|---|---|---|---|---|---|---|---|---|---|
| OBD116.89.91_4 | 1 | 0 | 0 | 1 | 0 | 0 | 0 | 1 | 0 | 0 | 0 | 0 |
| OBD116.89.91_8 | 0 | 0 | 0 | 0 | 0 | 0 | 0 | 1 | 0 | 0 | 0 | 0 |
| OBD116.89.91_16 | 0 | 0 | 0 | 0 | 0 | 0 | 0 | 0 | 0 | 0 | 0 | 0 |
| OBD116.89.91_32 | 0 | 0 | 0 | 0 | 0 | 0 | 0 | 0 | 0 | 0 | 0 | 0 |
| OBD116.89.91_64 | 0 | 0 | 0 | 0 | 0 | 0 | 0 | 0 | 0 | 0 | 0 | 0 |
| OBD116.89.103_2 | 1 | 1 | 1 | 1 | 1 | 1 | 1 | 1 | 0 | 1 | 1 | 1 |
| OBD116.89.103_4 | 1 | 1 | 1 | 0 | 1 | 1 | 1 | 1 | 0 | 0 | 1 | 0 |
| OBD116.89.103_8 | 0 | 1 | 1 | 0 | 1 | 0 | 0 | 0 | 0 | 0 | 0 | 0 |
| OBD116.89.103_16 | 0 | 0 | 1 | 0 | 1 | 0 | 0 | 0 | 0 | 0 | 0 | 0 |
| OBD116.89.103_32 | 0 | 0 | 0 | 0 | 0 | 0 | 0 | 0 | 0 | 0 | 0 | 0 |
| OBD116.89.103_64 | 0 | 0 | 0 | 0 | 0 | 0 | 0 | 0 | 0 | 0 | 0 | 0 |
| OBD116.113.87_2 | 1 | 1 | 1 | 1 | 1 | 1 | 1 | 1 | 1 | 1 | 1 | 1 |
| OBD116.113.87_4 | 1 | 1 | 1 | 1 | 1 | 1 | 1 | 1 | 1 | 1 | 1 | 1 |
| OBD116.113.87_8 | 1 | 1 | 1 | 1 | 1 | 1 | 1 | 1 | 1 | 1 | 1 | 1 |
| OBD116.113.87_16 | 0 | 1 | 1 | 1 | 0 | 1 | 1 | 1 | 1 | 0 | 1 | 0 |
| OBD116.113.87_32 | 0 | 0 | 1 | 0 | 0 | 0 | 1 | 0 | 0 | 0 | 0 | 0 |
| OBD116.113.87_64 | 0 | 0 | 0 | 0 | 0 | 0 | 0 | 0 | 0 | 0 | 0 | 0 |
| OBD116.129.131_2 | 1 | 1 | 1 | 1 | 1 | 1 | 1 | 1 | 1 | 1 | 1 | 1 |
| OBD116.129.131_4 | 0 | 1 | 1 | 1 | 1 | 0 | 1 | 1 | 1 | 1 | 0 | 1 |
| OBD116.129.131_8 | 0 | 1 | 1 | 1 | 0 | 0 | 1 | 1 | 1 | 1 | 0 | 1 |
| OBD116.129.131_16 | 0 | 0 | 1 | 0 | 0 | 0 | 0 | 1 | 1 | 0 | 0 | 1 |
| OBD116.129.131_32 | 0 | 0 | 1 | 0 | 0 | 0 | 0 | 1 | 1 | 0 | 0 | 1 |
| OBD116.129.131_64 | 0 | 0 | 0 | 0 | 0 | 0 | 0 | 1 | 1 | 0 | 0 | 1 |
| OBD116.161.163_2 | 1 | 1 | 1 | 1 | 1 | 1 | 1 | 1 | 1 | 1 | 1 | 1 |
| OBD116.161.163_4 | 0 | 1 | 1 | 1 | 1 | 1 | 1 | 1 | 1 | 1 | 1 | 1 |
| OBD116.161.163_8 | 0 | 1 | 0 | 0 | 1 | 0 | 0 | 1 | 1 | 1 | 1 | 1 |
| OBD116.161.163_16 | 0 | 0 | 0 | 0 | 1 | 0 | 0 | 1 | 1 | 1 | 1 | 0 |
| OBD116.161.163_32 | 0 | 0 | 0 | 0 | 0 | 0 | 0 | 0 | 0 | 0 | 0 | 0 |
| OBD116.161.163_64 | 0 | 0 | 0 | 0 | 0 | 0 | 0 | 0 | 0 | 0 | 0 | 0 |
| OBD116.173.175_2 | 1 | 0 | 0 | 1 | 0 | 0 | 1 | 0 | 0 | 1 | 0 | 1 |
| OBD116.173.175_4 | 1 | 0 | 0 | 1 | 0 | 0 | 1 | 0 | 0 | 0 | 0 | 1 |
| OBD116.173.175_8 | 0 | 0 | 0 | 1 | 0 | 0 | 1 | 0 | 0 | 0 | 0 | 1 |
| OBD116.173.175_16 | 0 | 0 | 0 | 0 | 0 | 0 | 1 | 0 | 0 | 0 | 0 | 1 |
| OBD116.173.175_32 | 0 | 0 | 0 | 0 | 0 | 0 | 0 | 0 | 0 | 0 | 0 | 1 |
| OBD116.173.175_64 | 0 | 0 | 0 | 0 | 0 | 0 | 0 | 0 | 0 | 0 | 0 | 0 |
| OBD116.177.179_2 | 1 | 1 | 1 | 1 | 1 | 1 | 1 | 1 | 1 | 1 | 1 | 1 |
| OBD116.177.179_4 | 1 | 1 | 0 | 1 | 1 | 1 | 1 | 1 | 1 | 1 | 1 | 1 |
| OBD116.177.179_8 | 1 | 0 | 0 | 0 | 0 | 1 | 1 | 1 | 0 | 1 | 1 | 1 |
| OBD116.177.179_16 | 0 | 0 | 0 | 0 | 0 | 0 | 1 | 0 | 0 | 1 | 1 | 0 |
| OBD116.177.179_32 | 0 | 0 | 0 | 0 | 0 | 0 | 1 | 0 | 0 | 1 | 1 | 0 |
| OBD116.177.179_64 | 0 | 0 | 0 | 0 | 0 | 0 | 0 | 0 | 0 | 0 | 0 | 0 |
| OBD116.185.187_2 | 1 | 1 | 1 | 1 | 1 | 1 | 1 | 1 | 1 | 1 | 1 | 0 |
| OBD116.185.187_4 | 1 | 1 | 1 | 1 | 1 | 1 | 1 | 1 | 1 | 1 | 1 | 0 |
| OBD116.185.187_8 | 0 | 0 | 1 | 0 | 1 | 0 | 1 | 0 | 0 | 1 | 1 | 0 |
| OBD116.185.187_16 | 0 | 0 | 1 | 0 | 1 | 0 | 1 | 0 | 0 | 1 | 1 | 0 |
| OBD116.185.187_32 | 0 | 0 | 0 | 0 | 0 | 0 | 0 | 0 | 0 | 1 | 1 | 0 |
| OBD116.185.187_64 | 0 | 0 | 0 | 0 | 0 | 0 | 0 | 0 | 0 | 0 | 0 | 0 |
| OBD116.197.199_2 | 0 | 0 | 1 | 1 | 1 | 1 | 1 | 0 | 1 | 1 | 1 | 1 |
| OBD116.197.199_4 | 0 | 0 | 1 | 1 | 1 | 1 | 1 | 0 | 0 | 1 | 0 | 1 |
| OBD116.197.199_8 | 0 | 0 | 0 | 0 | 0 | 1 | 0 | 0 | 0 | 0 | 0 | 0 |
| OBD116.197.199_16 | 0 | 0 | 0 | 0 | 0 | 0 | 0 | 0 | 0 | 0 | 0 | 0 |
| OBD116.197.199_32 | 0 | 0 | 0 | 0 | 0 | 0 | 0 | 0 | 0 | 0 | 0 | 0 |
| OBD116.197.199_64 | 0 | 0 | 0 | 1 | 0 | 0 | 0 | 0 | 0 | 0 | 0 | 0 |
| OBD116.261.263_2 | 0 | 1 | 1 | 1 | 1 | 1 | 1 | 1 | 0 | 1 | 0 | 0 |
| OBD116.261.263_4 | 0 | 0 | 0 | 0 | 0 | 0 | 1 | 1 | 0 | 0 | 0 | 0 |
| OBD116.261.263_8 | 0 | 0 | 0 | 0 | 0 | 0 | 1 | 1 | 0 | 0 | 0 | 0 |
| OBD116.261.263_16 | 0 | 0 | 0 | 0 | 0 | 0 | 1 | 0 | 0 | 0 | 0 | 0 |
| OBD116.261.263_32 | 0 | 0 | 0 | 0 | 0 | 0 | 0 | 0 | 0 | 0 | 0 | 0 |
| OBD116.261.263_64 | 0 | 0 | 0 | 0 | 0 | 0 | 0 | 0 | 0 | 0 | 0 | 0 |
| OBD116.301.303_2 | 1 | 1 | 0 | 1 | 1 | 1 | 1 | 1 | 1 | 1 | 1 | 1 |
| OBD116.301.303_4 | 1 | 1 | 0 | 0 | 0 | 1 | 1 | 1 | 0 | 1 | 1 | 0 |
| OBD116.301.303_8 | 0 | 1 | 0 | 0 | 0 | 0 | 1 | 0 | 0 | 0 | 0 | 0 |
| OBD116.301.303_16 | 0 | 1 | 0 | 0 | 0 | 0 | 0 | 0 | 0 | 0 | 0 | 0 |
| OBD116.301.303_32 | 0 | 1 | 0 | 0 | 0 | 0 | 0 | 0 | 0 | 0 | 0 | 0 |
| OBD116.301.303_64 | 0 | 0 | 0 | 0 | 0 | 0 | 0 | 0 | 0 | 0 | 0 | 0 |

| | State. 1 | | | | | | | | | | | |
|---|---|---|---|---|---|---|---|---|---|---|---|---|
| | Control | Control | Control | Control | Control | Control | Control | Control | Control | Control | Control | Control |
| | | | | | | State. 2 | | | | | | |
| | 30049 | 30062 | 30066 | 30067 | 30069 | 30070 | 30075 | 30077 | 30079 | 30080 | 30082 | 30085 |
| OBD116.1.3_2 | 0 | 1 | 1 | 1 | 1 | 1 | 1 | 1 | 1 | 1 | 1 | 1 |
| OBD116.1.3_4 | 0 | 0 | 0 | 0 | 1 | 1 | 1 | 1 | 1 | 0 | 1 | 1 |
| OBD116.1.3_8 | 0 | 0 | 0 | 0 | 1 | 0 | 1 | 1 | 0 | 0 | 1 | 0 |
| OBD116.1.3_16 | 0 | 0 | 0 | 0 | 0 | 0 | 1 | 1 | 0 | 0 | 1 | 0 |

TABLE 18-continued

Binary analysis results using the top 13 markers. Darker results showing a p-value > 0.3. Lighter results show best dilution.
OBD116 Gliwice results

| | | | | | | | | | | | | |
|---|---|---|---|---|---|---|---|---|---|---|---|---|
| OBD116.1.3_32 | 0 | 0 | 0 | 0 | 0 | 0 | 1 | 0 | 0 | 0 | 0 | 0 |
| OBD116.1.3_64 | 0 | 0 | 0 | 0 | 0 | 0 | 1 | 0 | 0 | 0 | 0 | 0 |
| OBD116.53.55_2 | 1 | 1 | 1 | 1 | 1 | 1 | 1 | 1 | 1 | 1 | 1 | 1 |
| OBD116.53.55_4 | 0 | 1 | 1 | 1 | 1 | 1 | 1 | 1 | 1 | 1 | 1 | 1 |
| OBD116.53.55_8 | 0 | 0 | 1 | 1 | 1 | 0 | 0 | 1 | 1 | 0 | 0 | 1 |
| OBD116.53.55_16 | 0 | 0 | 0 | 1 | 1 | 0 | 0 | 0 | 1 | 0 | 0 | 1 |
| OBD116.53.55_32 | 0 | 0 | 0 | 1 | 0 | 0 | 0 | 0 | 0 | 0 | 0 | 1 |
| OBD116.53.55_64 | 0 | 0 | 0 | 0 | 0 | 0 | 0 | 0 | 0 | 0 | 0 | 0 |
| OBD116.89.91_2 | 1 | 0 | 1 | 0 | 1 | 0 | 1 | 0 | 1 | 1 | 0 | 0 |
| OBD116.89.91_4 | 0 | 0 | 1 | 0 | 1 | 0 | 0 | 0 | 1 | 0 | 0 | 0 |
| OBD116.89.91_8 | 0 | 0 | 1 | 0 | 0 | 0 | 0 | 0 | 0 | 0 | 0 | 0 |
| OBD116.89.91_16 | 0 | 0 | 0 | 0 | 0 | 0 | 0 | 0 | 0 | 0 | 0 | 0 |
| OBD116.89.91_32 | 0 | 0 | 0 | 0 | 0 | 0 | 0 | 0 | 0 | 0 | 0 | 0 |
| OBD116.89.91_64 | 0 | 0 | 0 | 0 | 0 | 0 | 0 | 0 | 0 | 0 | 0 | 0 |
| OBD116.89.103_2 | 0 | 0 | 1 | 1 | 1 | 1 | 0 | 1 | 1 | 1 | 1 | 1 |
| OBD116.89.103_4 | 0 | 0 | 1 | 0 | 1 | 1 | 0 | 1 | 1 | 1 | 1 | 1 |
| OBD116.89.103_8 | 0 | 0 | 1 | 0 | 1 | 1 | 0 | 0 | 0 | 1 | 1 | 0 |
| OBD116.89.103_16 | 0 | 0 | 1 | 0 | 0 | 1 | 0 | 0 | 0 | 0 | 0 | 0 |
| OBD116.89.103_32 | 0 | 0 | 0 | 0 | 0 | 0 | 0 | 0 | 0 | 0 | 0 | 0 |
| OBD116.89.103_64 | 0 | 0 | 0 | 0 | 0 | 0 | 0 | 0 | 0 | 0 | 0 | 0 |
| OBD116.113.87_2 | 1 | 1 | 1 | 1 | 1 | 1 | 1 | 1 | 1 | 1 | 1 | 1 |
| OBD116.113.87_4 | 1 | 1 | 1 | 1 | 1 | 1 | 1 | 1 | 1 | 1 | 1 | 1 |
| OBD116.113.87_8 | 1 | 0 | 1 | 1 | 1 | 0 | 1 | 1 | 0 | 1 | 0 | 1 |
| OBD116.113.87_16 | 0 | 0 | 1 | 1 | 1 | 0 | 1 | 1 | 0 | 1 | 0 | 0 |
| OBD116.113.87_32 | 0 | 0 | 1 | 1 | 0 | 0 | 1 | 0 | 0 | 0 | 0 | 0 |
| OBD116.113.87_64 | 0 | 0 | 0 | 0 | 0 | 0 | 0 | 0 | 0 | 0 | 0 | 0 |
| OBD116.129.131_2 | 1 | 0 | 1 | 1 | 1 | 1 | 1 | 1 | 1 | 1 | 1 | 1 |
| OBD116.129.131_4 | 1 | 0 | 1 | 1 | 1 | 1 | 1 | 1 | 1 | 1 | 1 | 1 |
| OBD116.129.131_8 | 1 | 0 | 0 | 0 | 1 | 1 | 0 | 0 | 1 | 0 | 0 | 0 |
| OBD116.129.131_16 | 0 | 0 | 0 | 0 | 0 | 1 | 0 | 0 | 1 | 0 | 0 | 0 |
| OBD116.129.131_32 | 0 | 0 | 0 | 0 | 0 | 0 | 0 | 0 | 0 | 0 | 0 | 0 |
| OBD116.129.131_64 | 0 | 0 | 0 | 0 | 0 | 0 | 0 | 0 | 0 | 0 | 0 | 0 |
| OBD116.161.163_2 | 1 | 1 | 0 | 1 | 1 | 1 | 1 | 1 | 1 | 1 | 1 | 1 |
| OBD116.161.163_4 | 0 | 0 | 0 | 1 | 1 | 1 | 1 | 1 | 1 | 1 | 1 | 1 |
| OBD116.161.163_8 | 0 | 0 | 0 | 1 | 1 | 1 | 1 | 0 | 1 | 0 | 0 | 0 |
| OBD116.161.163_16 | 0 | 0 | 0 | 1 | 1 | 0 | 1 | 0 | 0 | 0 | 0 | 0 |
| OBD116.161.163_32 | 0 | 0 | 0 | 1 | 0 | 0 | 1 | 0 | 0 | 0 | 0 | 0 |
| OBD116.161.163_64 | 0 | 0 | 0 | 1 | 0 | 0 | 0 | 0 | 0 | 0 | 0 | 0 |
| OBD116.173.175_2 | 1 | 0 | 0 | 1 | 0 | 1 | 1 | 0 | 0 | 0 | 0 | 0 |
| OBD116.173.175_4 | 1 | 0 | 0 | 1 | 0 | 1 | 0 | 0 | 0 | 0 | 0 | 0 |
| OBD116.173.175_8 | 0 | 0 | 0 | 1 | 0 | 1 | 0 | 0 | 0 | 0 | 0 | 0 |
| OBD116.173.175_16 | 0 | 0 | 0 | 0 | 0 | 1 | 0 | 0 | 0 | 0 | 0 | 0 |
| OBD116.173.175_32 | 0 | 0 | 0 | 0 | 0 | 0 | 0 | 0 | 0 | 0 | 0 | 0 |
| OBD116.173.175_64 | 0 | 0 | 0 | 0 | 0 | 0 | 0 | 0 | 0 | 0 | 0 | 0 |
| OBD116.177.179_2 | 1 | 1 | 1 | 1 | 1 | 1 | 1 | 1 | 1 | 1 | 1 | 1 |
| OBD116.177.179_4 | 0 | 1 | 1 | 1 | 1 | 1 | 0 | 1 | 1 | 1 | 1 | 1 |
| OBD116.177.179_8 | 0 | 1 | 0 | 1 | 0 | 1 | 0 | 1 | 0 | 1 | 0 | 0 |
| OBD116.177.179_16 | 0 | 0 | 0 | 1 | 0 | 1 | 0 | 0 | 0 | 0 | 0 | 0 |
| OBD116.177.179_32 | 0 | 0 | 0 | 0 | 0 | 1 | 0 | 0 | 0 | 0 | 0 | 0 |
| OBD116.177.179_64 | 0 | 0 | 0 | 0 | 0 | 0 | 0 | 0 | 0 | 0 | 0 | 0 |
| OBD116.185.187_2 | 1 | 1 | 0 | 0 | 1 | 1 | 0 | 1 | 1 | 1 | 1 | 1 |
| OBD116.185.187_4 | 1 | 0 | 0 | 0 | 1 | 0 | 0 | 1 | 1 | 1 | 1 | 1 |
| OBD116.185.187_8 | 1 | 0 | 0 | 0 | 1 | 0 | 0 | 1 | 0 | 1 | 0 | 1 |
| OBD116.185.187_16 | 1 | 0 | 0 | 0 | 1 | 0 | 0 | 0 | 0 | 0 | 0 | 0 |
| OBD116.185.187_32 | 0 | 0 | 0 | 0 | 1 | 0 | 0 | 0 | 0 | 0 | 0 | 0 |
| OBD116.185.187_64 | 0 | 0 | 0 | 0 | 0 | 0 | 0 | 0 | 0 | 0 | 0 | 0 |
| OBD116.197.199_2 | 0 | 0 | 1 | 1 | 0 | 1 | 1 | 1 | 1 | 1 | 1 | 1 |
| OBD116.197.199_4 | 0 | 0 | 1 | 1 | 0 | 0 | 1 | 0 | 1 | 1 | 1 | 1 |
| OBD116.197.199_8 | 0 | 0 | 0 | 1 | 0 | 0 | 0 | 0 | 0 | 0 | 0 | 0 |
| OBD116.197.199_16 | 0 | 0 | 0 | 0 | 0 | 0 | 0 | 0 | 0 | 0 | 0 | 0 |
| OBD116.197.199_32 | 0 | 0 | 0 | 0 | 0 | 0 | 0 | 0 | 0 | 0 | 0 | 0 |
| OBD116.197.199_64 | 0 | 0 | 0 | 0 | 0 | 0 | 0 | 0 | 0 | 0 | 0 | 0 |
| OBD116.261.263_2 | 1 | 0 | 0 | 0 | 1 | 0 | 0 | 0 | 1 | 0 | 1 | 0 |
| OBD116.261.263_4 | 0 | 0 | 0 | 0 | 0 | 0 | 0 | 0 | 0 | 0 | 1 | 0 |
| OBD116.261.263_8 | 0 | 0 | 0 | 0 | 0 | 0 | 0 | 0 | 0 | 0 | 0 | 0 |
| OBD116.261.263_16 | 0 | 0 | 0 | 0 | 0 | 0 | 0 | 0 | 0 | 0 | 0 | 0 |
| OBD116.261.263_32 | 0 | 0 | 0 | 0 | 0 | 0 | 0 | 0 | 0 | 0 | 0 | 0 |
| OBD116.261.263_64 | 0 | 0 | 0 | 0 | 0 | 0 | 0 | 0 | 0 | 0 | 0 | 0 |
| OBD116.301.303_2 | 0 | 1 | 1 | 1 | 1 | 1 | 1 | 1 | 1 | 1 | 1 | 0 |
| OBD116.301.303_4 | 0 | 0 | 0 | 1 | 0 | 1 | 1 | 1 | 0 | 0 | 0 | 0 |
| OBD116.301.303_8 | 0 | 0 | 0 | 1 | 0 | 0 | 0 | 0 | 0 | 0 | 0 | 0 |
| OBD116.301.303_16 | 0 | 0 | 0 | 0 | 0 | 0 | 0 | 0 | 0 | 0 | 0 | 0 |
| OBD116.301.303_32 | 0 | 0 | 0 | 0 | 0 | 0 | 0 | 0 | 0 | 0 | 0 | 0 |
| OBD116.301.303_64 | 0 | 0 | 0 | 0 | 0 | 0 | 0 | 0 | 0 | 0 | 0 | 0 |

Example 3

The work described in the Example concerns 13 nested markers which are typed by polymerase chain reaction (PCR) and qPCR (please see the Table 19 below). These markers were developed to differentiate patients with breast cancer from non-malignant individuals.

| No | 3C interactions identified by nested PCR |
|---|---|
| 1 | ATM_11_108118137_108126372_108155279_108156687_RF |
| 2 | CDC6_17_38421089_38423079_38451196_38457050_FF |
| 3 | CDC6_17_38421089_38423079_38467677_38474960_FR |
| 4 | FOXC1_6_1577253_1581989_1604206_1605973_FR |
| 5 | MAP3K1_5_56102259_56110500_56140227_56144076_FF |
| 6 | ME3_11_86300063_86304401_86420537_86426200_FR |
| 7 | MELK_9_36577630_36579243_36637050_36643005_RF |
| 8 | MSH3_5_80021913_80025030_80153948_80159012_RF |
| 9 | NF1_17_29477103_29483764_29651799_29657368_FF |
| 10 | SLC16A10_6_111441989_111447305_111492951_111498421_FR |
| 11 | SRD5A1_5_6634973_6639025_6667775_6669711_RF |
| 12 | TSPYL5_8_98276431_98282736_98316421_98318720_FF |
| 13 | VAV3_1_108148303_108158073_108220200_108227533_RF |

The overview of the qPCR development is:
nested PCR primers
single-step SYBR PCR (temperature gradient optimised)
gel purification
fluorometer measurement, sequencing, homology and genomic mapping check
hydrolysis probe optimisation
std curve testing with patient samples.

The work was to identify epigenetic changes that can be used to discriminate breast cancer patients from non-malignant material using small volume blood samples.

Blood samples from the Asian cohort, which includes blood samples from the original test evaluation work, were to be used to validate the qPCR probe assays according to the MIQE (Minimum Information for the Publication of Quantitative Real-Time PCR Experiments) guidelines.

Each marker qPCR probe and individual detection assay was developed and tested across a temperature gradient on the representative pools of samples (4×4) to meet the following MIQE—compliant criteria for quality detection:
1. Specificity: the predicted PCR amplicon was validated with sequencing.
2. Linear standard curve ($R^2$>0.98).
3. Efficiency (E), E>90%.
4. Genomic non-specific cross reaction controls used with all assays.

The requirement was that at least 70% of the nested marker would be developed for detection using hydrolysis probes with the performance of the assays meeting the four criteria described above.

EpiSwitch™ qPCR Assay Development Data

CCS biomarkers were confirmed by nested PCR. All development PCRs were made using the QIAgility™. 3C sample templates at 10 ng per well were screened using a single step temperature gradient PCR and SYBR based detection, with concentration matched negative controls. 10 interactions were identified and sequenced. The sequencing data was submitted to ENSEMBL™ and the genomic location of each of the predicted 3C interactions was confirmed using ENSEMBL™ Blat™ and the Needleman-Wunsch algorithm. The hydrolysis probes were designed for the junction region of each confirmed interaction and optimized by temperature gradient. All samples were positive for a stable independent 3C interaction (MMP1). All assays were tested with n=8 patient samples (4=breast cancer, 4=non-malignant), standard curves and concentration matched negative controls.

The primer data from the development process including the original sequencing electropherograms and is presented in a clear easy to check format for each qPCR assay. The assays are in alphabetical order. Standards at $10^6$ copies were used as a positive control during the probe temperature gradient optimisation. Patient samples were tested with curves between 1-$10^6$ copies. Any variations in analysis of the standard curves during the patient screening are noted for each assay described in the report.

EpiSwitch™ Summary of qPCR Assays
ATM_11_108118137_108126372_108155279_1 08156687_RF i. The 3C template amplified at single step.
ii. Lab Chip image. Comments: the amplicon is visible in paraformaldehyde fixed samples only (10 ng of template). The single-step PCR product is of expected size, 472 bp.
iii. ENSEMBL™ BLAT™ (FIG. 1) after direct sequencing of the sample PCR product. Comments: the good quality sequencing (forward and reverse primers) has 100% homology to the predicted 3C interaction.
iv. The performance of the quantitative PCR assay standards. The standard curve is linear from $10^2$-$10^6$ copies. $R^2$=0.996.
v. One amplicon doubles to produce two=100% efficient. Efficiency of assay=91.7% (>90% MIQE guideline).
vi. The assay shows profound copy number differences (Table 20) between the patient (n=8) subsets (C01-C12=breast cancer, D01 to D12=non-malignant). SQ=starting quantity, copies in 20 ng of template. NaN=0 copies.

ENSEMBL™ BLATT™ after Direct Sequencing of the Sample PCR Product.

This PCR product was sequenced and mapped to chromosome 11q22.3. The two 3C fragments are ligated at Taq I (TCGA). Above the sequence traces are the ENSEMBL™ BLAT™ mapping data (sequence homologies in red).

TABLE 19

| Well | Fluor | Target | Content | Sample | Cq | Starting Quantity (SQ) |
|---|---|---|---|---|---|---|
| C01 | FAM™ | 032B 20 ng | Unkn | 032B 20 ng | 41.04 | 0.42 |
| C02 | FAM™ | 032B 20 ng | Unkn | 032B 20 ng | 39.89 | 0.89 |
| C03 | FAM™ | 032B 20 ng | Unkn | 032B 20 ng | 37.82 | 3.42 |
| C04 | FAM™ | 063B 20 ng | Unkn | 063B 20 ng | 37.92 | 3.19 |
| C05 | FAM™ | 063B 20 ng | Unkn | 063B 20 ng | 36.8 | 6.64 |
| C06 | FAM™ | 063B 20 ng | Unkn | 063B 20 ng | 36.78 | 6.72 |

TABLE 19-continued

| Well | Fluor | Target | Content | Sample | Cq | Starting Quantity (SQ) |
|---|---|---|---|---|---|---|
| C07 | FAM™ | 065A 20 ng | Unkn | 065A 20 ng | 37.5 | 4.21 |
| C08 | FAM™ | 065A 20 ng | Unkn | 065A 20 ng | 37.23 | 5.01 |
| C09 | FAM™ | 065A 20 ng | Unkn | 065A 20 ng | 37.33 | 4.68 |
| C10 | FAM™ | 124B 20 ng | Unkn | 124B 20 ng | 37.21 | 5.07 |
| C11 | FAM™ | 124B 20 ng | Unkn | 124B 20 ng | 37.33 | 4.69 |
| C12 | FAM™ | 124B 20 ng | Unkn | 124B 20 ng | NaN | NaN |
| D01 | FAM™ | 005B 20 ng | Unkn | 005B 20 ng | 38.6 | 2.06 |
| D02 | FAM™ | 005B 20 ng | Unkn | 005B 20 ng | NaN | NaN |
| D03 | FAM™ | 005B 20 ng | Unkn | 005B 20 ng | 37.12 | 5.4 |
| D04 | FAM™ | 007B 20 ng | Unkn | 007B 20 ng | NaN | NaN |
| D05 | FAM™ | 007B 20 ng | Unkn | 007B 20 ng | NaN | NaN |
| D06 | FAM™ | 007B 20 ng | Unkn | 007B 20 ng | NaN | NaN |
| D07 | FAM™ | 17B 20 ng | Unkn | 17B 20 ng | 37.98 | 3.07 |
| D08 | FAM™ | 17B 20 ng | Unkn | 17B 20 ng | NaN | NaN |
| D09 | FAM™ | 17B 20 ng | Unkn | 17B 20 ng | 38.63 | 2.01 |
| D10 | FAM™ | 022B 20 ng | Unkn | 022B 20 ng | NaN | NaN |
| D11 | FAM™ | 022B 20 ng | Unkn | 022B 20 ng | NaN | NaN |
| D12 | FAM™ | 022B 20 ng | Unkn | 022B 20 ng | NaN | NaN |
| E07 | FAM™ | Gen Neg Ctrl | Neg Ctrl | Gen Neg Ctrl | NaN | NaN |
| E08 | FAM™ | Gen Neg Ctrl | Neg Ctrl | Gen Neg Ctrl | NaN | NaN |
| E09 | FAM™ | No fix 20 ng | Neg Ctrl | No fix 20 ng | NaN | NaN |
| E10 | FAM™ | No fix 20 ng | Neg Ctrl | No fix 20 ng | NaN | NaN |
| E11 | FAM™ | ATE Ext | NTC | ATE Ext | NaN | NaN |
| E12 | FAM™ | ATE Ext | NTC | ATE Ext | NaN | NaN |
| F01 | FAM™ | ATE Post-PCR | NTC | ATE Post-PCR | NaN | NaN |
| F02 | FAM™ | ATE Post-PCR | NTC | ATE Post-PCR | NaN | NaN |
| F03 | FAM™ | Water | NTC | Water | NaN | NaN |
| F04 | FAM™ | Water | NTC | Water | NaN | NaN = 0 copies |

CDC6_17_38421089_38423079_38451196_38457050_FF
  i. The 3C template amplified at single step.
  ii. Lab Chip™ image. Comments: the band is visible in paraformaldehyde fixed samples only (10 ng of template). Single-step PCR product of expected size, 428 bp.
  iii. ENSEMBL™ BLAT™ after direct sequencing of the sample PCR product. Comments: the good quality sequencing (forward and reverse primers) has 100% homology to the predicted 3C interaction.
  iv. The performance of the quantitative PCR assay standards. The standard curve is linear from $10^1$-$10^6$ copies. $R^2$=0.99.
  v. One amplicon doubles to produce two=100% efficient. Efficiency 90.7% (>90% MIQE guideline).
  vi. The assay shows profound copy number differences (Table 2) between the patient (n=8) subsets (C01-C12=breast cancer, D01-D12=non-malignant). SQ=starting quantity, copies in 20 ng of template. NaN=0 copies.

TABLE 20

| Well | Fluor | Target | Content | Sample | Cq | Starting Quantity (SQ) |
|---|---|---|---|---|---|---|
| C01 | FAM™ | 032B 20 ng | Unkn | 032B 20 ng | 39.63 | 1.93 |
| C02 | FAM™ | 032B 20 ng | Unkn | 032B 20 ng | 38.14 | 5.05 |
| C03 | FAM™ | 032B 20 ng | Unkn | 032B 20 ng | 38.80 | 3.30 |
| C04 | FAM™ | 063B 20 ng | Unkn | 063B 20 ng | 37.18 | 9.40 |
| C05 | FAM™ | 063B 20 ng | Unkn | 063B 20 ng | 37.35 | 8.40 |
| C06 | FAM™ | 063B 20 ng | Unkn | 063B 20 ng | 37.41 | 8.10 |
| C07 | FAM™ | 065A 20 ng | Unkn | 065A 20 ng | 36.32 | 16.34 |
| C08 | FAM™ | 065A 20 ng | Unkn | 065A 20 ng | 36.36 | 15.92 |
| C09 | FAM™ | 065A 20 ng | Unkn | 065A 20 ng | 36.75 | 12.41 |
| C10 | FAM™ | 124B 20 ng | Unkn | 124B 20 ng | 34.76 | 44.71 |
| C11 | FAM™ | 124B 20 ng | Unkn | 124B 20 ng | NaN | NaN |
| C12 | FAM™ | 124B 20 ng | Unkn | 124B 20 ng | NaN | NaN |
| D01 | FAM™ | 005B 20 ng | Unkn | 005B 20 ng | 36.24 | 17.24 |
| D02 | FAM™ | 005B 20 ng | Unkn | 005B 20 ng | 36.14 | 18.42 |
| D03 | FAM™ | 005B 20 ng | Unkn | 005B 20 ng | 35.53 | 27.29 |
| D04 | FAM™ | 007B 20 ng | Unkn | 007B 20 ng | 36.57 | 13.97 |
| D05 | FAM™ | 007B 20 ng | Unkn | 007B 20 ng | 37.49 | 7.68 |
| D06 | FAM™ | 007B 20 ng | Unkn | 007B 20 ng | 36.60 | 13.68 |
| D07 | FAM™ | 17B 20 ng | Unkn | 17B 20 ng | 36.01 | 19.97 |
| D08 | FAM™ | 17B 20 ng | Unkn | 17B 20 ng | 37.43 | 8.01 |
| D09 | FAM™ | 17B 20 ng | Unkn | 17B 20 ng | 36.75 | 12.38 |
| D10 | FAM™ | 022B 20 ng | Unkn | 022B 20 ng | NaN | NaN |
| D11 | FAM™ | 022B 20 ng | Unkn | 022B 20 ng | 39.06 | 2.80 |
| D12 | FAM™ | 022B 20 ng | Unkn | 022B 20 ng | 36.75 | 12.41 |
| E07 | FAM™ | Gen Neg Ctrl | Neg Ctrl | Gen Neg Ctrl | NaN | NaN |
| E08 | FAM™ | Gen Neg Ctrl | Neg Ctrl | Gen Neg Ctrl | NaN | NaN |
| E09 | FAM™ | No fix 20 ng | Neg Ctrl | No fix 20 ng | NaN | NaN |
| E10 | FAM™ | No fix 20 ng | Neg Ctrl | No fix 20 ng | NaN | NaN |
| E11 | FAM™ | ATE Ext | NTC | ATE Ext | NaN | NaN |
| E12 | FAM™ | ATE Ext | NTC | ATE Ext | NaN | NaN |
| F01 | FAM™ | ATE Post-PCR | NTC | ATE Post-PCR | NaN | NaN |
| F02 | FAM™ | ATE Post-PCR | NTC | ATE Post-PCR | NaN | NaN |
| F03 | FAM™ | Water | NTC | Water | NaN | NaN |
| F04 | FAM™ | Water | NTC | Water | NaN | NaN = 0 copies |

FOXC1_61577253158198916042061605973F R.
  i. The 3C template amplified at single step.
  ii. Lab Chip' image. Comments: the band is visible in paraformaldehyde fixed samples only (10 ng of template). Single-step PCR product of expected size, 208 bp.
  iii. ENSEMBL™ BLAT™ after direct sequencing of the sample PCR product. Comments: the good quality sequencing (forward and reverse primers) has 100% homology to the predicted 3C interaction.
  iv. The performance of the quantitative PCR assay standards. The standard curve is linear from $10^1$-$10^6$ copies. $R^2$=0.992.
  v. One amplicon doubles to produce two=100% efficient. The efficiency of this assay was 101.6%, (>90% MIQE guideline).
  vi. The assay shows profound copy number differences (Table 21) between the patient (n=8) subsets (C01-C12=breast cancer, D01-D12=non-malignant). SQ=starting quantity, copies in 20 ng of template. NaN=0 copies.

ENSEMBL™ BLAT™ after direct sequencing of the sample PCR product.

The Lab Chip™ image of the FOXC1 well B7 208 bp single step amplification (inner primers). This PCR product was sequenced and mapped to chromosome 6p.

TABLE 21

| Well | Fluor | Target | Content | Sample | Cq | Starting Quantity (SQ) |
|---|---|---|---|---|---|---|
| C01 | FAM™ | 032B 20 ng | Unkn | 032B 20 ng | 36.16 | 3.05 |
| C02 | FAM™ | 032B 20 ng | Unkn | 032B 20 ng | NaN | NaN |
| C03 | FAM™ | 032B 20 ng | Unkn | 032B 20 ng | 35.80 | 3.92 |
| C04 | FAM™ | 063B 20 ng | Unkn | 063B 20 ng | 38.13 | 0.77 |
| C05 | FAM™ | 063B 20 ng | Unkn | 063B 20 ng | NaN | NaN |
| C06 | FAM™ | 063B 20 ng | Unkn | 063B 20 ng | 37.49 | 1.19 |

TABLE 21-continued

| Well | Fluor | Target | Content | Sample | Cq | Starting Quantity (SQ) |
|---|---|---|---|---|---|---|
| C07 | FAM ™ | 065A 20 ng | Unkn | 065A 20 ng | 33.48 | 19.86 |
| C08 | FAM ™ | 065A 20 ng | Unkn | 065A 20 ng | 35.45 | 4.99 |
| C09 | FAM ™ | 065A 20 ng | Unkn | 065A 20 ng | 37.30 | 1.36 |
| C10 | FAM ™ | 142 20 ng | Unkn | 142 20 ng | 34.89 | 7.39 |
| C11 | FAM ™ | 142 20 ng | Unkn | 142 20 ng | 34.05 | 13.35 |
| C12 | FAM ™ | 142 20 ng | Unkn | 142 20 ng | NaN | NaN |
| D01 | FAM ™ | 005B 20 ng | Unkn | 005B 20 ng | 34.05 | 13.38 |
| D02 | FAM ™ | 005B 20 ng | Unkn | 005B 20 ng | 33.72 | 16.81 |
| D03 | FAM ™ | 005B 20 ng | Unkn | 005B 20 ng | 33.52 | 19.37 |
| D04 | FAM ™ | 007B 20 ng | Unkn | 007B 20 ng | 34.87 | 7.54 |
| D05 | FAM ™ | 007B 20 ng | Unkn | 007B 20 ng | 35.17 | 6.08 |
| D06 | FAM ™ | 007B 20 ng | Unkn | 007B 20 ng | 33.62 | 18.02 |
| D07 | FAM ™ | 17B 20 ng | Unkn | 17B 20 ng | 33.57 | 18.72 |
| D08 | FAM ™ | 17B 20 ng | Unkn | 17B 20 ng | 35.18 | 6.04 |
| D09 | FAM ™ | 17B 20 ng | Unkn | 17B 20 ng | 34.50 | 9.71 |
| D10 | FAM ™ | 022B 20 ng | Unkn | 022B 20 ng | 35.58 | 4.57 |
| D11 | FAM ™ | 022B 20 ng | Unkn | 022B 20 ng | 33.97 | 14.13 |
| D12 | FAM ™ | 022B 20 ng | Unkn | 022B 20 ng | 34.97 | 7.00 |
| E07 | FAM ™ | Gen Neg Ctrl | Neg Ctrl | Gen Neg Ctrl | NaN | NaN |
| E08 | FAM ™ | Gen Neg Ctrl | Neg Ctrl | Gen Neg Ctrl | NaN | NaN |
| E09 | FAM ™ | No fix 20 ng | Neg Ctrl | No fix 20 ng | NaN | NaN |
| E10 | FAM ™ | No fix 20 ng | Neg Ctrl | No fix 20 ng | NaN | NaN |
| E11 | FAM ™ | ATE Ext | NTC | ATE Ext | NaN | NaN |
| E12 | FAM ™ | ATE Ext | NTC | ATE Ext | NaN | NaN |
| F01 | FAM ™ | ATE Post-PCR | NTC | ATE Post-PCR | NaN | NaN |
| F02 | FAM ™ | ATE Post-PCR | NTC | ATE Post-PCR | NaN | NaN |
| F03 | FAM ™ | Water | NTC | Water | NaN | NaN |
| F04 | FAM ™ | Water | NTC | Water | NaN | NaN = 0 copies |

MAP3K1_5_56102259_56110500_56140227_56144076_FF
  i. The 3C template amplified at single step.
  ii. Lab Chip™ image. Comments: the amplicon is visible in paraformaldehyde fixed samples only (10 ng of template). The single-step PCR product is of expected size, 495 bp.
  iii. ENSEMBL™ BLAT™ after direct sequencing of the sample PCR product. Comments: the good quality sequencing (forward and reverse primers) has 100% homology to the predicted 3C interaction.
  iv. The performance of the quantitative PCR assay standards. The standard curve is linear from $10^2$-$10^6$ copies. $R^2$=0.999.
  v. One amplicon doubles to produce two=100% efficient. Efficiency of assay=91.9% (>90% MIQE guideline).
  vi. Copy number differences (Table 22) between the patient (n=8) subsets (C01-C12=breast cancer, D01-D12=non-malignant). SQ=starting quantity, copies in 20 ng of template. NaN=0 copies.

ENSEMBL™ BLAT™ after direct sequencing of the sample PCR product.

This PCR product was sequenced and mapped to chromosome 5q11.2.

TABLE 22

| Well | Fluor | Target | Content | Sample | Cq | Starting Quantity (SQ) |
|---|---|---|---|---|---|---|
| C01 | FAM ™ | 032B 20 ng | Unkn | 032B 20 ng | NaN | NaN |
| C02 | FAM ™ | 032B 20 ng | Unkn | 032B 20 ng | 38.94 | 3.68 |
| C03 | FAM ™ | 032B 20 ng | Unkn | 032B 20 ng | 40.24 | 1.58 |
| C04 | FAM ™ | 063B 20 ng | Unkn | 063B 20 ng | 38.22 | 5.87 |
| C05 | FAM ™ | 063B 20 ng | Unkn | 063B 20 ng | 37.85 | 7.48 |
| C06 | FAM ™ | 063B 20 ng | Unkn | 063B 20 ng | 38.05 | 6.58 |
| C07 | FAM ™ | 065A 20 ng | Unkn | 065A 20 ng | 38.01 | 6.75 |
| C08 | FAM ™ | 065A 20 ng | Unkn | 065A 20 ng | 37.72 | 8.14 |
| C09 | FAM ™ | 065A 20 ng | Unkn | 065A 20 ng | 39.02 | 3.50 |
| C10 | FAM ™ | 142 20 ng | Unkn | 124B 20 ng | 37.40 | 10.02 |
| C11 | FAM ™ | 142 20 ng | Unkn | 124B 20 ng | 38.74 | 4.19 |
| C12 | FAM ™ | 142 20 ng | Unkn | 124B 20 ng | 39.94 | 1.92 |
| D01 | FAM ™ | 005B 20 ng | Unkn | 005B 20 ng | 42.07 | 0.48 |
| D02 | FAM ™ | 005B 20 ng | Unkn | 005B 20 ng | 37.03 | 12.77 |
| D03 | FAM ™ | 005B 20 ng | Unkn | 005B 20 ng | 38.12 | 6.29 |
| D04 | FAM ™ | 007B 20 ng | Unkn | 007B 20 ng | 39.94 | 1.92 |
| D05 | FAM ™ | 007B 20 ng | Unkn | 007B 20 ng | 39.27 | 2.97 |
| D06 | FAM ™ | 007B 20 ng | Unkn | 007B 20 ng | 37.04 | 12.66 |
| D07 | FAM ™ | 17B 20 ng | Unkn | 17B 20 ng | 36.62 | 16.75 |
| D08 | FAM ™ | 17B 20 ng | Unkn | 17B 20 ng | 38.11 | 6.33 |
| D09 | FAM ™ | 17B 20 ng | Unkn | 17B 20 ng | 38.06 | 6.54 |
| D10 | FAM ™ | 022B 20 ng | Unkn | 022B 20 ng | 37.38 | 10.18 |
| D11 | FAM ™ | 022B 20 ng | Unkn | 022B 20 ng | 38.85 | 3.90 |
| D12 | FAM ™ | 022B 20 ng | Unkn | 022B 20 ng | NaN | NaN |
| E07 | FAM ™ | Gen Neg Ctrl | Neg Ctrl | Gen Neg Ctrl | NaN | NaN |
| E08 | FAM ™ | Gen Neg Ctrl | Neg Ctrl | Gen Neg Ctrl | NaN | NaN |
| E09 | FAM ™ | No fix 20 ng | Neg Ctrl | No fix 20 ng | NaN | NaN |
| E10 | FAM ™ | No fix 20 ng | Neg Ctrl | No fix 20 ng | NaN | NaN |
| E11 | FAM ™ | ATE Ext | NTC | ATE Ext | NaN | NaN |
| E12 | FAM ™ | ATE Ext | NTC | ATE Ext | NaN | NaN |
| F01 | FAM ™ | ATE Post-PCR | NTC | ATE Post-PCR | NaN | NaN |
| F02 | FAM ™ | ATE Post-PCR | NTC | ATE Post-PCR | NaN | NaN |
| F03 | FAM ™ | Water | NTC | Water | NaN | NaN |
| F04 | FAM ™ | Water | NTC | Water | NaN | NaN = 0 copies |

ME3_11_86300063_86304401_86420537_86426200_FR
  i. The 3C template amplified at single step.
  ii. Lab Chip™ image. Comments: the amplicon is visible in paraformaldehyde fixed samples only (10 ng of template). The single-step PCR product is of expected size, 291 bp.
  iii. ENSEMBL™ BLAT™ after direct sequencing of the sample PCR product. Comments: the good quality sequencing (forward and reverse primers) has 100% homology to the predicted 3C interaction.
  iv. The performance of the quantitative PCR assay standards. The standard curve is linear from 10¹ $10^6$ copies. $R^2$=0.998.
  v. One amplicon doubles to produce two=100% efficient. Efficiency of assay=96.8% (>90% MIQE guideline).
  vi. The assay differences (Table 5) between the patient (n=8) subsets (C01-C12=breast cancer, D01-D12=non-malignant). SQ=starting quantity, copies in 20 ng of template. NaN=0 copies.

TABLE 23

| Well | Fluor | Target | Content | Sample | Cq | Starting Quantity (SQ) |
|---|---|---|---|---|---|---|
| C01 | FAM ™ | 032B 20 ng | Unkn | 032B 20 ng | NaN | NaN |
| C02 | FAM ™ | 032B 20 ng | Unkn | 032B 20 ng | NaN | NaN |
| C03 | FAM ™ | 032B 20 ng | Unkn | 032B 20 ng | 40.29 | 0.63 |
| C04 | FAM ™ | 063B 20 ng | Unkn | 063B 20 ng | 40.51 | 0.54 |
| C05 | FAM ™ | 063B 20 ng | Unkn | 063B 20 ng | 41.88 | 0.21 |
| C06 | FAM ™ | 063B 20 ng | Unkn | 063B 20 ng | 41.21 | 0.34 |
| C07 | FAM ™ | 065A 20 ng | Unkn | 065A 20 ng | 40.75 | 0.46 |
| C08 | FAM ™ | 065A 20 ng | Unkn | 065A 20 ng | 41.84 | 0.22 |
| C09 | FAM ™ | 065A 20 ng | Unkn | 065A 20 ng | 41.59 | 0.26 |
| C10 | FAM ™ | 142 20 ng | Unkn | 142 20 ng | NaN | NaN |
| C11 | FAM ™ | 142 20 ng | Unkn | 142 20 ng | NaN | NaN |
| C12 | FAM ™ | 142 20 ng | Unkn | 142 20 ng | NaN | NaN |

TABLE 23-continued

| Well | Fluor | Target | Content | Sample | Cq | Starting Quantity (SQ) |
|---|---|---|---|---|---|---|
| D01 | FAM™ | 005B 20 ng | Unkn | 005B 20 ng | 42.62 | 0.13 |
| D02 | FAM™ | 005B 20 ng | Unkn | 005B 20 ng | 39.44 | 1.11 |
| D03 | FAM™ | 005B 20 ng | Unkn | 005B 20 ng | NaN | NaN |
| D04 | FAM™ | 007B 20 ng | Unkn | 007B 20 ng | NaN | NaN |
| D05 | FAM™ | 007B 20 ng | Unkn | 007B 20 ng | NaN | NaN |
| D06 | FAM™ | 007B 20 ng | Unkn | 007B 20 ng | 43.48 | 0.07 |
| D07 | FAM™ | 17B 20 ng | Unkn | 17B 20 ng | NaN | NaN |
| D08 | FAM™ | 17B 20 ng | Unkn | 17B 20 ng | 41.34 | 0.31 |
| D09 | FAM™ | 17B 20 ng | Unkn | 17B 20 ng | 40.22 | 0.66 |
| D10 | FAM™ | 022B 20 ng | Unkn | 022B 20 ng | NaN | NaN |
| D11 | FAM™ | 022B 20 ng | Unkn | 022B 20 ng | NaN | NaN |
| D12 | FAM™ | 022B 20 ng | Unkn | 022B 20 ng | NaN | NaN |
| E07 | FAM™ | Gen Neg Ctrl | Neg Ctrl | Gen Neg Ctrl | NaN | NaN |
| E08 | FAM™ | Gen Neg Ctrl | Neg Ctrl | Gen Neg Ctrl | NaN | NaN |
| E09 | FAM™ | No fix 20 ng | Neg Ctrl | No fix 20 ng | NaN | NaN |
| E10 | FAM™ | No fix 20 ng | Neg Ctrl | No fix 20 ng | NaN | NaN |
| E11 | FAM™ | ATE Ext | NTC | ATE Ext | NaN | NaN |
| E12 | FAM™ | ATE Ext | NTC | ATE Ext | NaN | NaN |
| F01 | FAM™ | ATE Post-PCR | NTC | ATE Post-PCR | NaN | NaN |
| F02 | FAM™ | ATE Post-PCR | NTC | ATE Post-PCR | NaN | NaN = 0 copies |

MELK_9_36577630_36579243_36637050_36643005_RF
  i. The 3C template amplified at single step.
  ii. Lab Chip™ image. Comments: the amplicon is visible in paraformaldehyde fixed samples only (10 ng of template). The single-step PCR product is of expected size, 265 bp.
  iii. ENSEMBL™ BLAT™ after direct sequencing of the sample PCR product. Comments: the good quality sequencing (forward and reverse primers) has 100% homology to the predicted 3C interaction.
  iv. The performance of the quantitative PCR assay standards. The standard curve is linear from 10'-10$^6$ copies. $R^2=0.995$.
  v. One amplicon doubles to produce two=100% efficient. Efficiency of assay=91.3% (>90% MIQE guideline).
  vi. The assay differences (Table 24) between the patient (n=8) subsets (C01-C12=breast cancer, D01-D12=non-malignant). SQ=starting quantity, copies in 20 ng of template. NaN=0 copies.
ENSEMBL™ BLA™ after Direct Sequencing of the Sample PCR Product.
This PCR product was sequenced and mapped to chromosome 9p13.2.

TABLE 24

| Well | Fluor | Target | Content | Sample | Cq | Starting Quantity (SQ) |
|---|---|---|---|---|---|---|
| C01 | FAM™ | 032B 20 ng | Unkn | 032B 20 ng | NaN | NaN |
| C02 | FAM™ | 032B 20 ng | Unkn | 032B 20 ng | 38.94 | 3.68 |
| C03 | FAM™ | 032B 20 ng | Unkn | 032B 20 ng | 40.24 | 1.58 |
| C04 | FAM™ | 063B 20 ng | Unkn | 063B 20 ng | 38.22 | 5.87 |
| C05 | FAM™ | 063B 20 ng | Unkn | 063B 20 ng | 37.85 | 7.48 |
| C06 | FAM™ | 063B 20 ng | Unkn | 063B 20 ng | 38.05 | 6.58 |
| C07 | FAM™ | 065A 20 ng | Unkn | 065A 20 ng | 38.01 | 6.75 |
| C08 | FAM™ | 065A 20 ng | Unkn | 065A 20 ng | 37.72 | 8.14 |
| C09 | FAM™ | 065A 20 ng | Unkn | 065A 20 ng | 39.02 | 3.5 |
| C10 | FAM™ | 142 20 ng | Unkn | 124B 20 ng | 37.4 | 10.02 |
| C11 | FAM™ | 142 20 ng | Unkn | 124B 20 ng | 38.74 | 4.19 |
| C12 | FAM™ | 142 20 ng | Unkn | 124B 20 ng | 39.94 | 1.92 |

TABLE 24-continued

| Well | Fluor | Target | Content | Sample | Cq | Starting Quantity (SQ) |
|---|---|---|---|---|---|---|
| D01 | FAM™ | 005B 20 ng | Unkn | 005B 20 ng | 42.07 | 0.48 |
| D02 | FAM™ | 005B 20 ng | Unkn | 005B 20 ng | 37.03 | 12.77 |
| D03 | FAM™ | 005B 20 ng | Unkn | 005B 20 ng | 38.12 | 6.29 |
| D04 | FAM™ | 007B 20 ng | Unkn | 007B 20 ng | 39.94 | 1.92 |
| D05 | FAM™ | 007B 20 ng | Unkn | 007B 20 ng | 39.27 | 2.97 |
| D06 | FAM™ | 007B 20 ng | Unkn | 007B 20 ng | 37.04 | 12.66 |
| D07 | FAM™ | 17B 20 ng | Unkn | 17B 20 ng | 36.62 | 16.75 |
| D08 | FAM™ | 17B 20 ng | Unkn | 17B 20 ng | 38.11 | 6.33 |
| D09 | FAM™ | 17B 20 ng | Unkn | 17B 20 ng | 38.06 | 6.54 |
| D10 | FAM™ | 022B 20 ng | Unkn | 022B 20 ng | 37.38 | 10.18 |
| D11 | FAM™ | 022B 20 ng | Unkn | 022B 20 ng | 38.85 | 3.9 |
| D12 | FAM™ | 022B 20 ng | Unkn | 022B 20 ng | NaN | NaN |
| E07 | FAM™ | Gen Neg Ctrl | Neg Ctrl | Gen Neg Ctrl | NaN | NaN |
| E08 | FAM™ | Gen Neg Ctrl | Neg Ctrl | Gen Neg Ctrl | NaN | NaN |
| E09 | FAM™ | No fix 20 ng | Neg Ctrl | No fix 20 ng | NaN | NaN |
| E10 | FAM™ | No fix 20 ng | Neg Ctrl | No fix 20 ng | NaN | NaN |
| E11 | FAM™ | ATE Ext | NTC | ATE Ext | NaN | NaN |
| E12 | FAM™ | ATE Ext | NTC | ATE Ext | NaN | NaN |
| F01 | FAM™ | ATE Post-PCR | NTC | ATE Post-PCR | NaN | NaN |
| F02 | FAM™ | ATE Post-PCR | NTC | ATE Post-PCR | NaN | NaN |
| F03 | FAM™ | Water | NTC | Water | NaN | NaN |
| F04 | FAM™ | Water | NTC | Water | NaN | NaN = 0 copies |

MSH3_5_80021913_80025030_80153948_80159012_RF
  i. The 3C template amplified at single step.
  ii. Lab Chip™ image. Comments: the amplicon is visible in paraformaldehyde fixed samples only (10 ng of template). The single-step PCR product is of expected size, 207 bp.
  iii. ENSEMBL™ SLA™ after direct sequencing of the sample PCR product. Comments: the good quality sequencing (forward and reverse primers) has 100% homology to the predicted 3C interaction.
  iv. The performance of the quantitative PCR assay standards. The standard curve is linear from 10'-10$^6$ copies. $R^2=0.99$.
  v. One amplicon doubles to produce two=100% efficient. Efficiency of assay=97.1% (>90% MIQE guideline).
  vi. The assay differences (Table 25) between the patient (n=8) subsets (C01-C12=breast cancer, D01-D12=non-malignant). SQ=starting quantity, copies in 20 ng of template. NaN=0 copies.
ENSEMBL™ BLA™ after direct sequencing of the sample PCR product.
This PCR product was sequenced and mapped to chromosome 5q14.1.

TABLE 25

| Well | Fluor | Target | Content | Sample | Cq | Starting Quantity (SQ) |
|---|---|---|---|---|---|---|
| C01 | FAM™ | 032B 20 ng | Unkn | 032B 20 ng | NaN | NaN |
| C02 | FAM™ | 032B 20 ng | Unkn | 032B 20 ng | NaN | NaN |
| C03 | FAM™ | 032B 20 ng | Unkn | 032B 20 ng | NaN | NaN |
| C04 | FAM™ | 063B 20 ng | Unkn | 063B 20 ng | NaN | NaN |
| C05 | FAM™ | 063B 20 ng | Unkn | 063B 20 ng | 38.99 | 7.08 |
| C06 | FAM™ | 063B 20 ng | Unkn | 063B 20 ng | NaN | NaN |
| C07 | FAM™ | 065A 20 ng | Unkn | 065A 20 ng | NaN | NaN |
| C08 | FAM™ | 065A 20 ng | Unkn | 065A 20 ng | NaN | NaN |
| C09 | FAM™ | 065A 20 ng | Unkn | 065A 20 ng | NaN | NaN |
| C10 | FAM™ | 142 20 ng | Unkn | 142 20 ng | NaN | NaN |
| C11 | FAM™ | 142 20 ng | Unkn | 142 20 ng | NaN | NaN |
| C12 | FAM™ | 142 20 ng | Unkn | 142 20 ng | 41.30 | 1.48 |
| D01 | FAM™ | 005B 20 ng | Unkn | 005B 20 ng | NaN | NaN |

TABLE 25-continued

| Well | Fluor | Target | Content | Sample | Cq | Starting Quantity (SQ) |
|---|---|---|---|---|---|---|
| D02 | FAM ™ | 005B 20 ng | Unkn | 005B 20 ng | NaN | NaN |
| D03 | FAM ™ | 005B 20 ng | Unkn | 005B 20 ng | NaN | NaN |
| D04 | FAM ™ | 007B 20 ng | Unkn | 007B 20 ng | NaN | NaN |
| D05 | FAM ™ | 007B 20 ng | Unkn | 007B 20 ng | 41.01 | 1.80 |
| D06 | FAM ™ | 007B 20 ng | Unkn | 007B 20 ng | NaN | NaN |
| D07 | FAM ™ | 17B 20 ng | Unkn | 17B 20 ng | NaN | NaN |
| D08 | FAM ™ | 17B 20 ng | Unkn | 17B 20 ng | NaN | NaN |
| D09 | FAM ™ | 17B 20 ng | Unkn | 17B 20 ng | NaN | NaN |
| D10 | FAM ™ | 022B 20 ng | Unkn | 022B 20 ng | 39.09 | 6.63 |
| D11 | FAM ™ | 022B 20 ng | Unkn | 022B 20 ng | NaN | NaN |
| D12 | FAM ™ | 022B 20 ng | Unkn | 022B 20 ng | NaN | NaN |
| E07 | FAM ™ | Gen Neg Ctrl | Neg Ctrl | Gen Neg Ctrl | NaN | NaN |
| E08 | FAM ™ | Gen Neg Ctrl | Neg Ctrl | Gen Neg Ctrl | NaN | NaN |
| E09 | FAM ™ | No fix 20 ng | Neg Ctrl | No fix 20 ng | NaN | NaN |
| E10 | FAM ™ | No fix 20 ng | Neg Ctrl | No fix 20 ng | NaN | NaN |
| E11 | FAM ™ | ATE Ext | NTC | ATE Ext | NaN | NaN |
| E12 | FAM ™ | ATE Ext | NTC | ATE Ext | NaN | NaN |
| F01 | FAM ™ | ATE Post PCR | NTC | ATE Post PCR | NaN | NaN |
| F02 | FAM ™ | ATE Post PCR | NTC | ATE Post PCR | NaN | NaN |
| F03 | FAM ™ | Water | NTC | Water | NaN | NaN |
| F04 | FAM ™ | Water | NTC | Water | NaN | NaN = 0 copies |

NF1_17_29477103_29483764_29651799_29657368_FF
 i. The 3C template amplified at single step.
 ii. Lab Chip™ image. Comments: the amplicon of expected size is visible in paraformaldehyde fixed samples only (10 ng of template). The single-step PCR product is of expected size, 401 bp.
 iii. ENSEMBL™ BLAT™ after direct sequencing of the sample PCR product. Comments: the good quality sequencing (forward and reverse primers) has 100% homology to the predicted 3C interaction.
 iv. The performance of the quantitative PCR assay standards. The standard curve is linear from $10^1$-$10^6$ copies. $R^2$=0.987.
 v. One amplicon doubles to produce two=100% efficient. Efficiency of assay=99% (>90% MIQE guideline).
 vi. The assay shows differences (Table 26) between the patient (n=8) subsets (C01-C12=breast cancer, D01-D12=non-malignant). SQ=starting quantity, copies in 20 ng of template. NaN=0 copies.

TABLE 26

| Well | Fluor | Target | Content | Sample | Cq | Starting Quantity (SQ) |
|---|---|---|---|---|---|---|
| C01 | FAM ™ | 032B 20 ng | Unkn | 032B 20 ng | NaN | NaN |
| C02 | FAM ™ | 032B 20 ng | Unkn | 032B 20 ng | NaN | NaN |
| C03 | FAM ™ | 032B 20 ng | Unkn | 032B 20 ng | 38.29 | 3.69 |
| C04 | FAM ™ | 063B 20 ng | Unkn | 063B 20 ng | 38.94 | 2.36 |
| C05 | FAM ™ | 063B 20 ng | Unkn | 063B 20 ng | 36.45 | 13.11 |
| C06 | FAM ™ | 063B 20 ng | Unkn | 063B 20 ng | 39.37 | 1.76 |
| C07 | FAM ™ | 065A 20 ng | Unkn | 065A 20 ng | 41.96 | 0.30 |

TABLE 26-continued

| Well | Fluor | Target | Content | Sample | Cq | Starting Quantity (SQ) |
|---|---|---|---|---|---|---|
| C08 | FAM ™ | 065A 20 ng | Unkn | 065A 20 ng | NaN | NaN |
| C09 | FAM ™ | 065A 20 ng | Unkn | 065A 20 ng | 37.18 | 7.92 |
| C10 | FAM ™ | 142 20 ng | Unkn | 142 20 ng | NaN | NaN |
| C11 | FAM ™ | 142 20 ng | Unkn | 142 20 ng | NaN | NaN |
| C12 | FAM ™ | 142 20 ng | Unkn | 142 20 ng | 41.77 | 0.34 |
| D01 | FAM ™ | 005B 20 ng | Unkn | 005B 20 ng | 38.43 | 3.36 |
| D02 | FAM ™ | 005B 20 ng | Unkn | 005B 20 ng | NaN | NaN |
| D03 | FAM ™ | 005B 20 ng | Unkn | 005B 20 ng | NaN | NaN |
| D04 | FAM ™ | 007B 20 ng | Unkn | 007B 20 ng | NaN | NaN |
| D05 | FAM ™ | 007B 20 ng | Unkn | 007B 20 ng | 40.95 | 0.60 |
| D06 | FAM ™ | 007B 20 ng | Unkn | 007B 20 ng | NaN | NaN |
| D07 | FAM ™ | 17B 20 ng | Unkn | 17B 20 ng | 37.66 | 5.73 |
| D08 | FAM ™ | 17B 20 ng | Unkn | 17B 20 ng | NaN | NaN |
| D09 | FAM ™ | 17B 20 ng | Unkn | 17B 20 ng | NaN | NaN |
| D10 | FAM ™ | 022B 20 ng | Unkn | 022B 20 ng | 38.33 | 3.59 |
| D11 | FAM ™ | 022B 20 ng | Unkn | 022B 20 ng | NaN | NaN |
| D12 | FAM ™ | 022B 20 ng | Unkn | 022B 20 ng | NaN | NaN |
| E07 | FAM ™ | Gen Neg Ctrl | Neg Ctrl | Gen Neg Ctrl | NaN | NaN |
| E08 | FAM ™ | Gen Neg Ctrl | Neg Ctrl | Gen Neg Ctrl | NaN | NaN |
| E09 | FAM ™ | No fix 20 ng | Neg Ctrl | No fix 20 ng | NaN | NaN |
| E10 | FAM ™ | No fix 20 ng | Neg Ctrl | No fix 20 ng | NaN | NaN |
| E11 | FAM ™ | ATE Ext | NTC | ATE Ext | NaN | NaN |
| E12 | FAM ™ | ATE Ext | NTC | ATE Ext | NaN | NaN |
| F01 | FAM ™ | ATE Post PCR | NTC | ATE Post PCR | NaN | NaN |
| F02 | FAM ™ | ATE Post PCR | NTC | ATE Post PCR | NaN | NaN |
| F03 | FAM ™ | Water | NTC | Water | NaN | NaN |
| F04 | FAM ™ | Water | NTC | Water | NaN | NaN = 0 copies |

SRD5A$_1$_5_6634973_6639025_6667775_6669711_RF
 i. The 3C template amplified at single step.
 ii. Lab Chip™ image. Comments: the amplicon is visible in paraformaldehyde fixed samples only (10 ng of template). The single-step PCR product is of expected size, 219 bp.
 iii. ENSEMBL™ BLAT™ after direct sequencing of the sample PCR product. Comments: the good quality sequencing (forward and reverse primers) has 100% homology to the predicted 3C interaction.
 iv. The performance of the quantitative PCR assay standards. The standard curve is linear from $10^2$-$10^6$ copies. $R^2$=0.997.
 v. One amplicon doubles to produce two=100% efficient. Efficiency of assay=95.5% (>90% MIQE guideline).
TSPYL5_8_98276431_9828273698316421_98318720FF
 i. The 3C template amplified at single step.
 ii. Lab Chip™ image. Comments: the amplicon is visible in paraformaldehyde fixed samples only (10 ng of template). The single-step PCR product is of expected size, 507 bp.
 iii. ENSEMBL™ BLAT™ after direct sequencing of the sample PCR product. Comments: the good quality sequencing (forward and reverse primers) has 100% homology to the predicted 3C interaction.

iv. The performance of the quantitative PCR assay standards. The standard curve is linear from $10^2$-$10^6$ copies. $R^2$=0.998.
v. One amplicon doubles to produce two=100% efficient. Efficiency of assay=94.2% (>90% MIQE guideline).

Conclusions
1. The 3C markers ATM, FOXC1 and TSPYL1 produced single-step products for both sets of primers.
2. ATM copy number is increased in breast cancer (n=4, Table 1). Samples in row C (malignant late stage disease breast cancer) differ from row D (non-malignant early stage) with a p-value of 0.009037772.
3. CDC6_FF copy number is reduced in breast cancer (n=4, Table 2).
4. FOXC1_FR copy number is reduced in breast cancer. Row C differs from row D with a p-value of 0.004112668.

Name of the predicted interaction: ATM_11_108118137_108126372_108155279_108156687_RF
Sequence of the probe. TACGTTCAACTTCGACTGTATTCTACAA (SEQ ID NO: 26)
Sequence of forward primer. GCAAGTTCCTTAGTTGCTTAG (SEQ ID NO: 27)
Sequence of reverse primer. CAACCATCATCACTAATTCTGG (RC)(SEQ ID NO: 28),
CCAGAATTAGTGATGATGGTTG (SEQ ID NO: 29).
Position of PCR sequence BLAT™.

| Genomic Location | Over-lapping Gene(s) | Orientation | Query start | Query end | Query ori | Length | Score | E-val | % ID |
|---|---|---|---|---|---|---|---|---|---|
| 11:108285708-108285962 | ATM | Forward | 3 | 257 | Forward | 255 [Sequence] | 495 | 2.80 E-140 | 100.00 [Alignment] |
| 11:108247409-108247583 | ATM | Forward | 254 | 428 | Forward | 175 [Sequence] | 338 | 4.40 E-93 | 100.00 [Alignment] |
| 4:55715682-55715761 | | Forward | 345 | 424 | Forward | 80 [Sequence] | 97 | 2.30 E-20 | 81.25 [Alignment] |
| 1:10700828-10700899 | CASZ1 | Reverse | 345 | 419 | Forward | 75 [Sequence] | 85 | 6.20 E-17 | 81.33 [Alignment] |

Please note the first two rows are the true homologies.

>ATM_11_108118137_108126372_108155279_108156687_RF
Underlined=forward, Double underlined=reverse, Dotted Underlined=Taq I.

(SEQ ID NO: 30)
AAGGGATAAGTAACCAAACTTGGTCAATATTAGATAAACTTCAAGGGACCTTTTTTTTTTTAGTTTCCTAGTT

ATCTATATTGAACCAAGAAATGGAACAGCAAGTTCCTTAGTTGCTTAGGTGGACCTATTCAGAACTGGTTGTAA

GTCTGCAGTCTGAAGGGAAATGGTGAGCAGAGGACTCCTTTCCCAAAGACAGCTGGAACAGAAATAGGCACTCC

AGAGGTTATGGAATTTGAGAGAGATACTCAGCCTCTAGCCACTCCCATTCAATCTCCCAGCTTAGTCTTCTGAG

CATTCTTAATCTTACTATTCTTTTCTTAATGTATTCAAACCAAAAGACAGCAATTTTTAGAGCCTGAATAGGTT

TTGGAGGGAAAAGTAATTACGTTCAACTTCGACTGTATTCTACAAAGTGCTGGGATTACAGGCATGAGCCACCA

AGCCCAGTCTGTTTCTTTTTTGCAATTAAGCTAGAGTTCACATAGCATAAAATTCACGATTTTGAGTTGTACAT

TTCAGTGGTTTTTAGTATTTTTACTATGTTGTACAACCATCATCACTAATTCTGGAAACTTTTTTTATTTTATT

TTTATTTTTTTGAGATGGAGTCTTGCTCTGTCACCCAGGCTGGAGTGCAGTGGCACAATCTCCGCTCACTGCAA

CCTCCCTTTCCCGGGTTCAAGTGATTCTCCTGCATCAGCCTCCCGAGTAGCTGGGACTACAGGTGCCTGCCACC

ACGCCCAGCTAATTTTTGTTTTTTTAGTAGAGACTGGGTTTCACCATATTGGCCAGCCTA

Name of the predicted interaction: CDC6_17_38421089_38423079_38451196_38457050_FF
Sequence of the probe. AAAGAGAATGTGATCGATTTCTAAAATACT (SEQ ID NO: 31)
Sequence of forward primer. GGGTTCAAGAATGCAGGAATAG (SEQ ID NO: 32)
Sequence of reverse primer. GTATAGTCACATGGTGGCAA (RC)(SEQ ID NO: 33),
TTGCCACCATGTGACTATAC (SEQ ID NO: 34)
Genomic Position of PCRs

| Genomic Location | Over-lapping Gene(s) | Orientation | Query start | Query end | Query ori | Length | Score | E-val | % ID |
|---|---|---|---|---|---|---|---|---|---|
| 17:40266532-40266830 [Sequence] | WIPF2 | Reverse | 43 | 341 | Forward | 299 [Sequence] | 576 | 9.90 E-165 | 99.33 [Alignment] |
| 17:40300754-40300800 [Sequence] | CDC6 | Forward | 1 | 47 | Forward | 47 [Sequence] | 91 | 1.60 E-18 | 100.00 [Alignment] |

>CDC6_17_38421089_38423079_38451196_38457050_FF (SEQ ID NO: 35)
AGGTAAGTTAAAGACCAAGAACTGGCATTGGTCTTAGTATCATGGGACCCTTTTGAGTAGTTTCAGTGGAGTGG

TGGAGGGTGAAAGTGAAAGCTTAATTGGAGTGGGTTCAAGAATGCAGGAATAGGAGGAGAGAAATTGGAGATAG

CAATATAGAAATCTCTTAAAGAGTTCGCTGTAAAGTCCAGGAGAGAGGGGTGAAGATAAGTGAAGTGATTGTTG

GACGAAGATGTGGGGTTGAGAGTTGTTTTTTTCCCATCCCAAGATGGGAGACCTATTTGTATGCTGATGGAATG

AGTAGCATGAAACTTAGGAGAGAGGGAAAAAATTGAATCAGAAGAGAGGGAACAGATTGCCTGAATAATGACCT

GGAGGAGGCCAGAGAAAAGAGAATGTGATCGATTTCTAAAATACTGTGTGTGTGTATGTATGATGAGACAGATG

ATACTAAGTTTGAGCTAAAGGAAATTCAAGTATAGTCACATGGTGGCAAAGCAGAGGTTTTAAATCTCTAACCA

GAGGCCAAAGGATGAGAGATAATGCTATTCTCTTAAGGATGTCAAATAATGTGGGATGACTTGAAAAGTAGGG

TTACCCTTTCTCTGGGCCAAATAGTGAGCTGTTTTGTCCTATGGAATGTAATTTAATGTCAGAGGAACAAAACC

CACCTCATGAAAGGACCAGAGAACTACTGTATTTTTTTTGGGACAGGATCTCTGTCACTCAGGCTGGAGTACA

GTGGCACTATCATGGCTCACTGCAGCCTTGGCTTCCTGGGTTCAAGTGATCCTCCTGCCT

Name of the predicted interaction: FOXC1_6_1577253_1581989_1604206_1605973_FR.
Sequence of the probe: AACCGGTTTCGATGCTGTTGTGCCT (SEQ ID NO: 36)
Sequence of forward primer GGGACACACGTTAGTCAAG (SEQ ID NO: 37)
Sequence of reverse primer CTGGAAGGAATGCGTAGC (RC)(SEQ ID NO: 38),
GCTACGCATTCCTTCCAG (SEQ ID NO: 39).
Position of PCR sequence. BLAT™.

| Genomic Location | Over-lapping Gene(s) | Orientation | Query start | Query end | Query ori | Length | Score | E-val | % ID |
|---|---|---|---|---|---|---|---|---|---|
| 6:1603970-1604208 [Sequence] | | Forward | 157 | 395 | Forward | 239 [Sequence] | 465 | 3.90 E-131 | 100.00 [Alignment] |
| 6:1581597-1581752 [Sequence] | | Forward | 1 | 156 | Forward | 156 [Sequence] | 307 | 9.60 E-84 | 100.00 [Alignment] |

>FOXC1_6_1577253_1581989_1609206_1605973_FR (SEQ ID NO: 40)
CGCCGTCCCAGCAGCGCCCCATCTCACCAACTCCCACCTTCATGTGTGGCCGCCCACCTAGAGCCATGCCTGAA
GCCACTGTCCCTGACCACAAAGCTTTTGGCTGATAGGAAGCATGACAGCACTGGGGCCCTACACTGGAAGCGGG
ACCGTCCAGAGAAGAAGACTGCGCACAGGGATCGGGAGCTGGGACACACGTTAGTCAAGGTGTACGAGGGAGGA
ATCACCGCCATGTGGAGCCACTACTCGGGGAGGACGTGGGCCACCCGGAGCTCAGTGACAGTACTCCCGGGAGT
GTACATCGTTGGTAATGTCCACGACAGTGTCCCTGCCTGTGACCCAATAATTTCCCATCCAGGGACACACTTCA
CAGAAATGCACGCACAGGCACAACAGCATCGAAACCGGTTCTTTGGAGGCTCAGTTTTTGGTAATTAAGACTAA
GGAGTGTTTAAAAAACAGAAGTACATTTTCCTGGAAACCAGCAGTCTTTATTTGCAACTTTTATTGGCAAACCT
GGCTGCCAGTAAATACATTCCTTGGCATCTCCCACAATGTAATTCACTGGATGGAGCGGCCTTGCTTTTTCTGT
AACGTGTACGTCAATTAAAGGGCCGCCTGGAAGGAATGCGTAGCGGTGGCTGAAAGCCCCAGTCTCGGGTCAC
CTCCCTCCACTCCAGGAACAAAAGCGTCCGTGGTCTGTGCCTGGAAGTCTGAGAGGGTCTCCCCGATGGGGCTG
TTCCCGCCCGGACCCTGAGGGATGAGAGTTGCAGCCTAGAAAACCAGGTGCCAGGCCCTG

Name of the predicted interaction: MAP3K1_5_56102259_56110500_56140227_56144076_FF
Sequence of the probe AAAACTAAAGATCGAAAGTTTTTATTACTTC (SEQ ID NO: 41)
Sequence of forward primer GTGACATTACCGAGCACTTC (SEQ ID NO: 42)
Sequence of reverse primer GTAACTCAAACTCAGTGTGCT (RC)(SEQ ID NO: 43),
AGCACACTGAGTTTGAGTTAC (SEQ ID NO: 44)
Position of PCR sequence. BLAT™.

| Genomic Location | Gene(s) | Orientation | Query start | Query end | Query ori | Length | Score | E-val | % ID |
|---|---|---|---|---|---|---|---|---|---|
| 5:56848104-56848251 [Sequence] | MAP3K1, AC008937.2 | Reverse | 62 | 209 | Forward | 148 [Sequence] | 284 | 1.10 E-76 | 100.00 [Alignment] |
| 5:56814611-56814675 [Sequence] | | Forward | 1 | 65 | Forward | 65 [Sequence] | 127 | 2.00 E-29 | 100.00 [Alignment] |

>MAP3K1_5_56102259_56110500_56140227_56144076_FF (SEQ ID NO: 45)
AAACCAGCTGGAGGAAAGGAAAGGAAGGAAGAAATAAACGCAACACAGAAGTTCTCCTCAGTTGACAAAAGGTC
AAAAATCATTAACGTGTAAATGTTGCTTTTTCCATCCCAAAGCACCTTCTCACGTAGAGTCCAGGGACTAGGAG
GACTCACAACGCAGCGATGGGCAGCCAGGCCCTGCAGGAGTGGGGACAGAGGGAACCCGGCCGGTGGCCCGACC
CTGCAGGGAAGAAGGACGTGCGGCGAGAAGCATCGGATTCGGGGAGGGCCGGGACCTGGCCGAGGGTGACATTA
CCGAGCACTTCCTGGCACAGCGCTGGTCCCCTCCCCAAACGCGCTATATGTGGTTCTGTACGGGACTGCCTTTC
CCAAAGACAGCCAAGGAAAAACTAAAGATCGAAAGTTTTTATTACTTCCAAATTAGTAAATTTGTAACAATCAT
CAGGCAACTAACTATAATAAGAGGGAATTTACAAAAGACAGAGAGCTACTAGTCAGTATCAAATCATTCTTAAA
AGTGGCAACTCTGTATCAATTTTTTTTTTGCAGTCAATTACCTTTGACTCAGTCTATAAAGTACATGCCCAAAT
CTCCCTTTAGAGAAGAAAAGTGAATCAAAAAGAAAAATGTATATTAACTGTACAGTTCTCCTATACTAAATGTT
CTTACATGCTCAAAATGTATGAATATATTTAAAGCAACTGATCCTCTATTGAATACTGAATAAACTTGAAGGGA
TTTCTAAGTAAATTATTACTGGTAACTCAAACTCAGTGTGCTATAAATTTCAGACACCAC

Name of the predicted interaction: ME3_11_86300063_86304401_86420537_86426200_FR
Sequence of the probe. AATAAGGTATCGAGAAAGTATTCAAAGCA (SEQ ID NO: 46)
Sequence of forward primer. ACCCTCCTTCACTCACATAG (SEQ ID NO: 47)
Sequence of reverse primer. GTGATGTTAGGTAGATTAGGTGC (RC)(SEQ ID NO: 48),
GCACCTAATCTACCTAACATCAC (SEQ ID NO: 49)
Position of PCR sequence BLAT™.

| Genomic Location | Over-lapping Gene(s) | Orientation | Query start | Query end | Query ori | Length | Score | E-val | % ID |
|---|---|---|---|---|---|---|---|---|---|
| 11:86593191-86593357 [Sequence] | RP11-317J19.1, ME3 | Reverse | 78 | 244 | Forward | 167 [Sequence] | 325 | 4.40 E-89 | 100.00 [Alignment] |
| 11:86709494- [Sequence] | CTD-2005H7.1 | Reverse | 1 | 77 | Forward | 77 [Sequence] | 148 | 7.00 E-36 | 100.00 [Alignment] |
| 14:59850307-59850375 [Sequence] | RTN1 | Forward | 1 | 69 | Forward | 69 [Sequence] | 108 | 7.70 E-24 | 88.41 [Alignment] |
| 2:119300691-119300754 [Sequence] | | Forward | 1 | 64 | Forward | 64 [Sequence] | 100 | 2.60 E-21 | 89.06 [Alignment] |

Please note the first two rows are the true homologies.

>ME3_11_86300063_86304401_86420537_86426200_FR (SEQ ID NO: 50)

TAACCTTCCATAGGCCTCAGCTCCCTTATCTATTAACCTGGTGAAATGCAGACCCCTCTGCATGGGGTTACAAG

GTTTCAGCATGACTGGGTATGAAAAGAGAACAAAGAAGCTTCCTGGAGATGACTGTGGCCTTGGCTCACTGCCA

GGAAAATGACTCATTTCTGTATGCCAGGGTTATAGTTCACTGTTACCCTGACAAATGAATGTGGAAGACCCATG

ATTTCCTCCACCCTCCTTCACTCACATAGTAAAAGTTAGCTACTGCCTGCAACATACCAGGCACCGTACAACAC

GAAACTGTAGGCTCCCCCTCCAGGAAGTGACAATGTCATTCCTAACCTGTTGGAATTTTAACACCTGTCATAAA

AGGATCTCATGATGCTTTGAATACTTTCTCGATACCTTATTATAAAATCAGCTTTGTGTTGAATGATTTTTCCC

AGCTGTAGACTAATGTAAATGTTCTGAGCATGTTTAAGGTAGGCTAGTCTAAGCTGTGATGTTAGGTAGATTAG

GTGCATTTAAATGCATTTTCAATGATATTTTAAATTTGCAGTGGGTTTATCAGGATGTTACTCCAAGATGCTCC

TCCAAGGTGAGGGGCATCTGTGTTTTAGTCAGTGAAAATGTCTTGCAAAACTGAAGATAAAATAAATACAGTTA

GTCACACTTCACTTGCACTATAAGAAATTCTAAAGAAAAATTCTTCAAATTGAAGGAATATAATAACATAAATT

TATATCTACAGGAAGGAATAAAGAGCAAAGAAATGATAAACAAATCGCTTAAAGTGTTTA

Name of the predicted interaction: MELK_9_36577630_36579243_26637050_36643005_RF
Sequence of the probe. TGTAGTTTATTCACCTCGACTAGATTTTA (SEQ ID NO: 51)
Sequence of forward primer. ATGCTTGCTGGAATATGCTTAC (SEQ ID NO: 52)
Sequence of reverse primer. CAGCTTCGCTTGTTACCCAG (RC)(SEQ ID NO: 53),
CTGGGTAACAAGCGAAGCTG (SEQ ID NO: 54)
Position of PCR sequence BLAT™.

| Genomic Location | Over-lapping Gene(s) | Orientation | Query start | Query end | Query ori | Length | Score | E-val | % ID |
|---|---|---|---|---|---|---|---|---|---|
| 9:366472807-36643010 [Sequence] | MELK | Reverse | 13 | 215 | Forward | 204 [Sequence] | 368 | 5.60 E-102 | 98.04 [Alignment] |

Name of the predicted interaction: MELK_9_36577630_36579243_26637050_36643005_RF
Sequence of the probe. TGTAGTTTATTCACCTCGACTAGATTTTA (SEQ ID NO: 51)
Sequence of forward primer. ATGCTTGCTGGAATATGCTTAC (SEQ ID NO: 52)
Sequence of reverse primer. CAGCTTCGCTTGTTACCCAG (RC)(SEQ ID NO: 53),
CTGGGTAACAAGCGAAGCTG (SEQ ID NO: 54)
Position of PCR sequence BLAT™.

| Genomic Location | Over-lapping Gene(s) | Orientation | Query start | Query end | Length | Score | E-val | % ID |
|---|---|---|---|---|---|---|---|---|
| 9:36642851-36642992 [Sequence] | MELK | Forward | 1 | 142 | 142 [Sequence] | 270 | 1.30 E-72 | 100.00 [Alignment] |

MELK_9_36577630_36579243_36637050_36643005_RF (SEQ ID NO: 55)
AGTAGAGATGGGGTTTCACCATGCTGGCCAGGCCAGTCTCAAACTCCTGACCTCAGGTGATCTGCCCGCCCCAG

CCTCCCAAAATGCTAGAATTACAGGTGTGAACTATTGTGCCCGGCATTGTACAACCGAACTTTAACAACAGTTG

CTCAGATGATGATGGGGATAAAGAGTTGGGAAAGAGCACATCTTCTTGAAATGCTTGCTGGAATATGCTTACTT

CTTAAAAGATTATAGAGAATATTGATTCTTCCCCAAGAAATTGACAGATTCATGTTTTACATAATGATATTTGA

TTGTATAAAGTAATTATGCTGATTTTAAAATGTGAAAACATTGAATATATTTGTAATTTTTGTTAATAAAGTG

CATAATTTTTTTGTAGTTTATTCACCTCGACTAGATTTTAATTTTTAATTTTTATTTATTTTTTGAGACAC

AGCTTCGCTTGTTACCCAGGCTGGAGTGCAGTGGCATGATCTCGGCTCACCGCAACCTCTGCTTCCCGGGTTCA

AGTGATTCTCCTGCCTCAGCCTCCCTAGTAGCTGGGATTACAGGCATGGGCCACCACGCCTGGCTAATTTTTTA

TATTTTTAGTAGAGACGGGGTTTCTCCATGTTGGTCAGGCTGGTCTTGAACTCCCGACCTCAGGTGATCCGCCT

GCCTCAGCCTCCCAAAGTGCCGGGATTACAAGTGTGAGCCACTGCGCCTGGCTGTTTTTATTTTTAGTAGAGA

CAAGGTCTTGCTATATTGTCCTGGCTTGTCTTGAACTCCAGGCCTCAAGCAATCCTCCTG

Name of the predicted interaction: MSH3_5_80021913_80025030_80153948_80159012_RF
Sequence of the probe. ATTCCTGGTATCGAAATATTTTAGGTAATC (SEQ ID NO: 56)
Sequence of forward primer. AGGACCCATCACCTACATATA (SEQ ID NO: 57)
Sequence of reverse primer. CTCTTGGCATAAACTTGGCT RC (SEQ ID NO: 58),
AGCCAAGTTATGCCAAGAG (SEQ ID NO: 59)
Position of PCR sequence BLAT™.

| Genomic Location | Over-lapping Gene(s) | Orientation | Query start | Query end | Query ori | Length | Score | E-val | % ID |
|---|---|---|---|---|---|---|---|---|---|
| 5:80726093-80726216 [Sequence] | MSH3 | Reverse | 1 | 124 | Forward | 124 [Sequence] | 239 | 2.5. E-63 | 100.00 [Alignment] |
| 5:80863153-80863195 [Sequence] | MSH3 | Reverse | 121 | 163 | Forward | 43 [Sequence] | 84 | 2.10 E-16 | 100.00 [Alignment] |

MSH3_5_80021913_80025030_80153948_80159012_RF (SEQ ID NO: 60)
TAACAAAAATAAACTTTAAAATGGTGGAGGTGAGTGGGGAAAAGTGAAACCTCTGCTTTACAGAATACCAACGA

ATAAATGTAGGAAGAATTTTTTAATCAACATTTAATAACGACTATAATAATAACTGATTCAGACAGCAATGATC

AATAGATTATAAAACCTTTGGATGAAAGATTGTTGGAGAAAAGGATATTCATATATCT<u>AAAGTGTCATGCCAC</u>

<u>AGGT</u>TATTTATTAATTACAAAGGGAAAAGGTATAGTGAAGAAATCTAGTGGGTACCCTCTTCAACCAGATAATC

AAATTTGGCATCCCCAGTTATGTAAAACTGATATCACGTCCCACCTGATGTGATGCACTGGG<u>AAGGACCCATCA</u>

<u>CCTACATATAC</u>ATGGAATATTCCTGGTA<u>TCG</u>AAATATTTTAGGTAATCATTATTTGTCTAATTCACATGTCCAC

AATCAGGCATTAATGTTTACTTTCATTTGTACCTCACATTCCTGCCAGTCCAGCTTATGTTAGGGTCCATTTTG

TGGATGGTGAGGTGAATAGACATTTTCC<u>CTCTTGGCATAAACTTGGCTT</u>CACTCTAATCTTCATCCTACTCCAT

ATGGAGGAAATTTATCTCTGTCACATGCTAGAGAGTGTTCATCATCAGCTC<u>CCCATCACTGCTCCATTTAAG</u>CA

TCAGTGTCTAGTTAGCATTTCCTTGCATCTAGGCATCAGTGTCTTGTTAGCATGTCTCTTTAATTTCAT ATGC

CTTGGTCAAATAAAGTGTCTGAGCGTGTATCCCACTTCTTTTATTTTTTCTGTAAGGT

Name of the predicted interaction: NF1_17_29477103_29483764_29651799_29657368_FF
Sequence of the probe. AATTTAAAAATCGATTTTAGAAAATGGGAAGA (SEQ ID NO: 61)
Sequence Of forward primer. TGTAGTAGTTACCCTGTTGTTG (SEQ ID NO: 62)
Sequence Of reverse primer. CATAAGAGCACTGTGAGGC RC (SEQ ID NO: 63),
GCCTCACAGTGCTCTTATG (SEQ ID NO: 64)
Position of PCR sequence BLAT™.

| Genomic Location | Over-lapping Gene(s) | Orientation | Query start | Query end | Query ori | Length | Score | E-val | % ID |
|---|---|---|---|---|---|---|---|---|---|
| 17:31330152-31330352 [Sequence] | NF1 | Reverse | 54 | 254 | Forward | 201 [Sequence] | 385 | 4.00E-107 | 100.00 [Alignment] |
| 17:31156692-31156750 [Sequence] | NF1 | Forward | 1 | 59 | Forward | 59 [Sequence] | 113 | 2.90E-25 | 100.00 [Alignment] |

>NF1_17_29477103_29483764_29651799_29657368_FF (SEQ ID NO: 65)
ACTTTCATTTTAATTTATTATTTCCCTTAGAAACATCTCCTATCTTTTGTGACCATGTCTCCTTTTCCAGTATG

TTTCTTGAATTAGGATTTCATAGAGCTTTTGTGGCCTACACGAATTGACCACAGTAATCCATTACACATATTTT

TCTTTAGCATCTTGTTTGAATTTACTTACGGTTGTCCCAGCCCTAAGTAGATGATAAAATATGATCTCATAGTC

CTAAAATGTGGATTGATTTTTTATGAAGATATGTGTTT<u>TTCTTCCTTCTGTAACCTGTG</u>ACAGATT<u>CTGTAG</u>

<u>TAGTTACCCTGTTGTT</u>GAAACAGTTTTTCTCAAATACCAGTTTCATCAAATAATTCCACTGTTAAAAGCTCATA

ATTTCTTTCTTCTTCCCATTTTCTAAAA<u>TCG</u>ATTTTTAAATTAAAGGTACAAGTTAAGGCACACAGAAGATTAT

AGGCAGCTGACCTAGGAGAAAACACAAATGAAGTTGTTTTAAAACGTATTTTTCCTTATAGTTCCAAAATTTTT

TCATAACATACAATTTGTGATTCTGTTACAAAGTATGATCAACTATTTTAAATTTTATGATCAGTTAGAAATA

AGATGTTATAATTCTACAGTAAAACCAAAATACCCCTTAATCATTTAGGGATTTTATAAAAAGGGACACACTTG

ATATAAC<u>CATAAGAGCACTGTGAGGC</u>TCCTATGACAGAGGGGCGGGGTATAGGCTTTCCTAAAATACATCTCAC

TGAGACATAAAATATGAGAGGA<u>CTTATGGTCCTAATGTGGATCA</u>ATAGAAATTAAGTCAG

Name of the predicted interaction: SRD5A1_5_6634973_6639025_6667775_6669711_RF
Sequence of the probe. TACTAATTGTTACATCGAAAGTTCAAA (SEQ ID NO: 66)
Sequence of forward primer. GGCA-FGCT-FGCC-FATC (SEQ ID NO: 67)
Sequence Of reverse primer. CTCTACACCCAAGGAAGTTG RC (SEQ ID NO: 68),
CAACTTCCTTGGGTGTAGAG (SEQ ID NO: 69)
Position of PCR sequence BLAT™.

| Genomic Location | Over- lapping Gene(s) | Orientation | Query start | Query end | Query ori | Length | Score | E- val | % ID |
|---|---|---|---|---|---|---|---|---|---|
| 5:6634859- 6634948 [Sequence] | SRD5A1 | Forward | 75 | 164 | Forward | 90 [Sequence] | 174 | 1.60 E- 43 | 100.00 [Alignment] |
| 5:6669523- 6669602 [Sequence] | SRD5A1 | Forward | 1 | 80 | Forward | 80 [Sequence] | 153 | 2.10 E- 37 | 100.00 [Alignment] |

>sRD5A1_5_6634973_6639025_6667775_6669711_RF (SEQ ID NO: 70)
ACCACTTTTTAAGATTTATCCTGTTTGTTCTTTGTTGATTGAAACATAATAATTGTTAAAATTCTCTACAGCCT

TCTTTTTCTTCCATAGCTAATCTTCCTTCTAATAGTTTTTGCTTTCTGTTTTGCTGTTGTTGCTTTGCAAAGCT

TTCCCCTCATAGCCTGTACCTGTTATCAATATAAAATAATCTTCCTGTTGAATGCTTCATGACTTGAATTCTAC

TTTGATAAAAACATTGCCATACTGCTTTTTATCTTGATGAATTCATCTGGCATTGCTTTGCCTTATCATCTCAT

CTGGAGTTTTTAAATGCCATTTGTTTCAGTTGTCTTTAACAACATAATAAATAGACTTTGCCATTTAACAAGGT

AGCTCAAATTCTTTTACTAATTGTTACATCGAAAGTTCAAAATTAAATTTTAAACGTTTTCATTCAGGCTCTGG

AAAGCTTCACAGTTAAAAAGGATGTCTCTACACCCAAGGAAGTTGAACTCACTGGCTGTGTGACTATGGGCAGT

TTACCCAACCTTTCTGATTTGGGGTCCCACCTTAAAACACTCACTTCCCAGAGAGACAGGAAGAACTCAGTGTG

TGTTTATAAGCCTCTCTTCTTTCTCCTGGTGTCATGCATTCCAGCGAAGAGAAAGTACACAGCTCCACTACTTG

GAACCAGTGTTGTACCCAGCACAGTTTTTGGTACCTGAGTTCCCTGAAAACCAGCACCTTACCCTGTAACTGGT

GCAGTCTGTGTCCTCAGTGTGCTTTGATGACTTGCACTTTAAACAAGGGCAAGTCAACAT

Name of the predicted interaction: TSPYL5_8_98276431_98282736_98316421_98318720_FF
Sequence of the probe. AGGAATTCAAGACTCGAACTAAA (SEQ ID NO: 71)
Sequence Of forward primer. TTGAGTCCTGGCTCTACTAC (SEQ ID NO: 72)
Sequence Of reverse primer. GAACAAAGGACCAAGTATAGCT RC (SEQ ID NO: 73),
AGCTATACTTGGTCCTTTGTTC (SEQ ID NO: 74)
Position of PCR sequence BLAT™.

| Genomic Location | Over- lapping Gene(s) | Orientation | Query start | Query end | Query ori | Length | Score | E- val | % ID |
|---|---|---|---|---|---|---|---|---|---|
| 8:97306203- 9730649 [Sequence] | | Reverse | 170 | 461 | Forward | 292 [Sequence] | 571 | 4.60 E- 163 | 100.00 [Alignment] |
| 8:97270338- 97270510 [Sequence] | | Forward | 1 | 173 | Forward | 173 [Sequence] | 335 | 3.10 E- 92 | 100.00 [Alignment] |
| 18:68006367- 68006398 [Sequence] | | Reverse | 186 | 217 | Forward | 32 [Sequence] | 58 | 8.70 E- 09 | 96.88 [Alignment] |
| 22:34012396- 34012431 [Sequence] | | Reverse | 370 | 404 | Forward | 36 [Sequence] | 53 | 3.50 E- 07 | 91.67 [Alignment] |

-continued

Name of the predicted interaction: TSPYL5_8_98276431_98282736_98316421_98318720_FF
Sequence of the probe. AGGAATTCAAGACTCGAACTAAA (SEQ ID NO: 71)
Sequence Of forward primer. TTGAGTCCTGGCTCTACTAC (SEQ ID NO: 72)
Sequence Of reverse primer. GAACAAAGGACCAAGTATAGCT RC (SEQ ID NO: 73),
AGCTATACTTGGTCCTTTGTTC (SEQ ID NO: 74)
Position of PCR sequence BLAT™.

| Genomic Location | Over-lapping Gene(s) | Orientation | Query start | Query end | Query ori | Length | Score | E-val | % ID |
|---|---|---|---|---|---|---|---|---|---|
| 7:82655893-82655925 [Sequence] | | Forward | 180 | 212 | Forward [Sequence] | 33 | 49 | 6.90 E-06 | 87.88 [Alignment] |
| 2:37820936-37820959 [Sequence] | | Forward | 392 | 415 | Forward [Sequence] | 24 | 47 | 1.70 E-05 | 100.00 [Alignment] |

Please note the first two rows are the true homologies.

>TSPYL5_8_98276431_98282736_98316421_98318720_FF (SEQ ID NO: 75)
TAAAGAAGTTTCACATTCATATGCCAACTCAGATTGATGGGCAGCAACTGGATAATCCGCTGTGCAGAAAGTTA

AATACAGGTTCTGTGCAAAGAAGTGTCTAGATTCATAGTGCCAGACATCTGCCCTGGGCCACATGCTTACCGTC

CCATGGATGGATGGAACTTGGAATCAGAAGACCCAAGTTTGAGTCCTGGCTCTACTACTTTTGTGATTTTGGTC

ATTTAACCTCTTTGAGCCTTCTTATGGCATAGTAGTTATAATCAAGATAATATAAGTGAATGTGCTTTGTAAAC

CATGAAGTGTTGGTCACACAGATGATAGCTACTGTCTTATATTTGTCAAACCTCAGCTGAGGACCAGGTTGACA

GGATGGAGGAAGAGGAGGAATTCAAGACTCGAACTAAACAAAAGGAGATGATCCTGGGTGGGCTTGACTTAAT

CAAGTGAAAGCCTTAAAAGCAAGAGTCTCCTGCTAGTCTAGGAAAAGCAAACAGCCCTGCTATGAATGGCCTAT

AGAAAGGGGCAGCCTCTAGGAGCATGGGCCTCAGTCATATGCCCACGAGGAACTGAATATTGCCAGCAACCATG

TGAGCATGGAAGAGGACTCTAAGCCTCTGATGAGACCACAGCCCTGGCCAATGCTTTGATTGTGGCTCTGTGAG

GCCTTGAACAAAGGACCAAGTATAGCTATGCCAGGACTTCTGAACCACGGGAATGGTGAGATAATAAATGTTTG

GTGTTTTAAGCCACTAAGTTTGTGTTAATTTTTTATGCCGCAATAGAAAGCGAATACTAC

>CDC6_17_38421089_38423079_38467677_38474960_FR (SEQ ID NO: 76)
AGGTAAGTTAAAGACCAAGAACTGGCATTGGTCTTAGTATCATGGGACCCTTTTGAGTAGTTTCAGTGGAGTGG

TGGAGGGTGAAAGTGAAAGCTTAATTGGAGTGGGTTCAAGAATGCAGGAATAGGAGGAGAGAAATTGGAGATAG

CAATATAGAAATCTCTTAAAGAGTTCGCTGTAAAGTCCAGGAGAGAGGGGTGAAGATAAGTGAAGTGATTGTTG

GACGAAGATGTGGGGTTGAGAGTTGTTTTTTTCCCATCCCAAGATGGGAGACCTATTTGTATGCTGATGGAATG

AGTAGCATGAAACTTAGGAGAGAGGGAAAAAATTGAATCAGAAGAGAGGGAACAGATTGCCTGAATAATGACCT

GGAGGAGGCCAGAGAAAAGAGAATGTGATCGATGACCTTAATGTCAGTGTCACTGACTCTGACAAGGAGGAAAG

GACAGCGATGAGCCAGGCTGACCCCCGCCACCCCATTCCCATAGCCCACTTTCTTCTCTCTTCTTGTTCAGAA

ATGTTTCACTTTGCCTCATCTAGCCCCTTTGGCCAGTAGGTCACATCTGGGAGCTTCTGGGGGTGCCACATGTC

TGCCTCAATCTGGGCTGTTTCCTCCCCTCCAAGATATTTCACTGTCTCTGGGCTGGGCGCCAGGACTCCTGGGT

TTCCCTGCCTGTGGTGCAGGGCTCCCCTGCAGGGCTCCAGAGAGTCGCTTAGCTGGTTTCCTTCCTCCTTTGTG

GGGAGGGCCTTCCCCTAGGGCTGGGAGGTGTCAGGAATCCCAGGTGGGACAGGGGTGGGG

>SLC16A10_6_111441989_111147305_111492951_111998421_FR (SEQ ID NO: 77)
TTCAATTGCTATATAAAAAATGTAAAGTCTGTTTACTGCCTTAAACCTTCTGGTGTATTTTTATATAAAGTAAC

ACCCTTAATTCTAACTTGGCCAACAGGTAGGATGGTATTATTATTATCTTCATTGTACAGATAAGGAAACTGAG

GCTCAGATTGACTAGATCAAACAGGAGTTTTCTGGAAAACCTAGGACACAAGCCTAAATCTTTGAACTCAAATA

CTGCTCTACACTGAATTACAGTTATATACTGATTTCTGTTGTAAATTCTTAGAGAAGACAGACATAGAAATTAG

TAACTTGAGTCAGTAGCGGCTTTGTTCAAACACAGGCACATGCATATTTTATGGTATATGTTTATATCTGTGTA

ATACTCATCATAAATGTCAGATTTATAATCGAGATCACAGTGAGCTGAGATTGCACCACTGCACTCCAGCCTGG

GCAGCGGAGTGAGACCTTTTCTCAAAAAAAAAAAAAAAAAAGGCAAAAAATTAAATTATTAGTATGGTAAAGT

TTCGTTTGGACTTAATATGAAACTCATTTCTAGAAATGATGATCATTTGCATAGGGCTTAACTTCCTTTGCTAA

GAAAATAGAGTAGTATACTAGGAGACTTCCAGAGCTGCATAGAGCTTCAGGGTCATCTACCAAGACAGACAATT

TGTTGTCATCATCAGTGTTAAACTCTAAATTATTAAGTGCTTATGTGCCAGATACTGAAGTTTATATACACTTT

CTCTAATCTTTAATAATTCTAGAAAGGTATGTGTTTGATCCATTTTCAAGATAAGAAAAC

>VAV3_1_108148303_108158073_108220200_108227533_RF (SEQ ID NO: 78)
ATGAGGTTTTTTTCCAGCCTTCCTAAGGGCCTCAAAGTCATATCCAGCAGACTTGCAGGGTTCTCAGGTGAAAG

CAAATTGGAGAAATTTTTAAAATGTAATTTTGGTTTTTACTCCAACTACTTTCAACATGGATTTGTAAAAGACT

GCTAGGATCATTAAAATCAGCATTGAAGCTATGTTGAGCAAGATGGATAGCTGCACTAGAAAAGCTGTAACAAG

AGTCATTGTGAATGAAAGGAAAATTTTGCTCTAGATTTGTTGGTAGCCAAGGCACAAAAATTGGAAGCATAATG

AGTTACAGACTCATGTCTGATAATATGAAAGAACACTAATTTAAAGAAAAAATCTTTTCTGTCTGAAATTTTAT

AATTTAGAGGAACTCTATATAAACAACATCGAAACTTTGCTTCATGCACAAAATTTAAAATATTACATAAAATT

ACCTTCAGGCTTTGTGTATAAGATATATATAAAACATAAATAAATTTTGTGTTTACACTTGGGTTCCATCCTGA

ATATATCTCATGATGTTTATGCAAATATTCCAAAATCTGAAAAAATCTGAAATTCAAAACACTTCCGGTCCCAA

GCATTTTGAATAAGGGATACTCAACCTATAGCTGCATTAATTGAATTAAGACAACCACATAATCTACCTGTTAA

TTTTCTCTGGAGCCTTTTCTTCTGAGCCCTCCACGCTCTTCTAATTGATACTGCTTGCTCTACTAAGCCTGTTG

AATTACTGTAGTCCTGGGACTTCTCTTTGCTCCCCTTTCCTGGCTTCTATATCTCCCTCT

A dual label hydrolysis probe was used to detect the sequenced interaction labeled with 5'-FAM™/BHQ1™-3'. The probe was temperature gradient optimized and designed to span the junction of the 3C fragment making the detection of the 3C product totally specific. The qPCR standard curve ($10^6$ copies-1 copy) was produced from the sequenced product used in the reports figures.

MMP1 copy testing as an internal control for 3C library production.

The primer set and probe used are shown in the reference sequence below. The Taq I site is highlighted. The probe spans the junction of both fragments and is specific at an annealing temperature of 66.4° C.

(SEQ ID NO: 79)
GGGGAGTGGATGGGATAAGGTGGAATGTTGGGTGAACTAAAAGGCCTTTA

AGGCCCCTCTGAAATCCAGCATCGAAGAGGGAAACTGCATCACAGTTGAT

GGAAGTCTGTTGGCCTCTTAACAAAGCTAATGCTTGCCCTTCTGGCTTAG

CTTACATAAGAACCACAAGGAATCTTTGTTGAATTGTTTCTTTCAGATCA

-continued

TCGGGACAACTCTCCTTTTGATGGACCTGGAGGAAATCTTGCTCATGCTT

TTCAACCAGGCCCA

MMP 1-4 2F
                                                  (SEQ ID NO: 80)
5'-GGGGAGTGGATGGGATAAGGTG-3'

MPP 1F
                                                  (SEQ ID NO: 81)
5'-TGGGCCTGGTTGAAAAGCAT-3'

MMP1F1b2 probe
                                                  (SEQ ID NO: 82)
5'-FAM™-ATCCAGCATCGAAGAGGGAAACTGCATCA-BHQ1™-3'

The forward and reverse primer and probe sequences for the hydrolysis qPCRs are describes in the previous tables.

3C library copy number testing with the internal control marker MMP1.

A 3C interaction with MMP-1 was used as a internal control for the EpiSwitch™ library. A dual label 5'FAM-BHQ1-3' labeled hydrolysis probe was used to detect the sequenced interaction. Samples were screened at 20 ng and copy number recorded. The 264 bp product was quantified as above, all samples were run on LabChip™, prior to screening with the 3C target. The target was expressed as a MMP1 ratio for each experiment.

qPCR screening with standard curves and estimation of 3C fragment copy number.

qPCR templates were adjusted to 20 ng of 3C library DNA, and used with concentration-matched negative controls including 3C libraries derived from normal blood. Additional negative controls included patient material without formaldehdye fixation, digested and ligated library material, and normal genomic DNA. A 3C interaction MMP-1 was used as an internal control for the EpiSwitch™ library synthesis.

We have used HEX™, Texas Red™ and FAM™ fluorophores with matched quenchers.

| Abs [nm] | Em [nm] | 3' Quencher | Flurophore |
|---|---|---|---|
| FAM™ | 495 | 520 | TAM™, BHQ1™, DAB™, ECLIP™ |
| TET™ | 521 | 536 | TAM™, BHQ1™ |
| JOE™ | 520 | 548 | TAM™, BHQ1™, BHQ2™ |
| Yakima Yellow™ | 530 | 549 | BHQ1™, ECLIP™ |
| HEX™ | 535 | 556 | TAM™, BHQ1™, BHQ2™, ECLIP™, BBQ650™ |
| CYANINE3™ | 552 | 570 | BHQ1™, BHQ2™, BBQ650™ |
| ATTO 550™ | 554 | 576 | TAM™, BHQ2™ |
| TAMRA | 544 | 576 | BHQ2™ |
| ROX | 575 | 602 | TAM™, BHQ2™, BBQ650™ |
| TEXAS RED™ | 583 | 603 | BHQ2™, BBQ650™ |
| CYANINE3.5™ | 588 | 604 | BHQ2™ |
| LC 610™ | 590 | 610 | BHQ2™ |
| LC 640™ | 625 | 640 | BHQ2™, BBQ650™ |
| ATTO 647N™ | 644 | 669 | BHQ2™, BBQ650™ |
| CYANINE5™ | 649 | 670 | BHQ2™, BBQ650™ |
| CYANINE5.5™ | 675 | 694 | BHQ2™, BBQ650™ |
| ATTO 680™ | 680 | 700 | BBQ650™ |

The invention claimed is:

1. A method for selecting a human individual and treating the selected human individual, wherein the selected human individual is in need of therapy for breast cancer the method comprising: detecting the presence of a first chromosome interaction, the absence of a second chromosome interaction, the presence of a third chromosome interaction, and the presence of a fourth chromosome interaction in a sample from the human individual; selecting the human individual as in need of treatment for breast cancer based on the detection of the presence of the first chromosome interaction, the absence of the second chromosome interaction, the presence of the third chromosome interaction and the presence of the fourth chromosome interaction; and treating the selected human individual for breast cancer by administering an agent which is therapeutic for breast cancer;

wherein said detecting comprises:

(a) cross-linking of chromosome regions which have come together in a chromosome interaction wherein said cross-linking is carried out in a sample from the human individual;

(b) subjecting said cross-linked regions to cleavage;

(c) ligating the cross-linked cleaved DNA ends to form ligated nucleic acids; and (d) detecting the presence or absence of the ligated nucleic acids to thereby detect whether chromosome regions have been brought together in a chromosome interaction;

wherein:

the ligated nucleic acid corresponding to the first chromosome interaction is detected by the probe sequence:

(SEQ ID NO:109)
GGAGGAGGCCAGAGAAAAGAGAATGTGATCGATGACCTTAATGTCAGTG
TCACTGACTCT;

the ligated nucleic acid corresponding to the second chromosome interaction is detected by the probe sequence:

(SEQ ID NO:113)
CATAATTTTTTTTGTAGTTTATTCACCTCGACTAGATTTTAATTTTA
ATTTTTATTTA;

the ligated nucleic acid corresponding to the third chromosome interaction is detected by the probe sequence:

(SEQ ID NO:118)
GGATGGAGGAAGAGGAGGAATTCAAGACTCGAACTAAACAAAAAGGAGA
TGATCCTGGGT; and the ligated nucleic acid corresponding to the fourth chromosome interaction is detected by the probe sequence:

(SEQ ID NO:119)
AATTTAGAGGAACTCTATATAAACAACATCGAAACTTTGCTTCATGCAC
AAAATTTAAAA.

2. The method according to claim 1, wherein:
the method is carried out on an individual who has been selected based on gender or another physical characteristic.

3. The method according to claim 1, wherein one or more of the probe sequences comprises:
a fluorophore covalently attached to the 5' end of the probe sequence; and/or a quencher covalently attached to the 3' end of the probe sequence.

* * * * *